US 10,259,808 B2

(12) United States Patent
Fauber et al.

(10) Patent No.: US 10,259,808 B2
(45) Date of Patent: Apr. 16, 2019

(54) ARYL SULTAM DERIVATIVES AS RORC MODULATORS

(71) Applicant: Genentech, Inc., South San Francisco, CA (US)

(72) Inventors: Benjamin Fauber, Austin, TX (US); Emanuela Gancia, Essex (GB); Tammy Ladduwahetty, Essex (GB); David Vesey, Essex (GB); Paul Winship, Essex (GB); Olivier Rene, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/847,407

(22) Filed: Dec. 19, 2017

(65) Prior Publication Data

US 2018/0105516 A1    Apr. 19, 2018

Related U.S. Application Data

(63) Continuation of application No. PCT/EP2016/066271, filed on Jul. 8, 2016.

(60) Provisional application No. 62/190,071, filed on Jul. 8, 2015, provisional application No. 62/345,195, filed on Jun. 3, 2016.

(51) Int. Cl.

| C07D 417/12 | (2006.01) |
|---|---|
| C07D 417/14 | (2006.01) |
| C07D 417/10 | (2006.01) |
| A61K 31/541 | (2006.01) |
| A61P 19/02 | (2006.01) |
| A61P 17/06 | (2006.01) |

(52) U.S. Cl.
CPC .......... *C07D 417/14* (2013.01); *A61K 31/541* (2013.01); *A61P 17/06* (2018.01); *A61P 19/02* (2018.01); *C07D 417/10* (2013.01); *C07D 417/12* (2013.01)

(58) Field of Classification Search
CPC ... C07D 417/12; C07D 417/14; C07D 417/10
USPC .......................................... 544/3; 514/222.2
See application file for complete search history.

(56) References Cited

U.S. PATENT DOCUMENTS

| 9,115,101 B2 * | 8/2015 | Bodil van Niel .... C07D 417/10 |
| 9,751,873 B2 * | 9/2017 | Fauber ................ C07D 417/10 |
| 10,131,644 B2 * | 11/2018 | van Niel ............. C07D 279/02 |

FOREIGN PATENT DOCUMENTS

| WO | 2014/009447 A1 | 1/2014 |
| WO | 2015/104356 A1 | 7/2015 |
| WO | 2016/096936 A1 | 6/2016 |

OTHER PUBLICATIONS

PCT ISR and Written Opinion for PCT/EP2016/066271.

* cited by examiner

*Primary Examiner* — Venkataraman Balasubramanian
(74) *Attorney, Agent, or Firm* — Robert C. Hall

(57) ABSTRACT

Compounds of the formula I:

or pharmaceutically acceptable salts thereof, wherein m, n, p, q, r, $X^1$, $X^2$, $X^3$, $X^4$, Y, Z, A, Het, $R^1$, $R^2$, $R^3$, $R^4$, $R^5$, $R^6$, $R^7$, $R^8$, $R^9$, $R^{10}$, $R^{11}$, $R^{12}$ and $R^{13}$ are as defined herein. Also disclosed are methods of making the compounds and using the compounds for treatment of inflammatory diseases such as arthritis, muscular sclerosis and psoriasis.

11 Claims, No Drawings

ARYL SULTAM DERIVATIVES AS RORC MODULATORS

CROSS REFERENCE TO RELATED APPLICATIONS

This Application is a Continuation of International Patent Application PCT/EP/2016/066271 filed on Jul. 8, 2016 which is entitled to the benefit of U.S. Provisional Patent Applications No. 62/190,071 filed on Jul. 8, 2015, and U.S. Provisional Patent Applications No. 62/345,195 filed on Jun. 3, 2016, the disclosures of which are incorporated herein by reference

FIELD OF THE INVENTION

The invention pertains to compounds that modulate the function of retinoid-receptor related orphan receptor RORc (RORγ) and use of such compounds for treatment of auto-immune diseases

BACKGROUND OF THE INVENTION

T helper 17 cells (Th17) are interleukin (IL)-17 secreting CD4+ T cells involved in pathogenesis of autoimmune diseases such as rheumatoid arthritis, irritable bowel disease, psoriasis, psoriatic arthritis and spondyloarthridities. The retinoic acid-related orphan receptor γ (RORγ or RORc) is recognized as a transcription factor necessary for Th17 cell differentiation. RORc is an orphan member of the nuclear hormone receptor subfamily that includes RORα (RORa) and RORβ (RORb). RORc controls gene transcription by binding to DNA as a monomer. Selective modulation of RORc has been proposed as a route to discovery and development of Th17 cell-associated autoimmune diseases.

There is accordingly a need for compounds that inhibit RORc for use in treatment of autoimmune diseases such as rheumatoid arthritis, osteoarthritis, psoriatic arthritis, irritable bowel disease, asthma, COPD, psoriasis, lupus, Sjogren's disease, idiopathic pulmonary fibrosis, muscular sclerosis and spondyloarthritis.

SUMMARY OF THE INVENTION

The invention provides compounds of the formula I:

or a pharmaceutically acceptable salt thereof, wherein:
m is 0 or 1;
n is 0 or 1;
p is from 0 to 3;
q is 0, 1 or 2;
r is f1, 2 or 3;
A is:
a bond;
—$(CR_jR_k)_t$—;
—$C(O)$—$(CR_jR_k)_t$—;
—$(CR_jR_k)_t$—$C(O)$—;
—$NR^a$—$(CR_jR_k)_t$—;
—$(CR_jR_k)_t$—$NR^a$—;
—$C(O)NR^a$—$(CR_jR_k)_t$—;
—$(CR_jR_k)_t$—$NR^aC(O)$—;
—$O$—$(CR_jR_k)_t$—;
—$(CR_jR_k)_t$—$O$—;
—$S$—$(CR_jR_k)_t$—;
—$(CR_jR_k)_t$—$S$—;
—$SO_2$—$(CR_jR_k)_t$—;
—$(CR_jR_k)_t$—$SO_2$—; or
t is from 0 to 4;
W is:
—$CR^bR^c$—;
—$O$—;
—$S$—;
—$SO_2$—; or
—$NR^d$—;
one of $X^1$, $X^2$, $X^3$ and $X^4$ is N and the others are $CR^e$;
or two of $X^1$, $X^2$, $X^3$ and $X^4$ are N and the others are $CR^e$;
or three of $X^1$, $X^2$, $X^3$ and $X^4$ are N and the other is $CR^e$;
or each of $X^1$, $X^2$, $X^3$ and $X^4$ is $CR^e$;
Y is:
—$O$—;
—$S$—;
—$SO_2$—;
—$CR^fR^g$—; or
—$NR^h$—;
Z is:
a bond;
—$C_{1-6}$alkylene-;
—$NR^p$—$C_{1-6}$alkylene;
—$C_{1-6}$alkylene-$NR^p$—;
—$NR^p$—;
—$C(O)$—;
—$C(O)NR^p$—;
—$C(O)NR^p$—$C_{1-6}$alkylene;
—$NR^pC(O)$—;
—$NR^pC(O)$—$C_{1-6}$alkylene;
—$C_{1-6}$alkylene-$O$—;
—$O$—$C_{1-6}$alkylene-; or
—$C_{1-6}$alkylene-$O$—$C_{1-6}$alkylene-;
Het is:
heteroaryl selected from:
  oxazolyl;
  isoxazolyl;
  thiazolyl;
  isothiazolyl;
  pyrazolyl;
  triazolyl;
  oxadiazolyl;
  thiadiazolyl;
  pyridinyl;
  pyrimidinyl;
  pyrazinyl; or
  imidazolyl;
each of which heteroaryl may be unsubstituted or substituted one or more times with $R^m$; or
heterocyclyl selected from:
  oxetanyl;
  tetrahydrofuranyl;
  tetrahydropyranyl;
  pyrrolidinyl;

piperidinyl;
piperazinyl;
oxazolidinyl;
imidazolidinyl;
morpoholinyl;
thiomorpholinyl; or
1,1-dioxothiomorpholinyl;
each of which heterocyclyl may be unsubstituted or substituted one or more times with $R^n$;
$R^1$, $R^2$, $R^3$, $R^4$, $R^5$, $R^6$, $R^7$ and $R^8$ each independently is:
hydrogen; or
$C_{1-6}$alkyl which may be unsubstituted or substituted one or more times with halo;
or $R^3$ and $R^4$ together with the atom to which they are attached may form an ethylene group; or $R^3$ and $R^4$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or $R^5$ and $R^6$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or $R^7$ and $R^8$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^3$ and $R^4$ together with one of $R^5$ and $R^6$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^5$ and $R^6$ together with one of $R^7$ and $R^8$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
each $R^9$ is independently:
$C_{1-6}$alkyl;
halo;
$C_{1-6}$alkoxy; or
cyano;
wherein the $C_{1-6}$alkyl moieties may be unsubstituted or substituted one or more times with halo;
$R^{10}$ is:
hydrogen;
carboxy;
$C_{1-6}$alkyl-carbonyl;
$C_{1-6}$alkoxy-carbonyl;
oxo;
hydroxy;
aminocarbonyl;
N—$C_{1-6}$alkyl-aminocarbonyl;
N,N-di-$C_{1-6}$alkyl-aminocarbonyl;
cyano;
hydroxy-$C_{1-6}$alkyl;
N—$C_{1-6}$alkoxy-$C_{1-6}$alkyl-aminocarbonyl;
N-hydroxy-$C_{1-6}$alkyl-aminocarbonyl;
N—$C_{1-6}$alkoxy-aminocarbonyl;
halo; or
$C_{1-6}$alkyl which may be unsubstituted or substituted one or more times with halo or oxo;
$R^{11}$ is:
hydrogen;
halo;
carboxy;
$C_{1-6}$alkyl-carbonyl;
$C_{1-6}$alkoxy-carbonyl;
oxo;
hydroxy;
aminocarbonyl;
N—$C_{1-6}$alkyl-aminocarbonyl;
N,N-di-$C_{1-6}$alkyl-aminocarbonyl;
$C_{1-6}$alkyl-sulfonylamino;
$C_{1-6}$alkyl-sulfonylamino-$C_{1-6}$alkyl;
cyano;
hydroxy-$C_{1-6}$alkyl;
N—$C_{1-6}$alkoxy-$C_{1-6}$alkyl-aminocarbonyl;
N-hydroxy-$C_{1-6}$alkyl-aminocarbonyl;
N—$C_{1-6}$alkoxy-aminocarbonyl; or
$C_{1-6}$alkyl which may be unsubstituted or substituted one or more times with halo or oxo;
or $R^{10}$ and $R^{11}$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or $R^{10}$ and $R^{11}$ together with the atoms to which they are attached may form a double bond;
$R^{12}$ is:
hydrogen;
halo;
carboxy;
$C_{1-6}$alkyl-carbonyl;
$C_{1-6}$alkoxy-carbonyl;
oxo;
hydroxy;
aminocarbonyl;
N—$C_{1-6}$alkyl-aminocarbonyl;
N,N-di-$C_{1-6}$alkyl-aminocarbonyl;
cyano;
hydroxy-$C_{1-6}$alkyl;
N—$C_{1-6}$alkoxy-$C_{1-6}$alkyl-aminocarbonyl;
N-hydroxy-$C_{1-6}$alkyl-aminocarbonyl;
N—$C_{1-6}$alkoxy-aminocarbonyl; or
$C_{1-6}$alkyl which may be unsubstituted or substituted one or more times with halo or oxo;
$R^{13}$ is:
hydrogen; or
$C_{1-6}$alkyl which may be unsubstituted or substituted one or more times with halo;
$R^a$, $R^b$, $R^c$ and $R^d$ each independent is:
hydrogen; or
$C_{1-6}$alkyl which may be unsubstituted or substituted one or more times with halo;
or $R^b$ and $R^c$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^b$ and $R^c$ together with one of $R^7$ and $R^8$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

or one of R$^b$ and R$^c$ together with one of R$^5$ and R$^6$ and the atoms to which they are attached may form a three, four, five, six or seven membered saturated or partially saturated ring that may optionally include one or two heteroatoms selected from —O—, —NR$^a$— or —S—, and which may be optionally substituted one or more times with R$^i$;

each R$^e$ is independently:
hydrogen;
C$_{1-6}$alkyl;
halo;
C$_{1-6}$alkoxy; or
cyano;
wherein the C$_{1-6}$alkyl moieties may be unsubstituted or substituted one or more times with halo, hydroxy or C$_{1-6}$alkoxy;

R$^f$ is:
hydrogen;
halo;
C$_{1-6}$alkoxy; or
C$_{1-6}$alkyl which may be unsubstituted or substituted one or more times with halo, hydroxy, or C$_{1-6}$alkoxy;

R$^g$ is:
hydrogen;
C$_{1-6}$alkyl;
C$_{3-6}$cycloalkyl which may be unsubstituted or substituted once or twice with C$_{1-6}$alkyl;
C$_{2-6}$alkenyl;
C$_{3-6}$cycloalkenyl;
C$_{3-6}$cycloalkyl-C$_{1-6}$alkyl;
halo;
C$_{1-6}$alkyl-carbonyl;
C$_{3-6}$cycloalkyl-carbonyl;
C$_{3-6}$cycloalkyl-C$_{1-6}$alkyl-carbonyl;
cyano-C$_{1-6}$alkyl-carbonyl;
hydroxy-C$_{1-6}$alkyl-carbonyl;
C$_{1-6}$alkoxy-C$_{1-6}$alkyl-carbonyl;
carboxy;
N-cyano-aminocarbonyl;
N-cyano-N—C$_{1-6}$alkyl-aminocarbonyl;
N—C$_{1-6}$alkyl-acetimidamidyl;
N,N'-di-C$_{1-6}$alkyl-acetimidamidyl;
N'-cyano-N—C$_{1-6}$alkyl-acetimidamidyl;
N'-hydroxy-acetimidamidyl;
N'—C$_{1-6}$alkoxy-acetimidamidyl;
N'-hydroxy-N—C$_{1-6}$alkyl-acetimidamidyl;
N'—C$_{1-6}$alkoxy-N—C$_{1-6}$alkyl-acetimidamidyl;
2-nitro-1-N—C$_{1-6}$alkylamino-vinyl; formyl;
C$_{1-6}$alkyl-sulfonyl;
C$_{3-6}$cycloalkyl-sulfonyl;
C$_{3-6}$cycloalkyl-C$_{1-6}$alkyl-sulfonyl;
C$_{1-6}$alkyl-sulfonyl-C$_{1-6}$alkyl;
aminocarbonyl;
carbonylamino;
N-hydroxy-aminocarbonyl;
N—C$_{1-6}$alkoxy-aminocarbonyl;
N—C$_{1-6}$alkyl-aminocarbonyl;
aminocarbonyl-C$_{1-6}$alkyl;
N—C$_{1-6}$alkyl-aminocarbonyl-C$_{1-6}$alkyl;
N,N-di-C$_{1-6}$alkyl-aminocarbonyl-C$_{1-6}$alkyl;
C$_{1-6}$alkoxy-carbonyl;
N-hydroxy-N—C$_{1-6}$alkyl-aminocarbonyl;
N—C$_{1-6}$alkoxy-N—C$_{1-6}$alkyl-aminocarbonyl;
N,N-di-C$_{1-6}$alkyl-aminocarbonyl;
aminosulfonyl;
N—C$_{1-6}$alkyl-aminosulfonyl;
N,N-di-C$_{1-6}$alkyl-aminosulfonyl;
cyano;
C$_{1-6}$alkoxy;
C$_{1-6}$alkyl-sulfonylamino;
N—C$_{1-6}$alkyl-sulfonylaminocarbonyl;
N—(C$_{1-6}$alkyl-sulfonyl)-N—C$_{1-6}$alkyl-aminocarbonyl;
N—(C$_{1-6}$alkyl-sulfonyl)-amino-C$_{1-6}$alkyl; amino;
N—C$_{1-6}$alkyl-amino;
N,N-di-C$_{1-6}$alkyl-amino;
halo-C$_{1-6}$alkyl;
phenyl;
heterocyclyl;
heteroaryl;
C$_{1-6}$alkyl-carbonylamino;
carbonylamino; or
hydroxy;
wherein the C$_{1-6}$alkyl moieties may be unsubstituted or substituted one or more times with halo; and
wherein the phenyl, heterocyclyl, heteroaryl, C$_{3-6}$cycloalkyl, C$_{3-6}$cycloalkenyl and C$_{3-6}$cycloalkyl-C$_{1-6}$alkyl moieties may be unsubstituted or substituted one or more times with R$^i$;

or R$^f$ and R$^g$ together may form oxo;

or R$^f$ and R$^g$ together with the atoms to which they are attached may form a four, five, six or seven membered saturated or partially saturated ring that may optionally include one or two heteroatoms selected from —O—, —NR$^a$— or —S—, and which may be optionally substituted one or more times with R$^i$;

R$^h$ is:
hydrogen;
C$_{1-6}$alkyl;
C$_{3-6}$cycloalkyl;
C$_{3-6}$cycloalkenyl;
C$_{3-6}$cycloalkyl-C$_{1-6}$alkyl;
C$_{1-6}$alkyl-carbonyl;
C$_{3-6}$cycloalkyl-carbonyl;
C$_{3-6}$cycloalkyl-C$_{1-6}$alkyl-carbonyl;
cyano-C$_{1-6}$alkyl-carbonyl;
hydroxy-C$_{1-6}$alkyl-carbonyl;
C$_{1-6}$alkoxy-C$_{1-6}$alkyl-carbonyl;
N-cyano-aminocarbonyl;
N-cyano-N—C$_{1-6}$alkyl-aminocarbonyl;
N—C$_{1-6}$alkyl-acetimidamidyl;
N,N'-di-C$_{1-6}$alkyl-acetimidamidyl;
N'-cyano-N—C$_{1-6}$alkyl-acetimidamidyl;
N'-hydroxy-acetimidamidyl;
N'—C$_{1-6}$alkoxy-acetimidamidyl;
N'-hydroxy-N—C$_{1-6}$alkyl-acetimidamidyl;
N'—C$_{1-6}$alkoxy-N—C$_{1-6}$alkyl-acetimidamidyl;
2-nitro-1-N—C$_{1-6}$alkylamino-vinyl;
formyl;
C$_{1-6}$alkyl-sulfonyl;
C$_{3-6}$cycloalkyl-sulfonyl;
C$_{3-6}$cycloalkyl-C$_{1-6}$alkyl-sulfonyl;
C$_{1-6}$alkyl-sulfonyl-C$_{1-6}$alkyl;
aminocarbonyl;
N-hydroxy-aminocarbonyl;
N—C$_{1-6}$alkoxy-aminocarbonyl;
N—C$_{1-6}$alkyl-aminocarbonyl;
N-hydroxy-N—C$_{1-6}$alkyl-aminocarbonyl;
N—C$_{1-6}$alkoxy-N—C$_{1-6}$alkyl-aminocarbonyl;
N,N-di-C$_{1-6}$alkyl-aminocarbonyl;
aminosulfonyl;
N—C$_{1-6}$alkyl-aminosulfonyl;
N,N-di-C$_{1-6}$alkyl-aminosulfonyl;
cyano;

$C_{1-6}$alkyl-sulfonylamino;
$C_{1-6}$alkyl-sulfonylamino-$C_{1-6}$alkyl;
N—($C_{1-6}$alkyl-sulfonyl)aminocarbonyl;
N—($C_{1-6}$alkyl-sulfonyl)-N—$C_{1-6}$alkyl-aminocarbonyl;
N—($C_{1-6}$alkyl-sulfonyl)-amino-$C_{1-6}$alkyl;
aminocarbonyl-$C_{1-6}$alkyl;
N—$C_{1-6}$alkyl-aminocarbonyl-$C_{1-6}$alkyl;
N,N-di-$C_{1-6}$alkyl-aminocarbonyl-$C_{1-6}$alkyl;
$C_{1-6}$alkoxy-carbonyl;
phenyl;
heterocyclyl; or
heteroaryl;
  wherein the $C_{1-6}$alkyl moieties may be unsubstituted or substituted one or more times with halo; and
  wherein the phenyl, heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;
or $R^h$ and one of $R^{10}$ and $R^{11}$ together with the atoms to which they are attached may form a four, five, six or seven membered aromatic, partially saturated or unsaturated ring that may optionally include one or two additional heteroatom selected from —O—, —$NR^a$— or —S—, and which may be optionally substituted one or more times with $R^i$—;
or one of $R^f$ and $R^g$ and one of $R^{10}$ and $R^{11}$ together with the atoms to which they are attached may form a three, four, five, six or seven membered aromatic, partially saturated or unsaturated ring that may optionally include an additional heteroatom selected from —O—, —$NR^a$— or —S—, and which may be optionally substituted one or more times with $R^i$;
  $R^i$ is:
  $C_{1-6}$alkyl;
  halo-$C_{1-6}$alkyl;
  $C_{3-6}$cycloalkyl;
  halo;
  oxo;
  hydroxy;
  acetyl;
  $C_{1-6}$alkyl-carbonyl;
  amino-carbonyl;
  hydroxy-$C_{1-6}$alkyl;
  cyano;
  cyano-$C_{1-6}$alkyl;
  $C_{1-6}$alkoxy-$C_{1-6}$alkyl;
  carboxy; or
  $C_{1-6}$alkoxy;
  $R^j$ and $R^k$ each independent is:
  hydrogen; or
  $C_{1-6}$alkyl which may be unsubstituted or substituted one or more times with halo;
  each $R^m$ is independently:
  $C_{1-6}$alkyl;
  oxo;
  hydroxyl;
  amino;
  $C_{3-6}$cycloalkyl;
  amino-$C_{1-6}$alkyl;
  hydroxyl-$C_{1-6}$alkyl;
  hydroxyl-$C_{1-6}$alkenyl;
  $C_{1-6}$alkoxycarbonyl-$C_{1-6}$alkyl;
  halo;
  cyano-$C_{1-6}$alkyl;
  aminocarbonyl-$C_{1-6}$alkyl; or
  $C_{1-6}$alkoxycarbonyl;
  each $R^n$ is independently:
  $C_{1-6}$alkyl;
  oxo;
  hydroxyl;
  amino;
  $C_{3-6}$cycloalkyl;
  amino-$C_{1-6}$alkyl;
  hydroxyl-$C_{1-6}$alkyl;
  hydroxyl-$C_{1-6}$alkenyl;
  $C_{1-6}$alkoxycarbonyl-$C_{1-6}$alkyl;
  halo;
  aminocarbonyl-$C_{1-6}$alkyl; or
  $C_{1-6}$alkoxycarbonyl; and
  $R^p$ is:
  hydrogen; or
  $C_{1-6}$alkyl.

The invention also provides and pharmaceutical compositions comprising the compounds, methods of using the compounds, and methods of preparing the compounds.

In the compounds of the invention, the group Z of formula I is a quaternary carbon with a heteroaryl or heterocyclyl substituent. Surprisingly and unexpectedly, introduction of the heteroaryl or heterocyclyl group at the group Z, via direct bond or an intervening linker in accordance with the invention, results in compounds having improved selectivity for RORc (RORγ) over other receptor subtypes RORa and RORb (RORα and RORβ), as well as other improved properties, in comparison to analogous compounds that do not have a heteroaryl or heterocyclyl substituent at group Z.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein.

Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylalkyl" means a group of the formula —R—C(O)—R wherein R is alkylene and R' is alkyl as defined herein.

"Alkoxyalkylcarbonyl" means a moiety of the formula —C(O)—R—R', wherein R is alkylene and R' is alkoxy as defined herein.

"Alkoxycarbonylalkyl" means a group of the formula —R—C(O)—R wherein R is alkylene and R' is alkoxy as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R' wherein R is alkylene and R' and R" are alkyl as defined herein.

"Alkylsulfonyl" means a moiety of the formula —SO$_2$—R, wherein R is alkyl as defined herein.

"Alkylsulfonylalkyl means a moiety of the formula —R'—SO$_2$—R" where R' is alkylene and R" is alkyl as defined herein.

"Alkylsulfonylalkoxy" means a group of the formula —O—R—SO$_2$—R' wherein R is alkylene and R' is alkyl as defined herein.

"Amino means a moiety of the formula —NRR' wherein R and R' each independently is hydrogen or alkyl as defined herein. "Amino thus includes "alkylamino (where one of R and R' is alkyl and the other is hydrogen) and "dialkylamino (where R and R' are both alkyl.

"Aminocarbonyl" means a group of the formula —C(O)—R wherein R is amino as defined herein.

"N-hydroxy-aminocarbonyl" means a group of the formula —C(O)—NR—OH wherein R is hydrogen or alkyl as defined herein.

"N-alkoxy-aminocarbonyl" means a group of the formula —C(O)—NR—R' wherein R is hydrogen or alkyl and R' is alkoxy as defined herein.

"N-alkyl-aminocarbonyl means a group of the formula —C(O)—NH—R wherein R is alkyl as defined herein.

"N-hydroxy-N-alkylaminocarbonyl means a group of the formula —C(O)—NRR' wherein R is alkyl as defined herein and R' is hydroxy.

"N-alkoxy-N-alkylaminocarbonyl" means a group of the formula —C(O)—NRR' wherein R is alkyl and R' is alkoxy as defined herein.

"N,N-di-C$_{1-6}$alkyl-aminocarbonyl" means a group of the formula —C(O)—NRR' wherein R and R' are alkyl as defined herein.

"Aminosulfonyl" means a group of the formula —SO$_2$—NH$_2$.

"N-alkylaminosulfonyl" means a group of the formula —SO$_2$—NHR wherein R is alkyl as defined herein.

"N,N-dialkylaminosulfonyl" means a group of the formula —SO$_2$—NRR' wherein R and R' are alkyl as defined herein.

"Alkylsulfonylamino" means a group of the formula —NR'—SO$_2$—R wherein R id alkyl and R' is hydrogen or alkyl as defined herein.

"N-(alkylsulfonyl)-aminoalkyl" means a group of the formula —R—NH—SO$_2$—R' wherein R is alkylene and R' is alkyl as defined herein.

"N-(Alkylsulfonyl)aminocarbonyl" means a group of the formula —C(O)—NH—SO$_2$—R wherein wherein R is alkyl as defined herein.

"N-(Alkylsulfonyl)-N-alkylaminocarbonyl" means a group of the formula —C(O)—NR—SO$_2$—R' wherein R and R' are alkyl as defined herein.

"N-Alkoxyalkyl-aminocarbonyl" means a group of the formula —C(O)—NR—R'—OR" wherein R is hydrogen or alkyl, R' is alkylene, and R" is alkyl as defined herein.

"N-Hydroxyalkyl-aminocarbonyl" means a group of the formula —C(O)—NR—R'—OH" wherein R is hydrogen or alkyl and R' is alkylene as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein.

"Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'SO$_2$—R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substituted with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkenyl" means a cycloalkyl as defined herein that includes at least one double bond or unsaturation. Exemplary cycloalkenyl include cyclohexenyl, cyclopentenyl, cyclobutenyl and the like.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Cycloalkylcarbonyl" means a moiety of the formula —C(O)—R, wherein R is cycloalkyl as defined herein.

"$C_{3-6}$cycloalkyl-$C_{1-6}$alkyl-carbonyl" means a moiety of the formula —C(O)—R, wherein R is cycloalkylalkyl as defined herein.

"Cyanoalkylcarbonyl" means a moiety of the formula —C(O)—R—R', wherein R is alkylene as defined herein and R' is cyano or nitrile.

"N—Cyano-aminocarbonyl" means a moiety of the formula —C(O)—NHR, wherein R is cyano or nitrile.

"N—Cyano-N-alkyl-aminocarbonyl" means a moiety of the formula —C(O)—NRR'—R, wherein R' is alkyl as defined herein and R is cyano or nitrile.

"Cycloalkylsulfonyl" means a group of the formula —$SO_2$—R wherein R is cycloalkyl as defined herein.

"Cycloalkylalkylsulfonyl" means a group of the formula —$SO_2$—R wherein R is cycloalkylalkyl as defined herein.

"Formyl" means a moiety of the formula —C(O)—H.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzoxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

"Heteroarylalkyl" or "heteroaralkyl" means a group of the formula —R—R' wherein R is alkylene and R' is heteroaryl as defined herein.

"Heteroarylsulfonyl means a group of the formula —$SO_2$—R wherein R is heteroaryl as defined herein.

"Heteroaryloxy" means a group of the formula —O—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkylcarbonyl" means a moiety of the formula —C(O)—R—R', wherein R is alkylene as defined herein and R' is hydroxy.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Oxo" means a group of the formula =O (i.e., an oxygen with a double bond). Thus, for example, a 1-oxo-ethyl group is an acetyl group.

"Alkoxy hydroxyalkyl" and "hydroxy alkoxyalkyl", which may be used interchangeably, means an alkyl as defined herein that is substituted at least once with hydroxy and at least once with alkoxy.

"Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted" when used in association with an "aryl", phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Arthritis" means a disease or condition that causes damage to joints of the body and pain associated with such joint damage. Arthritis includes rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

"Respiratory disorder" refers to, without limitation, chronic obstructive pulmonary disease (COPD), asthma, bronchospasm, and the like.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature and chemical names used in this Application are based on ChembioOffice™ by CambridgeSoft™. Any open valency appearing on a carbon, oxygen sulfur or nitrogen atom in the structures herein indicates the presence of a hydrogen atom unless indicated otherwise. Where a nitrogen-containing heteroaryl ring is shown with an open valency on a nitrogen atom, and variables such as $R^a$, $R^b$ or $R^c$ are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structures herein are intended to encompass all naturally occurring isotopes of such atoms. Thus, for example, the hydrogen atoms represented herein are meant to include deuterium and tritium, and the carbon atoms are meant to include $C^{13}$ and $C^{14}$ isotopes. One or more carbon atom(s) of a compound of the invention may be replaced by a silicon atom(s), and it is contemplated that one or more oxygen atom(s) of a compound of the invention may be replaced by a sulfur or selenium atom(s).

Compounds of the Invention

The invention provides compounds of the formula I:

or a pharmaceutically acceptable salt thereof,
wherein:
m is 0 or 1;
n is 0 or 1;
p is from 0 to 3;
q is 0, 1 or 2;
r is f1, 2 or 3;
A is:
a bond;
—$(CR_jR_k)_t$—;
—C(O)—$(CR_jR_k)_t$—;
—$(CR_jR_k)_t$—C(O)—;
—$NR^a$—$(CR_jR_k)_t$—;
—$(CR_jR_k)_t$—$NR^a$—;
—C(O)$NR^a$—$(CR_jR_k)_t$—;
—$(CR_jR_k)_t$—$NR^aC(O)$—;
—O—$(CR_jR_k)_t$—;
—$(CR_jR_k)_t$—O—;
—S—$(CR_jR_k)_t$—;
—$(CR_jR_k)_t$—S—;
—$SO_2$—$(CR_jR_k)_t$—;
—$(CR_jR_k)_t$—$SO_2$—; or
t is from 0 to 4;
W is:
—$CR^bR^c$—;
—O—;
—S—;
—$SO_2$—; or
—$NR^d$—;
one of $X^1$, $X^2$, $X^3$ and $X^4$ is N and the others are $CR^e$;
or two of $X^1$, $X^2$, $X^3$ and $X^4$ are N and the others are $CR^e$;
or three of $X^1$, $X^2$, $X^3$ and $X^4$ are N and the other is $CR^e$;
or each of $X^1$, $X^2$, $X^3$ and $X^4$ is $CR^e$;
Y is:
—O—;
—S—;
—$SO_2$—;
—$CR^fR^g$—; or
—$NR^h$—;
Z is:
a bond;
—$C_{1-6}$alkylene-;
—$NR^p$—$C_{1-6}$alkylene;
—$C_{1-6}$alkylene-$NR^p$—;
—NR—;
—C(O)—;
—C(O)$NR^p$—;
—C(O)$NR^p$—$C_{1-6}$alkylene;
—$NR^pC(O)$—;
—$NR^pC(O)$—$C_{1-6}$alkylene;
—$C_{1-6}$alkylene-O—;

—O—$C_{1-6}$alkylene-; or
—$C_{1-6}$alkylene-O—$C_{1-6}$alkylene-;
Het is:
  heteroaryl selected from:
    oxazolyl;
    isoxazolyl;
    thiazolyl;
    isothiazolyl;
    pyrazolyl;
    triazolyl;
    oxadiazolyl;
    thiadiazolyl;
    pyridinyl;
    pyrimidinyl;
    pyrazinyl; or
    imidazolyl;
  each of which heteroaryl may be unsubstituted or substituted one or more times with $R^m$; or
  heterocyclyl selected from:
    oxetanyl;
    tetrahydrofuranyl;
    tetrahydropyranyl;
    pyrrolidinyl;
    piperidinyl;
    piperazinyl;
    oxazolidinyl;
    imidazolidinyl;
    morpoholinyl;
    thiomorpholinyl; or
    1,1-dioxothiomorpholinyl;
  each of which heterocyclyl may be unsubstituted or substituted one or more times with $R^n$;
$R^1$, $R^2$, $R^3$, $R^4$, $R^5$, $R^6$, $R^7$ and $R^8$ each independently is:
  hydrogen; or
  $C_{1-6}$alkyl which may be unsubstituted or substituted one or more times with halo;
  or $R^3$ and $R^4$ together with the atom to which they are attached may form an ethylene group; or $R^3$ and $R^4$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
  or $R^5$ and $R^6$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
  or $R^7$ and $R^8$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
  or one of $R^3$ and $R^4$ together with one of $R^5$ and $R^6$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
  or one of $R^5$ and $R^6$ together with one of $R^7$ and $R^8$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
    each $R^9$ is independently:
      $C_{1-6}$alkyl;
      halo;
      $C_{1-6}$alkoxy; or
      cyano;
      wherein the $C_{1-6}$alkyl moieties may be unsubstituted or substituted one or more times with halo;
    $R^{10}$ is:
      hydrogen;
      carboxy;
      $C_{1-6}$alkyl-carbonyl;
      $C_{1-6}$alkoxy-carbonyl;
      oxo;
      hydroxy;
      aminocarbonyl;
      N—$C_{1-6}$alkyl-aminocarbonyl;
      N,N-di-$C_{1-6}$alkyl-aminocarbonyl;
      cyano;
      hydroxy-$C_{1-6}$alkyl;
      N—$C_{1-6}$alkoxy-$C_{1-6}$alkyl-aminocarbonyl;
      N-hydroxy-$C_{1-6}$alkyl-aminocarbonyl;
      N—$C_{1-6}$alkoxy-aminocarbonyl;
      halo; or
      $C_{1-6}$alkyl which may be unsubstituted or substituted one or more times with halo or oxo;
    $R^{11}$ is:
      hydrogen;
      halo;
      carboxy;
      $C_{1-6}$alkyl-carbonyl;
      $C_{1-6}$alkoxy-carbonyl;
      oxo;
      hydroxy;
      aminocarbonyl;
      N—$C_{1-6}$alkyl-aminocarbonyl;
      N,N-di-$C_{1-6}$alkyl-aminocarbonyl;
      $C_{1-6}$alkyl-sulfonylamino;
      $C_{1-6}$alkyl-sulfonylamino-$C_{1-6}$alkyl;
      cyano;
      hydroxy-$C_{1-6}$alkyl;
      N—$C_{1-6}$alkoxy-$C_{1-6}$alkyl-aminocarbonyl;
      N-hydroxy-$C_{1-6}$alkyl-aminocarbonyl;
      N—$C_{1-6}$alkoxy-aminocarbonyl; or
      $C_{1-6}$alkyl which may be unsubstituted or substituted one or more times with halo or oxo;
    or $R^{10}$ and $R^{11}$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
    or $R^{10}$ and $R^{11}$ together with the atoms to which they are attached may form a double bond;
    $R^{12}$ is:
      hydrogen;
      halo;
      carboxy;
      $C_{1-6}$alkyl-carbonyl;
      $C_{1-6}$alkoxy-carbonyl;
      oxo;
      hydroxy;
      aminocarbonyl;
      N—$C_{1-6}$alkyl-aminocarbonyl;
      N,N-di-$C_{1-6}$alkyl-aminocarbonyl;
      cyano;

hydroxy-$C_{1-6}$alkyl;
N—$C_{1-6}$alkoxy-$C_{1-6}$alkyl-aminocarbonyl;
N-hydroxy-$C_{1-6}$alkyl-aminocarbonyl;
N—$C_{1-6}$alkoxy-aminocarbonyl; or
$C_{1-6}$alkyl which may be unsubstituted or substituted one or more times with halo or oxo;
$R^{13}$ is:
hydrogen; or
$C_{1-6}$alkyl which may be unsubstituted or substituted one or more times with halo;
$R^a$, $R^b$, $R^c$ and $R^d$ each independent is:
hydrogen; or
$C_{1-6}$alkyl which may be unsubstituted or substituted one or more times with halo;
or $R^b$ and $R^c$ together with the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^b$ and $R^c$ together with one of $R^7$ and $R^8$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
or one of $R^b$ and $R^c$ together with one of $R^5$ and $R^6$ and the atoms to which they are attached may form a three, four, five, six or seven membered saturated or partially saturated ring that may optionally include one or two heteroatoms selected from —O—, —$NR^a$— or —S—, and which may be optionally substituted one or more times with $R^i$;
each $R^e$ is independently:
hydrogen;
$C_{1-6}$alkyl;
halo;
$C_{1-6}$alkoxy; or
cyano;
wherein the $C_{1-6}$alkyl moieties may be unsubstituted or substituted one or more times with halo, hydroxy or $C_{1-6}$alkoxy;
$R^f$ is:
hydrogen;
halo;
$C_{1-6}$alkoxy; or
$C_{1-6}$alkyl which may be unsubstituted or substituted one or more times with halo, hydroxy, or $C_{1-6}$alkoxy;
$R^g$ is:
hydrogen;
$C_{1-6}$alkyl;
$C_{3-6}$cycloalkyl which may be unsubstituted or substituted once or twice with $C_{1-6}$alkyl;
$C_{2-6}$alkenyl;
$C_{3-6}$cycloalkenyl;
$C_{3-6}$cycloalkyl-$C_{1-6}$alkyl;
halo;
$C_{1-6}$alkyl-carbonyl;
$C_{3-6}$cycloalkyl-carbonyl;
$C_{3-6}$cycloalkyl-$C_{1-6}$alkyl-carbonyl;
cyano-$C_{1-6}$alkyl-carbonyl;
hydroxy-$C_{1-6}$alkyl-carbonyl;
$C_{1-6}$alkoxy-$C_{1-6}$alkyl-carbonyl;
carboxy;
N-cyano-aminocarbonyl;
N-cyano-N—$C_{1-6}$alkyl-aminocarbonyl;
N—$C_{1-6}$alkyl-acetimidamidyl;
N,N'-di-$C_{1-6}$alkyl-acetimidamidyl;
N'-cyano-N—$C_{1-6}$alkyl-acetimidamidyl;
N'-hydroxy-acetimidamidyl;
N'—$C_{1-6}$alkoxy-acetimidamidyl;
N'-hydroxy-N—$C_{1-6}$alkyl-acetimidamidyl;
N'—$C_{1-6}$alkoxy-N—$C_{1-6}$alkyl-acetimidamidyl;
2-nitro-1-N—$C_{1-6}$alkylamino-vinyl; formyl;
$C_{1-6}$alkyl-sulfonyl;
$C_{3-6}$cycloalkyl-sulfonyl;
$C_{3-6}$cycloalkyl-$C_{1-6}$alkyl-sulfonyl;
$C_{1-6}$alkyl-sulfonyl-$C_{1-6}$alkyl;
aminocarbonyl;
carbonylamino;
N-hydroxy-aminocarbonyl;
N—$C_{1-6}$alkoxy-aminocarbonyl;
N—$C_{1-6}$alkyl-aminocarbonyl;
aminocarbonyl-$C_{1-6}$alkyl;
N—$C_{1-6}$alkyl-aminocarbonyl-$C_{1-6}$alkyl;
N,N-di-$C_{1-6}$alkyl-aminocarbonyl-$C_{1-6}$alkyl;
$C_{1-6}$alkoxy-carbonyl;
N-hydroxy-N—$C_{1-6}$alkyl-aminocarbonyl;
N—$C_{1-6}$alkoxy-N—$C_{1-6}$alkyl-aminocarbonyl;
N,N-di-$C_{1-6}$alkyl-aminocarbonyl;
aminosulfonyl;
N—$C_{1-6}$alkyl-aminosulfonyl;
N,N-di-$C_{1-6}$alkyl-aminosulfonyl;
cyano;
$C_{1-6}$alkoxy;
$C_{1-6}$alkyl-sulfonylamino;
N—$C_{1-6}$alkyl-sulfonylaminocarbonyl;
N—($C_{1-6}$alkyl-sulfonyl)-N—$C_{1-6}$alkyl-aminocarbonyl;
N—($C_{1-6}$alkyl-sulfonyl)-amino-$C_{1-6}$alkyl; amino;
N—$C_{1-6}$alkyl-amino;
N,N-di-$C_{1-6}$alkyl-amino;
halo-$C_{1-6}$alkyl;
phenyl;
heterocyclyl;
heteroaryl;
$C_{1-6}$alkyl-carbonylamino;
carbonylamino; or
hydroxy;
wherein the $C_{1-6}$alkyl moieties may be unsubstituted or substituted one or more times with halo; and
wherein the phenyl, heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;
or $R^f$ and $R^g$ together may form oxo;
or $R^f$ and $R^g$ together with the atoms to which they are attached may form a four, five, six or seven membered saturated or partially saturated ring that may optionally include one or two heteroatoms selected from —O—, —$NR^a$— or —S—, and which may be optionally substituted one or more times with $R^i$;
$R^h$ is:
hydrogen;
$C_{1-6}$alkyl;
$C_{3-6}$cycloalkyl;
$C_{3-6}$cycloalkenyl;
$C_{3-6}$cycloalkyl-$C_{1-6}$alkyl;
$C_{1-6}$alkyl-carbonyl;
$C_{3-6}$cycloalkyl-carbonyl;
$C_{3-6}$cycloalkyl-$C_{1-6}$alkyl-carbonyl;
cyano-$C_{1-6}$alkyl-carbonyl;
hydroxy-$C_{1-6}$alkyl-carbonyl;
$C_{1-6}$alkoxy-$C_{1-6}$alkyl-carbonyl;
N-cyano-aminocarbonyl;
N-cyano-N—$C_{1-6}$alkyl-aminocarbonyl;

N—$C_{1-6}$alkyl-acetimidamidyl;
N,N'-di-$C_{1-6}$alkyl-acetimidamidyl;
N'-cyano-N—$C_{1-6}$alkyl-acetimidamidyl;
N'-hydroxy-acetimidamidyl;
N'—$C_{1-6}$alkoxy-acetimidamidyl;
N'-hydroxy-N—$C_{1-6}$ alkyl-acetimidamidyl;
N'—$C_{1-6}$alkoxy-N—$C_{1-6}$alkyl-acetimidamidyl;
2-nitro-1-N—$C_{1-6}$alkylamino-vinyl;
formyl;
$C_{1-6}$alkyl-sulfonyl;
$C_{3-6}$cycloalkyl-sulfonyl;
$C_{3-6}$cycloalkyl-$C_{1-6}$alkyl-sulfonyl;
$C_{1-6}$alkyl-sulfonyl-$C_{1-6}$alkyl;
aminocarbonyl;
N-hydroxy-aminocarbonyl;
N—$C_{1-6}$alkoxy-aminocarbonyl;
N—$C_{1-6}$alkyl-aminocarbonyl;
N-hydroxy-N—$C_{1-6}$alkyl-aminocarbonyl;
N—$C_{1-6}$alkoxy-N—$C_{1-6}$alkyl-aminocarbonyl;
N,N-di-$C_{1-6}$alkyl-aminocarbonyl;
aminosulfonyl;
N—$C_{1-6}$alkyl-aminosulfonyl;
N,N-di-$C_{1-6}$alkyl-aminosulfonyl;
cyano;
$C_{1-6}$alkyl-sulfonylamino;
$C_{1-6}$alkyl-sulfonylamino-$C_{1-6}$alkyl;
N—($C_{1-6}$alkyl-sulfonyl)aminocarbonyl;
N—($C_{1-6}$alkyl-sulfonyl)-N—$C_{1-6}$alkyl-aminocarbonyl;
N—($C_{1-6}$alkyl-sulfonyl)-amino-$C_{1-6}$alkyl;
aminocarbonyl-$C_{1-6}$alkyl;
N—$C_{1-6}$alkyl-aminocarbonyl-$C_{1-6}$alkyl;
N,N-di-$C_{1-6}$alkyl-aminocarbonyl-$C_{1-6}$alkyl;
$C_{1-6}$alkoxy-carbonyl;
phenyl;
heterocyclyl; or
heteroaryl;
  wherein the $C_{1-6}$alkyl moieties may be unsubstituted or substituted one or more times with halo; and
  wherein the phenyl, heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$;
or $R^h$ and one of $R^{10}$ and $R^{11}$ together with the atoms to which they are attached may form a four, five, six or seven membered aromatic, partially saturated or unsaturated ring that may optionally include one or two additional heteroatom selected from —O—, —$NR^a$— or —S—, and which may be optionally substituted one or more times with $R^i$—;
or one of $R^f$ and $R^g$ and one of $R^{10}$ and $R^{11}$ together with the atoms to which they are attached may form a three, four, five, six or seven membered aromatic, partially saturated or unsaturated ring that may optionally include an additional heteroatom selected from —O—, —$NR^a$— or —S—, and which may be optionally substituted one or more times with $R^i$;
  $R^i$ is:
  $C_{1-6}$alkyl;
  halo-$C_{1-6}$alkyl;
  $C_{3-6}$cycloalkyl;
  halo;
  oxo;
  hydroxy;
  acetyl;
  $C_{1-6}$alkyl-carbonyl;
  amino-carbonyl;
  hydroxy-$C_{1-6}$alkyl;
  cyano;
  cyano-$C_{1-6}$alkyl;
  $C_{1-6}$alkoxy-$C_{1-6}$alkyl;
  carboxy; or
  $C_{1-6}$alkoxy;
  $R^j$ and $R^k$ each independent is:
  hydrogen; or
  $C_{1-6}$alkyl which may be unsubstituted or substituted one or more times with halo;
  each $R^m$ is independently:
  $C_{1-6}$alkyl;
  oxo;
  hydroxyl;
  amino;
  $C_{3-6}$cycloalkyl;
  amino-$C_{1-6}$alkyl;
  hydroxyl-$C_{1-6}$alkyl;
  hydroxyl-$C_{1-6}$alkenyl;
  $C_{1-6}$alkoxycarbonyl-$C_{1-6}$alkyl;
  halo;
  cyano-$C_{1-6}$alkyl;
  aminocarbonyl-$C_{1-6}$alkyl; or
  $C_{1-6}$alkoxycarbonyl;
  each $R^n$ is independently:
  $C_{1-6}$alkyl;
  oxo;
  hydroxyl;
  amino;
  $C_{3-6}$cycloalkyl;
  amino-$C_{1-6}$alkyl;
  hydroxyl-$C_{1-6}$alkyl;
  hydroxyl-$C_{1-6}$alkenyl;
  $C_{1-6}$alkoxycarbonyl-$C_{1-6}$alkyl;
  halo;
  aminocarbonyl-$C_{1-6}$alkyl; or
  $C_{1-6}$alkoxycarbonyl; and
  $R^p$ is:
  hydrogen; or
  $C_{1-6}$alkyl.
In certain embodiments of formula I, m is 0.
In certain embodiments of formula I, m is 1.
In certain embodiments of formula I, n is 0.
In certain embodiments of formula I, n is 1.
In certain embodiments of formula I, p is from 0 to 2.
In certain embodiments of formula I, p is 0 or 1.
In certain embodiments of formula I, p is 0.
In certain embodiments of formula I, p is 1.
In certain embodiments of formula I, p is 2.
In certain embodiments of formula I, p is 3.
In certain embodiments of formula I, q is 0.
In certain embodiments of formula I, q is 1.
In certain embodiments of formula I, q is 2.
In certain embodiments of formula I, r is 1.
In certain embodiments of formula I, r is 2.
In certain embodiments of formula I, r is 3.
In certain embodiments of formula I, t is from 0 to 3.
In certain embodiments of formula I, t is 0.
In certain embodiments of formula I, t is 1.
In certain embodiments of formula I, t is 2.
In certain embodiments of formula I, t is 3.
In certain embodiments of formula I, A is: a bond; —$CH_2$—; —C(O)—; —$NR^a$—; —O—; —S—; or —$SO_2$—.
In certain embodiments of formula I, A is: a bond; —$(CR_jR_k)_t$—; —C(O)—$(CR_jR_k)_t$—; —$(CR_jR_k)_t$—C(O)—; —$(CR_jR_k)_t$—$NR^a$—; —C(O)$NR^a$—$(CR_jR_k)_t$—; —$(CR_jR_k)_t$—$NR^a$C(O)—; —$(CR_jR_k)_t$—O—; —$(CR_jR_k)_t$—S—; or —$(CR_jR_k)_t$—$SO_2$—.

In certain embodiments of formula I, A is: a bond; —C(O)—(CR$_j$R$_k$)$_t$—; —(CR$_j$R$_k$)$_t$—C(O)—; —(CR$_j$R$_k$)$_t$—NR$^a$—; —C(O)NR$^a$—(CR$_j$R$_k$)$_t$—; (CR$_j$R$_k$)$_t$—NR$^a$C(O)—; or —(CR$_j$R$_k$)$_t$—O—.

In certain embodiments of formula I, A is: a bond; —NR$^a$—; —O—; or —S—.

In certain embodiments of formula I, A is: a bond; —NR$^a$—; or —O—.

In certain embodiments of formula I, A is: a bond; or —(CR$_j$R$_k$)$_t$—O—.

In certain embodiments of formula I, A is a bond.

In certain embodiments of formula I, A is —CH$_2$—.

In certain embodiments of formula I, A is —C(O)—.

In certain embodiments of formula I, A is —NR$^a$—.

In certain embodiments of formula I, A is —O—.

In certain embodiments of formula I, A is —S—.

In certain embodiments of formula I, A is —SO$_2$—.

In certain embodiments of formula I, A is —C(O)NR$^a$—(CH$_2$)$_t$-.

In certain embodiments of formula I, A is —(CH$_2$)$_t$—NR$^a$C(O)—.

In certain embodiments of formula I, A is —(CR$_j$R$_k$)$_t$—.

In certain embodiments of formula I, A is —CR$_j$R$_k$—.

In certain embodiments of formula I, A is —C(O)—(CR$_j$R$_k$)$_t$—.

In certain embodiments of formula I, A is —(CR$_j$R$_k$)$_t$—C(O)—.

In certain embodiments of formula I, A is —NR$^a$—(CR$_j$R$_k$)$_t$—.

In certain embodiments of formula I, A is —(CR$_j$R$_k$)$_t$—NR$^a$—.

In certain embodiments of formula I, A is —C(O)NR$^a$—(CR$_j$R$_k$)$_t$—.

In certain embodiments of formula I, A is (CR$_j$R$_k$)$_t$—NR$^a$C(O)—.

In certain embodiments of formula I, A is —O—(CR$_j$R$_k$)$_t$—.

In certain embodiments of formula I, A is —(CR$_j$R$_k$)$_t$—O—.

In certain embodiments of formula I, A is —S—(CR$_j$R$_k$)$_t$—.

In certain embodiments of formula I, A is —(CR$_j$R$_k$)$_t$—S—.

In certain embodiments of formula I, A is —SO$_2$—(CR$_j$R$_k$)$_t$—.

In certain embodiments of formula I, A is —(CR$_j$R$_k$)$_t$—SO$_2$—.

In certain embodiments of formula I, A is —(CH$_2$)$_2$—O—.

In certain embodiments of formula I, A is —(CH$_2$)—O—.

In certain embodiments of formula I, A is —O—(CH$_2$)$_2$—.

In certain embodiments of formula I, A is —O—(CH$_2$)—.

In certain embodiments of formula I, A is —(CH$_2$)$_2$—C(O)—.

In certain embodiments of formula I, A is —(CH$_2$)—C(O)—.

In certain embodiments of formula I, A is —C(O)—(CH$_2$)$_2$—.

In certain embodiments of formula I, A is —C(O)—(CH$_2$)—.

In certain embodiments of formula I, A is —C(O)—NH—.

In certain embodiments of formula I, A is —CH$_2$—C(O)—NH—.

In certain embodiments of formula I, A is —NH—.

In certain embodiments of formula I, A is —(CH$_2$)$_2$—NH—.

In certain embodiments of formula I, A is —CH$_2$—NH—.

In certain embodiments of formula I, A is —NH—(CH$_2$)$_2$—.

In certain embodiments of formula I, A is —NH—CH$_2$—.

In certain embodiments of formula I, A is —NH—C(O)—.

In certain embodiments of formula I, t is from 0 to 3.

In certain embodiments of formula I, t is from 1 to 3.

In certain embodiments of formula I, t is from 0 to 2.

In certain embodiments of formula I, t is 0.

In certain embodiments of formula I, t is 1.

In certain embodiments of formula I, t is 2.

In certain embodiments of formula I, t is 3.

In certain embodiments of formula I, t is 4.

In certain embodiments of formula I, W is —CR$^b$R$^c$— or —O—.

In certain embodiments of formula I, W is —CR$^b$R$^c$—.

In certain embodiments of formula I, W is —O—.

In certain embodiments of formula I, W is —NR$^d$—.

In certain embodiments of formula I, W is —S—.

In certain embodiments of formula I, W is —SO$_2$—.

In certain embodiments of formula I, W is —CH$_2$—.

In certain embodiments of formula I, one or two of X$^1$, X$^2$, X$^3$ and X$^4$ is N and the others are CR$^e$.

In certain embodiments of formula I, three of X$^1$, X$^2$, X$^3$ and X$^4$ are CR$^e$ and the other is N.

In certain embodiments of formula I, X$^1$, X$^2$, X$^3$ and X$^4$ are CR$^e$.

In certain embodiments of formula I, X$^1$ is N and X$^2$, X$^3$ and X$^4$ are CR$^e$.

In certain embodiments of formula I, X$^2$ is N and X$^1$, X$^3$ and X$^4$ are CR$^e$.

In certain embodiments of formula I, X$^1$ and X$^4$ are N, and X$^2$ and X$^3$ are CR$^a$.

In certain embodiments of formula I, X$^2$ and X$^3$ are N, and X$^1$ and X$^4$ are CR$^e$.

In certain embodiments of formula I, X$^1$ and X$^2$ are N, and X$^3$ and X$^4$ are CR$^e$.

In certain embodiments of formula I, Y is —O—, —CR$^f$R$^g$— or —NR$^h$—.

In certain embodiments of formula I, Y is —CR$^f$R$^g$— or —NR$^h$—.

In certain embodiments of formula I, Y is —O—, or —CR$^f$R$^g$—.

In certain embodiments of formula I, Y is —O—.

In certain embodiments of formula I, Y is —S—.

In certain embodiments of formula I, Y is —SO$_2$—.

In certain embodiments of formula I, Y is —CR$^f$R$^g$—.

In certain embodiments of formula I, Y is —NR$^h$—.

In certain embodiments of formula I, Z is: a bond; —NR$^p$—C$_{1-6}$alkylene; —C(O)—; —C(O)NR$^p$—; —C(O)NR$^x$—C$_{1-6}$alkylene; —NR$^x$C(O)—; —NR$^x$—C$_{1-6}$alkylene; —NR$^x$—; or —NR$^x$C(O)—C$_{1-6}$alkylene.

In certain embodiments of formula I, Z is: a bond; —NR$^p$—C$_{1-6}$alkylene; —C(O)—; —C(O)NR$^p$—; —NR$^x$—C$_{1-6}$alkylene; or —C(O)NR$^p$—.

In certain embodiments of formula I, Z is: a bond; or —NR$^p$—C$_{1-6}$alkylene-.

In certain embodiments of formula I, Z is: a bond;

In certain embodiments of formula I, Z is: —C$_{1-6}$alkylene-;

In certain embodiments of formula I, Z is: —NR$^x$—C$_{1-6}$alkylene;

In certain embodiments of formula I, Z is: —$C_{1-6}$alkylene-NR—;

In certain embodiments of formula I, Z is: —$NR^x$—;

In certain embodiments of formula I, Z is: —C(O)—;

In certain embodiments of formula I, Z is: —C(O)NR—;

In certain embodiments of formula I, Z is: —C(O)$NR^x$—$C_{1-6}$alkylene;

In certain embodiments of formula I, Z is: —$NR^x$C(O)—;

In certain embodiments of formula I, Z is: —$NR^x$C(O)—$C_{1-6}$alkylene;

In certain embodiments of formula I, Z is: —$C_{1-6}$alkylene-O—;

In certain embodiments of formula I, Z is: —O—$C_{1-6}$alkylene-; or

In certain embodiments of formula I, Z is: —$C_{1-6}$alkylene-O—$C_{1-6}$alkylene-;

In certain embodiments of formula I, Het is heteroaryl selected from: oxazolyl; isoxazolyl; pyrazolyl; triazolyl; oxadiazolyl; pyridinyl; pyrimidinyl; pyrazinyl; or imidazolyl; each of which may be unsubstituted or substituted one or more times with $R^m$.

In certain embodiments of formula I, Het is heteroaryl selected from: oxazolyl; isoxazolyl; pyrazolyl; triazolyl; or oxadiazolyl; each of which may be unsubstituted or substituted one or more times with $R^m$.

In certain embodiments of formula I, Het is oxazolyl which may be unsubstituted or substituted once or twice times with $R^m$.

In certain embodiments of formula I, Het is isoxazolyl which may be unsubstituted or substituted once or twice times with $R^m$.

In certain embodiments of formula I, Het is thiazolyl which may be unsubstituted or substituted once or twice times with $R^m$.

In certain embodiments of formula I, Het is isothiazolyl which may be unsubstituted or substituted once or twice times with $R^m$.

In certain embodiments of formula I, Het is pyrazolyl which may be unsubstituted or substituted once or twice times with $R^m$.

In certain embodiments of formula I, Het is triazolyl which may be unsubstituted or substituted once or twice times with $R^m$.

In certain embodiments of formula I, Het is oxadiazolyl which may be unsubstituted or substituted once or twice times with $R^m$.

In certain embodiments of formula I, Het is thiadiazolyl which may be unsubstituted or substituted once or twice times with $R^m$.

In certain embodiments of formula I, Het is pyridinyl which may be unsubstituted or substituted once or twice times with $R^m$.

In certain embodiments of formula I, Het is pyrimidinyl which may be unsubstituted or substituted once or twice times with $R^m$.

In certain embodiments of formula I, Het is pyrazinyl which may be unsubstituted or substituted once or twice times with $R^m$.

In certain embodiments of formula I, Het is imidazolyl which may be unsubstituted or substituted once or twice times with $R^m$.

In certain embodiments of formula I, Het is oxetanyl which may be unsubstituted or substituted once or twice times with $R^m$.

In certain embodiments of formula I, Het is tetrahydrofuranyl which may be unsubstituted or substituted once or twice times with $R^m$.

In certain embodiments of formula I, Het is tetrahydropyranyl which may be unsubstituted or substituted once or twice times with $R^m$.

In certain embodiments of formula I, Het is pyrrolidinyl which may be unsubstituted or substituted once or twice times with $R^m$.

In certain embodiments of formula I, Het is piperidinyl which may be unsubstituted or substituted once or twice times with $R^m$.

In certain embodiments of formula I, Het is piperazinyl which may be unsubstituted or substituted once or twice times with $R^m$.

In certain embodiments of formula I, Het is oxazolidinyl which may be unsubstituted or substituted once or twice times with $R^m$.

In certain embodiments of formula I, Het is imidazolidinyl which may be unsubstituted or substituted once or twice times with $R^m$.

In certain embodiments of formula I, Het is morpholinyl which may be unsubstituted or substituted once or twice times with $R^m$.

In certain embodiments of formula I, Het is thiomorpholinyl which may be unsubstituted or substituted once or twice times with $R^m$.

In certain embodiments of formula I, Het is 1,1-dioxothiomorpholinyl which may be unsubstituted or substituted once or twice times with $R^m$.

In certain embodiments of formula I, Het is: 3H-1,3,4-oxadiazol-2-one-5-yl; 3-methyl-1,3,4-oxadiazol-2-one-5-yl; 4H-1,2,4-triazol-3-yl; 3H-1,3,4-oxadiazol-2-one-5-yl; pyrazine-2-yl; 5-methylisoxazol-3-yl; isoxazol-3-yl; 3-oxo-isoxazole-5-yl; oxazol-2-yl; 2-methyl-1,2,4-triazol-3-yl; oxazol-4-yl; 1H-pyrazol-5-yl; pyrimidin-2-yl; 1H-pyrazol-3-yl; 1,3,4-oxadiazole-2-carboxylate-5-yl; 3-aminopyrazol-1-yl; or N-methyl-1,2,4-oxadiazole-5-carboxamide-3-yl.

In certain embodiments of formula I, Het is 3H-1,3,4-oxadiazol-2-one-5-yl.

In certain embodiments of formula I, Het is 3-methyl-1,3,4-oxadiazol-2-one-5-yl.

In certain embodiments of formula I, Het is 4H-1,2,4-triazol-3-yl.

In certain embodiments of formula I, Het is pyrazine-2-yl.

In certain embodiments of formula I, Het is 5-methylisoxazol-3-yl.

In certain embodiments of formula I, Het is isoxazol-3-yl.

In certain embodiments of formula I, Het is 3-oxo-isoxazole-5-yl.

In certain embodiments of formula I, Het is oxazol-2-yl.

In certain embodiments of formula I, Het is 2-methyl-1,2,4-triazol-3-yl.

In certain embodiments of formula I, Het is oxazol-4-yl.

In certain embodiments of formula I, Het is 1H-pyrazol-5-yl.

In certain embodiments of formula I, Het is pyrimidin-2-yl; 1H-pyrazol-3-yl.

In certain embodiments of formula I, Het is 1,3,4-oxadiazole-2-cHet boxylate-5-yl.

In certain embodiments of formula I, Het is 3-aminopyrazol-1-yl.

In certain embodiments of formula I, Het is N-methyl-1,2,4-oxadiazole-5-cHet boxamide-3-yl.

In certain embodiments of formula I, $R^1$ is hydrogen.

In certain embodiments of formula I, $R^1$ is $C_{1-6}$alkyl.

In certain embodiments of formula I, $R^2$ is hydrogen.

In certain embodiments of formula I, $R^2$ is $C_{1-6}$alkyl.

In certain embodiments of formula I, $R^3$ is hydrogen.

In certain embodiments of formula I, $R^3$ is $C_{1-6}$alkyl.

In certain embodiments of formula I, $R^3$ is methyl.
In certain embodiments of formula I, $R^3$ is halo-$C_{1-6}$alkyl.
In certain embodiments of formula I, $R^3$ is difluoromethyl.
In certain embodiments of formula I, $R^3$ is trifluoromethyl.
In certain embodiments of formula I, $R^4$ is hydrogen.
In certain embodiments of formula I, $R^4$ is $C_{1-6}$alkyl.
In certain embodiments of formula I, $R^5$ is hydrogen.
In certain embodiments of formula I, $R^5$ is $C_{1-6}$alkyl.
In certain embodiments of formula I, $R^6$ is hydrogen.
In certain embodiments of formula I, $R^6$ is $C_{1-6}$alkyl.
In certain embodiments of formula I, $R^7$ is hydrogen.
In certain embodiments of formula I, $R^7$ is $C_{1-6}$alkyl.
In certain embodiments of formula I, $R^8$ is hydrogen.
In certain embodiments of formula I, $R^8$ is $C_{1-6}$alkyl.
In certain embodiments of formula I, $R^3$ and $R^4$ together with the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.
In certain embodiments of formula I, $R^3$ and $R^4$ together with the atoms to which they are attached form a three, four or five membered saturated ring.
In certain embodiments of formula I, $R^5$ and $R^6$ together with the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.
In certain embodiments of formula I, $R^5$ and $R^6$ together with the atoms to which they are attached form a three, four or five membered saturated ring.
In certain embodiments of formula I, $R^7$ and $R^8$ together with the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.
In certain embodiments of formula I, $R_7$ and $R^8$ together with the atoms to which they are attached form a three, four or five membered saturated ring.
In certain embodiments of formula I, one of $R^3$ and $R^4$ together with one of $R^5$ and $R^6$ and the atoms to which they are attached form a three, four, five, six or seven membered ring that may optionally include one or two heteroatoms selected from —O—, —$NR^a$— or —S—, and which may be optionally substituted one or more times with $R^i$.
In certain embodiments of formula I, one of $R^5$ and $R^6$ together with one of $R^7$ and $R^8$ and the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.
In certain embodiments of formula I, each $R^9$ is independently: $C_{1-6}$alkyl; halo; or halo-$C_{1-6}$alkyl.
In certain embodiments of formula I, $R^9$ is $C_{1-6}$alkyl.
In certain embodiments of formula I, $R^9$ is halo.
In certain embodiments of formula I, $R^9$ is $C_{1-6}$alkoxy.
In certain embodiments of formula I, $R^9$ is cyano.
In certain embodiments of formula I, $R^9$ is halo-$C_{1-6}$alkyl.
In certain embodiments of formula I, each $R^9$ is independently: fluoro; chloro; or trifluoromethyl.
In certain embodiments of formula I, $R^{10}$ is: hydrogen; halo; or $C_{1-6}$alkyl which may be unsubstituted or substituted one or more times with halo or oxo.

In certain embodiments of formula I, $R^{10}$ is: hydrogen or $C_{1-6}$alkyl.
In certain embodiments of formula I, $R^{10}$ is hydrogen.
In certain embodiments of formula I, $R^{10}$ is $C_{1-6}$alkyl.
In certain embodiments of formula I, $R^{10}$ is methyl.
In certain embodiments of formula I, $R^{10}$ is halo.
In certain embodiments of formula I, $R^{10}$ is carboxy.
In certain embodiments of formula I, $R^{10}$ is $C_{1-6}$alkyl-carbonyl.
In certain embodiments of formula I, $R^{10}$ is $C_{1-6}$alkoxy-carbonyl. In certain embodiments of formula I, $R^{10}$ is oxo.
In certain embodiments of formula I, $R^{10}$ is hydroxy.
In certain embodiments of formula I, $R^{10}$ is aminocarbonyl.
In certain embodiments of formula I, $R^{10}$ is N—$C_{1-6}$alkyl-aminocarbonyl.
In certain embodiments of formula I, $R^{10}$ is N,N-di-$C_{1-6}$alkyl-aminocarbonyl.
In certain embodiments of formula I, $R^{10}$ is cyano
In certain embodiments of formula I, $R^{10}$ is hydroxy-$C_{1-6}$alkyl.
In certain embodiments of formula I, $R^{10}$ is N—$C_{1-6}$alkoxy-$C_{1-6}$alkyl-aminocarbonyl.
In certain embodiments of formula I, $R^{10}$ is N-hydroxy-$C_{1-6}$alkyl-aminocarbonyl.
In certain embodiments of formula I, $R^{10}$ is N—$C_{1-6}$alkoxy-aminocarbonyl.
In certain embodiments of formula I, $R^{11}$ is: hydrogen; halo; oxo; hydroxy; or $C_{1-6}$alkyl which may be unsubstituted or substituted one or more times with halo; or oxo.
In certain embodiments of formula I, $R^{11}$ is: hydrogen; halo; carboxy; $C_{1-6}$alkyl-carbonyl; $C_{1-6}$ alkoxy-carbonyl; oxo; hydroxy; aminocarbonyl; N—$C_{1-6}$alkyl-aminocarbonyl; N,N-di-$C_{1-6}$alkyl-aminocarbonyl; or $C_{1-6}$alkyl which may be unsubstituted or substituted one or more times with halo or oxo.
In certain embodiments of formula I, $R^{11}$ is: hydrogen; halo; or $C_{1-6}$alkyl.
In certain embodiments of formula I, $R^{11}$ is: hydrogen; $C_{1-6}$alkyl; or halo.
In certain embodiments of formula I, $R^{11}$ is: hydrogen; or $C_{1-6}$alkyl.
In certain embodiments of formula I, $R^{11}$ is hydrogen.
In certain embodiments of formula I, $R^{11}$ is $C_{1-6}$alkyl
In certain embodiments of formula I, $R^{11}$ is methyl.
In certain embodiments of formula I, $R^{11}$ is halo.
In certain embodiments of formula I, $R^{11}$ is oxo.
In certain embodiments of formula I, $R^{11}$ is $C_{1-6}$alkyl-sulfonylamino.
In certain embodiments of formula I, $R^{11}$ is $C_{1-6}$alkyl-sulfonylamino-$C_{1-6}$alkyl.
In certain embodiments of formula I, $R^{11}$ is cyano.
In certain embodiments of formula I, $R^{11}$ is hydroxy-$C_{1-6}$alkyl.
In certain embodiments of formula I, $R^{11}$ is N—$C_{1-6}$alkoxy-$C_{1-6}$alkyl-aminocarbonyl.
In certain embodiments of formula I, $R^{11}$ is N-hydroxy-$C_{1-6}$alkyl-aminocarbonyl.
In certain embodiments of formula I, $R^{11}$ is N—$C_{1-6}$alkoxy-aminocarbonyl.
In certain embodiments of formula I, $R^{12}$ is: hydrogen; or $C_{1-6}$alkyl.
In certain embodiments of formula I, $R^{12}$ is hydrogen.
In certain embodiments of formula I, $R^{12}$ is halo.
In certain embodiments of formula I, $R^{12}$ is carboxy.
In certain embodiments of formula I, $R^{12}$ is $C_{1-6}$alkyl-carbonyl.

In certain embodiments of formula I, $R^{12}$ is $C_{1-6}$alkoxycarbonyl.

In certain embodiments of formula I, $R^{12}$ is oxo.

In certain embodiments of formula I, $R^{12}$ is hydroxy.

In certain embodiments of formula I, $R^{12}$ is aminocarbonyl.

In certain embodiments of formula I, $R^{12}$ is N—$C_{1-6}$alkyl-aminocarbonyl.

In certain embodiments of formula I, $R^{12}$ is N,N-di-$C_{1-6}$alkyl-aminocarbonyl.

In certain embodiments of formula I, $R^{12}$ is cyano.

In certain embodiments of formula I, $R^{12}$ is hydroxy-$C_{1-6}$alkyl.

In certain embodiments of formula I, $R^{12}$ is N—$C_{1-6}$alkoxy-$C_{1-6}$alkyl-aminocarbonyl.

In certain embodiments of formula I, $R^{12}$ is N-hydroxy-$C_{1-6}$alkyl-aminocarbonyl.

In certain embodiments of formula I, $R^{12}$ is N—$C_{1-6}$alkoxy-aminocarbonyl.

In certain embodiments of formula I, $R^{12}$ is $C_{1-6}$alkyl.

In certain embodiments of formula I, $R^{12}$ is methyl.

In certain embodiments of formula I, $R^{10}$ and $R^{11}$ together with the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.

In certain embodiments of formula I, $R^{10}$ and $R^{11}$ together with the atoms to which they are attached form a four, five, six or seven membered ring.

In certain embodiments of formula I, $R^{10}$ and $R^{11}$ together with the atoms to which they are attached form a double bond.

In certain embodiments of formula I, $R^{13}$ is hydrogen.

In certain embodiments of formula I, $R^{13}$ is $C_{1-6}$alkyl.

In certain embodiments of formula I, $R^a$, $R^b$, R and $R^d$ each independent is: hydrogen; or $C_{1-6}$ alkyl.

In certain embodiments of formula I, $R^a$ is hydrogen.

In certain embodiments of formula I, $R^a$ is $C_{1-6}$alkyl.

In certain embodiments of formula I, $R^b$ is hydrogen.

In certain embodiments of formula I, $R^b$ is $C_{1-6}$alkyl.

In certain embodiments of formula I, R is hydrogen.

In certain embodiments of formula I, R is $C_{1-6}$alkyl.

In certain embodiments of formula I, $R^b$ and $R^c$ together with the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.

In certain embodiments of formula I, one of $R^b$ and $R^c$ together with one of $R^7$ and $R^8$ and the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.

In certain embodiments of formula I, one of $R^b$ and $R^c$ together with one of $R^5$ and $R^6$ and the atoms to which they are attached form a three, four, five, six or seven membered saturated or partially saturated ring that may optionally include one or two heteroatoms selected from —O—, —$NR^a$— or —S—, and which may be optionally substituted one or more times with $R^i$.

In certain embodiments of formula I, $R^d$ is hydrogen.

In certain embodiments of formula I, $R^d$ is $C_{1-6}$alkyl.

In certain embodiments of formula I, each $R^e$ is independently: hydrogen; $C_{1-6}$alkyl; halo; or halo-$C_{1-6}$alkyl.

In certain embodiments of formula I, each $R^e$ is independently: hydrogen; $C_{1-6}$alkyl; or halo.

In certain embodiments of formula I, each $R^e$ is independently: hydrogen; or halo.

In certain embodiments of formula I, each $R^e$ is independently: hydrogen; or fluoro.

In certain embodiments of formula I, $R^e$ is hydrogen.

In certain embodiments of formula I, $R^e$ is $C_{1-6}$alkyl.

In certain embodiments of formula I, $R^e$ is halo.

In certain embodiments of formula I, $R^e$ is $C_{1-6}$alkoxy.

In certain embodiments of formula I, $R^e$ is cyano.

In certain embodiments of formula I, $R^e$ is halo-$C_{1-6}$alkyl.

In certain embodiments of formula I, $R^f$ is: hydrogen; halo; $C_{1-6}$alkyl; $C_{1-6}$alkoxy; or halo-$C_{1-6}$ alkyl.

In certain embodiments of formula I, $R^f$ is: hydrogen; $C_{1-6}$alkyl; or halo-$C_{1-6}$alkyl.

In certain embodiments of formula I, $R^f$ is: hydrogen; fluoro; methyl; methoxyl; or trifluoromethyl.

In certain embodiments of formula I, $R^f$ is: hydrogen; methyl; or trifluoromethyl.

In certain embodiments of formula I, $R^f$ is: hydrogen; or $C_{1-6}$alkyl.

In certain embodiments of formula I, $R^f$ is hydrogen.

In certain embodiments of formula I, $R^f$ is $C_{1-6}$alkyl.

In certain embodiments of formula I, $R^f$ is halo-$C_{1-6}$alkyl.

In certain embodiments of formula I, $R^f$ is halo.

In certain embodiments of formula I, $R^f$ is $C_{1-6}$alkoxy.

In certain embodiments of formula I, $R^f$ is methyl

In certain embodiments of formula I, $R^f$ is trifluoromethyl.

In certain embodiments of formula I, $R^f$ is methoxy.

In certain embodiments of formula I, $R^f$ is fluoro.

In certain embodiments of formula I, $R^g$ is: $C_{1-6}$alkyl; $C_{3-6}$cycloalkyl; $C_{3-6}$cycloalkenyl; $C_{3-6}$cycloalkyl-$C_{1-6}$alkyl; halo; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; carboxy; N-cyano-aminocarbonyl; N-cyano-N—$C_{1-6}$alkyl-aminocarbonyl; N—$C_{1-6}$alkyl-acetimidamidyl; N,N'-di-$C_{1-6}$ alkyl-acetimidamidyl; N'-cyano-N—$C_{1-6}$alkyl-acetimidamidyl; N'-hydroxy-acetimidamidyl; N'—$C_{1-6}$ alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkoxy; $C_{1-6}$alkyl-sulfonylamino; N—$C_{1-6}$alkyl-sulfonylaminocarbonyl; N—($C_{1-6}$alkyl-sulfonyl)-N—$C_{1-6}$alkyl-aminocarbonyl; N—($C_{1-6}$alkyl-sulfonyl)-amino-$C_{1-6}$alkyl; amino; N—$C_{1-6}$alkyl-amino; N,N-di-$C_{1-6}$ alkyl-amino; halo-$C_{1-6}$ alkyl; heterocyclyl; heteroaryl; or hydroxyl; wherein the $C_{1-6}$alkyl moieties may be unsubstituted or substituted one or more times with halo; and wherein the heterocyclyl, heteroaryl, $C_{3-6}$cycloalkyl, $C_{3-6}$ cycloalkenyl and $C_{3-6}$cycloalkyl-$C_{1-6}$alkyl moieties may be unsubstituted or substituted one or more times with $R^i$.

In certain embodiments of formula I, $R^g$ is: hydrogen; $C_{1-6}$alkyl; $C_{3-6}$cycloalkyl; $C_{3-6}$cycloalkyl-$C_{1-6}$ alkyl; halo; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$ alkyl-aminosulfonyl; cyano; $C_{1-6}$alkoxy; $C_{1-6}$alkyl-sulfonylamino; amino; N—$C_{1-6}$alkyl-amino; N,N-di-$C_{1-6}$ alkyl-amino; halo-$C_{1-6}$alkyl; or hydroxyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^i$.

In certain embodiments of formula I, $R^g$ is: hydrogen; halo; $C_{1-6}$alkyl; hydroxyl; $C_{1-6}$alkoxy; or halo-$C_{1-6}$alkyl.

In certain embodiments of formula I, $R^g$ is: hydrogen; $C_{1-6}$alkyl; halo; carbonylamino; $C_{1-6}$alkoxy; heteroaryl; $C_{1-6}$alkyl-carbonylamino; carbonylamino; or hydroxyl.

In certain embodiments of formula I, $R^g$ is hydrogen.

In certain embodiments of formula I, $R^g$ is $C_{1-6}$alkyl.

In certain embodiments of formula I, $R^g$ is $C_{3-6}$cycloalkyl which may be unsubstituted or substituted one or more times with $R^i$.

In certain embodiments of formula I, $R^g$ is $C_{3-6}$cycloalkyl-$C_{1-6}$alkyl which may be unsubstituted or substituted one or more times with $R^i$.

In certain embodiments of formula I, $R^g$ is halo.

In certain embodiments of formula I, $R^g$ is $C_{1-6}$alkyl-carbonyl.

In certain embodiments of formula I, $R^g$ is $C_{3-6}$cycloalkyl-carbonyl wherein the $C_{3-6}$cycloalkyl moeity may be unsubstituted or substituted one or more times with $R^i$.

In certain embodiments of formula I, $R^g$ is $C_{3-6}$cycloalkyl-$C_{1-6}$alkyl-carbonyl wherein the $C_{3-6}$ cycloalkyl-$C_{1-6}$alkyl moiety may be unsubstituted or substituted one or more times with $R^i$.

In certain embodiments of formula I, $R^g$ is $C_{1-6}$alkyl-sulfonyl.

In certain embodiments of formula I, $R^g$ is $C_{3-6}$cycloalkyl-sulfonyl.

In certain embodiments of formula I, $R^g$ is $C_{3-6}$cycloalkyl-$C_{1-6}$alkyl-sulfonyl.

In certain embodiments of formula I, $R^g$ is aminocarbonyl.

In certain embodiments of formula I, $R^g$ is N—$C_{1-6}$alkyl-aminocarbonyl.

In certain embodiments of formula I, $R^g$ is N,N-di-$C_{1-6}$ alkyl-aminocarbonyl.

In certain embodiments of formula I, $R^g$ is aminosulfonyl.

In certain embodiments of formula I, $R^g$ is N—$C_{1-6}$alkyl-aminosulfonyl.

In certain embodiments of formula I, $R^g$ is N,N-di-$C_{1-6}$ alkyl-aminosulfonyl.

In certain embodiments of formula I, $R^g$ is cyano.

In certain embodiments of formula I, $R^g$ is $C_{1-6}$alkoxy.

In certain embodiments of formula I, $R^g$ is $C_{1-6}$alkyl-sulfonylamino.

In certain embodiments of formula I, $R^g$ is amino.

In certain embodiments of formula I, $R^g$ is N—$C_{1-6}$alkyl-amino.

In certain embodiments of formula I, $R^g$ is N,N-di-$C_{1-6}$ alkyl-amino.

In certain embodiments of formula I, $R^g$ is halo-$C_{1-6}$alkyl.

In certain embodiments of formula I, $R^g$ is hydroxy.

In certain embodiments of formula I, $R^g$ is $C_{3-6}$cycloalkeny which may be unsubstituted or substituted one or more times with $R^i$.

In certain embodiments of formula I, $R^g$ is cyano-$C_{1-6}$alkyl-carbonyl.

In certain embodiments of formula I, $R^g$ is hydroxy-$C_{1-6}$alkyl-carbonyl.

In certain embodiments of formula I, $R^g$ is $C_{1-6}$alkoxy-$C_{1-6}$alkyl-carbonyl.

In certain embodiments of formula I, $R^g$ is carboxy.

In certain embodiments of formula I, $R^g$ is N-cyano-aminocarbonyl.

In certain embodiments of formula I, $R^g$ is N-cyano-N—$C_{1-6}$alkyl-aminocarbonyl.

In certain embodiments of formula I, $R^g$ is N—$C_{1-6}$alkyl-acetimidamidyl.

In certain embodiments of formula I, $R^g$ is N,N'-di-$C_{1-6}$ alkyl-acetimidamidyl.

In certain embodiments of formula I, $R^g$ is N'-cyano-N—$C_{1-6}$alkyl-acetimidamidyl.

In certain embodiments of formula I, $R^g$ is N'-hydroxy-acetimidamidyl.

In certain embodiments of formula I, $R^g$ is N'—$C_{1-6}$ alkoxy-acetimidamidyl.

In certain embodiments of formula I, $R^g$ is N'-hydroxy-N—$C_{1-6}$alkyl-acetimidamide; N'—$C_{1-6}$ alkoxy-N—$C_{1-6}$alkyl-acetimidamidyl.

In certain embodiments of formula I, $R^g$ is 2-nitro-1-N—$C_{1-6}$alkylamino-vinyl.

In certain embodiments of formula I, $R^g$ is $C_{1-6}$alkyl-sulfonyl-$C_{1-6}$alkyl.

In certain embodiments of formula I, $R^g$ is N-hydroxy-aminocarbonyl.

In certain embodiments of formula I, $R^g$ is N—$C_{1-6}$ alkoxy-aminocarbonyl.

In certain embodiments of formula I, $R^g$ is N-hydroxy-N—$C_{1-6}$alkyl-aminocarbonyl.

In certain embodiments of formula I, $R^g$ is N—$C_{1-6}$ alkoxy-N—$C_{1-6}$alkyl-aminocarbonyl.

In certain embodiments of formula I, $R^g$ is N—$C_{1-6}$alkyl-sulfonylaminocarbonyl.

In certain embodiments of formula I, $R^g$ is N—($C_{1-6}$alkyl-sulfonyl)-N—$C_{1-6}$alkyl-aminocarbonyl.

In certain embodiments of formula I, $R^g$ is aminocarbonyl-$C_{1-6}$alkyl.

In certain embodiments of formula I, $R^g$ is N—$C_{1-6}$alkyl-aminocarbonyl-$C_{1-6}$alkyl In certain embodiments of formula I, $R^g$ is N,N-di-$C_{1-6}$ alkyl-aminocarbonyl-$C_{1-6}$alkyl.

In certain embodiments of formula I, $R^g$ is $C_{1-6}$alkoxy-carbonyl.

In certain embodiments of formula I, $R^g$ is carbonylamino.

In certain embodiments of formula I, $R^g$ is heterocyclyl which may be unsubstituted or substituted one or more times with $R^i$.

In embodiments of formula I wherein $R^g$ is heterocyclyl, such heterocyclyl may be oxetanyl, tetrahydrofuranyl, tetrahydropyranyl, azetidinyl, pyrrolidinyl, piperidinyl, azepinyl or piperazinyl, each of which may be unsubstituted or substituted one or more times with $R^i$.

In certain embodiments of formula I, $R^g$ is heteroaryl which may be unsubstituted or substituted one or more times with $R^i$.

In embodiments of formula I wherein $R^g$ is heteroaryl, such heteroaryl may be pyridinyl, pyrimidinyl, triazinyl, pyrrolyl, imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In embodiments of formula I wherein $R^g$ is heteroaryl, such heteroaryl may be imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In certain embodiments of formula I, $R^g$ is triazolyl.

In certain embodiments of formula I, $R^g$ is [1,2,4]triazol-4-yl.

In certain embodiments of formula I, $R^g$ is [1,2,4]triazol-3-yl.

In certain embodiments of formula I, $R^g$ is 4-methyl-[1,2,4]triazol-3-yl.

In certain embodiments of formula I, $R^g$ is [1,2,4]triazol-1-yl.

In certain embodiments of formula I, $R^g$ is [1,2,3]triazol-1-yl.

In certain embodiments of formula I, $R^g$ is [1,2,3]triazol-4-yl.

In certain embodiments of formula I, $R^g$ is 4-methyl-[1,2,4]triazol-3-yl.

In certain embodiments of formula I, $R^g$ is pyrazolyl.

In certain embodiments of formula I, $R^g$ is pyrazol-3-yl.

In certain embodiments of formula I, $R^g$ is pyrazol-1-yl.

In certain embodiments of formula I, $R^g$ is pyrazol-4-yl.

In certain embodiments of formula I, $R^g$ is imidazolyl.

In certain embodiments of formula I, $R^g$ is imidazol-1-yl.

In certain embodiments of formula I, $R^g$ is 1-methyl-imidazol-2-yl.

In certain embodiments of formula I, $R^g$ is isoxazolyl.

In certain embodiments of formula I, $R^g$ is 3-hydroxy-isoxazol-5-yl.

In certain embodiments of formula I, $R^g$ is oxdiazolyl.

In certain embodiments of formula I, $R^g$ is [1,2,4]oxadiazol-5-yl.

In certain embodiments of formula I, $R^g$ is [1,2,4]oxadiazol-3-yl.

In certain embodiments of formula I, $R^g$ is [1,2,3]oxadiazol-2-yl.

In certain embodiments of formula I, $R^g$ is [1,2,3]oxadiazol-2-one-5-yl.

In certain embodiments of formula I, $R^g$ is tetrazolyl.

In certain embodiments of formula I, $R^g$ is tetrazol-5-yl.

In certain embodiments of formula I, $R^g$ is tetrazol-1-yl.

In certain embodiments of formula I, $R^g$ is tetrazol-2-yl.

In certain embodiments of formula I, $R^g$ is pyrazolyl.

In certain embodiments of formula I, $R^g$ is pyridazinyl.

In certain embodiments of formula I, $R^g$ is triazinyl.

In certain embodiments of formula I, $R^g$ is $C_{2-6}$alkenyl.

In certain embodiments of formula I, $R^f$ and $R^g$ together with the atoms to which they are attached form a three, four, five, six or seven membered saturated or partially saturated ring.

In certain embodiments of formula I, $R^f$ and $R^g$ together with the atoms to which they are attached form a three membered ring.

In certain embodiments of formula I, $R^f$ and $R^g$ together with the atoms to which they are attached form a four membered ring.

In certain embodiments of formula I, $R^f$ and $R^g$ together with the atoms to which they are attached form a five membered ring.

In certain embodiments of formula I, $R^f$ and $R^g$ together with the atoms to which they are attached form a six membered ring.

In certain embodiments of formula I, $R^f$ and $R^g$ together with the atoms to which they are attached form a seven membered ring.

In certain embodiments of formula I, $R^f$ and $R^g$ together with the atoms to which they are attached form oxo.

In certain embodiments of formula I, $R^h$ is: hydrogen; $C_{1-6}$alkyl; $C_{3-6}$cycloalkyl; $C_{3-6}$cycloalkenyl; $C_{3-6}$cycloalkyl-$C_{1-6}$alkyl; $C_{1-6}$alkyl-carbonyl; $C_{3-6}$cycloalkyl-carbonyl; $C_{3-6}$cycloalkyl-$C_{1-6}$alkyl-carbonyl; cyano-$C_{1-6}$alkyl-carbonyl; hydroxy-$C_{1-6}$alkyl-carbonyl; $C_{1-6}$alkoxy-$C_{1-6}$alkyl-carbonyl; N-cyano-aminocarbonyl; N-cyano-N—$C_{1-6}$alkyl-aminocarbonyl; N—$C_{1-6}$alkyl-acetimidamidyl; N,N'-di-$C_{1-6}$alkyl-acetimidamidyl; N'-cyano-N—$C_{1-6}$alkyl-acetimidamidyl; N'-hydroxy-acetimidamidyl; N'—$C_{1-6}$alkoxy-acetimidamidyl; N'-hydroxy-N—$C_{1-6}$alkyl-acetimidamidyl; N'—$C_{1-6}$alkoxy-N—$C_{1-6}$alkyl-acetimidamidyl; 2-nitro-1-N—$C_{1-6}$alkylamino-vinyl; formyl; $C_{1-6}$alkyl-sulfonyl; $C_{3-6}$cycloalkyl-sulfonyl; $C_{3-6}$cycloalkyl-$C_{1-6}$alkyl-sulfonyl; $C_{1-6}$alkyl-sulfonyl-$C_{1-6}$alkyl; aminocarbonyl; N-hydroxy-aminocarbonyl; N—$C_{1-6}$alkoxy-aminocarbonyl; N—$C_{1-6}$alkyl-aminocarbonyl; N-hydroxy-N—$C_{1-6}$alkyl-aminocarbonyl; N—$C_{1-6}$alkoxy-N—$C_{1-6}$alkyl-aminocarbonyl; N,N-di-$C_{1-6}$alkyl-aminocarbonyl; aminosulfonyl; N—$C_{1-6}$alkyl-aminosulfonyl; N,N-di-$C_{1-6}$alkyl-aminosulfonyl; cyano; $C_{1-6}$alkyl-sulfonylamino; $C_{1-6}$alkyl-sulfonylamino-$C_{1-6}$alkyl; N—($C_{1-6}$ alkyl-sulfonyl)aminocarbonyl; N—($C_{1-6}$ alkyl-sulfonyl)-N—$C_{1-6}$alkyl-aminocarbonyl; N—($C_{1-6}$ alkyl-sulfonyl)-amino-$C_{1-6}$alkyl; halo-$C_{1-6}$alkyl; heterocyclyl; or heteroaryl; wherein the $C_{1-6}$alkyl moieties may be unsubstituted or substituted one or more times with halo; and wherein the heterocyclyl, heteroaryl, $C_{3-6}$cycloalkyl, $C_{3-6}$cycloalkenyl and $C_{3-6}$cycloalkyl-$C_{1-6}$alkyl moieties may be unsubstituted or substituted one or more times with $R^i$.

In certain embodiments of formula I, $R^h$ is: hydrogen; $C_{1-6}$alkyl; $C_{3-6}$cycloalkyl; $C_{3-6}$cycloalkyl-$C_{1-6}$ alkyl; $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; N,N-di-$C_{1-6}$alkyl-aminocarbonyl; aminosulfonyl; N—$C_{1-6}$alkyl-aminosulfonyl; or N,N-di-$C_{1-6}$alkyl-aminosulfonyl; wherein the $C_{1-6}$alkyl moieties may be unsubstituted or substituted one or more times with halo; and wherein the $C_{3-6}$cycloalkyl, and $C_{3-6}$cycloalkyl-$C_{1-6}$alkyl moieties may be unsubstituted or substituted one or more times with $R^i$.

In certain embodiments of formula I, $R^h$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; $C_{3-6}$cycloalkyl-$C_{1-6}$alkyl-sulfonyl; aminocarbonyl; N—$C_{1-6}$alkyl-aminocarbonyl; or N,N-di-$C_{1-6}$alkyl-aminocarbonyl; aminosulfonyl; N—$C_{1-6}$alkyl-aminosulfonyl; or N,N-di-$C_{1-6}$ alkyl-aminosulfonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is: $C_{1-6}$alkyl-carbonyl; $C_{3-6}$cycloalkyl-carbonyl; $C_{3-6}$cycloalkyl-$C_{1-6}$alkyl-carbonyl; $C_{1-6}$alkyl-sulfonyl; $C_{3-6}$cycloalkyl-sulfonyl; or $C_{3-6}$cycloalkyl-$C_{1-6}$alkyl-sulfonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is: $C_{1-6}$alkyl-carbonyl; $C_{3-6}$cycloalkyl-carbonyl; or $C_{3-6}$cycloalkyl-$C_{1-6}$alkyl-carbonyl; wherein the $C_{3-6}$cycloalkyl, and $C_{3-6}$cycloalkyl-$C_{1-6}$alkyl moieties each may be unsubstituted or substituted one or more times with $R^i$.

In certain embodiments of formula I, $R^h$ is hydrogen.

In certain embodiments of formula I, $R^h$ is $C_{1-6}$alkyl.

In certain embodiments of formula I, $R^h$ is $C_{3-6}$cycloalkyl which may be unsubstituted or substituted one or more times with $R^i$.

In certain embodiments of formula I, $R^h$ is $C_{3-6}$cycloalkyl-$C_{1-6}$alkyl.

In certain embodiments of formula I, $R^h$ is $C_{1-6}$alkyl-carbonyl.

In certain embodiments of formula I, $R^h$ is $C_{3-6}$cycloalkyl-carbonyl.

In certain embodiments of formula I, $R^h$ is $C_{3-6}$cycloalkyl-$C_{1-6}$alkyl-carbonyl.

In certain embodiments of formula I, $R^h$ is $C_{1-6}$alkyl-sulfonyl.

In certain embodiments of formula I, $R^h$ is $C_{3-6}$cycloalkyl-sulfonyl.

In certain embodiments of formula I, $R^h$ is $C_{3-6}$cycloalkyl-$C_{1-6}$alkyl-sulfonyl.

In certain embodiments of formula I, $R^h$ is aminocarbonyl.

In certain embodiments of formula I, $R^h$ is N—$C_{1-6}$alkyl-aminocarbonyl.

In certain embodiments of formula I, $R^h$ is N,N-di-$C_{1-6}$alkyl-aminocarbonyl.

In certain embodiments of formula I, $R^h$ is aminosulfonyl.

In certain embodiments of formula I, $R^h$ is N—$C_{1-6}$alkyl-aminosulfonyl.

In certain embodiments of formula I, $R^h$ is or N,N-di-$C_{1-6}$alkyl-aminosulfonyl.

In certain embodiments of formula I, $R^h$ is $C_{3-6}$cycloalkenyl.

In certain embodiments of formula I, $R^h$ is cyano-$C_{1-6}$alkyl-carbonyl.

In certain embodiments of formula I, $R^h$ is hydroxy-$C_{1-6}$alkyl-carbonyl.

In certain embodiments of formula I, $R^h$ is $C_{1-6}$alkoxy-$C_{1-6}$alkyl-carbonyl.

In certain embodiments of formula I, $R^h$ is N-cyano-aminocarbonyl.

In certain embodiments of formula I, $R^h$ is N-cyano-N—$C_{1-6}$alkyl-aminocarbonyl.

In certain embodiments of formula I, $R^h$ is N—$C_{1-6}$alkyl-acetimidamidyl.

In certain embodiments of formula I, $R^h$ is N,N'-di-$C_{1-6}$alkyl-acetimidamidyl.

In certain embodiments of formula I, $R^h$ is N'-cyano-N—$C_{1-6}$alkyl-acetimidamidyl.

In certain embodiments of formula I, $R^h$ is N'-hydroxy-acetimidamidyl.

In certain embodiments of formula I, $R^h$ is N'—$C_{1-6}$alkoxy-acetimidamidyl.

In certain embodiments of formula I, $R^h$ is N'-hydroxy-N—$C_{1-6}$alkyl-acetimidamidyl.

In certain embodiments of formula I, $R^h$ is N'—$C_{1-6}$alkoxy-N—$C_{1-6}$alkyl-acetimidamidyl.

In certain embodiments of formula I, $R^h$ is 2-nitro-1-N—$C_{1-6}$alkylamino-vinyl.

In certain embodiments of formula I, $R^h$ is $C_{1-6}$alkyl-sulfonyl-$C_{1-6}$alkyl.

In certain embodiments of formula I, $R^h$ is N-hydroxy-aminocarbonyl.

In certain embodiments of formula I, $R^h$ is N—$C_{1-6}$alkoxy-aminocarbonyl.

In certain embodiments of formula I, $R^h$ is N-hydroxy-N—$C_{1-6}$alkyl-aminocarbonyl.

In certain embodiments of formula I, $R^h$ is N—$C_{1-6}$alkoxy-N—$C_{1-6}$alkyl-aminocarbonyl.

In certain embodiments of formula I, $R^h$ is $C_{1-6}$alkyl-sulfonylamino-$C_{1-6}$alkyl.

In certain embodiments of formula I, $R^h$ is N—($C_{1-6}$alkyl-sulfonyl)aminocarbonyl.

In certain embodiments of formula I, $R^h$ is N—($C_{1-6}$alkyl-sulfonyl)-N—$C_{1-6}$alkyl-aminocarbonyl.

In certain embodiments of formula I, $R^h$ is aminocarbonyl-$C_{1-6}$alkyl.

In certain embodiments of formula I, $R^h$ is N—$C_{1-6}$alkyl-aminocarbonyl-$C_{1-6}$alkyl In certain embodiments of formula I, $R^h$ is N,N-di-$C_{1-6}$alkyl-aminocarbonyl-$C_{1-6}$alkyl.

In certain embodiments of formula I, $R^h$ is $C_{1-6}$alkoxy-carbonyl.

In certain embodiments of formula I, $R^h$ is heterocyclyl which may be unsubstituted or substituted one or more times with $R^i$.

In certain embodiments of formula I, $R^h$ is heteroaryl which may be unsubstituted or substituted one or more times with $R^i$.

In embodiments of formula I wherein $R^h$ is heteroaryl, such heteroaryl may be pyridinyl, pyrimidinyl, pyrolyl, imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In embodiments of formula I wherein $R^h$ is heteroaryl, such heteroaryl may be imidazolyl, pyrazoyl, triazolyl, oxazolyl, thiazolyl, isoxazolyl, isothiazolyl, oxadiazolyl, thiadiazolyl or tetrazolyl, each of which may be unsubstituted or substituted one or more times with $R^i$.

In certain embodiments of formula I, $R^h$ is acetyl.

In certain embodiments of formula I, $R^h$ is methanesulfonyl.

In certain embodiments of formula I, $R^h$ is cyclopropylcarbonyl.

In certain embodiments of formula I, $R^h$ and one of $R^{10}$ and $R^{11}$ together with the atoms to which they are attached form a four, five, six or seven membered aromatic, partially saturated or unsaturated ring.

In certain embodiments of formula I, $R^h$ and one of $R^{10}$ and $R^{11}$ together with the atoms to which they are attached form a four membered ring.

In certain embodiments of formula I, $R^h$ and one of $R^{10}$ and $R^{11}$ together with the atoms to which they are attached form a five membered ring.

In certain embodiments of formula I, $R^h$ and one of $R^{10}$ and $R^{11}$ together with the atoms to which they are attached form a six membered ring.

In certain embodiments of formula I, $R^h$ and one of $R^{10}$ and $R^{11}$ together with the atoms to which they are attached form a seven membered ring.

In certain embodiments of formula I, one of $R^f$ and $R^g$ and one of $R^{10}$ and $R^{11}$ together with the atoms to which they are attached form a four, five, six or seven membered aromatic, partially saturated or unsaturated ring.

In certain embodiments of formula I, one of $R^f$ and $R^g$ and one of $R^{10}$ and $R^{11}$ together with the atoms to which they are attached form a five or six membered aromatic ring.

In certain embodiments of formula I, one of $R^f$ and $R^g$ and one of $R^{10}$ and $R^{11}$ together with the atoms to which they are attached form a five membered aromatic ring.

In certain embodiments of formula I, one of $R^f$ and $R^g$ and one of $R^{10}$ and $R^{11}$ together with the atoms to which they are attached form a six membered aromatic ring.

In certain embodiments of formula I, one of $R^f$ and $R^g$ and one of $R^{10}$ and $R^{11}$ together with the atoms to which they are attached form a five or six membered saturated ring.

In certain embodiments of formula I, one of $R^f$ and $R^g$ and one of $R^{10}$ and $R^{11}$ together with the atoms to which they are attached form a five membered saturated ring.

In certain embodiments of formula I, one of $R^f$ and $R^g$ and one of $R^{10}$ and $R^{11}$ together with the atoms to which they are attached form a six membered saturated ring.

In certain embodiments of formula I, one of $R^f$ and $R^g$ and one of $R^{10}$ and $R^{11}$ together with the atoms to which they are attached form a four membered ring.

In certain embodiments of formula I, one of $R^f$ and $R^g$ and one of $R^{10}$ and $R^{11}$ together with the atoms to which they are attached form a five membered ring.

In certain embodiments of formula I, one of $R^f$ and $R^g$ and one of $R^{10}$ and $R^{11}$ together with the atoms to which they are attached form a six membered ring.

In certain embodiments of formula I, one of $R^f$ and $R^g$ and one of $R^{10}$ and $R^{11}$ together with the atoms to which they are attached form a seven membered ring.

In certain embodiments of formula I, $R^i$ is: $C_{1-6}$alkyl; halo; oxo; hydroxy; acetyl; or $C_{1-6}$alkoxy.

In certain embodiments of formula I, $R^i$ is $C_{1-6}$alkyl.

In certain embodiments of formula I, $R^i$ is halo.

In certain embodiments of formula I, $R^i$ is $C_{1-6}$alkoxy.

In certain embodiments of formula I, $R^i$ is halo-$C_{1-6}$alkyl.

In certain embodiments of formula I, $R^i$ is oxo.

In certain embodiments of formula I, $R^i$ is hydroxy.

In certain embodiments of formula I, $R^i$ is acetyl.

In certain embodiments of formula I, $R^i$ is $C_{1-6}$alkyl-carbonyl.

In certain embodiments of formula I, $R^i$ is amino-carbonyl.

In certain embodiments of formula I, $R^i$ is hydroxy-$C_{1-6}$alkyl.

In certain embodiments of formula I, $R^i$ is cyano.

In certain embodiments of formula I, $R^i$ is halo-$C_{1-6}$alkyl.

In certain embodiments of formula I, $R^i$ is $C_{3-6}$cycloalkyl.

In certain embodiments of formula I, $R^j$ and $R^k$ each independent is: hydrogen; or methyl.

In certain embodiments of formula I, $R^j$ is hydrogen.

In certain embodiments of formula I, $R^k$ is hydrogen.

In certain embodiments of formula I, $R^m$ is: $C_{1-6}$alkyl; oxo; hydroxyl; amino; or hydroxyl-$C_{1-6}$ alkyl.

In certain embodiments of formula I, $R^m$ is: $C_{1-6}$alkyl; or oxo.

In certain embodiments of formula I, $R^m$ is $C_{1-6}$alkyl.

In certain embodiments of formula I, $R^m$ is oxo.

In certain embodiments of formula I, $R^m$ is hydroxyl.

In certain embodiments of formula I, $R^m$ is amino.

In certain embodiments of formula I, $R^m$ is $C_{3-6}$cycloalkyl.

In certain embodiments of formula I, $R^m$ is amino-$C_{1-6}$ alkyl.

In certain embodiments of formula I, $R^m$ is hydroxyl-$C_{1-6}$ alkyl.

In certain embodiments of formula I, $R^m$ is hydroxyl-$C_{1-6}$ alkenyl.

In certain embodiments of formula I, $R^m$ is $C_{1-6}$alkoxy-carbonyl-$C_{1-6}$alkyl.

In certain embodiments of formula I, $R^m$ is halo.

In certain embodiments of formula I, $R^m$ is aminocarbonyl-$C_{1-6}$alkyl.

In certain embodiments of formula I, $R^m$ is $C_{1-6}$alkoxy-carbonyl.

In certain embodiments of formula I, $R^m$ is cyano-$C_{1-6}$alkyl.

In certain embodiments of formula I, $R^n$ is $C_{1-6}$alkyl.

In certain embodiments of formula I, $R^n$ is oxo.

In certain embodiments of formula I, $R^n$ is hydroxyl.

In certain embodiments of formula I, $R^n$ is amino.

In certain embodiments of formula I, $R^n$ is $C_{3-6}$cycloalkyl.

In certain embodiments of formula I, $R^n$ is amino-$C_{1-6}$ alkyl.

In certain embodiments of formula I, $R^n$ is hydroxyl-$C_{1-6}$ alkyl.

In certain embodiments of formula I, $R^n$ is hydroxyl-$C_{1-6}$ alkenyl.

In certain embodiments of formula I, $R^n$ is $C_{1-6}$alkoxy-carbonyl-$C_{1-6}$alkyl.

In certain embodiments of formula I, $R^n$ is halo.

In certain embodiments of formula I, $R^n$ is aminocarbonyl-$C_{1-6}$alkyl.

In certain embodiments of formula I, $R^n$ is $C_{1-6}$alkoxy-carbonyl.

In certain embodiments of formula I, $R^p$ is hydrogen

In certain embodiments of formula I, $R^p$ is $C_{1-6}$alkyl.

In certain embodiments, the subject compounds may be of formula II:

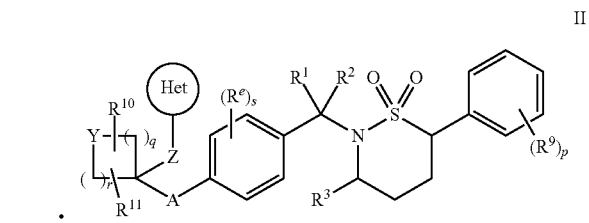

II wherein s is from 0 to 3 and $R^e$ is: $C_{1-6}$alkyl; $C_{1-6}$alkoxy; hydroxy; halo; hydroxy-$C_{1-6}$alkyl; or cyano; and p, q, r, A, Y, Z, Het, $R^1$, $R^2$, $R^3$, $R^9$, $R^{10}$, $R^{11}$, and $R^m$ are as defined herein.

In certain embodiments, the subject compounds may be of formula III:

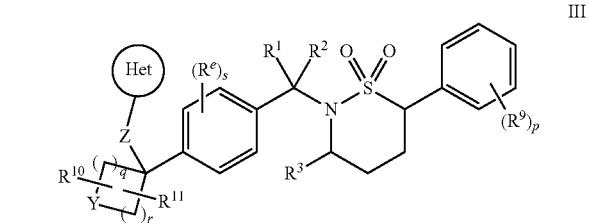

III wherein p, q, r, s, Y, Z, Het, $R^1$, $R^2$, $R^3$, $R^9$, $R^{10}$, $R^{11}$, $R^e$ and $R^m$ are as defined herein.

In certain embodiments, the subject compounds may be of formula IV:

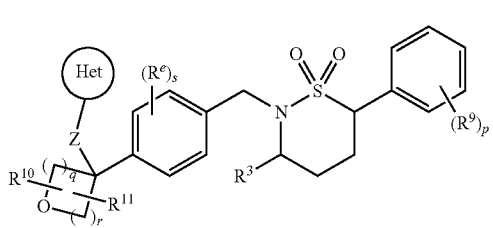

IV wherein p, q, r, s, Y, Z, Het, $R^3$, $R^9$, $R^{10}$, $R^{11}$, $R^e$ and $R^m$ are as defined herein.

In certain embodiments, the subject compounds may be of formula V:

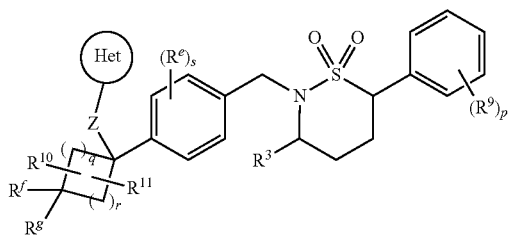

V wherein p, q, r, s, Z, Het, $R^3$, $R^9$, $R^{10}$, $R^{11}$, $R^e$, $R^f$, $R^g$, and $R^m$ are as defined herein.

In certain embodiments, the subject compounds may be of formula VI:

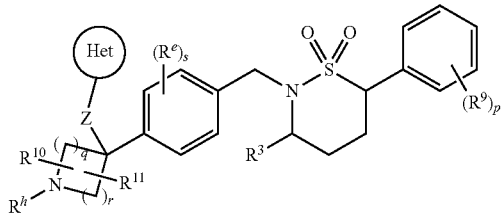

VI wherein p, q, r, s, Z, Het, $R^3$, $R^9$, $R^{10}$, $R^{11}$, $R^e$, $R^h$ and $R^m$ are as defined herein.

In certain embodiments, the subject compounds may be of formula VII:

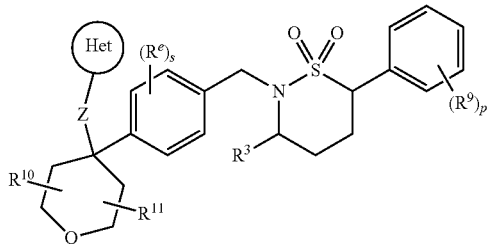

VII wherein p, q, r, s, Z, Het, $R^3$, $R^9$, $R^{10}$, $R^{11}$, $R^e$ and $R^m$ are as defined herein.

In certain embodiments, the subject compounds may be of formula VIII:

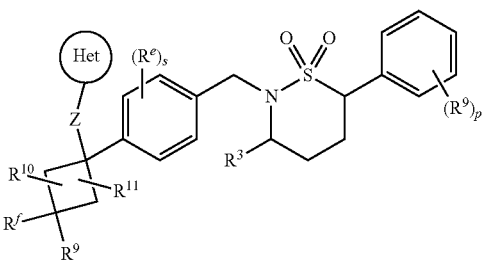

VIII wherein p, q, r, s, Z, Het, $R^3$, $R^9$, $R^{10}$, $R^{11}$, $R^e$, $R^f$, $R^g$, and $R^m$ are as defined herein.

In certain embodiments, the subject compounds may be of formula VIII:

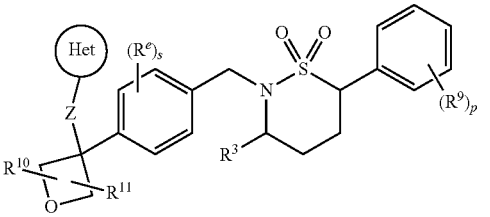

IX wherein p, q, r, s, Z, Ar, $R^3$, $R^9$, $R^{10}$, $R^{11}$, $R^e$, $R^f$, $R^g$, and $R^m$ are as defined herein.

In certain embodiments, the subject compounds may be of formula IIIa:

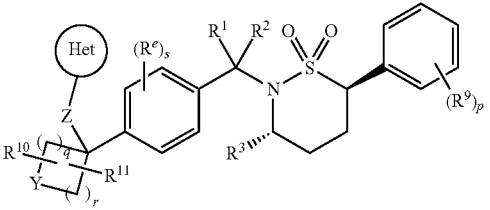

IIIa wherein p, q, r, s, Y, Z, Hetr, $R^1$, $R^2$, $R^3$, $R^9$, $R^{10}$, $R^{11}$, $R^e$ and $R^m$ are as defined herein.

In certain embodiments, the subject compounds may be of formula IVa:

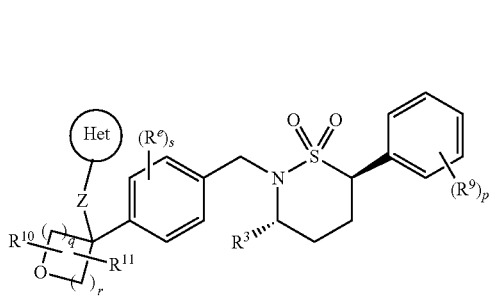

IVa wherein p, q, r, s, Y, Z, Het, $R^3$, $R^9$, $R^{10}$, $R^{11}$, $R^e$ and $R^m$ are as defined herein.

In certain embodiments, the subject compounds may be of formula Va:

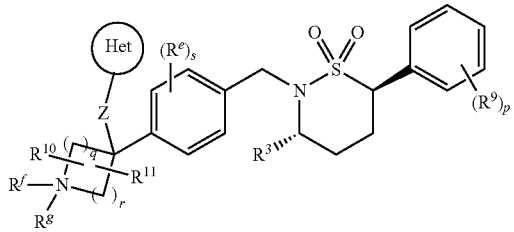

Va wherein p, q, r, s, Z, Het, $R^3$, $R^9$, $R^{10}$, $R^{11}$, $R^e$, $R^f$, $R^g$, and $R^m$ are as defined herein.

In certain embodiments, the subject compounds may be of formula VIa:

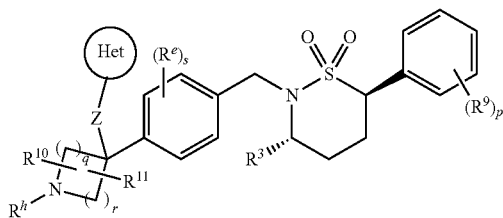

VIa wherein p, q, r, s, Z, Het, $R^3$, $R^9$, $R^{10}$, $R^{11}$, $R^e$, $R^h$ and $R^m$ are as defined herein.

In certain embodiments, the subject compounds may be of formula VIIa:

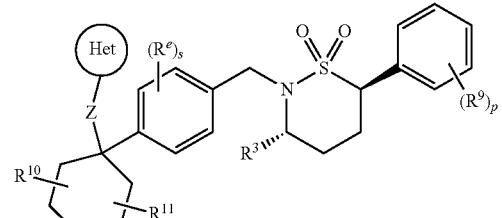

VIIa wherein p, q, r, s, Z, Het, $R^3$, $R^9$, $R^{10}$, $R^{11}$, $R^e$ and $R^f$ are as defined herein.

In certain embodiments, the subject compounds may be of formula VIIIa:

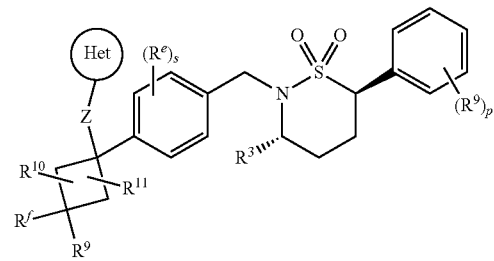

VIIIa wherein p, q, r, s, Z, Het, $R^3$, $R^9$, $R^{10}$, $R^{11}$, $R^e$, $R^f$, $R^g$, and $R^m$ are as defined herein.

In certain embodiments, the subject compounds may be of formula IXa:

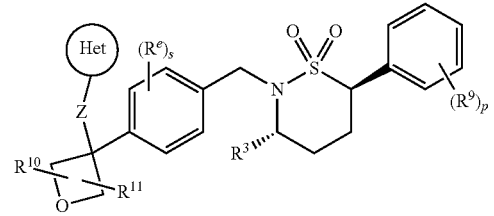

IXa wherein p, q, r, s, Z, Het, $R^3$, $R^9$, $R^{10}$, $R^{11}$, $R^e$, $R^f$, $R^g$, and $R^m$ are as defined herein.

Methods

The invention also provides a method for treating a disease or condition mediated by or otherwise associated with the RORc receptor, the method comprising administering to a subject in need thereof an effective amount of a compound of the invention.

The disease may be arthritis such as rheumatoid arthritis, spondyloarthritis or osteoarthritis.

The disease may be asthma or COPD.

The disease may be psoriasis, lupus, Sjogren's disease, irritable bowel disease or idiopathic pulmonary fibrosis.

The disease may be muscular sclerosis.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein LG is a leaving group such as halo, sulfonate, or the like, and m, n, p, q, A, $X^1$, $X^2$, $X^3$, $X^4$, Z, Ar, $R^1$, $R^2$, $R^3$, $R^4$, $R^5$, $R^6$, $R^7$, $R^8$, $R^9$, $R^{10}$, $R^b$ and $R^c$ are as defined herein.

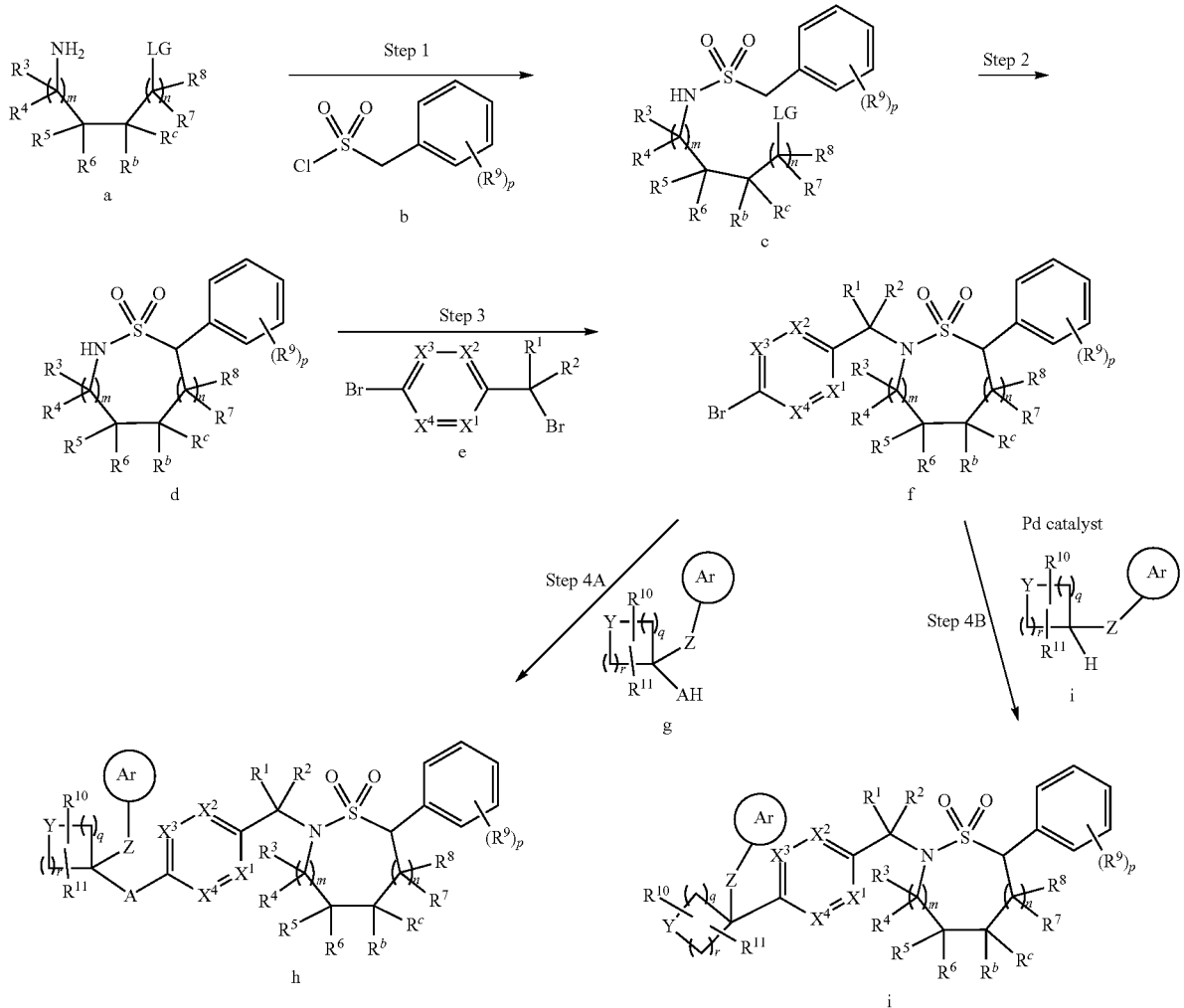

In step 1 of Scheme A, alkyl amine a is reacted with benzyl sulfonyl chloride b to form sulfonamide compound c. The reaction of step 1 may be carried out in a polar aprotic solvent such as THF or methylene chloride, and in the presence of a tertiary amine base or weak base such as potassium carbonate. The leaving group of compound a may be bromo in certain embodiments. Similarly, the chloro group of compound b may in certain embodiments be replaced by other halo or leaving group.

A cyclization reaction is carried out in step 2 to afford thiazinane compound d. The cyclization may be achieved in the presence of a strong base such as an alkyl lithium reagent, using polar aprotic solvent under anhydrous conditions.

In step 3, thiazinane compound c is reacted with aryalkyl halide compound e to yield aralkyl thiazinane f. The reaction of step 3 may be carried out in the presence of a strong base such as sodium hydride under anhydrous polar aprotic solvent conditions. The bromo groups of compound e may be replaced by other suitable leaving groups used in the art.

Thiazinane compound f may be treated with reagent g in step 4A to provide sultam compound h, which is a compound of formula I in accordance with the invention. In embodiments wherein A is oxygen such that reagent g is a cyclic alcohol, the reaction of step 4A may utilize a copper catalyst with hydrophobic solvent, in the presence of cesium carbonate or like base.

Alternatively, step 4B may be carried out wherein Thiazinane compound f undergoes an alkylation reaction with compound i to afford sultam compound j, which is a compound of formula I in accordance with the invention. The reaction of step may utilize a suitable palladium catalyst under Buchwald reaction conditions.

Scheme B below shows another synthetic procedure usable to prepare specific compounds of formula I, wherein TBS is tri-(tert-butyl)-silyl, and m, n, p, q, A, $X^1$, $X^2$, $X^3$, $X^4$, Y, $R^1$, $R^2$, $R^3$, $R^4$, $R^5$, $R^6$, $R^9$ and $R^{10}$ are as defined herein.

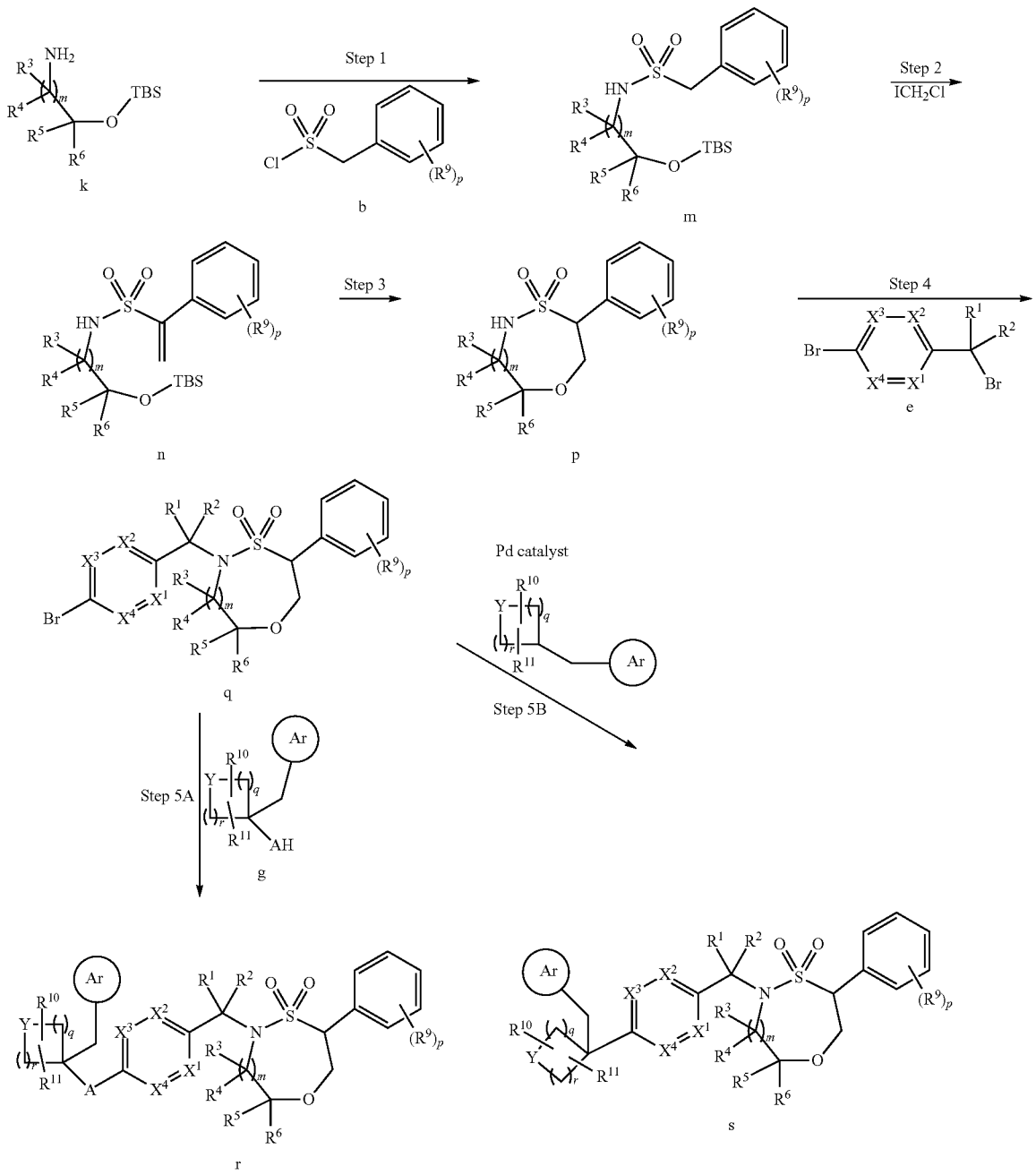

In step 1 of Scheme B, tri-(tert-butyl)-slilyloxy amine k is reacted with benzyl sulfonyl chloride b, as described above with reference to Scheme A, to form sulfonamide compound m. In certain embodiments the tri-(tert-butyl)-slilyloxy group may be replaced with other leaving groups.

In step 2, sulfonamide compound m is reacted with iodochloromethane to provide an alkenylsulfonamide compound n. This reaction may be achieved in the presence of a strong base such as an alkyl lithium reagent, using polar aprotic solvent such as THF under anhydrous conditions. In certain embodiments iodochloromethane may be replaced with other methylene reagents.

In step 3, a cyclization reaction is affected to provide oxathiazepane compound p. The cyclization may be carried out in the presence of an amine base under polar aprotic solvent conditions.

In step 4, oxathiazepane compound p is reacted with aryalkyl halide compound e to yield aralkyl oxathiazepane compound q, in the manner described above with reference to Scheme A.

Steps 5A or 5B may then be carried out by reaction of oxathiazepane compound q with reagents g and i respectively, in the manner described above with reference to Scheme A, to afford sultam compounds r and s respectively, which are compounds of formula I in accordance with the invention.

Many variations on the procedures of Scheme A and Scheme B are possible and will suggest themselves to those skilled in the art. Specific details for producing compounds of the invention are described in the Examples below.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, for example 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. A particular manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets may contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations may be in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described below.

Utility

The compounds of the invention are useful for treatment of immune disorders generally. The compounds may be used for treatment of arthritis, including rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

The compounds may be used for treatment of respiratory disorders such as chronic obstructive pulmonary disease (COPD), asthma, bronchospasm, and the like.

The compounds may be used for treatment of gastrointestinal disorder ("GI disorder") such as Irritable Bowel Syndrome (IBS), Inflammatory Bowel Disease (IBD), biliary colic and other biliary disorders, renal colic, diarrhea-dominant IBS, pain associated with GI distension, and the like.

The compounds may be used for treatment of pain conditions such as inflammatory pain; arthritic pain, surgical pain; visceral pain; dental pain; premenstrual pain; central pain; pain due to burns; migraine or cluster headaches; nerve injury; neuritis; neuralgias; poisoning; ischemic injury; interstitial cystitis; cancer pain; viral, parasitic or bacterial infection; post-traumatic injury; or pain associated with irritable bowel syndrome.

GENERAL EXPERIMENTAL

LCMS methods:

High Pressure Liquid Chromatography-Mass Spectrometry (LCMS) experiments to determine retention times (RT) and associated mass ions were performed using one of the following methods:

Method A: Compounds were analyzed using the following conditions: Experiments were performed on a Waters ZMD single quadrupole mass spectrometer linked to a Hewlett-Packard HP1100 LC system with UV diode array detector and 100 position autosampler. The spectrometer has an electrospray source operating in positive and negative ion mode. This system uses a Phenomenex Luna 3 μm C18(2) 30×4.6 mm column at ambient temperature and a 2.0 mL/min flow rate. The initial solvent system was 95% water containing 0.1% formic acid (solvent A) and 5% acetonitrile containing 0.1% formic acid (solvent B) for the first 0.5 min, followed by a gradient up to 5% solvent A and 95% solvent B over the next 4 min. This was maintained for 1 min before returning to 95% solvent A and 5% solvent B over the next 0.5 min. Total run time was 6 min.

Method B: Compounds were analysed using the following conditions: Experiments were performed on a Waters Micromass ZQ2000 quadrupole mass spectrometer linked to a Waters Acquity UPLC system with a PDA UV detector. The spectrometer has an electrospray source operating in positive and negative ion mode. This system uses an Acquity BEH C18 1.7 μm 100×2.1 mm column, maintained at 40° C. or an Acquity BEH Shield RP18 1.7 μm 100×2.1 mm column, maintained at 40° C. and a 0.4 mL/min flow rate. The initial solvent system was 95% water containing 0.1% formic acid (solvent A) and 5% acetonitrile containing 0.1% formic acid (solvent B) for the first 0.4 min followed by a gradient up to 5% solvent A and 95% solvent B over the next 5.6 min. This was maintained for 0.8 min before returning to 95% solvent A and 5% solvent B over the next 1.2 min. Total run time was 8 min.

Method C: Compounds were analysed using the following conditions: Experiments were performed on a Waters ZMD mass spectrometer linked to a Waters Acquity UPLC system with a PDA UV detector. The spectrometer has an electrospray source operating in positive and negative ion mode. This system uses an Acquity CSH C18 1.7 μm 50×2.1 mm column, maintained at 40° C. and a 1.0 mL/min flow rate. The initial solvent system was 97% water containing 0.1% formic acid (solvent A) and 3% acetonitrile containing 0.1% formic acid (solvent B) for the first 0.15 min followed by a gradient up to 1% solvent A and 99% solvent B over the next 1.85 min. This was maintained for 0.4 min before returning to 97% solvent A and 3% solvent B over the next 0.1 min. Total run time was 2.5 min.

NMR Methods:

$^1$H NMR spectra were recorded at ambient temperature, or at 80° C. where indicated, using one of the following machines: Varian Unity Inova (400 MHz) spectrometer with a triple resonance 5 mm probe, Bruker Avance DRX 400 (400 MHz) spectrometer with a triple resonance 5 mm probe, a Bruker Avance DPX 300 (300 MHz) equipped with a standard 5 mm dual frequency probe for detection of $^1$H and $^{13}$C, Bruker Fourier 300 MHz system equipped with a standard 5 mm $^1$H/$^{13}$C probe, a Bruker AVIII (400 MHz) using a BBI Broad Band Inverse 5 mm probe, or a Bruker AVIII (500 MHz) using a QNP (Quad Nucleus detect) 5 mm probe. Chemical shifts are expressed in ppm relative to an internal standard, tetramethylsilane (ppm=0.00). The following abbreviations have been used: br=broad signal, s=singlet, d=doublet, dd=double doublet, t=triplet, td=triplet doublet, dddd=doublet doublet doublet doublet, q=quartet, m=multiplet, or any combination thereof.

Microwave Reactor:

Microwave reactions were carried out using a Biotage® Initiator® in vials appropriate to the scale of the reaction and at the temperature and time described in the experimental details.

Purification Equipment:

Purifications were carried out using pre-packed silica gel cartridges either on a Teledyne ISCO CombiFlash® or Biotage® Isolera Four® or using compressed air to apply external pressure. Solvents and gradients shown in the experimental details were used.

Reverse Phase High Pressure Liquid Chromatography (HPLC) was used to purify compounds where indicated. Separation using gradient elution on a Phenomenex Gemini C18 column (250×21.2 mm, 5 micron) as stationary phase and using mobile phase indicated, operating at a 18 mL/min flow rate using a Gilson UV/Vis-155 dual channel detector and Gilson GX-271 automated liquid handler.

Phase separator cartridges are supplied by Biotage® as Isolute® phase separator cartridges.

Mass Directed Auto-Purification (MDAP) was used to purify compounds where indicated. Separation using Agilent 1260 Infinity Purifications System, XSelect CSH Prep C18 5 μm, 21×250 mm as the stationary phase, maintained at RT and a 19 mL/min flow. The initial solvent system was 90% water containing 0.1% formic acid (solvent A) and 10% acetonitrile containing 0.1% formic acid (solvent B), followed by a gradient up to 5% solvent A and 95% solvent B, centred around a specific focused gradient, over 22 min. Product collection was triggered by an Agilent 6100 series single Quadrupole LC/MS. The desired fractions were concentrated in vacuo at 40° C. and the residue freeze-dried from MeCN-water (1:1), except where stated otherwise.

List of Abbreviations

AcOH Acetic acid
AIBN 2,2'-Azobis(2-methylpropionitrile)
aq. Aqueous
Atm. Atmosphere
BOC tert-Butyloxycarbonyl group
(BOC)$_2$O Di-tert-butyl dicarbonate
CrO$_3$ Chromium(VI) oxide
CDCl$_3$ Deuterated chloroform
DavePhos 2-Dicyclohexylphosphino-2'-(N,N-dimethylamino)biphenyl
DCM Dichloromethane/methylene chloride
DMA N,N-Dimethylacetamide
DIAD Di-iso-propyl azodicarboxylate
DIPEA Di-iso-propylethylamine
DMAP 4-Dimethylaminopyridine
DME 1,2-Dimethoxyethane
DMF N,N-Dimethylformamide
DMSO Dimethyl sulfoxide
DPPF 1,1'-Bis(diphenylphosphino)ferrocene
ES Electrospray
Et$_2$O Diethyl ether
Et$_3$N Triethylamine
EtOH Ethanol/Ethyl alcohol
EtOAc Ethyl acetate
H$_2$O Water
H$_2$SO$_4$ Sulfuric acid
HATU 2-(1H-7-Azabenzotriazol-1-yl)-1,1,3,3-tetramethyl uronium hexafluorophosphate methanaminium
HBTU O-Benzotriazol-1-yl-N,N,N',N'-tetramethyluronium hexafluorophosphate HCO₂H Formic acid
HCl Hydrochloric acid
HOBT 1-Hydroxybenzotriazole
HPLC High pressure liquid chromatography
RP HPLC Reverse phase high pressure liquid chromatography
IBX 2-Iodoxybenzoic acid
IMS Industrial methylated spirit
KOH Potassium hydroxide
K₂CO₃ Potassium carbonate
LDA Lithium diisopropylamide
i-PrOH Isopropanol/isopropyl alcohol/propan-2-ol
LCMS Liquid Chromatograph/Mass Spectroscopy
LiOH Lithium hydroxide
MDAP Mass-directed autopurification system (preparative LCMS)
MgSO₄ Magnesium sulphate
MeOH Methanol/Methyl alcohol
MW Microwaves
NaH Sodium hydride
NaCl Sodium chloride
NaOH Sodium hydroxide
Na₂SO₄ Sodium sulfate
Na₂CO₃ Sodium carbonate
NaHCO₃ Sodium bicarbonate/Sodium hydrogen carbonate
NBS N-Bromosuccinimide
NH₄Cl Ammonium chloride
NMP 1-Methyl-2-pyrrolidinone
POCl₃ Phosphorus oxychloride
PhCH₃ Toluene
Pd₂(dba)₃ Tris(dibenzylideneacetone)dipalladium(O)
PSI Pound per square inch
RT Room temperature
sat. Saturated
SCX-2 Pre-packed Isolute® silica-based sorbent with a chemically bonded propylsulfonic acid functional group
SFC Supercritical fluid chiral chromatography
TBDMS tert-Butyldimethylsilyl
TFA Trifluoroacetic acid
THF Tetrahydrofuran
TIPS Triisopropylsilyl
TLC Thin layer chromatography
XantPhos 4,5-Bis(diphenylphosphino)-9,9-dimethylxanthene Preparations 1 and 2: (3R)-3-Aminobutan-1-ol and (3S)-3-Aminobutan-1-ol

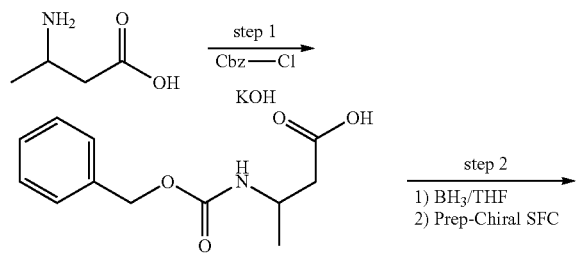

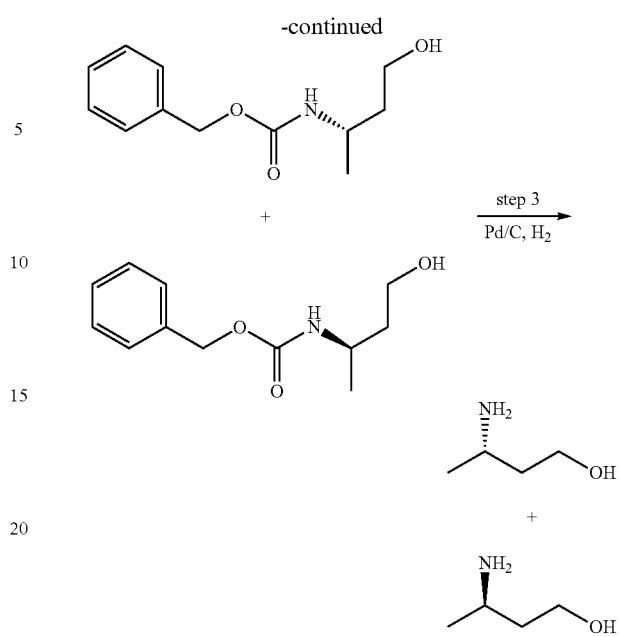

Step 1 3-[[(Benzyloxy)carbonyl]amino]butanoic Acid

Into a 2000-mL 4-necked round-bottom flask was placed a solution of 3-aminobutanoic acid (100 g, 969.75 mmol, 1.00 equiv) in water (1000 mL), followed by the addition of potassium hydroxide (136 g, 2.42 mol, 2.50 equiv) in several batches. To this was added benzyl chloroformate (247 g, 1.45 mol, 1.50 equiv) dropwise with stirring at 0-5° C. The resulting solution was stirred at 25° C. for 5 h. The reaction progress was monitored by LCMS. The resulting solution was extracted with dichloromethane and the aqueous layers were combined. The pH value of the water phase was adjusted to 3 with hydrogen chloride (2 mol/L). The precipitates were collected by filtration and dried to afford 102 g (44%) of 3-[[(benzyloxy)carbonyl]amino]butanoic acid as a white solid.

Step 2: Benzyl N-[(2S)-4-hydroxybutan-2-yl]carbamate and Benzyl N-[(2R)-4-hydroxybutan-2-yl]carbamate Into a 2000-mL 3-necked round-bottom flask purged and maintained with an inert atmosphere of nitrogen was placed a solution of 3-[[(benzyloxy)carbonyl]amino]butanoic acid (102 g, 429.92 mmol, 1.00 equiv) in THF (300 mL), followed by the addition of BH₃/THF (1N) (645 mL, 1.50 equiv) dropwise with stirring at 0-5° C. The resulting solution was stirred at 40° C. for 2 h, quenched by the addition of 200 mL of methanol and concentrated under vacuum. The residue was purified on a silica gel column eluting with ethyl acetate: petroleum ether (1:2). The crude product (70 g) was purified by Prep-SFC with the following conditions (prep SFC): Column, Phenomenex Lux 5u Cellulose-4, 2.12*25.5 um; mobile phase, CO₂ (85%), ethanol (15%); Detector, UV 254 nm. This resulted in 30 g (31.5%) of benzyl N-[(2R)-4-hydroxybutan-2-yl]carbamate as an off-white solid and 30 g (31.5%) of benzyl N-[(2S)-4-hydroxybutan-2-yl]carbamate as an off-white solid.

Step 3: (3R)-3-Aminobutan-1-ol and (3S)-3-Aminobutan-1-ol

Into a 1000-mL round-bottom flask was placed a solution of benzyl N-[(2S)-4-hydroxybutan-2-yl]carbamate (30 g, 134.4 mmol, 1.00 equiv) in methanol (500 mL) and palladium carbon (3 g, 0.10 equiv). The resulting solution was stirred at 25° C. for 12 h under an atmosphere of hydrogen. The solids were filtered out and the filtrate was concentrated under vacuum to afford 11.7 g (92%) of (3S)-3-aminobutan-1-ol as an oil. $^1$H NMR (300 MHz, DMSO, ppm): δ 4.48 (3H, s), 3.47 (2H, s), 2.96 (1H, s), 1.47-1.41 (2H, q), 1.02-0.99 (3H, d); LCMS (ESI), m/z, 90 [M+H]$^+$; measured $[\alpha]_D^{20.2}$+11.65° (C=1.22 g/100 mL in EtOH), lit. $[\alpha]_D^{20}$+ 16.3° (c=4.5 in EtOH) (*J. Org. Chem.* 1996, 61, 2293-2304.).

Using the above procedure, 12.0 g 12 g (94%) of (3R)-3-aminobutan-1-ol was isolated as an oil. $^1$H NMR (300 MHz, DMSO, ppm): δ 4.48 (3H, s), 3.47 (2H, s), 2.96 (1H, s), 1.47-1.41 (2H, q), 1.02-0.99 (3H, d); LCMS (ESI), m/z, 90 [M+H]$^+$; measured $[\alpha]_D^{20.2}$-11.1° (C=0.32 g/100 mL in EtOH), lit. $[\alpha]_D^{25}$ -25° (c=1.25 in EtOH) (*Tetrahedron: Asymmetry* 1999, 10, 2213-2224.).

Preparation 3: (R)—N-(4-Chlorobutan-2-yl)-1-phenylmethanesulfonamide

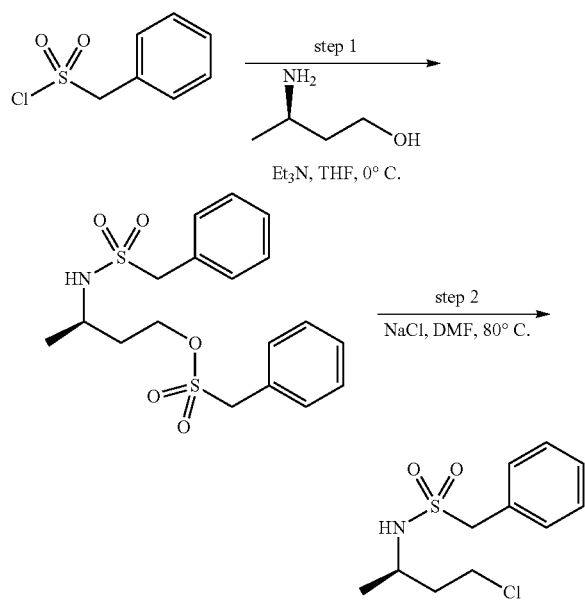

Step 1: (R)-3-(Phenylmethylsulfonamido)butyl phenylmethanesulfonate

To a solution of (3R)-3-aminobutan-1-ol (1.0 g, 11.2 mmol) and triethylamine (3.3 mL, 23.6 mmol) in tetrahydrofuran (37 mL) at 0° C. was slowly added phenylmethanesulfonyl chloride (4.49 g, 23.6 mmol) and the reaction was stirred at room temperature for 16 hours. MTBE (100 mL) was then added and the Et$_3$N—HCl salt was removed by filtration. The filtrate was then concentrated to give crude (R)-3-(phenylmethylsulfonamido)butyl phenylmethanesulfonate which was used without purification.

LCMS (ESI), m/z, 398 [M+H]+.

Step 2: (R)—N-(4-Chlorobutan-2-yl)-1-phenylmethanesulfonamide

To the crude (R)-3-(phenylmethylsulfonamido)butyl phenylmethanesulfonate (23.6 mmol) was added sodium chloride (984 mg, 16.8 mmol) and dimethylformamide (37 mL) and the reaction was stirred at 80° C. for 16 hours. The reaction was then diluted with EtOAc, washed with water (×2) and brine, dried with MgSO$_4$, concentrated and purified by silica gel column chromatography (0-50% Acetone in Heptane, 216 nM) to give (R)—N-(4-chlorobutan-2-yl)-1-phenylmethanesulfonamide (1.71 g, 6.53 mmol, 58% yield over 2 steps). LCMS (ESI), m/z, 261 [M+H]+.

Additional compounds made using the above procedure are shown in Table 1.

TABLE 1

| | Structure | Name | LCMS (ESI), m/z, [M + H]+ |
|---|---|---|---|
| 4 | 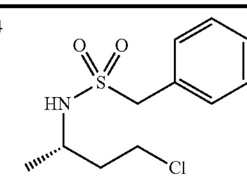 | (S)-N-(4-chlorobutan-2-yl)-1-phenyl-methanesulfonamide | 261 |
| 5 | 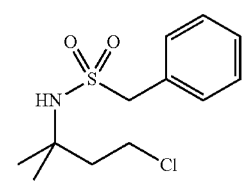 [SMILES: CC(C)(CCCl)NS(=O)(=O)Cc1ccccc1] | N-(4-chloro-2-methylbutan-2-yl)-1-phenylmethane-sulfonamide | 275 |
| 6 | 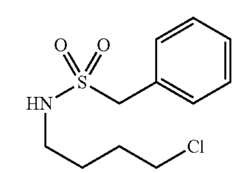 [SMILES: O=S(=O)(Cc1ccccc1)NCCCCCl] | N-(4-chlorobutyl)-1-phenylmethane-sulfonamide | 261 |

Preparation 7: N-(2-bromoethyl)(phenyl)methanesulfonamide

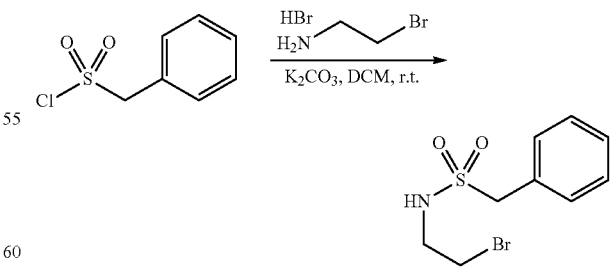

K$_2$CO$_3$ (8.7 g, 62 mmol) was added into a mixture of phenylmethanesulfonyl chloride (6 g, 31 mmol) and 2-bromoethanamine hydrobromide (6.4 g, 31 mmol) in DCM (100 mL) at 0° C. And the resulting mixture was stirred at r.t. for 4 hours and left standing overnight. Upon the completion of reaction, water (100 mL) was added in and DCM phase was separated. The aqueous phase was extracted with DCM. The combined organic phase was dried over Na$_2$SO$_4$, filtered and concentrated in vacuo to provide a crude which was separated with column chromatography (silica gel with 200-300 mesh, 0 to 50% of EtOAc in petroleum ether) to provide compound N-(2-bromoethyl)(phenyl)methanesulfonamide (7.0 g, 80%) as a pale yellow solid. $^1$H NMR (300 MHz, CDCl$_3$) δ 7.40 (m, 5H), 4.58 (m, 1H), 4.29 (s, 2H), 3.34-3.29 (m, 4H). LCMS (ESI), 300, 302 [M+Na]$^+$, Br pattern found.

Preparation 8
N-(2-bromoethyl)(4-fluorophenyl)methanesulfonamide

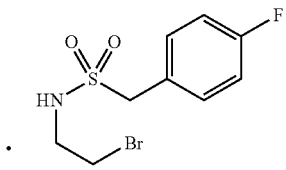 [SMILES: O=S(=O)(Cc1ccc(F)cc1)NCCBr]

N-(2-bromoethyl)(4-fluorophenyl)methanesulfonamide was also made using the above procedure, replacing phenylmethanesulfonyl chloride with 4-fluoro-phenylmethanesulfonyl chloride. $^1$H NMR (300 MHz, CDCl$_3$) δ 7.43-7.38 (m, 2H), 7.13-7.07 (m, 2H), 4.62 (br s, 1H), 4.26 (s, 2H), 3.41-3.32 (m, 4H).

Preparation 9:
N-(3-bromopropyl)(phenyl)methanesulfonamide

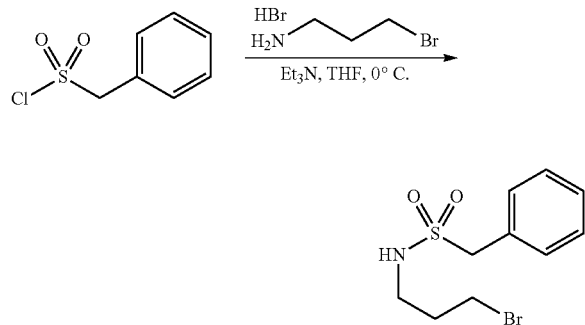

A solution of phenylmethanesulfonyl chloride (2.19 g, 10 mmol) was added into a suspension of 3-bromopropan-1-amine hydrobromide (2.19 g, 10 mmol) and Et$_3$N (2.02 g, 20 mmol) in THF (50 mL) at 0° C. The mixture was stirred at 0° C. for 5 min. TLC confirmed the completion of reaction. Solid was filtered out with suction, and the filtrate was concentrated to provide compound N-(3-bromopropyl)(phenyl)methanesulfonamide (2.7 g, quant.) as a pale yellow solid which was used in the next step without further purification. $^1$H NMR (300 MHz, CDCl$_3$) δ 7.40 (m, 5H), 4.48 (m, 1H), 4.27 (s, 2H), 3.41 (t, J=6.6 Hz, 2H), 3.16 (q, 2H), 2.01 (m, 2H). LCMS (ESI), m/z, 314 and 316 [M+Na]$^+$, Br pattern found.

Preparation 10: N-(3-bromopropyl)(4-fluorophenyl)methanesulfonamide

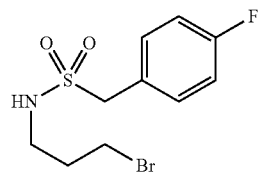 [SMILES: O=S(=O)(Cc1ccc(F)cc1)NCCCBr]

N-(3-bromopropyl)(4-fluorophenyl)methanesulfonamide was prepared using the above procedure. $^1$H NMR (300 MHz, CDCl$_3$) δ 7.42-7.37 (m, 2H), 7.13-7.07 (m, 2H), 4.26 (m, 1H), 4.24 (s, 2H), 3.46-3.42 (m, 2H), 3.20-3.16 (m, 2H), 2.05-2.00 (m, 2H).

Preparation 11: 6-Phenyl-1,2-thiazinane 1,1-dioxide

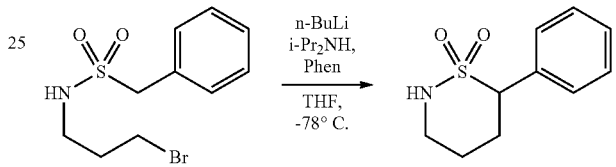

To a solution of N-(3-bromopropyl)-1-phenylmethanesulfonamide (2.3 g, 7.9 mmol), diisopropylamine (0.28 mL, 2.0 mmol) and 1,10-phenanthroline (3.6 mg, 0.02 mmol) in tetrahydrofuran (26 mL) at −78° C. was added n-BuLi (6.8 mL, 2.5 M in hexanes) dropwise and the reaction was stirred for 16 hours. Saturated NH$_4$Cl was then added and the reaction was diluted with EtOAc, washed with water and brine, dried with MgSO$_4$, concentrated and purified by silica gel column chromatography (0-50% EtOAc/heptane) to 6-Phenyl-1,2-thiazinane 1,1-dioxide (1.3 g, 80% yield). $^1$H NMR (300 MHz, DMSO-d$_6$) δ 7.40-7.35 (m, 5H), 6.98 (m, 1H), 4.12 (dd, 1H), 3.26-3.20 (m, 2H), 2.40-2.30 (m, 1H), 2.16-2.12 (m, 1H), 1.77-1.65 (m, 2H). LCMS (ESI), m/z, 234 [M+Na]$^+$. (Reference: D. Askin, et al. *Org. Lett.* 2003, 4175.)

Additional compounds made using the above procedure are shown in Table 2.

TABLE 2

| | Structure | Name | LCMS (ESI), m/z, [M + H]$^+$ |
|---|---|---|---|
| 12 | 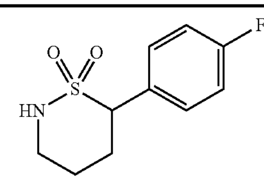 | 6-(4-fluorophenyl)-1,2-thiazinane 1,1-dioxide | 230 |
| 13 | 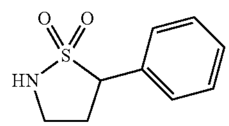 [SMILES: O=S1(=O)NCCC1c1ccccc1] | 5-phenyl-isothiazolidine 1,1-dioxide | 198 |

TABLE 2-continued

| | Structure | Name | LCMS (ESI), m/z, [M + H]+ |
|---|---|---|---|
| 14 | 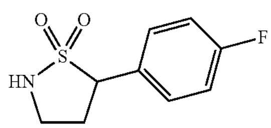 [SMILES: O=S1(=O)NCCC1c1ccc(F)cc1] | 5-(4-fluorophenyl) isothiazolidine 1,1-dioxide | 216 |
| 15 | 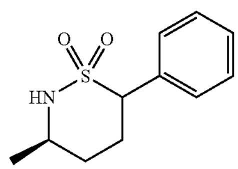 | (3R)-3-methyl-6-phenyl-1,2-thiazinane 1,1-dioxide | 226 |
| 16 | 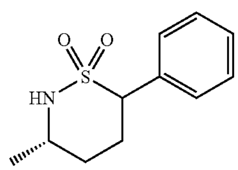 | (3S)-3-methyl-6-phenyl-1,2-thiazinane 1,1-dioxide | 226 |
| 17 | 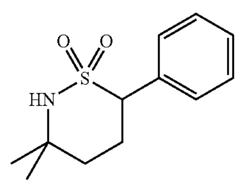 [SMILES: CC1(C)CCC(c2ccccc2)S(=O)(=O)N1] | 3,3-dimethyl-6-phenyl-1,2-thiazinane 1,1-dioxide | 240 |
| 18 | 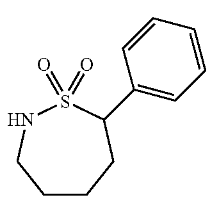 [SMILES: O=S1(=O)NCCCCC1c1ccccc1] | 7-phenyl-1,2-thiazepane 1,1-dioxide | 226 |

Preparation 19: 3-Phenyl-1,4,5-oxathiazepane 4,4-dioxide

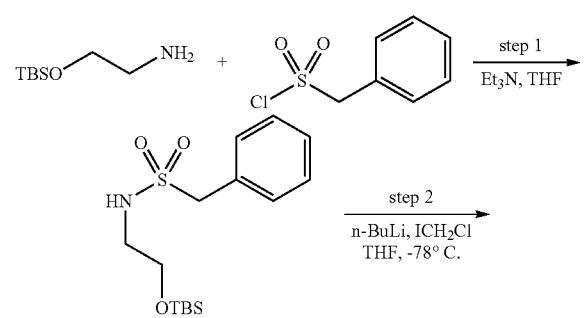

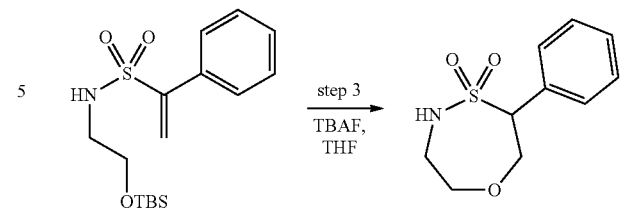

Step 1: N-(2-((Tert-butyldimethylsilyl)oxy)ethyl)-1-phenylmethanesulfonamide To a solution of 2-((tert-butyldimethylsilyl)oxy)ethanamine (11.7 g, 66.6 mmol) and triethylamine (11.2 mL, 79.9 mmol) in tetrahydrofuran (222 mL) at 0° C. was slowly added phenylmethanesulfonyl chloride (12.7 g, 66.6 mmol) portion wise and the reaction was stirred at room temperature for 16 hours. MTBE was then added and the Et$_3$N.HCl salt was removed by filtration. The filtrate was then concentrated and purified by silica gel column chromatography (0-30% Acetone in heptane, 216 nM) to N-(2-((tert-butyldimethylsilyl)oxy)ethyl)-1-phenylmethanesulfonamide (17.8 g, 81% yield). LCMS (ESI), m/z, 330. [M+H]+.

Step 2: N-(2-((Tert-butyldimethylsilyl)oxy)ethyl)-1-phenylethenesulfonamide

To a solution of N-[2-[tert-butyl(dimethyl)silyl]oxyethyl]-1-phenyl-methanesulfonamide (33 g, 100.2 mmol) in tetrahydrofuran (334 mL) at −78° C. was slowly added n-BuLi (2.5 M in hexanes) (100 mL, 250 mmol) via cannula and the reaction was stirred at −78° C. was 2 hours. Chloroiodomethane (8.3 mL, 110 mmol) was then slowly added and the reaction was stirred at −78° C. for one hour, then allowed to warm to room temperature and aged for 16 hours. The reaction was then quenched with saturated NH$_4$Cl and extracted with dichloromethane, dried with MgSO$_4$, concentrated and purified by silica gel column chromatography (0-60% EtOAc in heptane) to give N-[2-[tert-butyl(dimethyl)silyl]oxyethyl]-1-phenyl-ethenesulfonamide (24 g, 70% yield). LCMS (ESI), m/z, 342. [M+H]+.

Step 3: 3-Phenyl-1,4,5-oxathiazepane 4,4-dioxide

To a solution of N-(2-((Tert-butyldimethylsilyl)oxy)ethyl)-1-phenylethenesulfonamide (717 mg, 2.1 mmol) in tetrahydrofuran (7 mL) at 0° C. was added tetrabutylammonium fluoride (1.0 M in THF) (2.2 mL, 2.2 mmol) dropwise and the reaction was stirred at room temperature for 16 hours. Saturated NH$_4$Cl was then added and the product was extracted with dichloromethane (×2), dried with MgSO$_4$, concentrated and purified by silica gel column chromatography (0-100% EtOAc in heptane) to give 3-phenyl-1,4,5-oxathiazepane 4,4-dioxide (401 mg, 84% yield). (24 g, 70% yield). LCMS (ESI), m/z, 228. [M+H]+. (Reference: P. Hansen, et al. *Org. Lett.* 2008, 2951).

Additional compounds made using the above procedure are shown in Table 3.

TABLE 3

| | Structure | Name | LCMS (ESI), m/z, [M + H]+ |
|---|---|---|---|
| 20 | 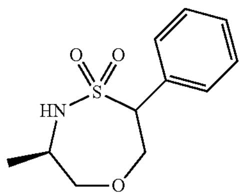 [SMILES: C[C@@H]1COCC(c2ccccc2)S(=O)(=O)N1] | (6R)-6-methyl-3-phenyl-1,4,5-oxathiazepane 4,4-dioxide | 242 |
| 21 | 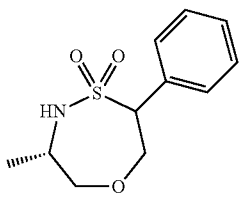 [SMILES: C[C@H]1COCC(c2ccccc2)S(=O)(=O)N1] | (6S)-6-methyl-3-phenyl-1,4,5-oxathiazepane 4,4-dioxide | 242 |
| 22 | 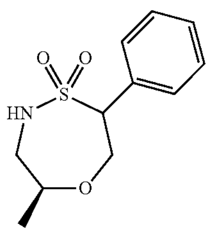 [SMILES: C[C@H]1CNS(=O)(=O)C(c2ccccc2)CO1] | (7S)-7-methyl-3-phenyl-1,4,5-oxathiazepane 4,4-dioxide | 242 |
| 23 | 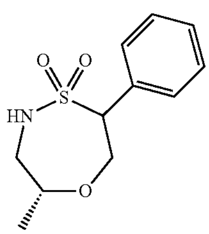 [SMILES: C[C@@H]1CNS(=O)(=O)C(c2ccccc2)CO1] | (7R)-7-methyl-3-phenyl-1,4,5-oxathiazepane 4,4-dioxide | 242 |

Example 1: (3S,6R)-2-[[2,5-difluoro-4-[3-[(5-methylisoxazol-3-yl)methoxy]oxetan-3-yl]phenyl]methyl]-3-methyl-6-phenyl-thiazinane 1,1-dioxide

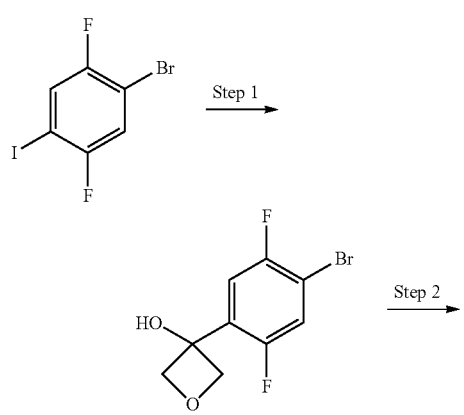

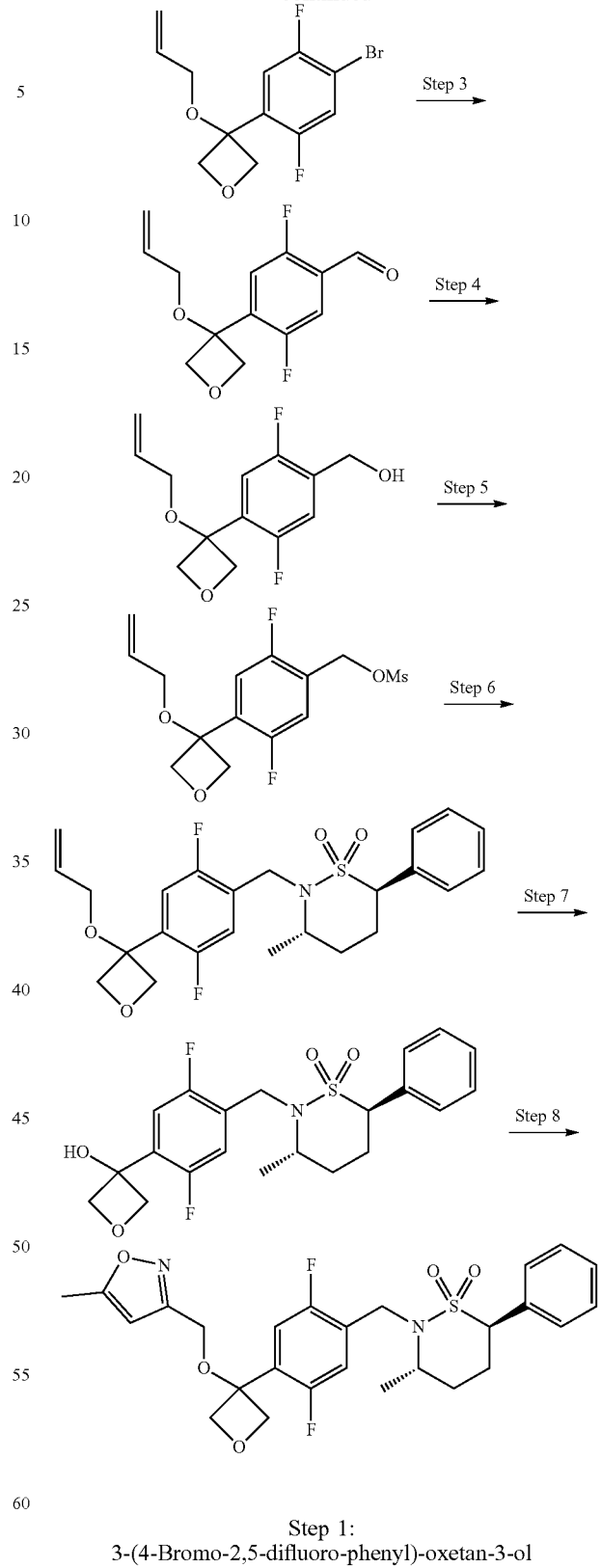

Step 1:
3-(4-Bromo-2,5-difluoro-phenyl)-oxetan-3-ol

To a stirred solution of 4-bromo-2,5-difluoroiodobenzene (5.0 g, 15.7 mmol) in dry THF (45 mL) at −30° C. was added isopropylmagnesium chloride (10.2 mL, 20.4 mmol, 2.0 M in THF) over 5 min. A solution of oxetan-3-one (1.47 g, 20.4 mmol) in dry THF (20 mL) was added drop-wise after 1 h and the reaction stirred for 0.5 h before warming to RT. After 16 h, the reaction was quenched with saturated aqueous NH$_4$Cl (30 mL), extracted with EtOAc, dried over Na$_2$SO$_4$ and concentrated in vacuo. Purification by flash chromatography (0-80% EtOAc/cyclohexane) gave the title compound as a pale yellow oil (2.65 g). $^1$H NMR (300 MHz, CDCl$_3$) δ 7.35 (1H, dd, J=5.4, 9.6 Hz), 7.17 (1H, dd, J=6.6, 8.4 Hz), 5.11-5.06 (2H, m), 4.85-4.79 (2H, m), 3.25 (1H, s).

Step 2:
3-Allyloxy-3-(4-bromo-2,5-difluoro-phenyl)-oxetan

To a stirred solution of 3-(4-bromo-2,5-difluoro-phenyl)-oxetan-3-ol (2.00 g, 7.55 mmol) in dry DMA (22 mL) at 0° C. was added sodium hydride (453 mg, 11.3 mmol of a 60% disp. in mineral oil) portion-wise. The reaction was stirred for 0.5 h before allyl bromide (0.973 mL, 11.3 mmol) was added and the reaction stirred at RT for 1 h. The reaction was quenched with brine (30 mL), extracted with EtOAc, dried over Na$_2$SO$_4$ and concentrated in vacuo. Purification by flash chromatography (0-80% EtOAc/cyclohexane) gave the title compound as an oil (2.12 g). $^1$H NMR (300 MHz, CDCl$_3$) δ 7.34 (1H, dd, J=5.7, 9.3 Hz), 7.02 (1H, dd, J=6.3, 8.4 Hz), 5.87 (1H, ddt, J=5.4, 10.2, 17.3 Hz), 5.27 (1H, dq, J=1.5, 17.3 Hz), 5.16 (1H, dq, J=1.5, 10.2 Hz), 5.00-4.90 (4H, m), 3.83-3.77 (2H, m).

Step 3: 4-(3-Allyloxy-oxetan-3-yl)-2,5-difluoro-benzaldehyde

To a stirred solution of 3-allyloxy-3-(4-bromo-2,5-difluoro-phenyl)-oxetan (2.12 g, 6.95 mmol) in dry THF (55 mL) at −78° C. was added n-butyllithium (6.50 mL, 10.4 mmol, 1.6 M solution in hexanes) drop-wise. The reaction was stirred for 0.5 h before dry DMF (2.25 mL, 27.8 mmol) was added and the reaction was allowed to warm to RT after 0.5 h. The reaction was quenched with saturated aqueous NH$_4$Cl (30 mL) after 1 h, extracted with EtOAc, dried over Na$_2$SO$_4$ and concentrated in vacuo.

Step 4: [4-(3-Allyloxy-oxetan-3-yl)-2,5-difluoro-phenyl]-methanol

The residue from step 3 was dissolved in MeOH (35 mL), cooled to 0° C., and sodium borohydride (1.05 mg, 27.8 mmol) added portion-wise. The reaction was quenched with H$_2$O (20 mL) after 0.5 h, extracted with EtOAc, and the combined extracts were washed with brine, dried over Na$_2$SO$_4$ and concentrated in vacuo. Purification by flash chromatography (0-80% EtOAc/cyclohexane) gave the title compound as an oil (900 mg). $^1$H NMR (300 MHz, CDCl$_3$) δ 7.23 (1H, dd, J=5.7, 10.2), 6.92 (1H, dd, J=6.0, 9.6 Hz), 5.87 (1H, ddt, J=5.4, 10.2, 17.3 Hz), 5.27 (1H, dq, J=1.5, 17.3 Hz), 5.16 (1H, dq, J=1.5, 10.2 Hz), 5.03-4.90 (4H, m), 4.77 (2H, d, J=5.7 Hz), 3.82-3.76 (2H, m), 1.87 (1H, t, J=6.0 Hz).

Step 5: Methanesulfonic acid 4-(3-allyloxy-oxetan-3-yl)-2,5-difluoro-benzyl Ester To a stirred solution of [4-(3-allyloxy-oxetan-3-yl)-2,5-difluoro-phenyl]-methanol (900 mg, 3.51 mmol) in DCM (35 mL) at 0° C. was added methanesulfonyl chloride (0.347 mL, 4.57 mmol) followed by triethylamine (0.732 mL, 5.27 mmol). After 1 h, the reaction was concentrated in vacuo and the residue was filtered through a phase separator and purified using flash chromatography (0-70% EtOAc/cyclohexane) to give the title compound as an oil (927 mg). $^1$H NMR (300 MHz, CDCl$_3$) δ 7.23 (1H, dd, J=5.7, 9.6 Hz), 7.01 (1H, dd, J=6.0, 9.6 Hz), 5.87 (1H, ddt, J=5.4, 10.5, 17.3 Hz), 5.32-5.23 (3H, m), 5.16 (1H, dq, J=1.5, 10.5 Hz), 5.03-4.91 (4H, m), 3.84-3.78 (2H, m), 3.07 (3H, s).

Step 6: (3S,6R)-2-[4-(3-Allyloxy-oxetan-3-yl)-2,5-difluoro-benzyl]-3-methyl-6-phenyl-[1,2]thiazinane 1,1-dioxide A mixture of the product from step 5 (871 mg, 2.61 mmol), Cs$_2$CO$_3$ (1.28 g, 3.92 mmol), DMA (5 mL) and (3S,6R)-3-methyl-6-phenyl-thiazinane 1,1-dioxide (528 mg, 2.34 mmol) was stirred for 4 h. The reaction was quenched with H$_2$O, extracted into EtOAc, dried over MgSO$_4$ and concentrated in vacuo. Purification by crystallisation (EtOAc-heptane) gave the title compound (950 mg).

Step 7: 3-[2,5-Difluoro-4-((3S,6R)-3-methyl-1,1-dioxo-6-phenyl-1lambda*6*-[1,2]thiazinan-2-ylmethyl)-phenyl]-oxetan-3-ol A mixture of the product from step 6 (100 mg, 0.216 mmol), triphenyl phosphine (23 mg, 0.02 mmol) and K$_2$CO$_3$ (13 mg, 0.82 mmol) in EtOH (5 mL) was heated at reflux for 0.5 h. The reaction was quenched with H$_2$O, extracted into EtOAc, dried over MgSO$_4$ and concentrated in vacuo. Purification by flash chromatography (1:1 EtOAc/cyclohexane) and crystallised (EtOAc-cyclohexanes) to give the title compound (50 mg). $^1$H NMR (400 MHz, DMSO-d$_6$) δ 7.46-7.20 (6H, m), 6.44 (1H, s), 4.91 (2H, d, J=6.8 Hz), 4.63 (2H, d, J=6.9 Hz), 4.56-4.47 (2H, m), 4.35 (1H, d, J=17.8 Hz), 4.15-4.07 (1H, m), 2.43-2.37 (1H, m), 2.11-2.05 (1H, m), 1.84-1.72 (1H, m), 1.68-1.60 (1H, m), 1.09 (3H, d, J=6.8 Hz). LCMS (ESI): m/z=424.1 [M+H]$^+$.

Step 8: (3S,6R)-2-[[2,5-difluoro-4-[3-[(5-methyl-isoxazol-3-yl)methoxy]oxetan-3-yl]phenyl]methyl]-3-methyl-6-phenyl-thiazinane 1,1-dioxide To a solution of the product from step 7 (0.4 g, 0.95 mmol) in DMA (3 mL) at 0° C. was added NaH (40 mg, 1.0 mmol, 60% dispersion in mineral oil). 3-Chloromethyl-5-methylisoxazole was added after 0.5 h and the reaction allowed to warm to room temperature and stirring continued for 45 min. The reaction was quenched with H$_2$O, extracted into EtOAc, dried over MgSO$_4$ and concentrated in vacuo. Purification by flash chromatography (1:2-1:1 EtOAc/cyclohexane) and crystallisation (EtOAc-cyclohexanes) to gave the title compound (48 mg). LCMS (ESI): m/z=519.1 [M+H]$^+$.

Example 2: trans 5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3H-1,3,4-oxadiazol-2-one

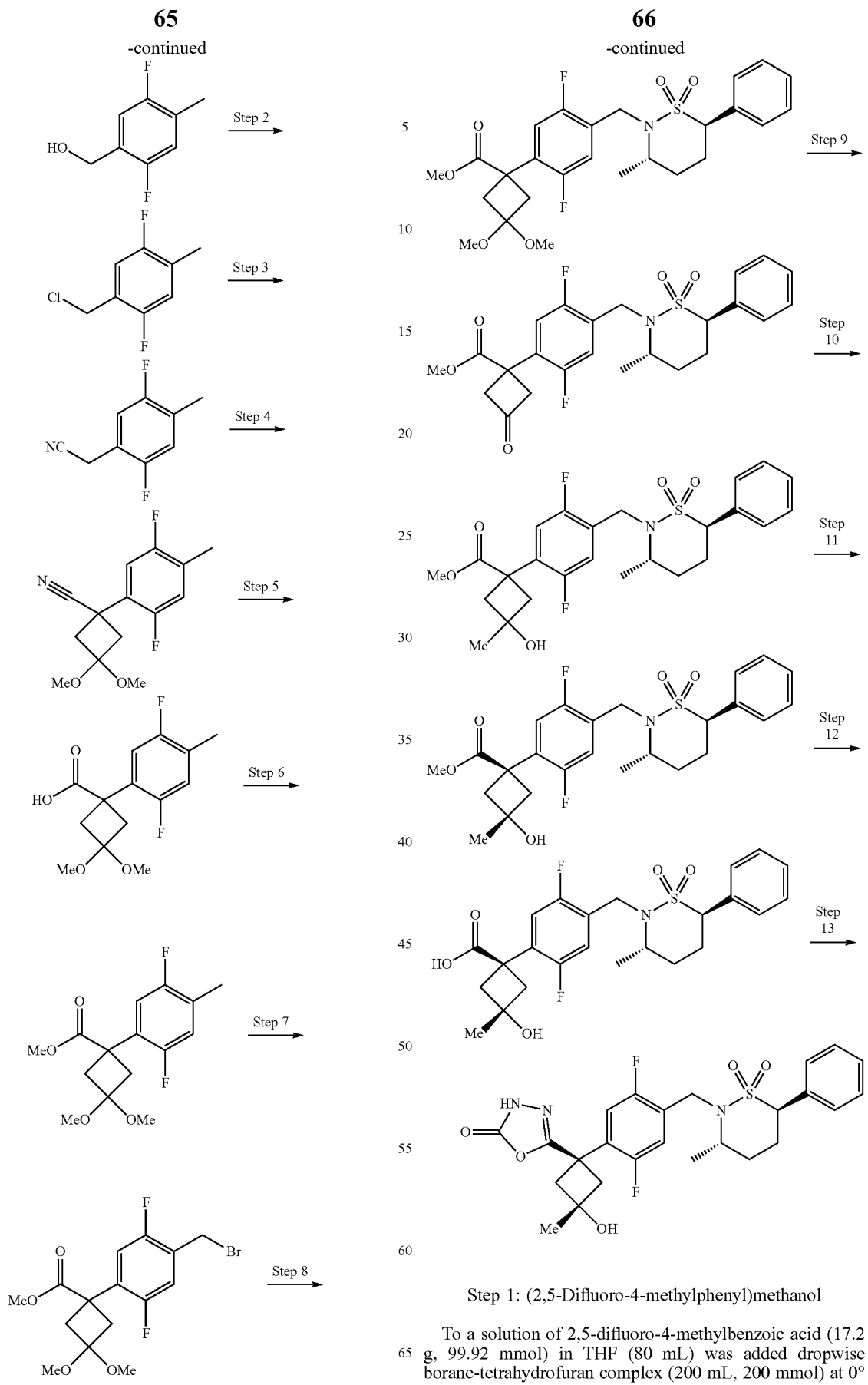
Step 1: (2,5-Difluoro-4-methylphenyl)methanol
To a solution of 2,5-difluoro-4-methylbenzoic acid (17.2 g, 99.92 mmol) in THF (80 mL) was added dropwise borane-tetrahydrofuran complex (200 mL, 200 mmol) at 0° C. over 30 min, then the mixture was heated at 60° C. for 2 h. The reaction was cooled to RT and the reaction was quenched with brine. The resulting mixture was poured into water, extracted with EtOAc (2×100 mL). The organic extracts were combined and washed with brine (2×50 mL), dried over $Na_2SO_4$, filtered, and concentrated under reduced pressure. The residue was purified by silica gel chromatography using petroleum ether/EtOAc (3/1) as eluting solvents to afford the title compound as a white solid. (15.5 g, 98% yield).

LCMS (ESI): m/z=141.2 [M-OH]+.

Step 2:
1-(Chloromethyl)-2,5-difluoro-4-methylbenzene

A mixture of (2,5-difluoro-4-methylphenyl)methanol (15.5 g, 98.1 mmol) in $SOCl_2$ (60 mL) was stirred at RT for 12 h. The solvent was removed under reduced pressure to obtain the crude product as yellow oil (16 g, 93% yield). The crude compound was used in next step without further purification.

Step 3: 2-(2,5-Difluoro-4-methylphenyl)acetonitrile

A mixture of 1-(chloromethyl)-2,5-difluoro-4-methylbenzene (18 g, 102.3 mmol), NaCN (30.1 g, 613.6 mmol) and TBAB (3.29 g, 10.2 mmol) in DCM/water (1:1, 240 mL) were stirred at RT for 12 h. The reaction was poured into water (150 mL) and extracted with DCM (2×100 mL). The combined extracts were washed with brine (2×50 mL), dried over $Na_2SO_4$, filtered, and concentrated under reduced pressure. The residue was purified by silica gel chromatography using petroleum ether/EtOAc (3/1) as eluting solvents to afford the title compound as a yellow solid. (16.4 g, 96% yield). LCMS (ESI): m/z=168.1 [M+H]+.

Step 4: 1-(2,5-Difluoro-4-methylphenyl)-3,3-dimethoxycyclobutanecarbonitrile

To a solution of 2-(2,5-difluoro-4-methylphenyl)acetonitrile (16.7 g, 100 mmol) in DMSO (200 mL) was added NaH (8 g, 200 mmol, 60% oil dispersion), portion-wise, at RT. The reaction was stirred for 1 h at RT, and then 1,3-dibromo-2,2-dimethoxypropane (39.3 g, 150 mmol) was added. The mixture was heated at 60° C. for 6 h. The reaction was quenched with water (100 mL) at 0° C. and extracted with EtOAc (2×100 mL). The organic extracts were combined and washed with brine (2×50 mL), dried over $Na_2SO_4$, filtered, and concentrated under reduced pressure. The residue was purified by silica gel chromatography using petroleum ether/EtOAc (4/1) as eluting solvents to afford the title compound as a yellow solid (12 g, 45% yield). $^1$H NMR (400 MHz, DMSO-$d_6$) δ 7.36-7.28 (m, 2H), 3.18 (s, 3H), 3.05 (s, 3H), 3.03 (d, J=13.6 Hz, 2H), 2.77 (d, J=13.6 Hz, 2H), 2.24 (d, J=1.6 Hz, 3H). LCMS (ESI): m/z=268.0 [M+H]+.

Step 5:1-(2,5-Difluoro-4-methylphenyl)-3,3-dimethoxycyclobutanecarboxylic Acid

A solution of 1-(2,5-difluoro-4-methylphenyl)-3,3-dimethoxycyclobutanecarbonitrile (6.7 g, 25.1 mmol) and KOH (50% aqueous, 15 g) in n-BuOH (30 ml) were heated at 125° C. for 16 h. The reaction mixture was concentrated under reduced pressure. Water (100 mL) was added and extracted with EtOAc (2×100 mL). The aqueous phase was adjusted to pH~2 with aqueous 2N HCl and extracted with EtOAc (3×100 mL). The organic phase was dried over $Na_2SO_4$, filtered, and concentrated under reduced pressure to obtain the title product as a yellow solid (6.2 g, 86% yield). The crude product was used in next step without further purification.

LCMS (ESI): m/z=309.0 [M+Na]+.

Step 6: Methyl 1-(2,5-difluoro-4-methylphenyl)-3,3-dimethoxycyclobutane-1-carboxylate To a solution of 1-(2,5-difluoro-4-methylphenyl)-3,3-dimethoxycyclobutanecarboxylic acid (6 g, 21 mmol) in methanol (25 mL) was added $SOCl_2$ (3.74 g, 31.5 mmol), and the reaction mixture was stirred at RT for 12 h. The solvent was removed under reduced pressure, and the residue was purified by silica gel chromatography using petroleum ether/EtOAc (8/1) as eluting solvents to afford the title compound as light yellow oil (5.5 g, 87% yield). $^1$H NMR (400 MHz, DMSO-$d_6$) δ 7.22 (dd, J=10 Hz, J=6.4 Hz, 1H), 7.13 (dd, J=11.2 Hz, J=6.4 Hz, 1H), 3.58 (s, 3H), 3.07 (s, 3H), 3.02 (s, 3H), 2.93 (d, J=13.2 Hz, 2H), 2.59 (d, J=12.8 Hz, 2H), 2.21 (d, J=1.6 Hz, 3H). LCMS (ESI): m/z=323.0 [M+Na]+.

Step 7: 1-(4-Bromomethyl-2,5-difluoro-phenyl)-3,3-dimethoxy-cyclobutanecarboxylic Acid Methyl Ester A solution of 1-(2,5-difluoro-4-methyl-phenyl)-3,3-dimethoxy-cyclobutanecarboxylic acid methyl ester (3.0 g, 10.0 mmol) in $CHCl_3$ (100 mL) was treated with NBS (2.13 g, 12.0 mmol) followed by benzoyl peroxide (165 mg, 0.68 mmol) and the solution refluxed for 2 h. The reaction was concentrated in vacuo and purified by silica gel column chromatography (cyclohexane-EtOAc/cyclohexane 1:3) to give the title compound as a yellow oil (3.0 g). LCMS (ESI): m/z=479.2 [M+H]+.

Step 8: 1-[2,5-Difluoro-4-((3S,6R)-3-methyl-1,1-dioxo-6-phenyl-1lambda*6*-[1,2]thiazinan-2-ylmethyl)-phenyl]-3,3-dimethoxy-cyclobutanecarboxylic Acid Methyl Ester A mixture of the product from step 7 (3.0 g, 7.9 mmol), (3S,6R)-3-methyl-6-phenyl-thiazinane 1,1-dioxide (1.2 g, 5.3 mmol), cesium carbonate (2.3 g, 7.5 mmol), and anhydrous DMF (20 mL) was stirred at RT for 16 h. The reaction was diluted with EtOAc (150 mL) and washed with $H_2O$ (150 mL) then brine (100 mL), dried over $MgSO_4$, evaporated and purified using flash chromatography (EtOAc/cyclohexane 1:4-1:2) to give the title compound as a yellow oil (2.9 g).

Step 9: 1-[2,5-Difluoro-4-((3S,6R)-3-methyl-1,1-dioxo-6-phenyl-1lambda*6*-[1,2]thiazinan-2-ylmethyl)-phenyl]-3-oxo-cyclobutanecarboxylic Acid Methylester A solution of the product from step 8 (2.9 g) in acetone (100 mL) was treated with conc. $H_2SO_4$ (5 drops). The solution was refluxed for 45 min and $H_2O$ was added to the hot solution until a precipitate started to form. On evaporation of some of the solvent, a white solid was obtained which was collected by filtration to give the title compound as an off-white solid (1.7 g). $^1$H NMR (300 MHz, $CDCl_3$) δ 7.50-7.36 (6H, m), 6.94 (1H, dd, J=6.2, 10.1 Hz), 4.49 (2H, dd, J=15.3, 41.5 Hz), 4.28-4.25 (1H, m), 4.00 (1H, dd, J=3.4, 12.9 Hz), 3.91-3.81 (2H, m), 3.74-3.73 (3H, m), 3.51 (2H, dd, J=2.6, 17.0 Hz), 2.74-2.58 (1H, m), 2.29-2.16 (1H, m), 1.84-1.73 (2H, m), 1.17 (3H, d, J=7.0 Hz). LCMS (ESI), m/z, 500 [M+Na]+.

Step 10: 1-[2,5-Difluoro-4-((3S,6R)-3-methyl-1,1-dioxo-6-phenyl-1lambda*6*-[1,2]thiazinan-2-ylmethyl)-phenyl]-3-hydroxy-3-methyl-cyclobutanecarboxylic Acid Methyl Ester A solution of the product from step 9 (763 mg, 1.6 mmol) in PhCH$_3$ (20 mL) was stirred at 0° C. and treated with methyl magnesium bromide (1.0 mL, 3M solution in Et$_2$O) and stirring continued for 0.75 h. The reaction was quenched with MeOH (1 mL) and then 0.1 N aqueous HCl (70 mL), diluted with EtOAc (2×70 mL) and the organic phase was dried (MgSO$_4$), filtered, concentrated in vacuo and purified using flash chromatography (1:2 to 1:1 EtOAc-cyclohexanes to give the title compound as a foam (550 mg).

Step 11: trans-1-[2,5-Difluoro-4-((3S,6R)-3-methyl-1,1-dioxo-6-phenyl-1lambda*6*-[1,2]thiazinan-2-ylmethyl)-phenyl]-3-hydroxy-3-methyl-cyclobutanecarboxylic Acid Methyl Ester A solution of the product from step 10 (0.75 g, 1.5 mmol) in THF (10 mL) was treated with a solution of lithium hydroxide (72 mg, 3.0 mmol) in water (10 mL) and stirring continued for 1 h. The reaction was diluted with H$_2$O (50 mL), extracted into EtOAc (50 mL), dried (MgSO$_4$) and evaporated in vacuo to give the title compound as a colourless oil (330 mg). $^1$H NMR (400 MHz, DMSO-d$_6$) δ 7.49-7.35 (6H, m), 7.23-7.15 (2H, m), 5.08 (1H, s), 4.60-4.48 (2H, m), 4.40-4.33 (1H, m), 4.18-4.07 (1H, m), 3.58 (3H, s), 2.90-2.82 (2H, m), 2.47-2.38 (1H, m), 2.14-2.06 (1H, m), 1.85-1.63 (2H, m), 1.40 (3H, s), 1.13 (3H, d, J=7.4 Hz).

Step 12: trans-1-[2,5-Difluoro-4-((3S,6R)-3-methyl-1,1-dioxo-6-phenyl-1lambda*6*-[1,2]thiazinan-2-ylmethyl)-phenyl]-3-hydroxy-3-methyl-cyclobutanecarboxylic Acid To a solution of the product from step 11 (330 mg, 0.69 mmol) in MeOH (18 mL) was added 1N aqueous NaOH (3.5 mL, 3.5 mmol). The reaction was held at RT for 18 h, heated at 35° C. for 7 h then held at RT for 56 h. The reaction was diluted with 1N aqueous HCl (50 mL), extracted into EtOAc (70 mL) and also CH$_2$Cl$_2$ (50 mL). The combined organics were dried (MgSO$_4$) and evaporated to give the title compound.

Step 13: trans-5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3H-1,3,4-oxadiazol-2-one To a solution of the product from step 12 (260 mg, 0.54 mmol) in THF (7 mL) at 0° C. was added Et$_3$N (104 μL, 0.73 mmol). Isobutyl chloroformate (104 μl, 0.66 mmol) was added followed after 0.5 h by hydrazine hydrate (153 μl, 1.6 mmol) and the reaction allowed to warm to RT. The reaction was diluted with EtOAc (70 mL) and washed with sat. aqueous NaHCO$_3$ (40 mL), dried (MgSO$_4$) and evaporated in vacuo. The residue was dissolved in dry DMF (1.5 mL), cooled to 0° C. and Et$_3$N (91 μL, 0.66 mmol) followed by 1,1-carbonyl diimidazole (89 mg, 0.55 mmol) was added. The reaction was diluted with EtOAc (70 mL), washed with H$_2$O (2×50 mL), dried (MgSO$_4$) and evaporated. Purification by flash chromatography (EtOAc/cyclohexane 1:2-1:1) followed by crystallisation from EtOAc/cyclohexane gave the title compound as a white solid (46 mg). $^1$H NMR (400 MHz, DMSO-d$_6$) δ 7.48-7.44 (2H, m), 7.43-7.35 (3H, m), 7.29-7.18 (2H, m), 5.19-5.18 (1H, m), 4.61-4.49 (2H, m), 4.41-4.34 (1H, m), 4.16-4.10 (1H, m), 2.94 (2H, d, J=13.2 Hz), 2.66 (2H, d, J=13.2 Hz), 2.47-2.37 (1H, m), 2.14-2.06 (1H, m), 1.86-1.73 (1H, m), 1.67 (1H, dd, J=2.4, 14.2 Hz), 1.27 (3H, s), 1.13 (3H, d, J=7.3 Hz). LCMS (ESI): m/z=520.1 [M+H]+.

Example 3: cis-5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3H-1,3,4-oxadiazol-2-one

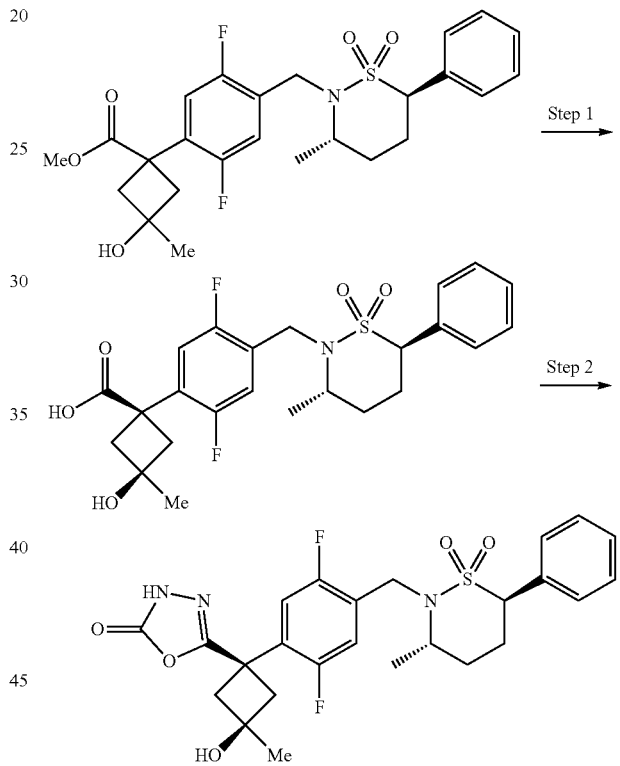

Step 1: cis-1-[2,5-Difluoro-4-((3S,6R)-3-methyl-1,1-dioxo-6-phenyl-1lambda*6*-[1,2]thiazinan-2-ylmethyl)-phenyl]-3-hydroxy-3-methyl-cyclobutanecarboxylic Acid The aqueous phase from example 2, step 11, was acidified, extracted with EtOAc and CH$_2$Cl$_2$ and the combined extracts dried (MgSO$_4$) and evaporated to give the title compound as a solid (390 mg).

Step 2: cis-5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3H-1,3,4-oxadiazol-2-one The product from step 1 was reacted as described in example 2, step 13, to give the title compound. $^1$H NMR (400 MHz, DMSO-$d_6$) δ 12.23-12.11 (1H, m), 7.48-7.35 (6H, m), 7.27-7.20 (1H, m), 5.22-5.20 (1H, m), 4.61-4.50 (2H, m), 4.38 (1H, d, J=17.6 Hz), 4.16-4.02 (1H, m), 2.90-2.82 (2H, m), 2.70 (2H, dd, J=4.2, 12.0 Hz), 2.48-2.38 (1H, m), 2.14-2.06 (1H, m), 1.85-1.63 (2H, m), 1.15-1.08 (6H, m); LCMS (ESI): m/z=520.1 [M+H]$^+$.

Example 4: 5-[1-[2,5-difluoro-4-[[(3S,6R)-3-methyl-1,1-dioxo-6-phenyl-thiazinan-2-yl]methyl]phenyl]-3,3-dimethoxy-cyclobutyl]-3H-1,3,4-oxadiazol-2-one

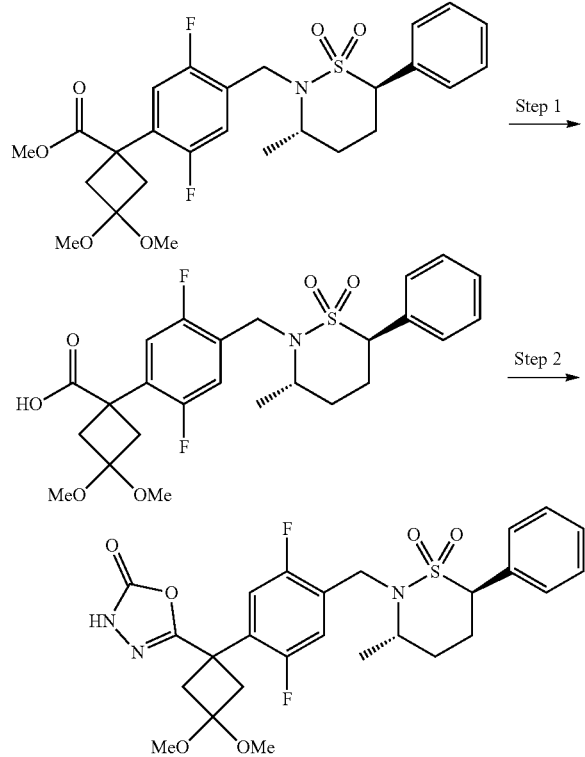

Step 1: 1-[2,5-Difluoro-4-((3S,6R)-3-methyl-1-dioxo-6-phenyl-1lambda*6*-[1,2]thiazinan-2-ylmethyl)-phenyl]-3,3-dimethoxy-cyclobutanecarboxylic Acid To a solution of 1-[2,5-difluoro-4-((3S,6R)-3-methyl-1,1-dioxo-6-phenyl-1lambda*6*-[1,2]thiazinan-2-ylmethyl)-phenyl]-3,3-dimethoxy-cyclobutanecarboxylic acid methyl ester (2.18 g, 4.17 mmol) in THF (20 mL) and H$_2$O (20 mL was added LiOH (0.2 g, 8.34 mmol). After 16 h the reaction was concentrated in vacuo and used directly in the next step. LCMS (ESI): m/z=532 [M+Na]$^+$.

Step 2: 5-[1-[2,5-difluoro-4-[[(3S,6R)-3-methyl-1,1-dioxo-6-phenyl-thiazinan-2-yl]methyl]phenyl]-3,3-dimethoxy-cyclobutyl]-3H-1,3,4-oxadiazol-2-one The product from step 1 was reacted as described in example 2, step 13, to give the title compound. $^1$H NMR (400 MHz, DMSO-$d_6$) δ 7.45-7.29 (6H, m), 7.21 (1H, dd, J=6.2, 11.1 Hz), 4.57-4.46 (2H, m), 4.35 (1H, d, J=17.8 Hz), 4.13-3.93 (1H, m), 3.05-2.99 (9H, m), 2.74 (2H, dd, J=4.5, 12.0 Hz), 2.44-2.35 (1H, m), 2.11-2.03 (1H, m), 1.83-1.70 (1H, m), 1.64 (1H, dd, J=2.3, 14.2 Hz), 1.12-1.08 (3H, m); LCMS (ESI), m/z, 542 [M+H]+.

Example 5: 5-[1-[2,5-difluoro-4-[[(3S,6R)-3-methyl-1,1-dioxo-6-phenyl-thiazinan-2-yl]methyl]phenyl]-3-oxo-cyclobutyl]-3H-1,3,4-oxadiazol-2-one

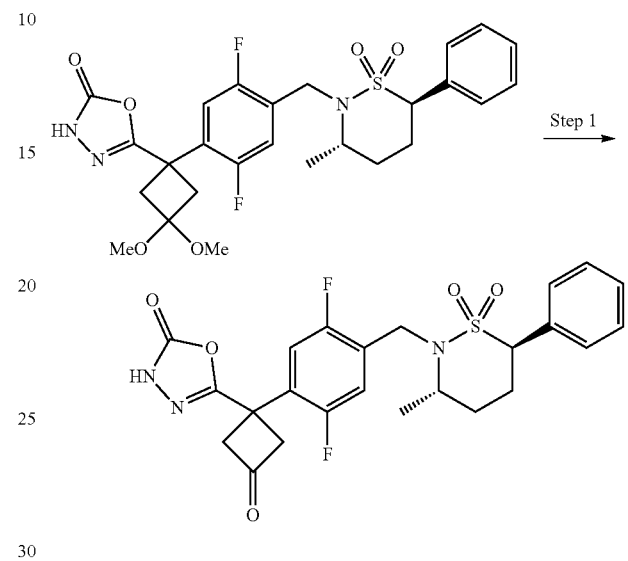

Step 1: 5-[1-[2,5-difluoro-4-[[(3S,6R)-3-methyl-1,1-dioxo-6-phenyl-thiazinan-2-yl]methyl]phenyl]-3-oxo-cyclobutyl]-3H-1,3,4-oxadiazol-2-one To a solution of 5-[1-[2,5-difluoro-4-[[(3S,6R)-3-methyl-1,1-dioxo-6-phenyl-thiazinan-2-yl]methyl]phenyl]-3,3-dimethoxy-cyclobutyl]-3H-1,3,4-oxadiazol-2-one (0.27 g, 0.5 mmol) in acetone (15 mL) was added conc. H$_2$SO$_4$ (2 drops) and the reaction stirred at reflux for 2 h. The reaction was quenched by addition of EtOAc (30 mL). The acetone was removed in vacuo and the reaction was washed with aqueous NaHCO$_3$, dried (Na$_2$SO$_4$) and concentrated under reduced pressure to give the title compound. $^1$H NMR (400 MHz, DMSO-$d_6$) δ 7.49-7.27 (7H, m), 4.62-4.53 (2H, m), 4.41 (1H, d, J=17.9 Hz), 4.18-4.10 (1H, m), 3.95-3.81 (3H, m), 2.48-2.40 (1H, m), 2.14-2.08 (1H, m), 1.91-1.76 (1H, m), 1.68 (1H, dd, J=2.3, 14.2 Hz), 1.40 (1H, s), 1.18-1.07 (3H, m). LCMS (ESI): m/z=504 [M+H]$^+$.

Example 6: trans-5-[1-[2,5-difluoro-4-[[(3S,6R)-3-methyl-1,1-dioxo-6-phenyl-thiazinan-2-yl]methyl]phenyl]-3-hydroxy-cyclobutyl]-3H-1,3,4-oxadiazol-2-one

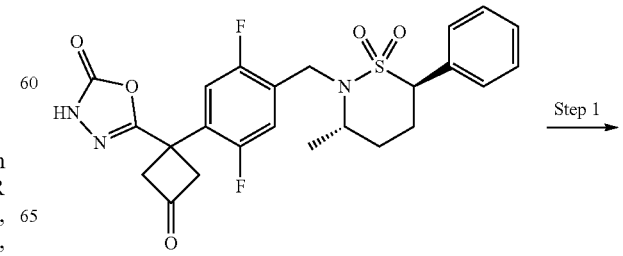

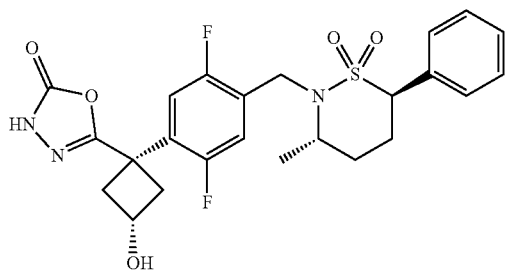

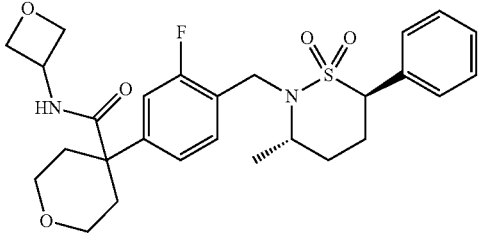

Step 1: trans-5-[1-[2,5-difluoro-4-[[(3S,6R)-3-methyl-1,1-dioxo-6-phenyl-thiazinan-2-yl]methyl]phenyl]-3-hydroxy-cyclobutyl]-3H-1,3,4-oxadiazol-2-one To a solution of 5-[1-[2,5-difluoro-4-[[(3S,6R)-3-methyl-1,1-dioxo-6-phenyl-thiazinan-2-yl]methyl]phenyl]-3-oxo-cyclobutyl]-3H-1,3,4-oxadiazol-2-one (245 mg, 0.5 mmol) in MeOH (2.5 mL) and THF (2.5 mL) was added NaBH$_4$ (38 mg, 1 mmol). After 2 h, the reaction was diluted with EtOAc (10 mL) and H$_2$O (10 mL), and the organic phase washed with brine, dried (MgSO$_4$) and evaporated. Purification by SFC gave the title compound as a white solid (68 mg). $^1$H NMR (400 MHz, DMSO-d$_6$) δ 7.46-7.34 (5H, m), 7.22-7.14 (2H, m), 5.30 (1H, d, J=6.9 Hz), 4.57-4.47 (2H, m), 4.38-4.23 (2H, m), 4.14-4.04 (1H, m), 3.12-3.03 (2H, m), 2.45-2.32 (3H, m), 2.11-2.05 (1H, m), 1.84-1.71 (1H, m), 1.64 (1H, dd, J=2.3, 14.2 Hz), 1.12-1.08 (3H, m); LCMS (ESI), m/z, 506 [M+H]$^+$.

Example 7: 4-[3-Fluoro-4-[[(3S,6R)-3-methyl-1,1-dioxo-6-phenyl-thiazinan-2-yl]methyl]phenyl]-N-(oxetan-3-yl)tetrahydropyran-4-carboxamide

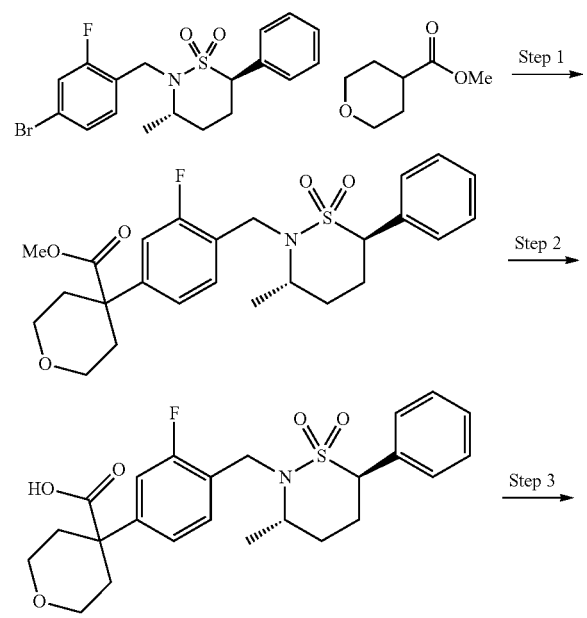

Step 1: Methyl 4-(3-fluoro-4-(((3S,6R)-3-methyl-1,1-dioxido-6-phenyl-1,2-thiazinan-2-yl)methyl)phenyl)tetrahydro-2H-pyran-4-carboxylate A flask was charged with (3S,6R)-2-[(4-bromo-2-fluoro-phenyl)methyl]-3-methyl-6-phenyl-thiazinane 1,1-dioxide (10 g, 24 mmol), bis(dibenzylideneacetone)palladium (1.39 g, 2.4 mmol) and 2-dicyclohexylphosphino-2',6'-di-i-propoxy-1,1'-biphenyl (1.15 g, 2.4 mmol) and purged with nitrogen for 2 min. THF (120 mL), methyl tetrahydropyran-4-carboxylate (8.1 mL, 61 mmol) and zinc chloro 2,2,6,6-tetramethylpiperidide lithium chloride complex (93 mL, 0.65 M in THF) were subsequently added and the reaction was stirred at 60° C. for 2 h. The reaction was cooled to RT, quenched with saturated aqueous NH$_4$Cl (100 mL), and extracted with EtOAc (3×100 mL). The combined organic extracts were dried with MgSO$_4$, filtered, concentrated and purified by silica gel column chromatography (0% to 100% EtOAc in heptane) to give the title compound (6.5 g, 56% yield). $^1$H NMR (400 MHz, DMSO-d$_6$) δ 7.55-7.48 (m, 1H), 7.48-7.43 (m, 2H), 7.43-7.33 (m, 3H), 7.26-7.20 (m, 1H), 7.18-7.12 (m, 1H), 4.58-4.47 (m, 2H), 4.41-4.32 (m, 1H), 4.20-4.06 (m, 1H), 3.85-3.75 (m, 2H), 3.66-3.60 (s, 3H), 3.47-3.36 (m, 2H), 2.47-2.31 (m, 3H), 2.15-2.05 (m, 1H), 1.96-1.74 (m, 3H), 1.71-1.61 (m, 1H), 1.15-1.07 (d, J=6.9 Hz, 3H).

Step 2: 4-(3-Fluoro-4-(((3S,6R)-3-methyl-1,1-dioxido-6-phenyl-1,2-thiazinan-2-yl)methyl)phenyl)tetrahydro-2H-pyran-4-carboxylic Acid To a solution of methyl 4-[3-fluoro-4-[[(3S,6R)-3-methyl-1,1-dioxo-6-phenyl-thiazinan-2-yl]methyl]phenyl]tetrahydropyran-4-carboxylate (5.67 g, 12 mmol) in THF (60 mL) and water (20 mL) was added lithium hydroxide hydrate (5.0 g, 119 mmol) and the reaction was stirred at RT for 72 h. The reaction was diluted with water (50 mL) and the pH was adjusted to 1 using 1N aqueous HCl. The product was extracted with EtOAc (3×75 mL), dried with MgSO$_4$, filtered, concentrated, and purified by silica gel chromatography (0% to 100% EtOAc in heptane) to give the title compound (4.0 g, 73% yield). $^1$H NMR (400 MHz, DMSO-d$_6$) δ 7.54-7.43 (m, 3H), 7.43-7.33 (m, 3H), 7.28-7.23 (m, 1H), 7.18-7.12 (m, 1H), 4.58-4.46 (m, 2H), 4.42-4.32 (m, 1H), 4.19-4.05 (m, 1H), 3.84-3.74 (m, 2H), 3.51-3.38 (m, 2H), 2.47-2.41 (m, 1H), 2.38-2.30 (m, 2H), 2.16-2.06 (m, 1H), 1.88-1.74 (m, 3H), 1.72-1.61 (m, 1H), 1.15-1.05 (d, J=6.8 Hz, 3H).

Step 3: 4-(3-Fluoro-4-(((3S,6R)-3-methyl-1,1-dioxido-6-phenyl-1,2-thiazinan-2-yl)methyl)phenyl)-N-(oxetan-3-yl)tetrahydro-2H-pyran-4-carboxamide A vial was charged with 4-[3-fluoro-4-[[(3S,6R)-3-methyl-1,1-dioxo-6-phenyl-thiazinan-2-yl]methyl]phenyl]

tetrahydropyran-4-carboxylic acid (50 mg, 0.11 mmol), oxetan-3-amine (24 mg, 0.33 mmol), N,N-dimethylformamide (14 mL) and triethylamine (0.045 mL, 0.33 mmol). To the reaction mixture was then added HATU (63 mg, 0.16 mmol) and the reaction was stirred at RT for 16 h. The reaction was partitioned between water and dichloromethane, and the organic layer was separated using a phase-separation cartridge, concentrated, and purified by preparative HPLC to give the title compound (17.9 mg, 32% yield). $^1$H NMR (400 MHz, DMSO-$d_6$) δ 8.28 (d, J=5.9 Hz, 1H), 7.53-7.43 (m, 3H), 7.43-7.33 (m, 3H), 7.20 (dd, J=8.3, 1.8 Hz, 1H), 7.11 (dd, J=12.2, 1.9 Hz, 1H), 4.81-4.68 (m, 1H), 4.64 (t, J=6.8 Hz, 2H), 4.58-4.45 (m, 2H), 4.43-4.31 (m, 3H), 4.20-4.05 (m, 1H), 3.84-3.68 (m, 2H), 3.51-3.36 (m, 2H), 2.47-2.35 (m, 3H), 2.16-2.07 (m, 1H), 1.92-1.73 (m, 3H), 1.72-1.60 (m, 1H), 1.10 (d, J=6.8 Hz, 3H).

Example 8: trans-[3-[2,5-Difluoro-4-((3S,6R)-3-methyl-1,1-dioxo-6-phenyl-1λ$^6$-[1,2]thiazinan-2-ylmethyl)-phenyl]-3-(5-oxo-4,5-dihydro-[1,3,4]oxadiazol-2-yl)-cyclobutyl]-acetonitrile and cis-[3-[2,5-difluoro-4-((3S,6R)-3-methyl-1,1-dioxo-6-phenyl-1λ$^6$-[1,2]thiazinan-2-ylmethyl)-phenyl]-3-(5-oxo-4,5-dihydro-[1,3,4]oxadiazol-2-yl)-cyclobutyl]-acetonitrile

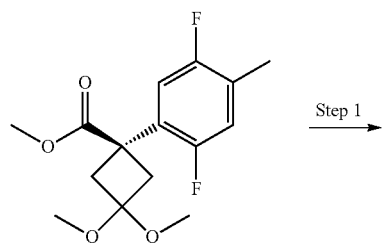

Step 1

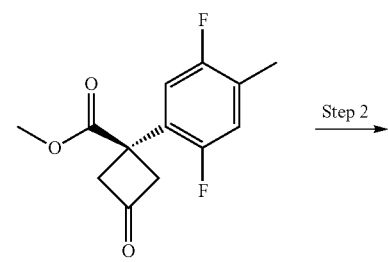

Step 2

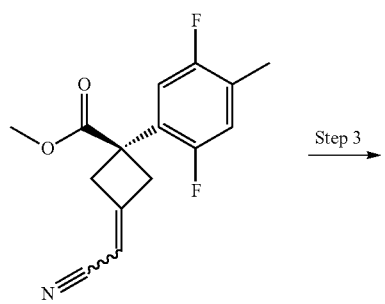

Step 3

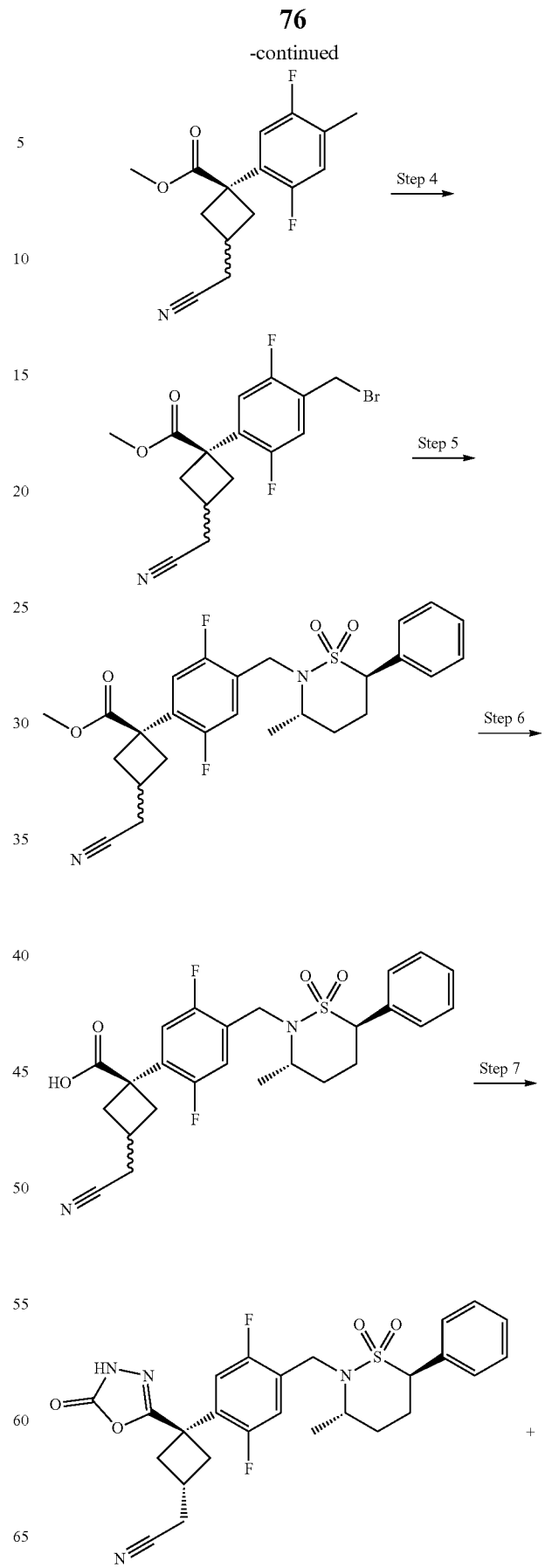

-continued

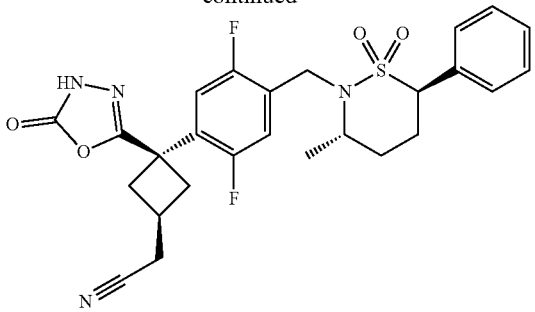

Step 1: 1-(2,5-Difluoro-4-methyl-phenyl)-3-oxo-cyclobutanecarboxylic Acid Methyl Ester 1-(2,5-difluoro-4-methylphenyl)-3,3-dimethoxycyclobutanecarboxylic acid methyl ester (4.50 g, 15.0 mmol) was reacted as described in example 2, step 9, to give the title compound as a solid (3.80 g). $^1$H NMR (300 MHz, CDCl$_3$) δ 6.96-6.89 (2H, m), 3.89-3.82 (2H, m), 3.74 (3H, s), 3.55-3.47 (2H, m), 2.28 (3H, d, J=1.8 Hz). LCMS (ESI): m/z=276.9 [M+Na]$^+$.

Step 2: 3-Cyanomethylene-1-(2,5-difluoro-4-methyl-phenyl)-cyclobutanecarboxylic Acid Methyl Ester To a solution of diethyl cyanophosphonate (585 mg, 3.31 mmol) in dry THF (15 mL) at 0° C. was added potassium tert-butoxide (3.31 mL, 3.31 mmol, 1 M in THF). The reaction was stirred at 0° C. for 5 min before a solution of the product from step 1 (700 mg, 2.76 mmol) in dry THF (15 mL) was added. The reaction was warmed to RT for 2 h, quenched with NH$_4$Cl (sat., aq., 30 mL) and extracted with EtOAc (2×40 mL). The combined organics were dried over Na$_2$SO$_4$ and concentrated in vacuo. Purification by flash chromatography (0-60% EtOAc/cyclohexane) gave the title compound as an oil (730 mg). $^1$H NMR (300 MHz, CDCl$_3$) δ 6.94-6.84 (2H, m), 5.28 (1H, dd, J=2.3, 2.3 Hz), 3.81-3.64 (5H, m), 3.49-3.12 (2H, m), 2.26 (3H, d, J=1.8 Hz).

Step 3: (cis/trans)-3-Cyanomethyl-1-(2,5-difluoro-4-methyl-phenyl)-cyclobutanecarboxylic Acid Methyl Ester A flask containing a solution of the product from step 2 (720 mg, 2.60 mmol) in EtOAc (10 mL) and MeOH (2.0 mL) was degassed with argon before palladium on carbon (551 mg, 0.331 mmol, 5% wt) was added. The mixture was degassed with H$_2$ and stirred under a hydrogen atmosphere for 2 h at RT. The reaction was filtered through celite and concentrated in vacuo. Purification by flash chromatography (0-60% EtOAc/cyclohexane) gave the title compound as an oil (658 mg) as a 2:1 mixture of diastereomers. $^1$H NMR (300 MHz, CDCl$_3$) δ 7.02-6.77 (2H, m), 3.70-3.66 (3H, m), 3.08-2.92 (1H, m), 2.76-2.57 (4.67H, m), 2.44 (0.67H, d, J=6.0 Hz), 2.35-2.22 (3.66H, m).

Step 4: (cis/trans)-1-(4-Bromomethyl-2,5-difluoro-phenyl)-3-cyanomethyl-cyclobutanecarboxylic Acid Methyl Ester The product from step 3 (658 mg, 2.36 mmol) was reacted as described in example 2, step 7, to give the title compound as a 2:1 mixture of diastereomers (870 mg). $^1$H NMR (300 MHz, CDCl$_3$) δ 7.14-6.83 (2H, m), 4.47-4.43 (2H, m), 3.73-3.67 (3H, m), 3.10-2.98 (1H, m), 2.77-2.58 (4.33H, m), 2.46 (0.67H, d, J=5.8 Hz), 2.36-2.24 (1H, m).

Step 5: (cis/trans)-3-Cyanomethyl-1-[2,5-difluoro-4-((3S,6R)-3-methyl-1,1-dioxo-6-phenyl-1λ$^6$-[1,2]thiazinan-2-ylmethyl)-phenyl]-cyclobutanecarboxylic Acid Methyl Ester The product from step 4 (870 mg) was reacted as described in example 2, step 8, to give the title compound as an oil (797 mg) as a 2:1 mixture of diastereomers. $^1$H NMR (300 MHz, CDCl$_3$) δ 7.50-7.35 (6H, m), 7.00 (0.67H, dd, J=6.2, 10.4 Hz), 6.83 (0.33H, dd, J=6.2, 10.1 Hz), 4.58-4.35 (2H, m), 4.32-4.22 (1H, m), 4.04-3.96 (1H, m), 3.68 (1H, s), 3.6 (2H, s), 3.07-2.92 (1H, m), 2.74-2.57 (5.66H, m), 2.45 (0.67H, d, J=6.0 Hz), 2.34-2.18 (1.67H, m), 1.82-1.73 (2H, m), 1.18 (3H, d, J=6.6 Hz).

Step 6: (cis/trans)-3-Cyanomethyl-1-[2,5-difluoro-4-((3S,6R)-3-methyl-1,1-dioxo-6-phenyl-1λ$^6$-[1,2]thiazinan-2-ylmethyl)-phenyl]-cyclobutanecarboxylic Acid The product from step 5 (797 mg, 1.59 mmol) was reacted as described in example 2, step 12, at 50° C. to give the title compound as an oil (736 mg) as a 2:1 mixture of diastereomers. LCMS (ESI): m/z=489.2 [M+H]$^+$.

Step 7: trans-[3-[2,5-Difluoro-4-((3S,6R)-3-methyl-1,1-dioxo-6-phenyl-1λ$^6$-[1,2]thiazinan-2-ylmethyl)-phenyl]-3-(5-oxo-4,5-dihydro-[1,3,4]oxadiazol-2-yl)-cyclobutyl]-acetonitrile and cis-[3-[2,5-difluoro-4-((3S,6R)-3-methyl-1,1-dioxo-6-phenyl-1λ$^6$-[1,2]thiazinan-2-ylmethyl)-phenyl]-3-(5-oxo-4,5-dihydro-[1,3,4]oxadiazol-2-yl)-cyclobutyl]-acetonitrile The product from step 6 (736 mg, 1.51 mmol) was reacted as described in example 2, step 13, to give the title compound as a 2:1 mixture of diastereomers. The diastereomers were separated by chiral SFC purification. trans-[3-[2,5-Difluoro-4-((3S,6R)-3-methyl-1,1-dioxo-6-phenyl-1λ$^6$-[1,2]thiazinan-2-ylmethyl)-phenyl]-3-(5-oxo-4,5-dihydro-[1,3,4]oxadiazol-2-yl)-cyclobutyl]-acetonitrile $^1$H NMR (400 MHz, DMSO-d$_6$) δ 12.26 (1H, s), 7.48-7.36 (5H, m), 7.25-7.18 (2H, m), 4.61-4.49 (2H, m), 4.37 (1H, d, J=17.9 Hz), 4.17-4.09 (1H, m), 2.94 (2H, dd, J=8.5, 10.4 Hz), 2.85-2.74 (1H, m), 2.69 (2H, d, J=6.7 Hz), 2.47-2.36 (3H, m), 2.14-2.07 (1H, m), 1.86-1.63 (2H, m), 1.13 (3H, d, J=6.9 Hz). LCMS (ESI): m/z=529.2 [M+H]$^+$. cis-[3-[2,5-Difluoro-4-((3S,6R)-3-methyl-1,1-dioxo-6-phenyl-1λ$^6$-[1,2]thiazinan-2-ylmethyl)-phenyl]-3-(5-oxo-4,5-dihydro-[1,3,4]oxadiazol-2-yl)-cyclobutyl]-acetonitrile $^1$H NMR (400 MHz, DMSO-d$_6$) δ 12.23-12.23 (1H, s), 7.51-7.36 (6H, m), 7.25 (1H, dd, J=6.2, 11.3 Hz), 4.61-4.51 (2H, m), 4.40 (1H, d, J=17.8 Hz), 4.16-4.08 (1H, m), 2.85-2.81 (2H, m), 2.73 (2H, d, J=6.2 Hz), 2.68-2.54 (3H, m), 2.48-2.38 (1H, m), 2.14-2.07 (1H, m), 1.87-1.75 (1H, m), 1.71-1.64 (1H, m), 1.14 (3H, d, J=6.9 Hz). LCMS (ESI): m/z=529.2 [M+H]$^+$.

Example 9: trans-5-{1-[2,5-Difluoro-4-((3S,6R)-3-methyl-1,1-dioxo-6-phenyl-1λ⁶-[1,2]thiazinan-2-ylmethyl)-phenyl]-3-hydroxy-3-methyl-cyclobutyl}-2-methyl-2,4-dihydro-[1,2,4]triazol-3-one and cis-5-{1-[2,5-Difluoro-4-((3S,6R)-3-methyl-1,1-dioxo-6-phenyl-1λ⁶-[1,2]thiazinan-2-ylmethyl)-phenyl]-3-hydroxy-3-methyl-cyclobutyl}-2-methyl-2,4-dihydro-[1,2,4]triazol-3-one

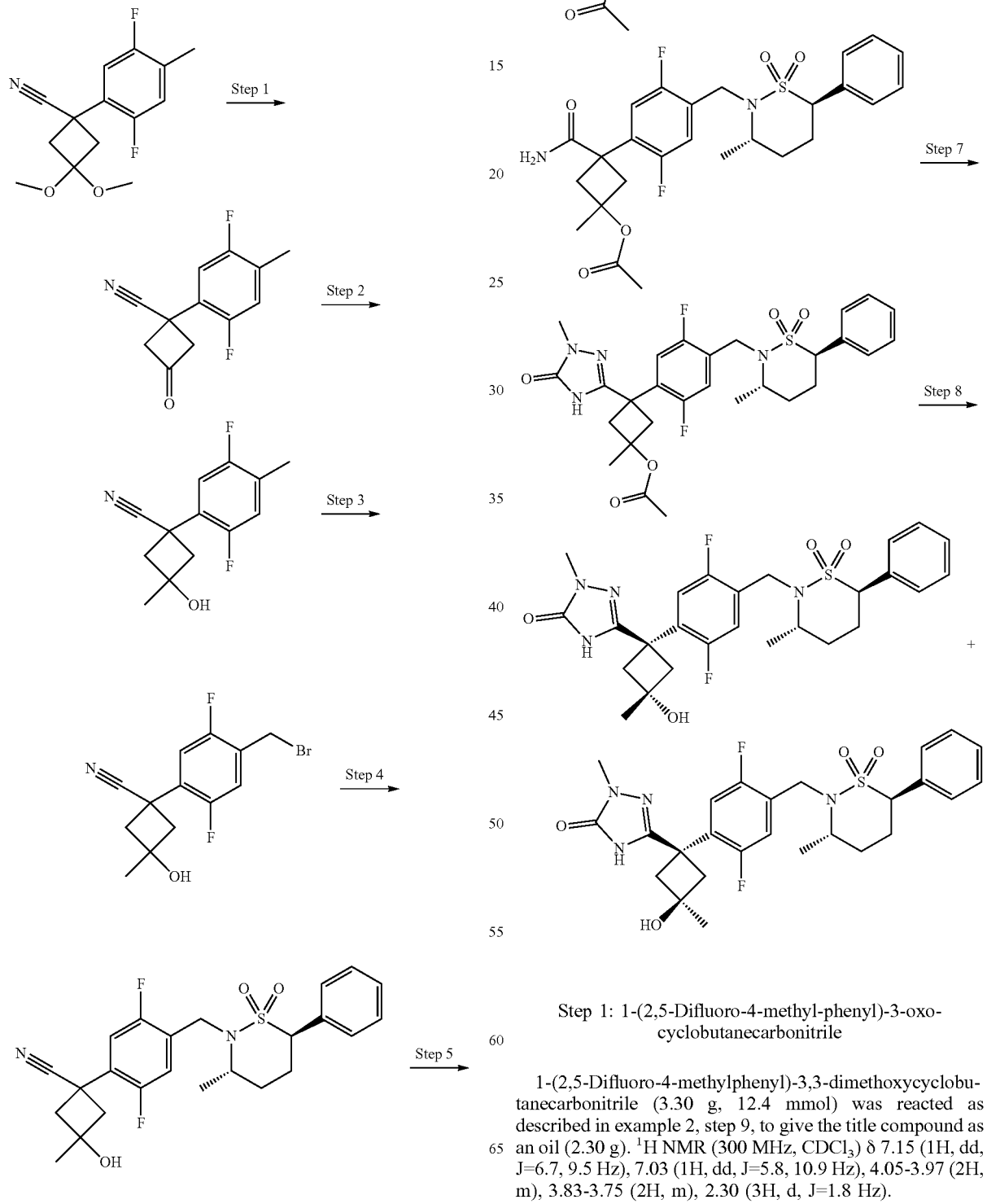

Step 1: 1-(2,5-Difluoro-4-methyl-phenyl)-3-oxo-cyclobutanecarbonitrile 1-(2,5-Difluoro-4-methylphenyl)-3,3-dimethoxycyclobutanecarbonitrile (3.30 g, 12.4 mmol) was reacted as described in example 2, step 9, to give the title compound as an oil (2.30 g). ¹H NMR (300 MHz, CDCl₃) δ 7.15 (1H, dd, J=6.7, 9.5 Hz), 7.03 (1H, dd, J=5.8, 10.9 Hz), 4.05-3.97 (2H, m), 3.83-3.75 (2H, m), 2.30 (3H, d, J=1.8 Hz).

Step 2: (cis/trans)-1-(25-Difluoro-4-methyl-phenyl)-3-hydroxy-3-methyl-cyclobutanecarbonitrile To a solution of the product from step 1 (2.30 g, 10.4 mmol) in toluene (80 mL) and THF (20 mL) at −78° C. was added methylmagnesium bromide (4.51 mL, 13.5 mmol, 3.0 M in THF). The reaction was stirred at −78° C. for 45 min, quenched with NaHCO$_3$ (sat., aq., 100 mL), warmed to RT and extracted with EtOAc (150 mL). The organics were dried over Na$_2$SO$_4$ and concentrated in vacuo. Purification by flash chromatography (0-50% EtOAc/cyclohexane) gave the title compound as an oil (1.53 g). LCMS (ESI): m/z=238.1 [M+H]$^+$.

Step 3: (cis/trans)-1-(4-Bromomethyl-2,5-difluoro-phenyl)-3-hydroxy-3-methyl-cyclobutanecarbonitrile The product from step 2 (1.53 g, 6.45 mmol) was reacted as described in example 2, step 7, to give the title compound as a 1:1 mixture of diastereomers (1.95 g). $^1$H NMR (300 MHz, CDCl$_3$) δ 7.25-7.14 (1H, m), 7.05-6.96 (1H, m), 4.46-4.44 (2H, m), 3.07-2.98 (2H, m), 2.80-2.74 (2H, m), 2.27 (1H, t, J=2.3 Hz), 1.75 (1.5H, s), 1.35 (1.5H, s).

Step 4: (cis/trans)-1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutanecarbonitrile The product from step 3 (1.95 g) was reacted as described in example 2, step 8, to give the title compound as a 1:1 mixture of diastereomers (1.50 g). $^1$H NMR (300 MHz, CDCl$_3$) δ 7.49-7.36 (6H, m), 6.99-6.89 (1H, m), 4.53 (1H, d, J=17.3 Hz), 4.40 (1H, d, J=17.1 Hz), 4.32-4.23 (1H, m), 4.04-3.97 (1H, m), 3.06-2.95 (2H, m), 2.82-2.63 (3H, m), 2.29-2.19 (1H, m), 1.97 (0.5H, s), 1.88 (0.5H, s), 1.82-1.78 (2H, m), 1.74 (1.5H, s), 1.33 (1.5H, s), 1.19-1.14 (3H, m).

Step 5: (cis/trans)-Acetic acid 3-cyano-3-[2,5-difluoro-4-((3S,6R)-3-methyl-1,1-dioxo-6-phenyl-1λ$^6$-[1,2]thiazinan-2-ylmethyl)-phenyl]-1-methyl-cyclobutyl Ester To a solution of the product from step 4 (200 mg, 0.435 mmol) in DCM (5 mL) was added acetic anhydride (0.164 mL, 1.74 mmol), Et$_3$N (0.303 mL, 2.18 mmol) and DMAP (8.0 mg, 0.065 mmol). The reaction was stirred at RT for 1 h before the solvent was removed in vacuo. Purification by flash chromatography (0-50% EtOAc/cyclohexane) gave the title compound as an oil (180 mg). LCMS (ESI): m/z=503.0 [M+H]$^+$.

Step 6: (cis/trans)-Acetic acid 3-carbamoyl-3-[2,5-difluoro-4-((3S,6R)-3-methyl-1,1-dioxo-6-phenyl-1λ$^6$-[1,2]thiazinan-2-ylmethyl)-phenyl]-1-methyl-cyclobutyl Ester To a solution of the product from step 5 (180 mg, 0.359 mmol) in IMS (2 mL) and H$_2$O (0.5 mL) was added hydrido(dimethylphosphinous acid-kP) [hydrogen bis(dimethylphosphinito-kP)]platinum(II) (1.5 mg, 3.6 μmol). The reaction was heated to 85° C. for 2 h then cooled to RT for 16 h. The reaction was concentrated in vacuo and the crude material taken up in EtOAc (40 mL). The organics were washed with brine, dried over Na$_2$SO$_4$ and concentrated in vacuo to give the title compound as an oil (186 mg). LCMS (ESI): m/z=521.0 [M+H]$^+$.

Step 7: (cis/trans)-Acetic acid 3-[2,5-difluoro-4-((3S,6R)-3-methyl-1,1-dioxo-6-phenyl-1λ$^6$-[1,2]thiazinan-2-ylmethyl)-phenyl]-1-methyl-3-(1-methyl-5-oxo-4,5-dihydro-1H-[1,2,4]triazol-3-yl)-cyclobutyl Ester To an degassed solution of the product from step 6 (186 mg, 0.358 mmol) in dry 1,2-dichloroethane (4.0 mL) was added oxalyl chloride (41 μL, 0.49 mmol). The reaction was heated for 0.5 h at RT before being heated to 75° C. for 15 min. The mixture was cooled to RT and the solvent removed in vacuo. The crude was immediately taken up in dry DCM (4 mL) and 1-Boc-2-methylhydrazine (65 mg, 0.44 mmol) was added. The reaction was stirred for 15 min at RT before the solvent was removed in vacuo. The crude was taken up in DCM (4 mL) and TFA (2 mL) and the reaction stirred for 1 h at RT. The solvent was removed in vacuo and the crude was taken up in EtOAc (30 mL). The organics were washed with NaHCO$_3$ (sat., aq., 30 mL), dried over Na$_2$SO$_4$ and concentrated in vacuo. Purification by flash chromatography (0-100% EtOAc/cyclohexane then 0-10% MeOH:DCM) gave the title compound as an oil (138 mg). LCMS (ESI): m/z=575.0 [M+H]$^+$.

Step 8: trans-5-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobut}-2-methyl-2,4-dihydro-[1,2,4]triazol-3-one and cis-5-{1-[2,5-difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-2-methyl-2,4-dihydro-[1,2,4]triazol-3-one To a solution of the product from step 7 (138 mg, 0.240 mmol) in MeOH (1.5 mL) was added K$_2$CO$_3$ (63 mg, 0.45 mmol). The reaction was stirred for 3 h before a solution of NaOH (18 mg, 0.45 mmol) in H$_2$O (1.5 mL) was added. The reaction was heated to 35° C. for 1.5 h before being cooled to RT and neutralised with HCl (1 M, aq., 10 mL). The mixture was extracted with EtOAc (2×30 mL) and the combined organics dried over Na$_2$SO$_4$ and concentrated in vacuo. The diastereomers were separated by MDAP purification. trans-5-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-2-methyl-2,4-dihydro-[1,2,4]triazol-3-one $^1$H NMR (400 MHz, DMSO-d$_6$) δ 11.53 (1H, s), 7.48-7.36 (5H, m), 7.21-7.12 (2H, m), 5.07 (1H, s), 4.59-4.46 (2H, m), 4.35 (1H, d, J=17.8 Hz), 4.15-4.08 (1H, m), 3.21 (3H, s), 2.92 (2H, d, J=12.5 Hz), 2.61-2.54 (2H, m), 2.47-2.31 (1H, m), 2.13-2.06 (1H, m), 1.85-1.62 (2H, m), 1.16 (3H, s), 1.12 (3H, d, J=6.8 Hz). LCMS (ESI): m/z=533.3 [M+H]$^+$. cis-5-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-2-methyl-2,4-dihydro-[1,2,4]triazol-3-one $^1$H NMR (400 MHz, DMSO-d$_6$) δ 7.49-7.35 (5H, m), 7.28 (1H, dd, J=6.7, 10.6 Hz), 7.17 (1H, dd, J=6.2, 11.2 Hz), 4.59-4.48 (2H, m), 4.37 (1H, d, J=17.7 Hz), 4.16-4.07 (1H, m), 3.16 (3H, s), 2.79 (2H, d, J=11.2 Hz), 2.66 (2H, d, J=11.7 Hz), 2.47-2.39 (1H, m), 2.14-2.06 (1H, m), 1.86-1.73 (1H, m), 1.67 (1H, dd, J=2.1, 14.2 Hz), 1.13 (3H, d, J=7.2 Hz), 1.08 (3H, s), NH and OH not observed. LCMS (ESI): m/z=533.3 [M+H]$^+$.

83
Example 10: trans-5-{1-[2,5-Difluoro-4-((3S,6R)-3-methyl-1,1-dioxo-6-phenyl-1λ⁶-[1,2]thiazinan-2-ylmethyl)-phenyl]-3-hydroxy-3-methoxymethyl-cyclobutyl}-3H-[1,3,4]oxadiazol-2-one

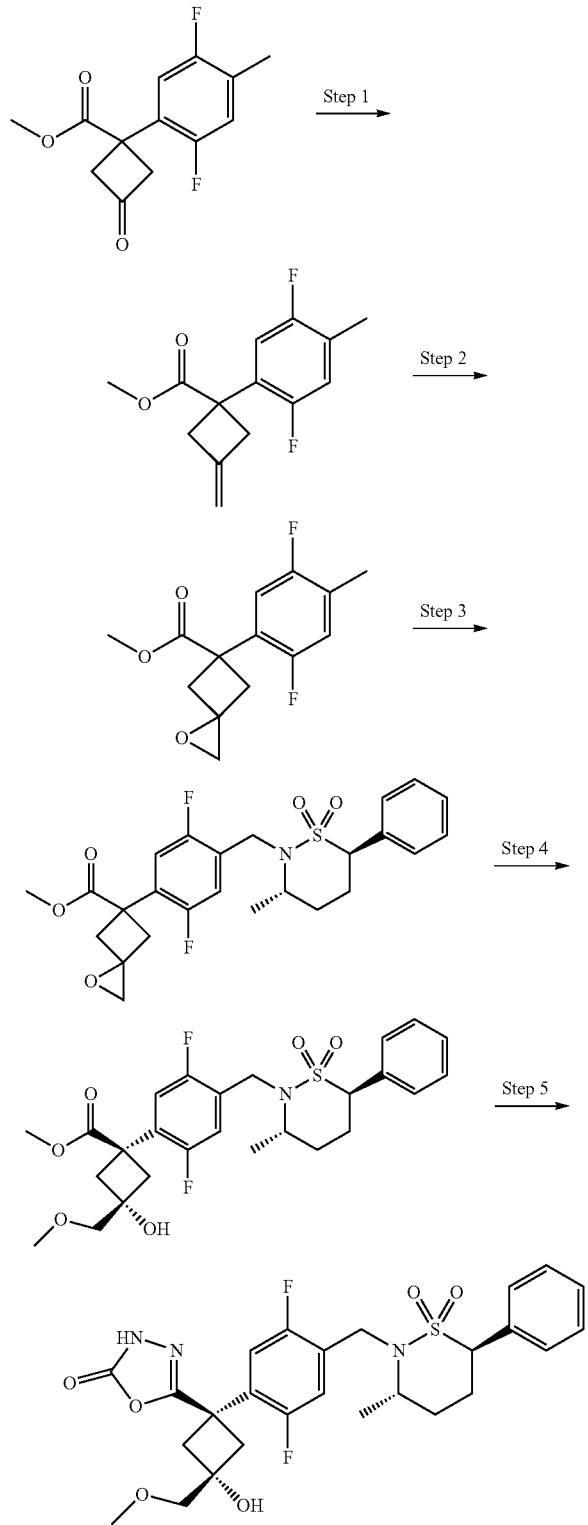

84

Step 1: 1-(2,5-Difluoro-4-methyl-phenyl)-3-methylene-cyclobutanecarboxylic Acid Methyl Ester To a solution of methyltriphenylphosphonium bromide (4.08 g, 11.4 mmol) in THF (40 mL) was added potassium tert-butoxide (12.0 mL, 12.0 mmol, 1 M in THF). The reaction was heated to 40° C. for 45 min. After cooling to 0° C., a solution of 1-(2,5-difluoro-4-methyl-phenyl)-3-oxo-cyclobutanecarboxylic acid methyl ester (2.40 g, 9.52 mmol) in THF (40 mL) was added. The reaction was warmed to RT and stirred for 1 h before brine (90 mL) was added. The mixture was extracted with EtOAc (120 mL) and the organics dried over Na₂SO₄ and concentrated in vacuo. Purification by flash chromatography (0-25% EtOAc/cyclohexane) gave the title compound as an oil (2.00 g). LCMS (ESI): m/z=253.2 [M+H]⁺.

Step 2: (cis/trans)-5-(25-Difluoro-4-methyl-phenyl)-1-oxa-spiro[2.3]hexane-5-carboxylic Acid Methyl Ester To a solution of the product from step 1 (1.20 g, 4.76 mmol) in DCM (60 mL) was added 3-chloroperbenzoic acid (1.17 g, 5.24 mmol). The reaction was stirred at RT for 6 h before being diluted with DCM (80 mL) and washed with Na₂S₂O₅ (sat., aq., 50 mL), NaHCO₃ (sat., aq., 50 mL), dried over Na₂SO₄ and concentrated in vacuo. Purification by flash chromatography (0-25% EtOAc/cyclohexane) gave the title compound as an oil (1.10 g, 65%) as a 2:1 mixture of diastereomers. LCMS (ESI): m/z=291.0 [M+Na]⁺.

Step 3: 5-(4-Bromomethyl-2,5-difluoro-phenyl)-1-oxa-spiro[2.3]hexane-5-carboxylic Acid Methyl Ester To a solution of the product from step 2 (1.60 g, 5.97 mmol) in CHCl₃ (80 mL) was added NBS (1.17 g, 6.57 mmol) and benzoyl peroxide (159 mg, 0.657 mmol). The reaction was heated at 70° C. for 4 h before being cooled to RT for 16 h. The reaction was further heated to 70° C. for 1 h before being cooled to RT and the solvent removed in vacuo. Purification by flash chromatography (0-25% EtOAc/cyclohexane) gave 1.90 g of a crude residue. The residue was taken up in DMA (15 mL) before (3S,6R)-3-methyl-6-phenyl-thiazinane-1,1-dioxide (820 mg, 3.65 mmol) and cesium carbonate (1.95 g, 5.97 mmol) were added. The reaction was stirred at RT for 16 h before EtOAc (400 mL) was added. The organics were washed with H₂O (2×400 mL), dried over Na₂SO₄ and concentrated in vacuo. Purification by flash chromatography (25-70% EtOAc/cyclohexane) gave the title compound as a foam (1.20 g) as a 2:1 mixture of diastereomers. LCMS (ESI): m/z=492.0 [M+H]⁺.

Step 4: trans-1-[2,5-Difluoro-4-((3S,6R)-3-methyl-1,1-dioxo-6-phenyl-1λ⁶-[1,2]thiazinan-2-ylmethyl)-phenyl]-3-hydroxy-3-methoxymethyl-cyclobutanecarboxylic Acid Methyl Ester To a solution of the product from step 3 (300 mg, 0.611 mmol) in MeOH (20 mL) was added sodium hydride (98 mg, 2.4 mmol, 60% dispersion). The reaction was stirred at RT for 15 min before being heated to 50° C. for 3 h. The reaction was cooled to RT and the solvent removed in vacuo. Purification by flash chromatography (50-100% EtOAc/cyclohexane then 10% MeOH:EtOAc) gave the title compound as an oil (140 mg) as a single diastereomer. LCMS (ESI): m/z=524.2 [M+H]⁺.

Step 5: trans-5-{1-[2,5-Difluoro-4-((3S,6R)-3-methyl-1,1-dioxo-6-phenyl-1λ⁶-[1,2]thiazinan-2-ylmethyl)-phenyl]-3-hydroxy-3-methoxymethyl-cyclobutyl}-3H-[1,3,4]oxadiazol-2-one To a solution of product from step 4 (140 mg, 0.268 mmol) in DMA (0.5 mL) was added hydrazine hydrate (0.5 mL). The mixture was heated at 50° C. for 16 h before being cooled to RT and diluted with EtOAc (40 mL). The organics were washed with H₂O (2×40 mL), dried over Na₂SO₄ and concentrated in vacuo. The crude material was taken up in DMF (1.5 mL) before Et₃N (50 µL, 0.45 mmol) and CDI (56 mg, 0.32 mmol) were added. The reaction was stirred at RT for 0.5 h before EtOAc (40 mL) was added. The organics were washed with H₂O (40 mL), dried over Na₂SO₄ and concentrated in vacuo. Purification by flash chromatography (50-80% EtOAc/cyclohexane) followed by trituration with Et₂O/cyclohexane gave the title compound as a solid (38 mg). ¹H NMR (400 MHz, DMSO-d₆) δ 12.21 (1H, s), 7.48-7.36 (5H, m), 7.31 (1H, dd, J=6.5, 10.3 Hz), 7.23 (1H, dd, J=6.2, 11.0 Hz), 5.29 (1H, s), 4.61-4.49 (2H, m), 4.38 (1H, d, J=17.9 Hz), 4.18-4.08 (1H, m), 3.30 (2H, s), 3.28 (3H, s), 3.04 (2H, d, J=13.7 Hz), 2.57 (2H, d, J=14.0 Hz), 2.47-2.39 (1H, m), 2.13-2.06 (1H, m), 1.85-1.74 (1H, m), 1.67 (1H, dd, J=2.2, 14.3 Hz), 1.14 (3H, d, J=6.5 Hz). LCMS (ESI): m/z=550.3 [M+H]⁺.

Example 11: trans-3-[2,5-Difluoro-4-((3S,6R)-3-methyl-1,1-dioxo-6-phenyl-1λ⁶-[1,2]thiazinan-2-ylmethyl)-phenyl]-1-methyl-3-[(3-methyl-oxetan-3-ylmethyl)-amino]-cyclobutanol

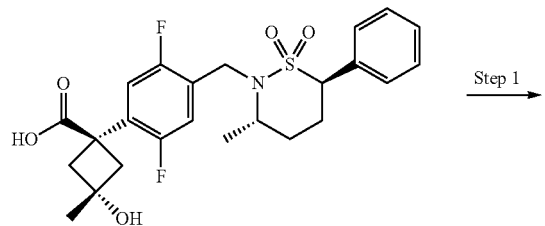

Step 1

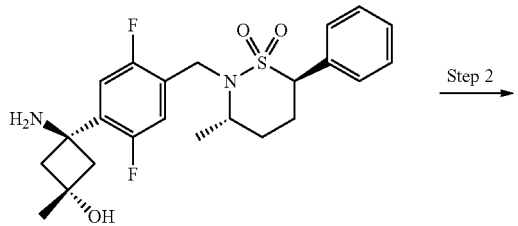

Step 2

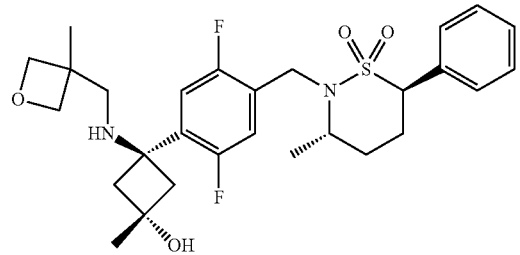

Step 1: 3-Amino-3-[2,5-difluoro-4-((3S,6R)-3-methyl-11-dioxo-6-phenyl-1λ⁶-[1,2]thiazinan-2-ylmethyl)-phenyl]-1-methyl-cyclobutanol To a solution of trans-1-[2,5-difluoro-4-((3S,6R)-3-methyl-1,1-dioxo-6-phenyl-1λ⁶-[1,2]thiazinan-2-ylmethyl)-phenyl]-3-hydroxy-3-methyl-cyclobutanecarboxylic acid (1.50 g, 3.13 mmol) in dioxane (50 mL) was added Et₃N (0.872 mL, 6.26 mmol) and diphenylphosphoryl azide (0.809 mL, 3.75 mmol). The reaction was heated at 80° C. for 45 min before being cooled to RT and HCl (aq., 1 M, 30 mL) added. The reaction was stirred at RT for 45 min before being extracted with Et₂O (30 mL). The aqueous layer was basified with NaOH (aq., 1 M) and extracted with EtOAc (2×40 mL). The combined organics were dried over Na₂SO₄ and concentrated in vacuo to give the title compound as a solid. ¹H NMR (400 MHz, DMSO-d₆) δ 7.48-7.35 (5H, m), 7.15 (1H, dd, J=6.2, 11.2 Hz), 7.02 (1H, dd, J=6.5, 10.6 Hz), 4.70 (1H, s), 4.57-4.46 (2H, m), 4.34 (1H, d, J=17.7 Hz), 4.16-4.09 (1H, m), 2.47-2.38 (3H, m), 2.20 (2H, d, J=11.6 Hz), 2.14-2.07 (1H, m), 2.00-1.95 (2H, m), 1.91-1.75 (1H, m), 1.70-1.63 (1H, m), 1.48 (3H, s), 1.11 (3H, d, J=6.9 Hz).

Step 2: trans-3-[2,5-Difluoro-4-((3S,6R)-3-methyl-1,1-dioxo-6-phenyl-1λ⁶-[1,2]thiazinan-2-ylmethyl)-phenyl]-1-methyl-3-[(3-methyl-oxetan-3-ylmethyl)-amino]-cyclobutanol To a solution of the product from step 1 (100 mg, 0.222 mmol) in 2,2,2-trifluoroethanol (2.0 mL) was added 3-methyloxetane-3-carbaldehyde (40 mg, 0.40 mmol). The reaction was heated to 40° C. for 15 min before sodium borohydride (15 mg, 0.40 mmol) was added. The reaction was heated at 40° C. for 15 min and the solvent removed in vacuo. Purification by flash chromatography (100% EtOAc) followed by trituration with Et₂O gave the title compound as a solid (37 mg). ¹H NMR (400 MHz, DMSO-d₆) δ 7.49-7.36 (5H, m), 7.16 (1H, dd, J=6.1, 11.1 Hz), 7.03 (1H, dd, J=6.4, 10.5 Hz), 4.82 (1H, s), 4.59-4.46 (2H, m), 4.36 (1H, d, J=17.7 Hz), 4.23 (2H, d, J=5.6 Hz), 4.14-4.10 (3H, m), 2.47-2.39 (1H, m), 2.36-2.22 (6H, m), 2.14-2.06 (1H, m), 2.00 (1H, dd, J=8.1, 8.1 Hz), 1.86-1.74 (1H, m), 1.67 (1H, dd, J=2.2, 14.2 Hz), 1.45 (3H, s), 1.14 (3H, s), 1.12 (3H, d, J=7.0 Hz). LCMS (ESI): m/z=535.1 [M+H]⁺.

Example 12: trans-1-{1-[2,5-Difluoro-4-((3S,6R)-3-methyl-1-dioxo-6-phenyl-1λ⁶-[1,2]thiazinan-2-ylmethyl)-phenyl]-3-hydroxy-3-methyl-cyclobutylmethyl}-1H-pyrazin-2-one

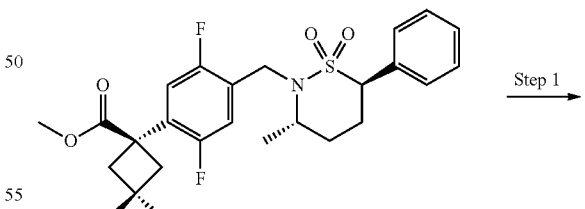

Step 1

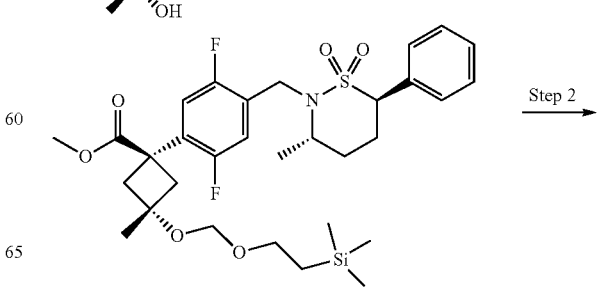

Step 2

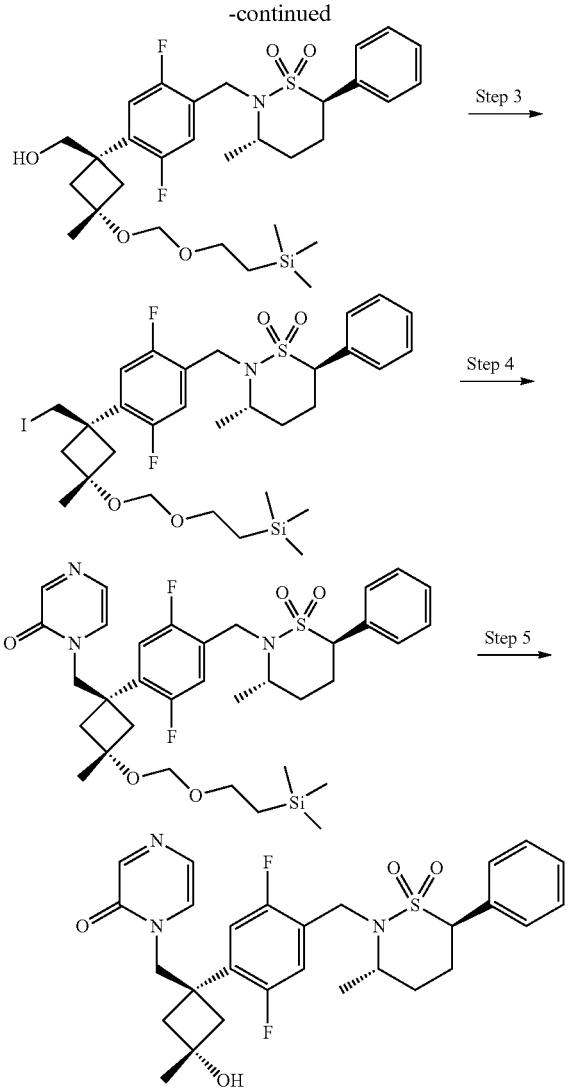

Step 1: trans-1-[2,5-Difluoro-4-((3S,6R)-3-methyl-1,1-dioxo-6-phenyl-1λ⁶-[1,2]thiazinan-2-ylmethyl)-phenyl]-3-methyl-3-(2-trimethylsilanyl-ethoxymethoxy)-cyclobutanecarboxylic Acid Methyl Ester To a solution of trans-1-[2,5-difluoro-4-((3S,6R)-3-methyl-1,1-dioxo-6-phenyl-1λ⁶-[1,2]thiazinan-2-ylmethyl)-phenyl]-3-hydroxy-3-methyl-cyclobutanecarboxylic acid methyl ester (2.50 g, 5.07 mmol) in DCM (50 mL) was added 2-(trimethylsilyl)ethylmethyl chloride (2.25 mL, 12.7 mmol) and diisopropylethylamine (1.76 mL, 10.1 mmol). The reaction was stirred at RT for 16 hr. The mixture was diluted with DCM (50 mL) and the organics washed with brine (50 mL), dried over Na₂SO₄ and concentrated in vacuo. Purification by flash chromatography (0-50% EtOAc/cyclohexane) gave the title compound as an oil (1.40 g). ¹H NMR (300 MHz, CDCl₃) δ 7.51-7.34 (6H, m), 6.94 (1H, dd, J=6.6, 10.4 Hz), 4.68 (2H, s), 4.52 (1H, d, J=17.3 Hz), 4.40 (1H, d, J=17.2 Hz), 4.33-4.23 (1H, m), 4.00 (1H, dd, J=3.5, 12.9 Hz), 3.68 (3H, s), 3.62-3.55 (2H, m), 3.03-2.93 (2H, m), 2.73 (2H, d, J=12.1 Hz), 2.69-2.59 (1H, m), 2.30-2.19 (1H, m), 1.82-1.74 (2H, m), 1.48 (3H, s), 1.17 (3H, d, J=6.9 Hz), 0.93-0.86 (2H, m), 0.00 (9H, s). LCMS (ESI): m/z=646.3 [M+Na]⁺.

Step 2: trans-[1-[2,5-Difluoro-4-((3S,6R)-3-methyl-1,1-dioxo-6-phenyl-1λ⁶-[1,2]thiazinan-2-ylmethyl)-phenyl]-3-methyl-3-(2-trimethylsilanyl-ethoxymethoxy)-cyclobutyl]-methanol To a solution of the product from step 1 (1.40 g, 2.25 mmol) in DCM (23 mL) at 0° C. was added DIBAL-H (6.7 mL, 6.7 mmol, 1.0 M in DCM). The reaction was warmed to RT and stirred for 1 hr. The reaction was quenched with potassium sodium tartarate (sat., aq., 20 mL) and stirred for 30 minutes. The layers were separated and the organics dried over Na₂SO₄ and concentrated in vacuo. Purification by flash chromatography (0-60% EtOAc/cyclohexane) gave the title compound as an oil (1.20 g). ¹H NMR (300 MHz, CDCl₃) δ 7.51-7.35 (6H, m), 6.85 (1H, dd, J=6.3, 10.4 Hz), 4.69 (2H, s), 4.53 (1H, d, J=17.1 Hz), 4.39 (1H, d, J=17.2 Hz), 4.34-4.22 (1H, m), 4.01 (1H, dd, J=3.9, 12.7 Hz), 3.77 (2H, d, J=5.9 Hz), 3.61-3.54 (2H, m), 2.71-2.58 (3H, m), 2.50-2.41 (2H, m), 2.25 (1H, ddd, J=3.5, 7.0, 14.1 Hz), 1.84-1.74 (2H, m), 1.53 (3H, s), 1.37 (1H, t, J=6.1 Hz), 1.19 (3H, d, J=6.9 Hz), 0.92-0.86 (2H, m), 0.02-0.00 (9H, m). LCMS (ESI): m/z=618.4 [M+Na]⁺.

Step 3: trans-(3S,6R)-2-{2,5-Difluoro-4-[1-iodomethyl-3-methyl-3-(2-trimethylsilanyl-ethoxymethoxy)-cyclobutyl]-benzyl}-3-methyl-6-phenyl-[1,2]thiazinane 1,1-dioxide To a solution of the product from step 2 (1.20 g, 2.02 mmol) in toluene (30 mL) was added triphenylphosphine (1.06 g, 4.03 mmol), imidazole (274 mg, 4.03 mmol) and iodine (872 mg, 3.43 mmol). The reaction was heated to 70° C. for 2 hr, before being cooled to RT, quenched with Na₂S₂O₃ (0.1 M, aq., 30 mL) and extracted with EtOAc (100 mL). The organics were dried over Na₂SO₄ and concentrated in vacuo. Purification by flash chromatography (0-60% EtOAc/cyclohexane) gave the title compound as an oil (1.32 g). ¹H NMR (400 MHz, DMSO-d₆) δ 7.51-7.39 (5H, m), 7.39-7.33 (1H, m), 6.83 (1H, dd, J=6.5, 10.4 Hz), 4.67 (2H, s), 4.54 (1H, d, J=16.9 Hz), 4.42 (1H, d, J=16.9 Hz), 4.33-4.24 (1H, m), 4.01 (1H, dd, J=3.6, 12.9 Hz), 3.68 (2H, s), 3.59-3.52 (2H, m), 2.77 (2H, d, J=12.5 Hz), 2.72-2.60 (1H, m), 2.45 (2H, d, J=14.2 Hz), 2.30-2.21 (1H, m), 1.84-1.75 (2H, m), 1.55 (3H, s), 1.18 (3H, d, J=7.0 Hz), 0.92-0.85 (2H, m), 0.00 (9H, s). (ESI): m/z=728.3 [M+Na]⁺.

Step 4: trans-1-[1-[2,5-Difluoro-4-((3S,6R)-3-methyl-1,1-dioxo-6-phenyl-1λ⁶-[1,2]thiazinan-2-ylmethyl)-phenyl]-3-methyl-3-(2-trimethylsilanyl-ethoxymethoxy)-cyclobutylmethyl]-1H-pyrazin-2-one To a solution of the product from step 3 (200 mg, 0.284 mmol) in DMA (1.0 mL) was added 2-hydroxypyrazine (82 mg, 0.85 mmol) and cesium carbonate (277 mg, 0.851 mmol). The reaction was heated to 80° C. for 16 h before being cooled to RT, diluted with H₂O (10 mL) and extracted with EtOAc (50 mL). The organics were washed with brine (3×30 mL), dried over Na₂SO₄ and concentrated in vacuo. Purification by flash chromatography (20-100% EtOAc/cyclohexane) gave the title compound as an oil (47 mg). ¹H NMR (300 MHz, CDCl₃) δ 8.12 (1H, d, J=1.0 Hz), 7.53-

7.39 (6H, m), 6.93 (1H, d, J=4.4 Hz), 6.63 (1H, dd, J=6.3, 10.2 Hz), 6.08 (1H, dd, J=1.0, 4.4 Hz), 4.67 (2H, s), 4.55 (1H, d, J=17.0 Hz), 4.44-4.36 (2H, m), 4.35-4.24 (2H, m), 4.03 (1H, dd, J=3.5, 12.8 Hz), 3.59-3.52 (2H, m), 2.81-2.61 (5H, m), 2.32-2.22 (1H, m), 1.85-1.76 (2H, m), 1.71 (3H, s), 1.17 (3H, d, J=6.9 Hz), 0.92-0.84 (2H, m), 0.00 (9H, s). LCMS (ESI): m/z=674.3 [M+H]+.

Step 5: trans-1-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutylmethyl}-1H-pyrazin-2-one To a solution of the product from step 4 (47 mg, 70 μmol) in MeOH (3.0 mL) was added HCl (4.0 M in dioxane, 2.0 mL). The reaction was stirred at RT for 0.5 h before the solvent was removed in vacuo. The crude was taken up in EtOAc (30 mL) and NaHCO$_3$ (sat., aq., 30 mL) and the layers separated. The organics were dried over Na$_2$SO$_4$ and concentrated in vacuo. Purification by MDAP gave the title compound as a solid. $^1$H NMR (400 MHz, DMSO-d$_6$) δ 7.87 (1H, d, J=1.1 Hz), 7.49-7.37 (5H, m), 7.11 (1H, dd, J=6.2, 11.2 Hz), 6.97 (1H, d, J=4.4 Hz), 6.82 (1H, dd, J=6.4, 10.6 Hz), 6.72 (1H, dd, J=1.0, 4.4 Hz), 4.91 (1H, s), 4.56-4.44 (2H, m), 4.34 (1H, d, J=17.4 Hz), 4.25 (2H, s), 4.11 (1H, ddd, J=1.8, 6.9, 11.9 Hz), 2.72-2.63 (2H, m), 2.48-2.38 (3H, m), 2.14-2.06 (1H, m), 1.87-1.77 (1H, m), 1.66 (1H, dd, J=2.2, 14.3 Hz), 1.42 (3H, s), 1.08 (3H, d, J=6.8 Hz). LCMS (ESI): m/z=544.3 [M+H]+.

Example 13: trans-3-[2,5-Difluoro-4-((3S,6R)-3-methyl-1,1-dioxo-6-phenyl-1λ$^6$-[1,2]thiazinan-2-ylmethyl)-phenyl]-1-methyl-3-(pyrazin-2-yloxymethyl)-cyclobutanol

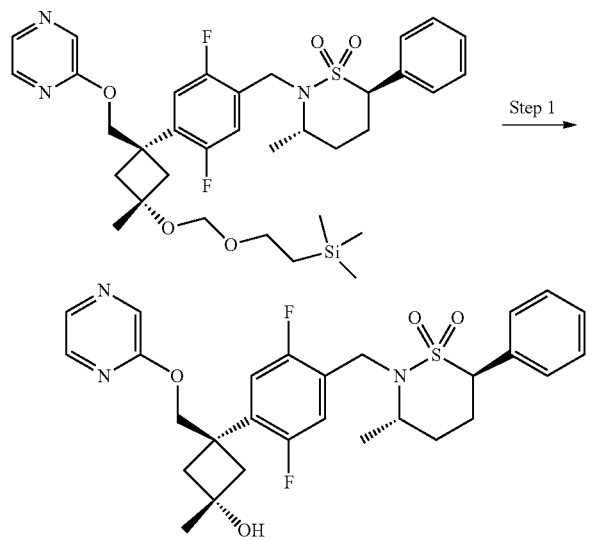

Step 1: trans-3-[2,5-Difluoro-4-((3S,6R)-3-methyl-1,1-dioxo-6-phenyl-1λ$^6$-[1,2]thiazinan-2-ylmethyl)-phenyl]-1-methyl-3-(pyrazin-2-yloxymethyl)-cyclobutanol (3S,6R)-2-{2,5-Difluoro-4-[3-methyl-1-(pyrazin-2-yloxymethyl)-3-(2-trimethylsilanyl-ethoxymethoxy)-cyclobutyl]-benzyl}-3-methyl-6-phenyl-[1,2]thiazinane 1,1-dioxide (87 mg, 0.13 mmol), also isolated from example 12, step 4, was reacted and purified as described in example 12, step 5, to give the title compound as a solid. $^1$H NMR (400 MHz, DMSO-d$_6$) δ 8.17 (1H, d, J=1.4 Hz), 8.13 (1H, d, J=2.6 Hz), 8.08 (1H, dd, J=1.4, 2.8 Hz), 7.48-7.36 (5H, m), 7.14 (1H, dd, J=6.2, 11.2 Hz), 7.07 (1H, dd, J=6.7, 10.5 Hz), 4.98 (1H, s), 4.57-4.44 (4H, m), 4.33 (1H, d, J=17.8 Hz), 4.15-4.07 (1H, m), 2.57-2.52 (2H, m), 2.49-2.38 (3H, m), 2.13-2.06 (1H, m), 1.85-1.72 (1H, m), 1.69-1.62 (1H, m), 1.37 (3H, s), 1.08 (3H, d, J=6.8 Hz). LCMS (ESI): m/z=544.3 [M+H]+.

Example 14: 5-{(R)-1-[2,5-Difluoro-4-((3S,6R)-3-methyl-1,1-dioxo-6-phenyl-1λ$^6$-[1,2]thiazinan-2-ylmethyl)-phenyl]-3-methyl-cyclobut-2-enyl}-3H-[1,3,4]oxadiazol-2-one and 5-{(S)-1-[2,5-difluoro-4-((3S,6R)-3-methyl-1,1-dioxo-6-phenyl-1λ$^6$-[1,2]thiazinan-2-ylmethyl)-phenyl]-3-methyl-cyclobut-2-enyl}-3H-[1,3,4]oxadiazol-2-one

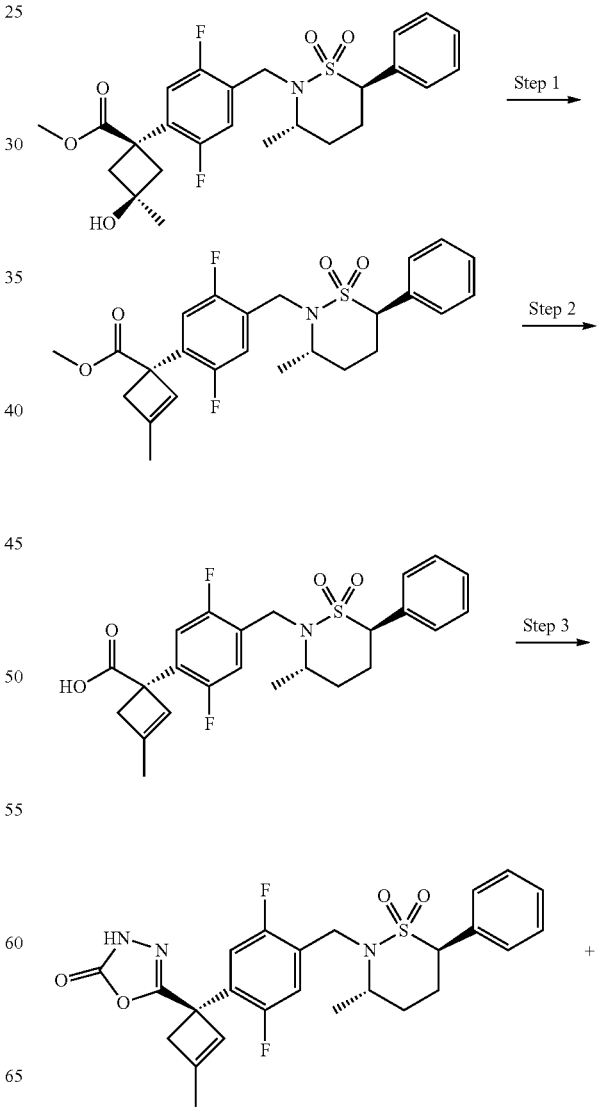

-continued

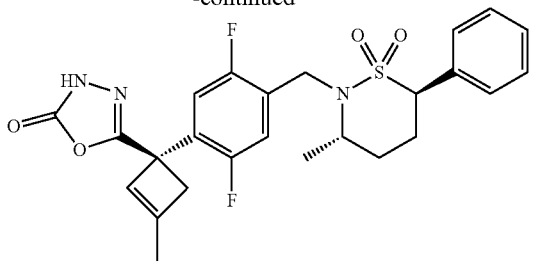

Step 1: (R/S)-1-[2,5-Difluoro-4-((3S,6R)-3-methyl-1,1-dioxo-6-phenyl-1λ⁶-[1,2]thiazinan-2-ylmethyl)-phenyl]-3-methyl-cyclobut-2-enecarboxylic Acid Methyl Ester To a solution of cis-1-[2,5-difluoro-4-((3S,6R)-3-methyl-1,1-dioxo-6-phenyl-1λ⁶-[1,2]thiazinan-2-ylmethyl)-phenyl]-3-hydroxy-3-methyl-cyclobutanecarboxylic acid methyl ester (2.00 g, 4.06 mmol) in DCM (50 mL) was added thionyl chloride (5.0 mL). The reaction was stirred at RT for 4 hr before the solvent was removed in vacuo. Purification by flash chromatography (25-70% EtOAc/cyclohexane) gave the title compound as an oil (1.30 g) as a mixture of alkene isomers. LCMS (ESI): m/z=476.3 [M+H]⁺.

Step 2: (R/S)-1-[2,5-Difluoro-4-((3S,6R)-3-methyl-1-dioxo-6-phenyl-1λ⁶-[1,2]thiazinan-2-ylmethyl)-phenyl]-3-methyl-cyclobut-2-enecarboxylic Acid The product from step 1 (650 mg, 1.37 mmol) was reacted as described in example 2, step 12, at 50° C. to give the title compound as a mixture of alkene isomers (580 mg). LCMS (ESI): m/z=462.3 [M+H]⁺.

Step 3: 5-{(R)-1-[2,5-Difluoro-4-((3S,6R)-3-methyl-1,1-dioxo-6-phenyl-1λ⁶-[1,2]thiazinan-2-ylmethyl)-phenyl]-3-methyl-cyclobut-2-enyl}-3H-[1,3,4]oxadiazol-2-one and 5-{(S)-1-[2,5-difluoro-4-((3S,6R)-3-methyl-1,1-dioxo-6-phenyl-1λ⁶-[1,2]thiazinan-2-ylmethyl)-phenyl]-3-methyl-cyclobut-2-enyl}-3H-[1,3,4]oxadiazol-2-one The product from step 2 (580 mg, 1.26 mmol) was reacted as described in example 2, step 13, to give the title compound as a mixture of alkene isomers. The isomers were separated by chiral SFC purification. 5-{(R)-1-[2,5-Difluoro-4-((3S,6R)-3-methyl-1,1-dioxo-6-phenyl-1λ⁶-[1,2]thiazinan-2-ylmethyl)-phenyl]-3-methyl-cyclobut-2-enyl}-3H-[1,3,4]oxadiazol-2-one ¹H NMR (400 MHz, DMSO-d₆) δ 12.15 (1H, br. s), 7.49-7.35 (5H, m), 7.31 (1H, dd, J=6.3, 10.2 Hz), 7.25 (1H, dd, J=5.9, 10.6 Hz), 6.32 (1H, s), 4.60-4.50 (2H, m), 4.38 (1H, d, J=17.8 Hz), 4.16-4.08 (1H, m), 3.25 (1H, d, J=14.7 Hz), 2.83 (1H, d, J=13.6 Hz), 2.48-2.39 (1H, m), 2.13-2.07 (1H, m), 1.86-1.74 (4H, m), 1.67 (1H, dd, J=2.2, 14.3 Hz), 1.13 (3H, d, J=6.9 Hz). LCMS (ESI): m/z=524.2 [M+Na]⁺. 5-{(S)-1-[2,5-Difluoro-4-((3S,6R)-3-methyl-1,1-dioxo-6-phenyl-1λ⁶-[1,2]thiazinan-2-ylmethyl)-phenyl]-3-methyl-cyclobut-2-enyl}-3H-[1,3,4]oxadiazol-2-one ¹H NMR (400 MHz, DMSO-d₆) δ 12.15 (1H, br. s), 7.49-7.34 (5H, m), 7.31 (1H, dd, J=6.3, 10.2 Hz), 7.25 (1H, dd, J=6.0, 10.5 Hz), 6.33 (1H, s), 4.61-4.50 (2H, m), 4.38 (1H, d, J=17.8 Hz), 4.15-4.08 (1H, m), 3.26 (1H, d, J=14.8 Hz), 2.83 (1H, d, J=13.5 Hz), 2.47-2.39 (1H, m), 2.14-2.07 (1H, m), 1.86-1.74 (4H, m), 1.71-1.64 (1H, m), 1.12 (3H, d, J=6.8 Hz). LCMS (ESI): m/z=524.2 [M+Na]⁺.

Example 15: trans-3-[2,5-Difluoro-4-((3S,6R)-3-methyl-1,1-dioxo-6-phenyl-1λ⁶-[1,2]thiazinan-2-ylmethyl)-phenyl]-3-[(S)-1-hydroxy-2-(1H-[1,2,4]triazol-3-yl)-ethyl]-1-methyl-cyclobutanol and trans-3-[2,5-difluoro-4-((3S,6R)-3-methyl-1,1-dioxo-6-phenyl-1λ⁶-[1,2]thiazinan-2-ylmethyl)-phenyl]-3-[(R)-1-hydroxy-2-(1H-[1,2,4]triazol-3-yl)-ethyl]-1-methyl-cyclobutanol

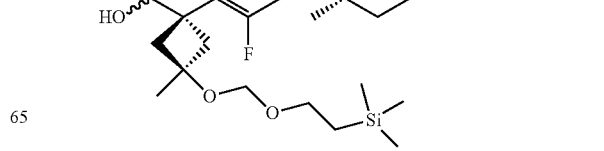

-continued

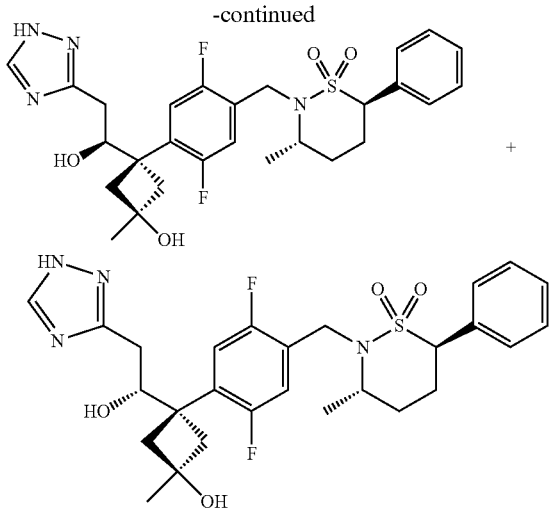

Step 1: trans-1-[2,5-Difluoro-4-((3S,6R)-3-methyl-1,1-dioxo-6-phenyl-1λ⁶-[1,2]thiazinan-2-ylmethyl)-phenyl]-3-methyl-3-(2-trimethylsilanyl-ethoxymethoxy)-cyclobutanecarbaldehyde To a solution of trans-[1-[2,5-difluoro-4-((3S,6R)-3-methyl-1,1-dioxo-6-phenyl-1λ⁶-[1,2]thiazinan-2-ylmethyl)-phenyl]-3-methyl-3-(2-trimethylsilanyl-ethoxymethoxy)-cyclobutyl]-methanol (700 mg, 1.18 mmol) in DCM (20 mL) was added Dess-Martin periodinane (698 mg, 1.65 mmol). The reaction was stirred at RT for 1.5 h before being diluted with DCM (50 mL). The organics were washed with Na₂S₂O₅ (sat., aq., 40 mL), NaHCO₃ (sat., aq., 40 mL), dried over Na₂SO₄ and concentrated in vacuo. Purification by flash chromatography (0-70% EtOAc/cyclohexane) gave the title compound as an oil (660 mg). ¹H NMR (300 MHz, CDCl₃) δ 9.62 (1H, d, J=1.8 Hz), 7.50-7.38 (6H, m), 6.84 (1H, dd, J=6.0, 10.1 Hz), 4.70 (2H, s), 4.53 (1H, d, J=17.2 Hz), 4.40 (1H, d, J=17.1 Hz), 4.34-4.22 (1H, m), 4.01 (1H, dd, J=3.5, 12.8 Hz), 3.63-3.56 (2H, m), 2.90 (2H, dd, J=1.0, 13.7 Hz), 2.65 (3H, d, J=13.6 Hz), 2.24 (1H, ddd, J=3.5, 7.1, 14.2 Hz), 1.83-1.74 (2H, m), 1.40 (3H, s), 1.16 (3H, d, J=6.9 Hz), 0.93-0.86 (2H, m), 0.00 (9H, s). LCMS (ESI): m/z=616.4 [M+Na]⁺.

Step 2: (R/S)-trans-3-[1-[2,5-Difluoro-4-((3S,6R)-3-methyl-1,1-dioxo-6-phenyl-1λ⁶-[1,2]thiazinan-2-ylmethyl)-phenyl]-3-methyl-3-(2-trimethylsilanyl-ethoxymethoxy)-cyclobutyl]-3-hydroxy-propionic Acid Ethyl Ester To a solution of LDA (696 µL, 1.39 mmol, 2.0 M in THF/heptane/ethylbenzene) in THF (3.0 mL) at −78° C. was added EtOAc (162 µL, 1.67 mmol). The reaction was stirred at −78° C. for 0.5 h before a solution of the product from step 1 (330 mg, 0.556 mmol) in THF (1.0 mL) was added. The reaction was stirred at −78° C. for 0.5 h before being quenched with H₂O (8 mL) and warmed to RT. The mixture was extracted with EtOAc (20 mL) and the organics washed with NaHCO₃ (sat., aq., 10 mL), dried over Na₂SO₄ and concentrated in vacuo. Purification by flash chromatography (0-70% EtOAc/cyclohexane) gave the title compound as an oil (310 mg). LCMS (ESI): m/z=704.5 [M+Na]⁺.

Step 3: (R/S)-trans-3-[1-[2,5-Difluoro-4-((3S,6R)-3-methyl-1,1-dioxo-6-phenyl-1λ⁶-[1,2]thiazinan-2-ylmethyl)-phenyl]-3-methyl-3-(2-trimethylsilanyl-ethoxymethoxy)-cyclobutyl]-3-hydroxy-propionamide To a solution of the product from step 2 (240 mg, 0.352 mmol) in MeOH (3.5 mL) and THF (1.25 mL) was added a solution of NaOH (28 mg, 0.70 mmol) in H₂O (3.5 mL). The reaction was heated at 50° C. for 1 h before being cooled to RT and diluted with EtOAc (50 mL). The mixture was washed with HCl (1 M, aq., 15 mL), brine (15 mL), dried over Na₂SO₄ and concentrated in vacuo. The crude material was taken up in DMF (0.8 mL) before diisopropylethylamine (184 µL, 1.06 mmol), HATU (187 mg, 0.493 mmol) and NH₄OH (59 µL, 0.53 mmol) were added sequentially. The reaction was stirred at RT for 1 h before being diluted with H₂O (5 mL) and extracted with EtOAc (20 mL). The organics were washed with brine (3×10 mL), dried over Na₂SO₄ and concentrated in vacuo. Purification by flash chromatography (50-100% EtOAc/cyclohexane) gave the title compound as an oil (230 mg). LCMS (ESI): m/z=653.4 [M+H]⁺.

Step 4: (R/S)-trans-1-[1-[2,5-Difluoro-4-((3S,6R)-3-methyl-1,1-dioxo-6-phenyl-1λ⁶-[1,2]thiazinan-2-ylmethyl)-phenyl]-3-methyl-3-(2-trimethylsilanyl-ethoxymethoxy)-cyclobutyl]-2-(1H-[1,2,4]triazol-3-yl)-ethanol A solution of the product from step 3 (230 mg, 0.352 mmol) in dimethylformamide dimethylacetal (3.8 mL) was heated at 70° C. for 1.5 h before being cooled to RT and the solvent removed in vacuo. The crude was azeotroped with toluene before being taken up in acetic acid (3.8 mL) and hydrazine hydrate (191 µL, 2.68 mmol). The reaction was heated at 70° C. for 1.5 h before being cooled to RT and the solvent removed in vacuo. Purification by flash chromatography (20-90% EtOAc/cyclohexane) gave the title compound as an oil (120 mg). LCMS (ESI): m/z=677.4 [M+H]⁺.

Step 5: trans-3-[2,5-Difluoro-4-((3S,6R)-3-methyl-1,1-dioxo-6-phenyl-1λ⁶-[1,2]thiazinan-2-ylmethyl)-phenyl]-3-[(S)-1-hydroxy-2-(1H-[1,2,4]triazol-3-yl)-ethyl]-1-methyl-cyclobutanol and trans-3-[2,5-difluoro-4-((3S,6R)-3-methyl-1,1-dioxo-6-phenyl-1λ⁶-[1,2]thiazinan-2-ylmethyl)-phenyl]-3-[(R)-1-hydroxy-2-(1H-[1,2,4]triazol-3-yl)-ethyl]-1-methyl-cyclobutanol The product from step 4 (120 mg, 0.220 mmol) was reacted and purified as described in example 12, step 5, to give the title compounds as a solid. The diastereomers were separated by chiral SFC purification. trans-3-[2,5-Difluoro-4-((3S,6R)-3-methyl-1,1-dioxo-6-phenyl-1λ⁶-[1,2]thiazinan-2-ylmethyl)-phenyl]-3-[(S)-1-hydroxy-2-(1H-[1,2,4]triazol-3-yl)-ethyl]-1-methyl-cyclobutanol ¹H NMR (400 MHz, DMSO-d₆) δ 13.58-13.45 (1H, m), 7.75 (1H, s), 7.49-7.37 (5H, m), 7.16 (1H, dd, J=6.2, 11.2 Hz), 6.99 (1H, dd, J=6.3, 11.0 Hz), 5.34-5.30 (1H, m), 4.77 (1H, s), 4.60-4.48 (2H, m), 4.37 (1H, d, J=17.8 Hz), 4.17-4.11 (2H, m), 2.68-2.62 (2H, m), 2.47-2.28 (4H, m), 2.22-2.07 (2H, m), 1.86-1.65 (2H, m), 1.31 (3H, s), 1.15 (3H, d, J=6.8 Hz). LCMS (ESI): m/z=547.3 [M+H]⁺. trans-3-[2,5-Difluoro-4-((3S,6R)-3-methyl-1,1-dioxo-6-phenyl-1λ⁶-[1,2]thiazinan-2-ylmethyl)-phenyl]-3-[(R)-1-hydroxy-2-(1H-[1,2,4]triazol-3-yl)-ethyl]-1-methyl-cyclobutanol ¹H NMR (400

MHz, DMSO-d$_6$) δ 13.58-13.46 (1H, m), 7.74 (1H, s), 7.49-7.37 (5H, m), 7.16 (1H, dd, J=6.1, 11.2 Hz), 6.99 (1H, dd, J=6.4, 11.0 Hz), 5.32-5.29 (1H, m), 4.80-4.72 (1H, m), 4.60-4.48 (2H, m), 4.37 (1H, d, J=17.7 Hz), 4.18-4.09 (2H, m), 2.68-2.63 (2H, m), 2.47-2.30 (4H, m), 2.21-2.06 (2H, m), 1.87-1.76 (1H, m), 1.72-1.64 (1H, m), 1.31 (3H, s), 1.15 (3H, d, J=6.9 Hz). LCMS (ESI): m/z=547.3 [M+H]$^+$.

Example 16: (R/S)-trans-3-[2,5-Difluoro-4-((3S, 6R)-3-methyl-1,1-dioxo-6-phenyl-1λ$^6$-[1,2]thiazinan-2-ylmethyl)-phenyl]-3-[2-hydroxy-2-(1H-[1,2,4]triazol-3-yl)-ethyl]-1-methyl-cyclobutanol

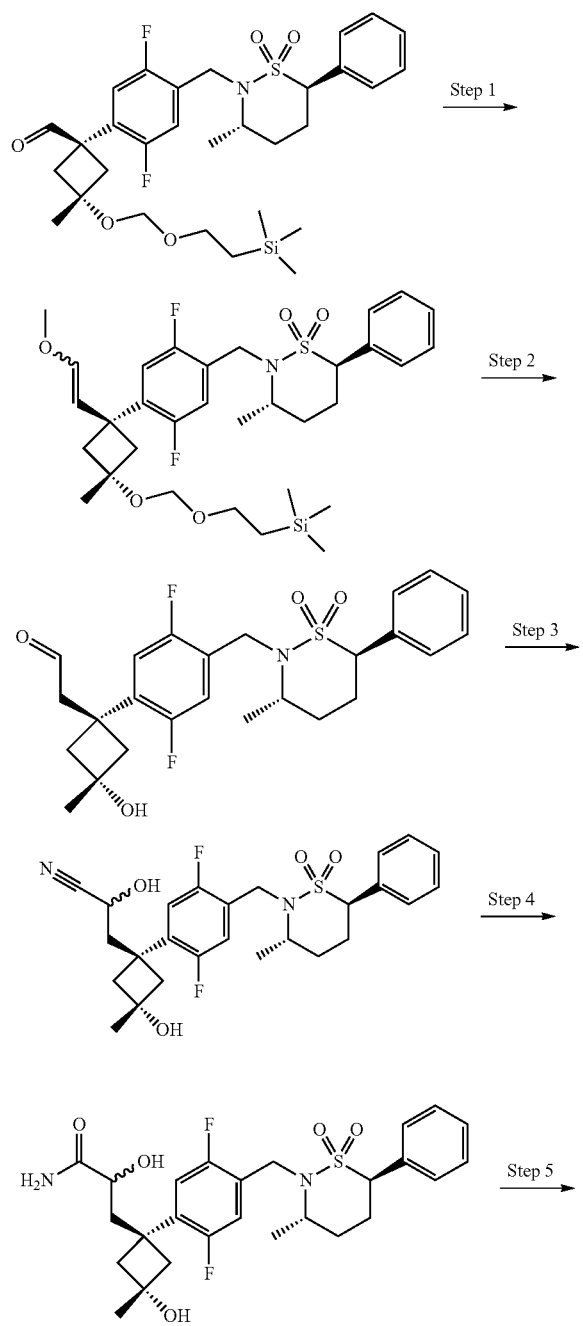

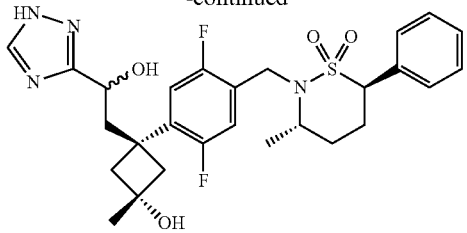

Step 1: trans-(3S,6R)-2-{2,5-Difluoro-4-[1-(-2-methoxy-vinyl)-3-methyl-3-(2-trimethylsilanyl-ethoxymethoxy)-cyclobutyl]-benzyl}-3-methyl-6-phenyl-[1,2]thiazinane 1,1-dioxide To a solution of (methyoxymethyl)triphenylphosphonium chloride (1.36 g, 4.42 mmol) in THF (20 mL) at 0° C. was added potassium tert-butoxide (2.95 mL, 2.95 mmol, 1.0 M in THF). The reaction was stirred at 0° C. for 0.5 h before a solution of 1-[2,5-difluoro-4-((3S,6R)-3-methyl-1,1-dioxo-6-phenyl-1λ$^6$-[1,2]thiazinan-2-ylmethyl)-phenyl]-3-methyl-3-(2-trimethylsilanyl-ethoxymethoxy)-cyclobutanecarbaldehyde (875 mg, 1.47 mmol) in THF (5 mL) was added. The mixture was stirred for 20 min at 0° C. before being quenched with brine (30 mL), warmed to RT and extracted with EtOAc (60 mL). The organics were dried over Na$_2$SO$_4$ and concentrated in vacuo. Purification by flash chromatography (0-60% EtOAc/cyclohexane) gave the title compound as an oil (774 mg) as a 60:40 mixture of alkene isomers. $^1$H NMR (300 MHz, CDCl$_3$) δ 7.51-7.24 (6H, m), 6.93 (0.4H, dd, J=6.2, 10.8 Hz), 6.75 (0.6H, dd, J=6.3, 10.5 Hz), 6.27 (0.6H, d, J=12.8 Hz), 5.74 (0.4H, d, J=6.3 Hz), 5.06 (0.6H, d, J=12.9 Hz), 4.73 (0.4H, dd, J=2.0, 6.3 Hz), 4.69 (2H, s), 4.51 (1H, d, J=17.1 Hz), 4.38 (1H, d, J=17.1 Hz), 4.32-4.20 (1H, m), 4.03-3.95 (1H, m), 3.64-3.55 (2H, m), 3.50 (1.2H, s), 3.49 (1.8H, s), 2.78-2.46 (5H, m), 2.28-2.17 (1H, m), 1.83-1.72 (2H, m), 1.55 (1.2H, s), 1.53 (1.8H, s), 1.16 (3H, d, J=6.9 Hz), 0.94-0.86 (2H, m), 0.00 (9H, s). LCMS (ESI) m/z=639.7 [M+H$_2$O]$^+$.

Step 2: {1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-acetaldehyde To a flask containing the product from step 1 (774 mg, 1.24 mmol) was added HCl (4.0 M in dioxane, 12.4 mL) and HCl (2.0 M, aq., 12.4 mL). The reaction was stirred at RT for 1 h before being neutralised with NaHCO$_3$ (sat., aq., to pH 10). The mixture was extracted with EtOAc (2×30 mL) and the organics dried over Na$_2$SO$_4$ and concentrated in vacuo. Purification by flash chromatography (0-60% EtOAc/cyclohexane) gave the title compound as a solid (574 mg). LCMS (ESI): m/z=500.2 [M+Na]$^+$.

Step 3: (R/S)-trans-3-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-2-hydroxy-propionitrile To a solution of the product from step 2 (574 mg, 1.20 mmol) in DCM (24 mL) was added trimethylsilyl cyanide (0.226 mL, 1.80 mmol) and Et$_3$N (0.251 mL, 1.80 mmol). The reaction was stirred at RT for 1 h before being quenched with K$_2$CO$_3$ (2.0 M, aq., 20 mL) and further stirred for 0.5 h. The reaction was extracted with DCM (2×30 mL) and the combined organics dried over Na$_2$SO$_4$ and concentrated in vacuo. The crude material was taken up in MeOH (3.0 mL) and HCl (4.0 M in dioxane, 12.4 mL) and stirred for 0.5 h before the solvent was removed in vacuo. Purification by flash chromatography (0-70% EtOAc/cyclohexane) gave the title compound as a solid (554 mg). LCMS (ESI): m/z=527.3 [M+Na]$^+$.

Step 4: (R/S)-trans-3-{1-[2,5-Difluoro-4-((3S,6R)-3-methyl-11-dioxo-6-phenyl-1λ$^6$-[1,2]thiazinan-2-ylmethyl)-phenyl]-3-hydroxy-3-methyl-cyclobutyl}-2-hydroxy-propionamide The product from step 3 (360 mg, 0.714 mmol) was reacted as described in example 9, step 6, to give the title compound (200 mg). $^1$H NMR (400 MHz, DMSO-d$_6$) δ 7.48-7.36 (5H, m), 7.16-7.09 (2H, m), 7.05-6.96 (2H, m), 5.17 (1H, d, J=5.9 Hz), 4.74 (1H, s), 4.58-4.46 (2H, m), 4.35 (1H, d, J=17.6 Hz), 4.15-4.10 (1H, m), 2.68-2.61 (1H, m), 2.48-2.31 (5H, m), 2.14-2.07 (2H, m), 1.95-1.76 (2H, m), 1.71-1.63 (1H, m), 1.31 (3H, s), 1.12 (3H, dd, J=1.5, 6.8 Hz). NH$_2$ not observed. LCMS (ESI): m/z=523.2 [M+H]$^+$.

Step 5: (R/S)-trans-3-[2,5-Difluoro-4-((3S,6R)-3-methyl-1,1-dioxo-6-phenyl-1λ$^6$-[1,2]thiazinan-2-ylmethyl)-phenyl]-3-[2-hydroxy-2-(1H-[1,2,4]triazol-3-yl)-ethyl]-1-methyl-cyclobutanol The product from step 3 (150 mg, 0.287 mmol) was reacted as described in example 15, step 4, to give the title compound (46 mg). $^1$H NMR (400 MHz, DMSO-d$_6$) δ 13.70 (1H, br. s), 7.74 (1H, br. s), 7.49-7.36 (5H, m), 7.17-7.10 (1H, m), 6.98-6.97 (1H, m), 5.52 (1H, br. s), 4.74 (1H, s), 4.59-4.46 (2H, m), 4.35 (1H, dd, J=3.3, 17.6 Hz), 4.22 (1H, br. s), 4.17-4.09 (1H, m), 2.68-2.61 (1H, m), 2.48-2.39 (2H, m), 2.34-2.23 (3H, m), 2.15-2.06 (2H, m), 1.87-1.76 (1H, m), 1.71-1.63 (1H, m), 1.32 (3H, s), 1.13 (3H, d, J=6.8 Hz). LCMS (ESI): m/z=547.1 [M+H]$^+$.

Example 17: trans-(R)-5-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-oxazolidin-2-one and trans-(S)-5-{1-[2,5-difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-oxazolidin-2-one

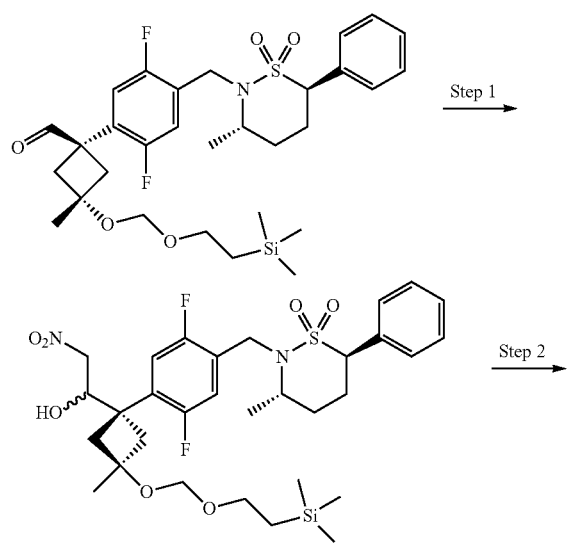

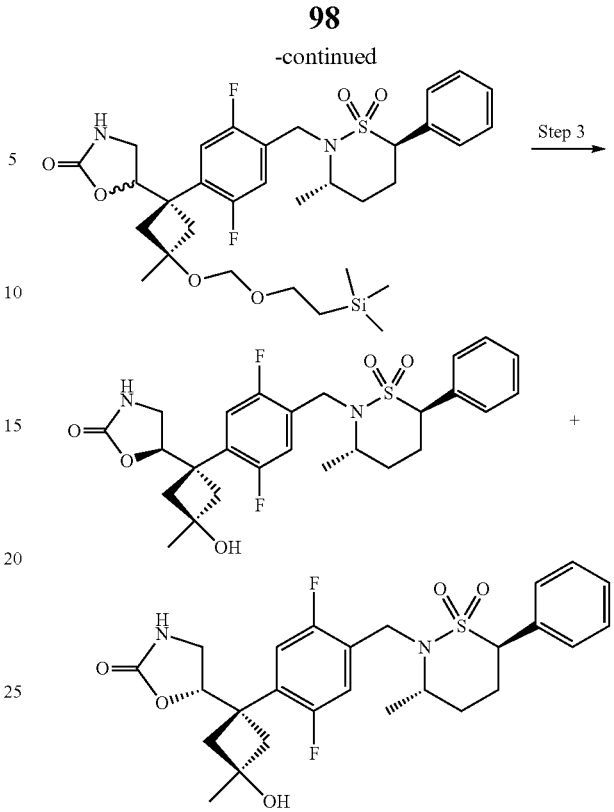

Step 1: (R/S)-trans-1-[1-[2,5-Difluoro-4-((3S,6R)-3-methyl-1,1-dioxo-6-phenyl-1λ$^6$-[1,2]thiazinan-2-ylmethyl)-phenyl]-3-methyl-3-(2-trimethylsilanyl-ethoxymethoxy)-cyclobutyl]-2-nitro-ethanol To a solution of 1-[2,5-difluoro-4-((3S,6R)-3-methyl-1,1-dioxo-6-phenyl-1λ$^6$-[1,2]thiazinan-2-ylmethyl)-phenyl]-3-methyl-3-(2-trimethylsilanyl-ethoxymethoxy)-cyclobutanecarbaldehyde (649 mg, 1.09 mmol) in nitromethane (5.0 mL) was added diisopropylethylamine (568 µL, 3.27 mmol). The reaction was stirred at RT for 4 h before the solvent was removed in vacuo. Purification by flash chromatography (0-70% EtOAc/cyclohexane) gave the title compound as a solid (660 mg). LCMS (ESI): m/z=677.4 [M+Na]$^+$.

Step 2: (R/S)-trans-2-Amino-1-[1-[2,5-difluoro-4-((3S,6R)-3-methyl-1,1-dioxo-6-phenyl-1λ$^6$-[1,2]thiazinan-2-ylmethyl)-phenyl]-3-methyl-3-(2-trimethylsilanyl-ethoxymethoxy)-cyclobutyl]-ethanol To a solution of the product from step 1 (200 mg, 0.306 mmol) in IMS (2.4 mL) was added NH$_4$Cl (100 mg, 1.86 mmol) in H$_2$O (0.8 mL). The reaction was stirred vigorously before iron powder (68 mg, 1.2 mmol) was added and the reaction heated at 85° C. for 0.5 h. The reaction was cooled to RT, filtered through a plug of celite and the solvent removed in vacuo. The crude was taken up in EtOAc (20 mL) and the organics washed with brine (20 mL), dried over Na$_2$SO$_4$ and concentrated in vacuo. The crude residue was taken up in DMF (0.7 mL) before 1,1-carbonyldiimidazole (74 mg, 0.46 mmol) and Et$_3$N (64 µL, 0.46 mmol) were added. The reaction was stirred at RT for 16 h before being diluted with EtOAc (30 mL). The organics were washed with brine (4×10 mL), dried over Na$_2$SO$_4$ and concentrated in vacuo. Purification by flash chromatography (0-90%

EtOAc/cyclohexane) gave the title compound as an oil (152 mg). $^1$H NMR (300 MHz, CDCl$_3$) δ 7.52-7.36 (6H, m), 6.92 (1H, dd, J=6.1, 10.4 Hz), 5.58 (1H, d, J=15.7 Hz), 4.86 (1H, dt, J=2.5, 8.1 Hz), 4.68-4.65 (2H, m), 4.59-4.48 (1H, m), 4.45-4.34 (1H, m), 4.34-4.24 (1H, m), 4.03 (1H, td, J=2.9, 12.9 Hz), 3.58-3.47 (2H, m), 3.31-3.08 (2H, m), 2.80-2.56 (5H, m), 2.31-2.20 (1H, m), 1.85-1.73 (2H, m), 1.53 (3H, d, J=2.2 Hz), 1.18 (3H, t, J=6.3 Hz), 0.93-0.83 (2H, m), 0.02-0.01 (9H, m). LCMS (ESI): m/z=673.3 [M+Na]$^+$.

Step 3: trans-(R)-5-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-oxazolidin-2-one and trans-(S)-5-{1-[2,5-difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-oxazolidin-2-one To a solution of the product from step 2 (152 mg, 0.234 mmol) in MeOH (2.0 mL) was added HCl (4.0 M in dioxane, 2.0 mL). The reaction was stirred for 0.5 h before the solvent was removed in vacuo. The crude was taken up in EtOAc (20 mL) and the organics washed with NaHCO$_3$ (sat., aq., 15 mL), dried over Na$_2$SO$_4$ and concentrated in vacuo. The diastereomers were separated by chiral SFC purification. trans-(R)-5-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-oxazolidin-2-one $^1$H NMR (400 MHz, DMSO-d$_6$) δ 7.48-7.35 (6H, m), 7.17 (2H, ddd, J=6.3, 11.3, 13.3 Hz), 4.89 (1H, s), 4.79-4.73 (1H, m), 4.59-4.47 (2H, m), 4.36 (1H, d, J=17.7 Hz), 4.14-4.07 (1H, m), 3.30-3.26 (1H, m), 3.02 (1H, dd, J=7.1, 8.7 Hz), 2.49-2.45 (3H, m), 2.44-2.32 (2H, m), 2.14-2.06 (1H, m), 1.86-1.74 (1H, m), 1.67 (1H, dd, J=2.0, 14.2 Hz), 1.30 (3H, s), 1.12 (3H, d, J=6.8 Hz). LCMS (ESI): m/z=521.2 [M+H]$^+$. trans-(S)-5-{1-[2,5-Difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutyl}-oxazolidin-2-one $^1$H NMR (400 MHz, DMSO-d$_6$) δ 7.48-7.35 (6H, m), 7.22-7.13 (2H, m), 4.89 (1H, s), 4.75 (1H, dd, J=6.6, 8.8 Hz), 4.59-4.47 (2H, m), 4.36 (1H, d, J=17.8 Hz), 4.13 (1H, ddd, J=2.0, 6.9, 11.8 Hz), 3.30-3.25 (1H, m), 3.01 (1H, dd, J=6.9, 8.7 Hz), 2.57-2.52 (1H, m), 2.48-2.34 (4H, m), 2.14-2.06 (1H, m), 1.87-1.75 (1H, m), 1.67 (1H, dd, J=2.2, 14.2 Hz), 1.31 (3H, s), 1.12 (3H, d, J=6.8 Hz). LCMS (ESI): m/z=521.2 [M+H]$^+$.

Example 18: trans-N-[3-[2,5-Difluoro-4-((3S,6R)-3-methyl-11-dioxo-6-phenyl-1λ$^6$-[1,2]thiazinan-2-ylmethyl)-phenyl]-1-methyl-3-(5-oxo-4,5-dihydro-[1,3,4]oxadiazol-2-yl)-cyclobutyl]-acetamide

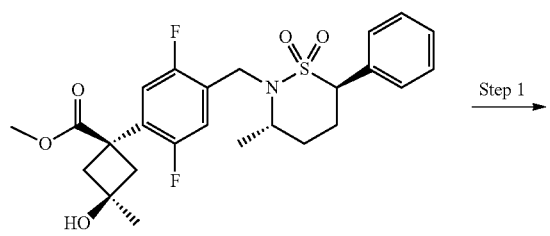

Step 1 →

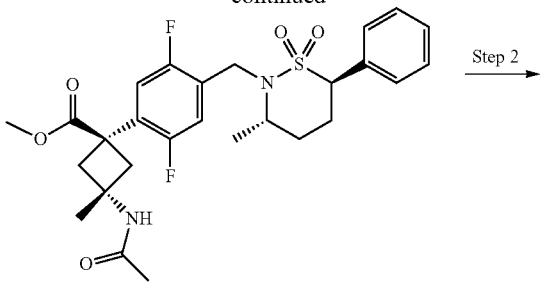

Step 2 →

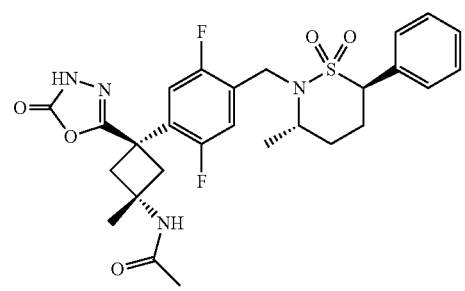

Step 1: trans-3-Acetylamino-1-[2,5-difluoro-4-((3S,6R)-3-methyl-1,1-dioxo-6-phenyl-1λ$^6$-[1,2]thiazinan-2-ylmethyl)-phenyl]-3-methyl-cyclobutanecarboxylic Acid Methyl Ester To a solution of 1-[2,5-difluoro-4-((3S,6R)-3-methyl-1,1-dioxo-6-phenyl-1λ$^6$-[1,2]thiazinan-2-ylmethyl)-phenyl]-3-hydroxy-3-methyl-cyclobutanecarboxylic acid methyl ester (500 mg, 1.01 mmol) in MeCN (20 mL) was added H$_2$SO$_4$ (conc., 200 µL). The reaction was stirred at 50° C. for 1 h before being quenched with H$_2$O (5 mL) and extracted with EtOAc (100 mL). The organic layer was washed with H$_2$O (70 mL), NaHCO$_3$ (sat., aq., 30 mL), dried over Na$_2$SO$_4$ and concentrated in vacuo. Trituration with Et$_2$O gave the title compound as a solid (400 mg). $^1$H NMR (400 MHz, DMSO-d$_6$) δ 7.92 (1H, s), 7.48-7.36 (5H, m), 7.22-7.15 (2H, m), 4.60-4.48 (2H, m), 4.37 (1H, d, J=17.8 Hz), 4.15-4.08 (1H, m), 3.59 (3H, s), 2.80 (4H, s), 2.48-2.38 (1H, m), 2.14-2.06 (1H, m), 1.81-1.75 (1H, m), 1.67 (4H, s), 1.38 (3H, s), 1.13 (3H, d, J=6.9 Hz). LCMS (ESI): m/z=535.2 [M+H]$^+$.

Step 2: trans-N-[3-[2,5-Difluoro-4-((3S,6R)-3-methyl-1,1-dioxo-6-phenyl-1λ$^6$-[1,2]thiazinan-2-ylmethyl)-phenyl]-1-methyl-3-(5-oxo-4,5-dihydro-[1,3,4]oxadiazol-2-yl)-cyclobutyl]-acetamide The product from step 1 (300 mg, 0.561 mmol) was reacted as described in example 10, step 5, to give the title compound as a solid. $^1$H NMR (400 MHz, DMSO-d$_6$) δ 12.25 (1H, s), 7.96 (1H, s), 7.48-7.36 (5H, m), 7.27-7.19 (2H, m), 4.60-4.49 (2H, m), 4.37 (1H, d, J=17.8 Hz), 4.17-4.09 (1H, m), 3.01-2.86 (4H, m), 2.48-2.38 (1H, m), 2.14-2.06 (1H, m), 1.86-1.75 (1H, m), 1.68-1.62 (4H, m), 1.39 (3H, s), 1.13 (3H, d, J=6.9 Hz). LCMS (ESI): m/z=561.2 [M+H]$^+$.

Example 19: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)oxazol-2(3H)-one

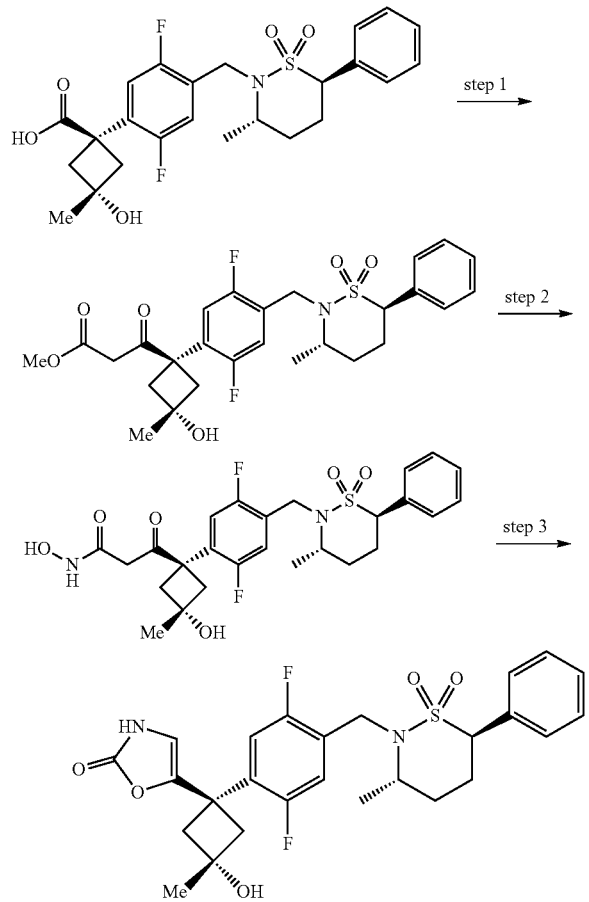

Step 1: Methyl 3-((1R,3S)-1-(2,5-difluoro-4-(((3S,6R)-3-methyl-1,1-dioxido-6-phenyl-1,2-thiazinan-2-yl)methyl)phenyl)-3-hydroxy-3-methylcyclobutyl)-3-oxopropanoate A round-bottom flask was charged with 1-(2,5-difluoro-4-(((3S,6R)-3-methyl-1,1-dioxo-6-phenyl-thiazinan-2-yl)methyl)phenyl)-3-hydroxy-3-methyl-cyclobutanecarboxylic acid (550 mg, 1.15 mmol) and tetrahydrofuran (10 mL), followed by 1,1'-carbonyldiimidazole (199 mg, 1.20 mmol), and the reaction was stirred at room temperature for 2 hours. Magnesium chloride (126 mg, 1.32 mmol) and potassium 3-methoxy-3-oxopropanoate (210 mg, 1.32 mmol) were added and the reaction was heated to 50° C. and stirred at that temperature for 16 hours. The reaction mixture was then filtered, concentrated on silica gel and purified by silica gel column chromatography (i-PrOAc 0-100%/heptane) to give the title compound as a white solid (454 mg). LCMS ES$^+$ 536.1 [M+1]$^+$.

Step 2: 3-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)-N-hydroxy-3-oxopropanamide A round bottom flask was charged with methyl 3-(1-(2,5-difluoro-4-(((3S,6R)-3-methyl-1,1-dioxo-6-phenyl-thiazinan-2-yl)methyl)phenyl)-3-hydroxy-3-methyl-cyclobutyl)-3-oxo-propanoate (266 mg, 0.50 mmol) and methanol (3 mL), and the resulting solution was cooled to −30° C. To the cooled solution was added sodium hydroxide (0.25M in MeOH, 2.2 mL) and the reaction was stirred at −30° C. for 10 minutes. To this solution was then added a solution of hydroxylamine hydrochloride (86 mg, 1.24 mmol) in sodium hydroxide (0.25M in MeOH, 5.0 mL) and water (1 mL). The resulting mixture was stirred at −30° C. for 10 minutes and then aged in a freezer at −25° C. for 16 hours. The reaction was diluted with saturated aqueous ammonium chloride (20 mL), extracted with i-PrOAc (3×5 mL) and CH$_2$Cl$_2$ (10 mL), dried with MgSO$_4$, concentrated and purified by silica gel column chromatography (MeOH 0-30%/CH$_2$Cl$_2$) to give to give the title compound as a white solid (140 mg). LCMS ES$^+$ 537.1 [M+1]$^+$.

Step 3: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)oxazol-2(3H)-one A solution of 3-(1-(2,5-difluoro-4-(((3S,6R)-3-methyl-1,1-dioxo-6-phenyl-thiazinan-2-yl)methyl)phenyl)-3-hydroxy-3-methyl-cyclobutyl)-3-oxo-propenehydroxamic acid (372 mg, 0.69 mmol) in tetrahydrofuran (7 mL) was cooled to 0° C. N,N-Diisopropylethylamine (0.31 mL, 1.7 mmol) was added, followed by 4-nitrobenzenesulfonyl chloride (188 mg, 0.76 mmol) and the reaction was stirred at 0° C. to room temperature for 16 hours. The resulting mixture was quenched with saturated aqueous ammonium chloride (20 mL), extracted with CH$_2$Cl$_2$ (3×10 mL), dried with MgSO$_4$, concentrated and purified by reverse phase preparative HPLC (acetonitrile 20-60%/0.1% formic acid in water) to give the title compound (30 mg). $^1$H NMR (400 MHz, DMSO-d6) δ 10.39 (s, 1H), 7.51-7.43 (m, 2H), 7.43-7.33 (m, 3H), 7.23-7.05 (m, 2H), 6.82 (s, 1H), 5.06 (s, 1H), 4.56 (dd, J=12.6, 3.5 Hz, 1H), 4.50 (d, J=17.7 Hz, 1H), 4.35 (d, J=17.9 Hz, 1H), 4.20-4.03 (m, 1H), 2.72 (d, J=13.0 Hz, 2H), 2.57 (d, J=12.6 Hz, 2H), 2.47-2.36 (m, 1H), 2.15-2.06 (m, 1H), 1.89-1.72 (m, 1H), 1.72-1.61 (m, 1H), 1.26 (s, 3H), 1.12 (d, J=6.8 Hz, 3H); LCMS ES$^+$ 519.2 [M+1]$^+$.

Example 20: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)-3-methyloxazol-2(3H)-one

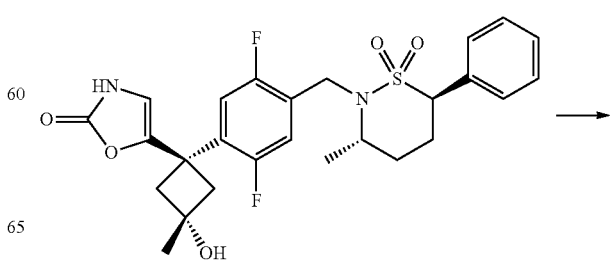

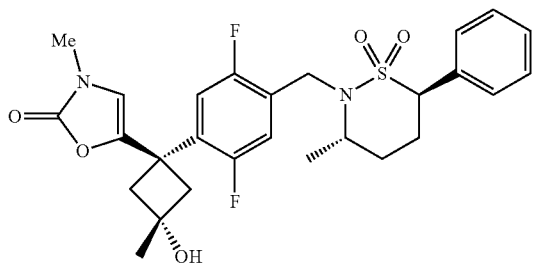

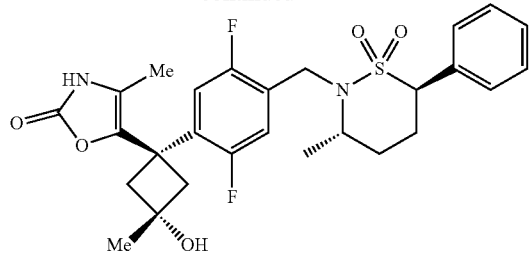

To a solution of 5-(1-(2,5-difluoro-4-(((3S,6R)-3-methyl-1,1-dioxo-6-phenyl-thiazinan-2-yl)methyl)phenyl)-3-hydroxy-3-methyl-cyclobutyl)-3H-oxazol-2-one (15 mg, 0.029 mmol) in N,N-dimethylformamide (0.5 mL) at room temperature was added potassium carbonate (14.0 mg, 0.174 mmol) and the reaction was stirred for 2 minutes. Iodomethane (0.086 mL, 0.054 mmol) was then added and the reaction was stirred at room temperature for 2 hours. The resulting mixture was filtered through Celite®, concentrated and purified by reverse phase preparative HPLC (acetonitrile 20-60%/0.1% formic acid in water) to give the title compound as a white solid (11.6 mg). $^1$H NMR (400 MHz, DMSO-$d_6$) δ 7.49-7.43 (m, 2H), 7.43-7.35 (m, 3H), 7.15 (ddd, J=19.5, 10.8, 6.3 Hz, 2H), 6.90 (s, 1H), 5.08 (s, 1H), 4.56 (dd, J=12.9, 3.5 Hz, 1H), 4.50 (d, J=18.0 Hz, 1H), 4.35 (d, J=17.6 Hz, 1H), 4.19-4.02 (m, 1H), 3.05 (s, 3H), 2.71 (d, J=13.0 Hz, 2H), 2.59 (d, J=12.9 Hz, 2H), 2.47-2.38 (m, 1H), 2.16-2.05 (m, 1H), 1.86-1.72 (m, 1H), 1.71-1.61 (m, 1H), 1.27 (s, 3H), 1.13 (d, J=6.9 Hz, 3H); LCMS ES$^+$ 533.2 [M+1]$^+$.

Example 21: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)-4-methyloxazol-2(3H)-one

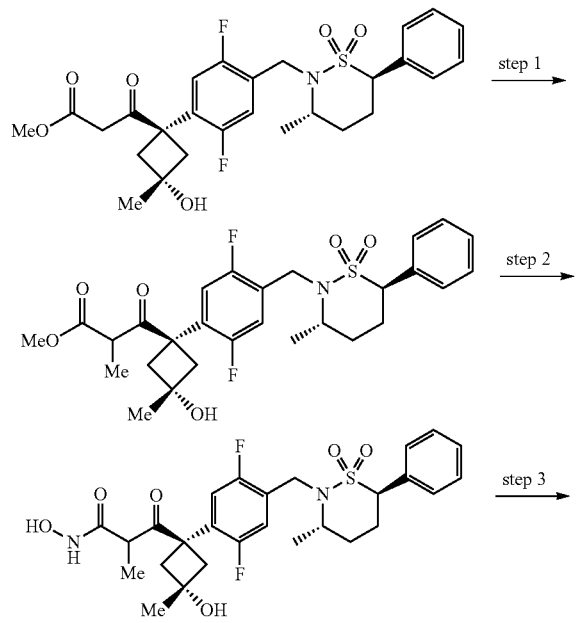

Step 1: Methyl 3-((1R,3S)-1-(2,5-difluoro-4-(((3S,6R)-3-methyl-1,1-dioxido-6-phenyl-1,2-thiazinan-2-yl)methyl)phenyl)-3-hydroxy-3-methylcyclobutyl)-2-methyl-3-oxopropanoate To a solution of methyl 3-(1-(2,5-difluoro-4-(((3S,6R)-3-methyl-1,1-dioxo-6-phenyl-thiazinan-2-yl)methyl)phenyl)-3-hydroxy-3-methyl-cyclobutyl)-3-oxo-propanoate (490 mg, 0.91 mmol) in N,N-dimethylformamide (4.5 mL) was added cesium carbonate (656 mg, 2.0 mmol) and the reaction was stirred at room temperature for 10 minutes. Iodomethane (0.06 mL, 1.0 mmol) was then added and the reaction was stirred at room temperature for 16 hours. The resulting mixture was quenched with saturated aqueous ammonium chloride (10 mL), and the pH was adjusted to 1 with concentrated aqueous hydrochloric acid. The product was extracted with $CH_2Cl_2$ (3×10 mL), dried with $MgSO_4$, concentrated and purified by silica gel column chromatography (i-PrOAc 0-100%/heptane) to give the title compound as white solid (378 mg). LCMS ES$^+$ 550.1 [M+1]$^+$.

Step 2: 3-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)-N-hydroxy-2-methyl-3-oxopropanamide A round bottom flask was charged with methyl 3-((1R,3S)-1-(2,5-difluoro-4-(((3S,6R)-3-methyl-1,1-dioxido-6-phenyl-1,2-thiazinan-2-yl)methyl)phenyl)-3-hydroxy-3-methylcyclobutyl)-2-methyl-3-oxopropanoate (378 mg, 0.69 mmol) and methanol (3 mL), and the resulting solution was cooled to −30° C. To the cooled solution was added sodium hydroxide (0.25M in MeOH, 3.0 mL) and the reaction was stirred at −30° C. for 10 minutes. To this solution was then added a solution of hydroxylamine hydrochloride (124 mg, 1.7 mmol) in sodium hydroxide (0.25M in MeOH, 6.9 mL) and water (0.5 mL). The resulting mixture was stirred at −30° C. for 10 minutes and then aged in a freezer at −25° C. for 16 hours. The reaction was diluted with saturated aqueous ammonium chloride (10 mL), extracted with i-PrOAc (3×5 mL) and $CH_2Cl_2$ (5 mL), dried with $MgSO_4$, concentrated and purified by silica gel column chromatography (MeOH 0-30%/$CH_2Cl_2$) to give the title compound as a white solid (153 mg). LCMS ES$^+$ 551.1 [M+1]$^+$.

Step 3: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)-4-methyloxazol-2(3H)-one A solution of 3-((1R,3S)-1-(2,5-difluoro-4-(((3S,6R)-3-methyl-1,1-dioxido-6-phenyl-1,2-thiazinan-2-yl)methyl)phenyl)-3-hydroxy-3-methylcyclobutyl)-N-hydroxy-2- methyl-3-oxopropanamide (153 mg, 0.83 mmol) in tetrahydrofuran (3.0 mL) was cooled to 0° C. N,N-Diisopropylethylamine (0.12 mL, 0.69 mmol) was added, followed by 4-nitrobenzenesulfonyl chloride (75 mg, 0.31 mmol) and the reaction was stirred at 0° C. to room temperature for 16 hours. The resulting mixture was quenched with saturated aqueous ammonium chloride (10 mL), extracted with $CH_2Cl_2$ (3×5 mL), dried with $MgSO_4$, concentrated and purified by reverse phase preparative HPLC (acetonitrile 20-60%/0.1% formic acid in water) to give the title compound as a white solid (13.8 mg). $^1$H NMR (400 MHz, DMSO-d6) δ 7.50-7.43 (m, 2H), 7.43-7.33 (m, 3H), 7.30-7.21 (m, 1H), 7.15 (dd, J=11.2, 6.1 Hz, 1H), 5.00 (s, 1H), 4.61-4.46 (m, 2H), 4.35 (d, J=17.9 Hz, 1H), 4.18-4.04 (m, 1H), 2.98-2.88 (m, 2H), 2.66-2.57 (m, 2H), 2.46-2.36 (m, 1H), 2.16-2.05 (m, 1H), 1.88-1.72 (m, 1H), 1.71-1.60 (m, 1H), 1.43 (s, 3H), 1.18 (s, 3H), 1.11 (d, J=6.8 Hz, 3H); LCMS ES$^+$ 533.2 [M+1]$^+$.

Examples 21 and 22: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)-2-methylisoxazol-3(2H)-one and (3S,6R)-2-(2,5-difluoro-4-((1R,3S)-3-hydroxy-1-(3-methoxyisoxazol-5-yl)-3-methylcyclobutyl)benzyl)-3-methyl-6-phenyl-1,2-thiazinane 1,1-dioxide

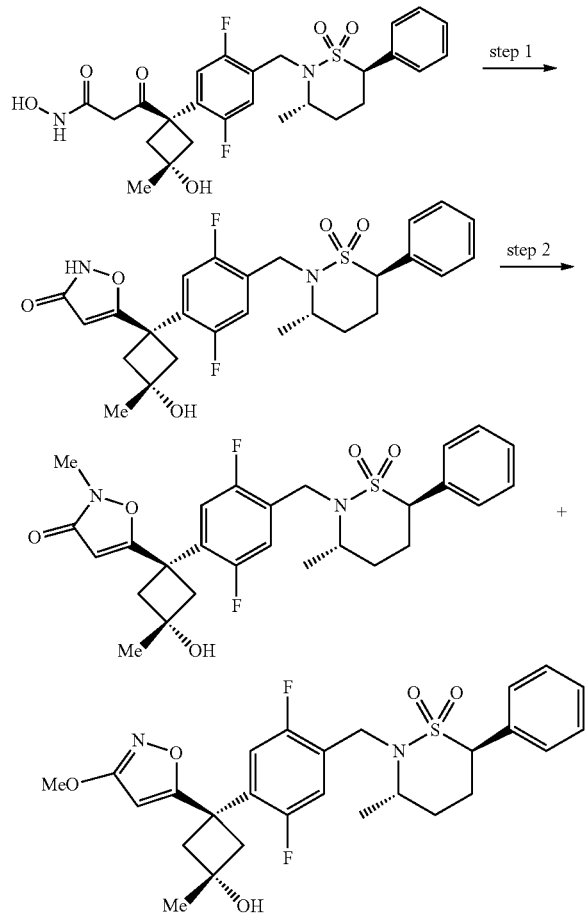

Step 1: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)isoxazol-3 (2H)-one To a round bottom flask holding 4-(2,5-difluoro-4-(((3S,6R)-3-methyl-1,1-dioxo-6-phenyl-thiazinan-2-yl)methyl)phenyl)-3-oxo-pentanehydroxamic acid (500 mg, 0.93 mmol) were added methanol (5 mL) and concentrated aqueous hydrochloric acid (1.5 mL). The reaction was stirred at 80° C. for 2 hour. The resulting mixture was cooled to room temperature, diluted with water (20 mL), extracted with i-PrOAc (3×5 mL) and $CH_2Cl_2$ (10 mL), dried with $MgSO_4$, and purified by reverse phase preparative HPLC (acetonitrile 20-60%/0.1% formic acid in water) to give the title compound (213 mg). LCMS ES$^+$ 519.1 [M+1]$^+$.

Step 2: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)-2-methylisoxazol-3(2H)-one and (3S,6R)-2-(2,5-difluoro-4-((1R,3S)-3-hydroxy-1-(3-methoxyisoxazol-5-yl)-3-methylcyclobutyl)benzyl)-3-methyl-6-phenyl-1,2-thiazinane 1,1-dioxide To a solution of 5-(1-(2,5-difluoro-4-(((3S,6R)-3-methyl-1,1-dioxo-6-phenyl-thiazinan-2-yl)methyl)phenyl)-3-hydroxy-3-methyl-cyclobutyl)isoxazol-3-one (213 mg, 0.41 mmol) in methanol (1.5 m) and tetrahydrofuran (1.5 m) at room temperature was added (trimethylsilyl)diazomethane (2.0 M in hexanes, ~1.0 mL) dropwise, until a yellow color persisted for more than 10 seconds. The reaction was stirred at room temperature for an additional 30 minutes. The resulting mixture was quenched with saturated aqueous ammonium chloride (20 mL), extracted with $CH_2Cl_2$ (3×10 mL), dried with $MgSO_4$, concentrated and purified by reverse phase preparative HPLC (acetonitrile 20-60%/0.1% formic acid in water) to give the title compounds.

5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-methylcyclobutyl)-2-methylisoxazol-3(2H)-one as a white solid (68 mg). $^1$H NMR (400 MHz, DMSO-d6) δ 7.49-7.43 (m, 2H), 7.43-7.33 (m, 3H), 7.27-7.17 (m, 2H), 5.17 (s, 1H), 4.57 (dd, J=12.8, 3.4 Hz, 1H), 4.51 (d, J=17.9 Hz, 1H), 4.36 (d, J=18.0 Hz, 1H), 4.19-4.06 (m, 1H), 3.30 (s, 3H), 2.94-2.83 (m, 2H), 2.76-2.63 (m, 2H), 2.15-2.06 (m, 1H), 1.88-1.71 (m, 1H), 1.71-1.62 (m, 1H), 1.24 (s, 3H), 1.13 (d, J=6.9 Hz, 3H); LCMS ES$^+$ 533.2 [M+1]$^+$. (3S,6R)-2-(2,5-Difluoro-4-((1R,3S)-3-hydroxy-1-(3-methoxyisoxazol-5-yl)-3-methylcyclobutyl)benzyl)-3-methyl-6-phenyl-1,2-thiazinane 1,1-dioxide as a white solid (56 mg). $^1$H NMR (400 MHz, DMSO-d6) δ 7.50-7.43 (m, 2H), 7.43-7.33 (m, 3H), 7.23 (dd, J=10.5, 6.4 Hz, 1H), 7.18 (dd, J=11.0, 6.2 Hz, 1H), 6.22 (s, 1H), 5.14 (s, 1H), 4.56 (dd, J=12.6, 3.6 Hz, 1H), 4.50 (d, J=17.8 Hz, 1H), 4.35 (d, J=17.7 Hz, 1H), 4.20-4.04 (m, 1H), 3.82 (s, 3H), 2.95-2.85 (m, 2H), 2.77-2.69 (m, 2H), 2.47-2.36 (m, 1H), 2.15-2.07 (m, 1H), 1.88-1.72 (m, 1H), 1.71-1.61 (m, 1H), 1.18 (s, 3H), 1.12 (d, J=6.9 Hz, 3H); LCMS ES$^+$ 533.2 [M+1]$^+$.

Example 23: (S)-5-((1R,3S)-1-(2,5-Difluoro-4-(((3S,6R)-3-methyl-1,1-dioxido-6-phenyl-1,2-thiazinan-2-yl)methyl)phenyl)-3-hydroxycyclobutyl)oxazolidin-2-one

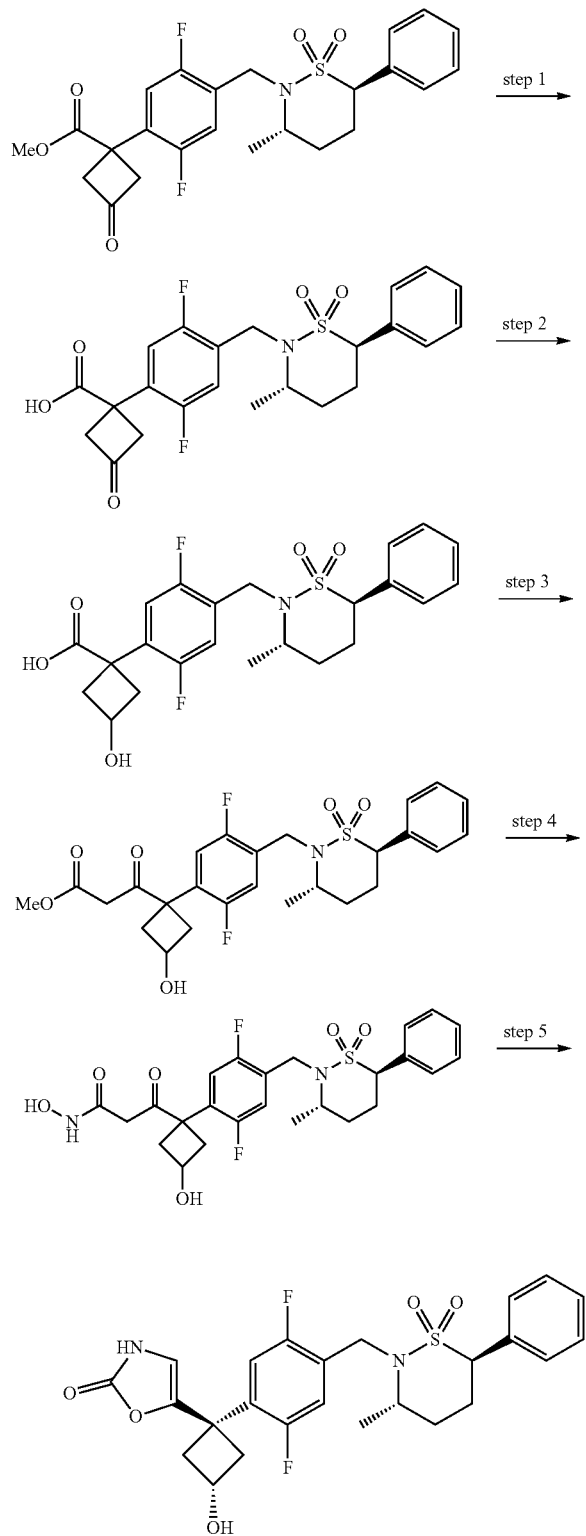

Step 1: 1-(2,5-Difluoro-4-(((3S,6R)-3-methyl-1,1-dioxido-6-phenyl-1,2-thiazinan-2-yl)methyl)phenyl)-3-oxacyclobutane-1-carboxylic Acid To a solution of methyl 1-(2,5-difluoro-4-(((3S,6R)-3-methyl-1,1-dioxo-6-phenyl-thiazinan-2-yl)methyl)phenyl)-3-oxo-cyclobutanecarboxylate (12.1 g, 25.3 mmol) in tetrahydrofuran (90 mL) and water (30 mL) was added lithium hydroxide (10.9 g, 253 mmol) and the reaction was stirred at room temperature for 4 hours. The resulting mixture was diluted with water (200 mL) and the pH was adjusted to 1 with concentrated aqueous hydrochloric acid. The reaction mixture was then extracted with i-PrOAc (2×100 mL) and CH$_2$Cl$_2$ (50 mL), dried with MgSO$_4$ and concentrated to give the title compound (9.2 g). LCMS ES$^+$ 464.1 [M+1]$^+$.

Step 2: 1-(2,5-Difluoro-4-(((3S,6R)-3-methyl-1,1-dioxido-6-phenyl-1,2-thiazinan-2-yl)methyl)phenyl)-3-hydroxycyclobutane-1-carboxylic Acid To a solution of 1-(2,5-difluoro-4-(((3S,6R)-3-methyl-1,1-dioxo-6-phenyl-thiazinan-2-yl)methyl)phenyl)-3-oxo-cyclobutanecarboxylic acid (1.0 g, 2.1 mmol) in ethanol (11 mL) was added sodium borohydride (250 mg, 6.47 mmol) at room temperature. Gas evolution occurred and lasted for about 5 minutes. The reaction was stirred at room temperature for an additional 30 minutes. The resulting mixture was quenched with a dropwise addition of concentrated aqueous hydrochloric acid until gas evolution ceased and a white suspension became a homogenous solution. The solution was diluted with water (100 mL), which resulted in the formation of a white precipitate, and extracted with a 10:1 mixture of CH$_2$Cl$_2$ and MeOH (5×25 mL), dried with MgSO$_4$, concentrated and purified by silica gel column chromatography (MeOH 0-30%/CH$_2$Cl$_2$) to give the title compound as a white solid (640 mg). LCMS ES$^+$ 466.1 [M+1]$^+$.

Step 3: Methyl 3-(1-(2,5-difluoro-4-(((3S,6R)-3-methyl-1,1-dioxido-6-phenyl-1,2-thiazinan-2-yl)methyl)phenyl)-3-hydroxycyclobutyl)-3-oxopropanoate A round-bottom flask was charged with 1-(2,5-difluoro-4-(((3S,6R)-3-methyl-1,1-dioxido-6-phenyl-1,2-thiazinan-2-yl)methyl)phenyl)-3-hydroxycyclobutane-1-carboxylic acid (630 mg, 1.35 mmol) and tetrahydrofuran (10 mL), followed by 1,1'-carbonyldiimidazole (235 mg, 1.42 mmol), and the reaction was stirred at room temperature for 2 hours. Magnesium chloride (148 mg, 1.55 mmol) and potassium 3-methoxy-3-oxopropanoate (248 mg, 1.55 mmol) were added and the reaction was heated to 50° C. and stirred at that temperature for 16 hours. The reaction mixture was then filtered, concentrated on silica gel and purified by silica gel column chromatography (i-PrOAc 0-100%/heptane) to give the title compound as a white solid (241 mg). LCMS ES$^+$ 522.1 [M+1]$^+$.

Step 4: 3-(1-(2,5-Difluoro-4-(((3S,6R)-3-methyl-1,1-dioxido-6-phenyl-1,2-thiazinan-2-yl)methyl)phenyl)-3-hydroxycyclobutyl)-N-hydroxy-3-oxopropanamide A round bottom flask was charged with methyl 3-(1-(2,5-difluoro-4-(((3S,6R)-3-methyl-1,1-dioxido-6-phenyl-1,2-thiazinan-2-yl)methyl)phenyl)-3-hydroxycyclobutyl)-3-oxopropanoate (240 mg, 0.46 mmol) and methanol (3 mL), and the resulting solution was cooled to −30° C. To the cooled solution was added sodium hydroxide (0.25M in MeOH, 2.0 mL) and the reaction was stirred at −30° C. for 10 minutes. To this solution was then added a solution of hydroxylamine hydrochloride (83 mg, 1.15 mmol) in sodium hydroxide (0.25M in MeOH, 4.6 mL) and water (1 mL). The resulting mixture was stirred at −30° C. for 10 minutes and then aged in a freezer at −25° C. for 16 hours. The reaction was diluted with saturated aqueous ammonium chloride (20 mL), extracted with i-PrOAc (3×5 mL) and CH$_2$Cl$_2$ (10 mL), dried with MgSO$_4$, concentrated and purified by silica gel column chromatography (MeOH 0-30%/CH$_2$Cl$_2$) to give the title compound as a white solid (122 mg). LCMS ES$^+$ 523.1 [M+1]$^+$.

Step 5: 5-((1R,3S)-1-(2,5-Difluoro-4-(((3S,6R)-3-methyl-1,1-dioxido-6-phenyl-1,2-thiazinan-2-yl)methyl)phenyl)-3-hydroxycyclobutyl)oxazol-2(3H)-one A solution of 3-(1-(2,5-difluoro-4-(((3S,6R)-3-methyl-1,1-dioxido-6-phenyl-1,2-thiazinan-2-yl)methyl)phenyl)-3-hydroxycyclobutyl)-N-hydroxy-3-oxopropanamide (122 mg, 0.23 mmol) in tetrahydrofuran (2.5 mL) was cooled to 0° C. N,N-Diisopropylethylamine (0.10 mL, 0.58 mmol) was added, followed by 4-nitrobenzenesulfonyl chloride (63 mg, 0.25 mmol) and the reaction was stirred at 0° C. to room temperature for 16 hours. The resulting mixture was quenched with saturated aqueous ammonium chloride (10 mL), extracted with CH$_2$Cl$_2$ (3×5 mL), dried with MgSO$_4$, concentrated and purified by chiral supercritical fluid chromatography to give the title compound as a single diastereomer (12.1 mg).
$^1$H NMR (400 MHz, DMSO-d$_6$) δ 10.37 (s, 1H), 7.49-7.44 (m, 2H), 7.43-7.35 (m, 3H), 7.17 (dd, J=11.0, 6.1 Hz, 1H), 7.07 (dd, J=10.3, 6.3 Hz, 1H), 6.76 (s, 1H), 5.20 (d, J=7.1 Hz, 1H), 4.56 (dd, J=12.6, 3.5 Hz, 1H), 4.50 (d, J=17.9 Hz, 1H), 4.35 (d, J=17.9 Hz, 1H), 4.28-4.06 (m, 2H), 2.97-2.86 (m, 2H), 2.47-2.40 (m, 1H), 2.33-2.23 (m, 2H), 2.15-2.07 (m, 1H), 1.88-1.73 (m, 1H), 1.71-1.62 (m, 1H), 1.12 (d, J=7.0 Hz, 3H); LCMS ES$^+$ 505.2 [M+1]$^+$.

Example 24: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-vinylcyclobutyl)oxazol-2(3H)-one

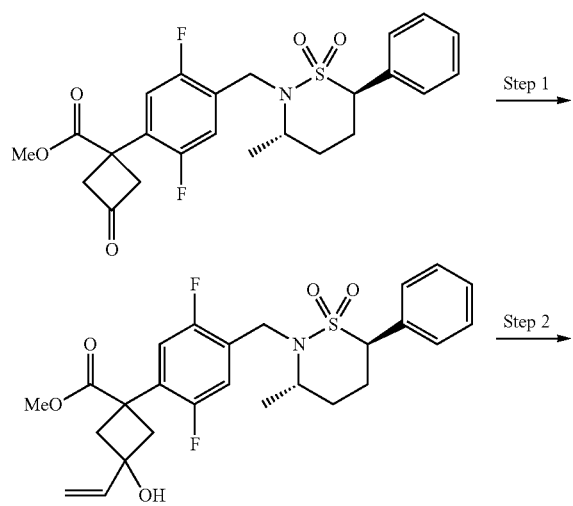

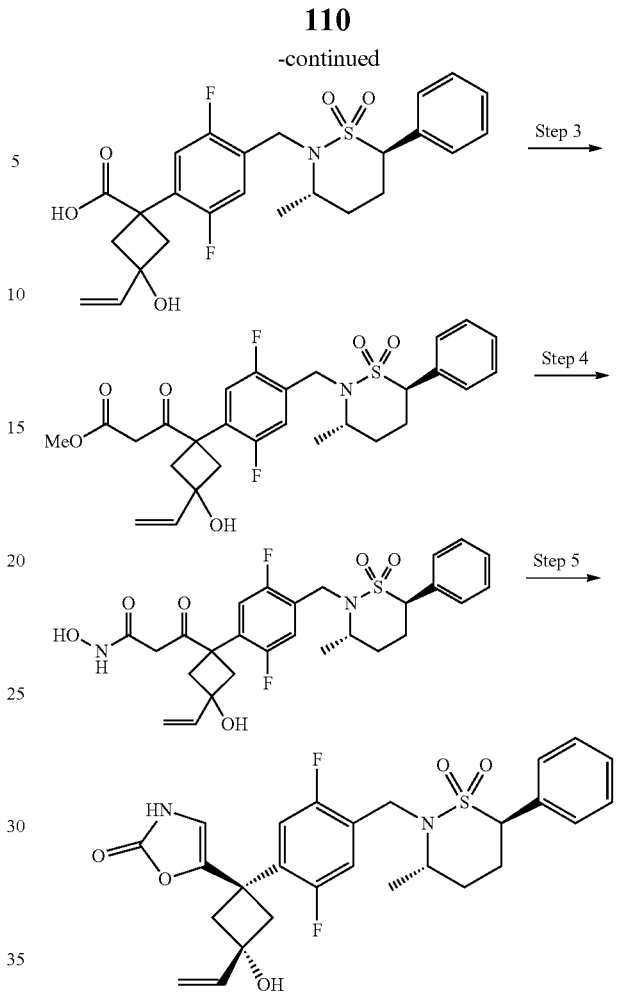

Step 1: Methyl 1-(2,5-difluoro-4-(((3S,6R)-3-methyl-1,1-dioxido-6-phenyl-1,2-thiazinan-2-yl)methyl)phenyl)-3-hydroxy-3-vinylcyclobutane-1-carboxylate A solution of methyl 1-(2,5-difluoro-4-(((3S,6R)-3-methyl-1,1-dioxido-6-phenyl-1,2-thiazinan-2-yl)methyl)phenyl)-3-oxacyclobutane-1-carboxylate (10.0 g, 20.9 mmol) in anisole (300 mL) and tetrahydrofuran (100 mL) was cooled to −30° C. Vinylmagnesium bromide (1.0M in THF, 52 mL) was then added dropwise and the reaction was stirred at −30° C. for 60 minutes. The resulting mixture was quenched with saturated aqueous ammonium chloride (200 mL) and the product was extracted with i-PrOAc (3×50 mL) and CH$_2$Cl$_2$ (50 mL), dried with MgSO$_4$, concentrated and purified by silica gel column chromatography (i-PrOAc 30-60%/heptane) to give the title compound as a white solid (8.3 g). LCMS ES$^+$ 506.1 [M+1]$^+$.

Step 2: 1-(2,5-Difluoro-4-(((3S,6R)-3-methyl-1,1-dioxido-6-phenyl-1,2-thiazinan-2-yl)methyl)phenyl)-3-hydroxy-3-vinylcyclobutane-1-carboxylic Acid To a solution of methyl 1-(2,5-difluoro-4-(((3S,6R)-3-methyl-1,1-dioxido-6-phenyl-1,2-thiazinan-2-yl)methyl)phenyl)-3-hydroxy-3-vinylcyclobutane-1-carboxylate (8.3 g, 16 mmol) in tetrahydrofuran (100 mL) and water (30 mL) was added lithium hydroxide (14.0 g, 330 mmol) and the reaction was stirred at 60° C. for 16 hours. The resulting mixture was diluted with more water (100 mL) and the pH was adjusted to 1 with concentrated aqueous hydrochloric acid. The product was extracted with CH$_2$Cl$_2$ (3×50 mL), dried with MgSO$_4$ and concentrated to give the title compound (8.1 g). LCMS ES$^+$ 592.1 [M+1]$^+$.

Step 3: Methyl 3-(1-(2,5-difluoro-4-(((3S,6R)-3-methyl-1,1-dioxido-6-phenyl-1,2-thiazinan-2-yl) methyl)phenyl)-3-hydroxy-3-vinylcyclobutyl)-3-oxopropanoate A round-bottom flask was charged with 1-(2,5-difluoro-4-(((3S,6R)-3-methyl-1,1-dioxido-6-phenyl-1,2-thiazinan-2-yl)methyl)phenyl)-3-hydroxy-3-vinylcyclobutane-1-carboxylic acid (8.1 g, 16.6 mmol) and tetrahydrofuran (55 mL), followed by 1,1'-carbonyldiimidazole (2.88 g, 17.4 mmol), and the reaction was stirred at room temperature for 5 hours. Magnesium chloride (18.1 g, 19.0 mmol) and potassium 3-methoxy-3-oxopropanoate (3.03 g, 19.0 mmol) were added and the reaction was heated to 50° C. and stirred at that temperature for 16 hours. The reaction mixture was then filtered, concentrated on silica gel and purified by silica gel column chromatography (i-PrOAc 0-100%/heptane) to give the title compound as a white solid (2.59 g). LCMS ES$^+$ 548.1 [M+1]$^+$.

Step 4: 3-(1-(2,5-Difluoro-4-(((3S,6R)-3-methyl-1,1-dioxido-6-phenyl-1,2-thiazinan-2-yl)methyl)phenyl)-3-hydroxy-3-vinylcyclobutyl)-N-hydroxy-3-oxopropanamide A round bottom flask was charged with methyl 3-(1-(2,5-difluoro-4-(((3S,6R)-3-methyl-1,1-dioxido-6-phenyl-1,2-thiazinan-2-yl)methyl)phenyl)-3-hydroxy-3-vinylcyclobutyl)-3-oxopropanoate (2.59 g, 4.73 mmol) and methanol (25 mL), and the resulting solution was cooled to −30° C. To the cooled solution was added sodium hydroxide (0.25M in MeOH, 21 mL) and the reaction was stirred at −30° C. for 10 minutes. To this solution was then added a solution of hydroxylamine hydrochloride (856 mg, 11.8 mmol) in sodium hydroxide (0.25M in MeOH, 47 mL) and water (5 mL). The resulting mixture was stirred at −30° C. for 10 minutes and then aged in a freezer at −25° C. for 16 hours. The reaction was diluted with saturated aqueous ammonium chloride (100 mL), extracted with i-PrOAc (3×20 mL) and CH$_2$Cl$_2$ (50 mL), dried with MgSO$_4$, concentrated and purified by silica gel column chromatography (MeOH 0-30%/CH$_2$Cl$_2$) to give the title compound as a white solid (1.81 g). LCMS ES$^+$ 549.1 [M+1]$^+$.

Step 5: 5-((1R,3S)-1-(2,5-Difluoro-4-(((3S,6R)-3-methyl-1,1-dioxido-6-phenyl-1,2-thiazinan-2-yl) methyl)phenyl)-3-hydroxy-3-vinylcyclobutyl)oxazol-2(3H)-one A solution of 3-(1-(2,5-difluoro-4-(((3S,6R)-3-methyl-1,1-dioxido-6-phenyl-1,2-thiazinan-2-yl)methyl)phenyl)-3-hydroxy-3-vinylcyclobutyl)-N-hydroxy-3-oxopropanamide (1.81 g, 3.30 mmol) in tetrahydrofuran (17 mL) was cooled to 0° C. N,N-Diisopropylethylamine (1.45 mL, 8.25 mmol) was added, followed by 4-nitrobenzenesulfonyl chloride (894 mg, 3.63 mmol) and the reaction was stirred at 0° C. to room temperature for 16 hours. The resulting mixture was quenched with saturated aqueous ammonium chloride (75 mL), extracted with CH$_2$Cl$_2$ (3×25 mL), dried with MgSO$_4$, concentrated and purified by chiral supercritical fluid chromatography to give the title compound as a single diastereomer (829 mg). $^1$H NMR (400 MHz, DMSO-d6) δ 10.38 (s, 1H), 7.51-7.43 (m, 2H), 7.43-7.32 (m, 3H), 7.25-7.09 (m, 2H), 6.75 (s, 1H), 6.03 (dd, J=17.3, 10.7 Hz, 1H), 5.34 (s, 1H), 5.17 (dd, J=17.1, 1.9 Hz, 1H), 4.97 (dd, J=10.6, 1.9 Hz, 1H), 4.62-4.45 (m, 2H), 4.36 (d, J=17.7 Hz, 1H), 4.22-4.02 (m, 1H), 2.96-2.86 (m, 2H), 2.71-2.61 (m, 2H), 2.47-2.37 (m, 1H), 2.18-2.07 (m, 1H), 1.88-1.73 (m, 1H), 1.72-1.60 (m, 1H), 1.13 (d, J=6.9 Hz, 3H); LCMS ES$^+$ 531.2 [M+1]$^+$.

Example 25: 5-((1R,3S)-3-cyclopropyl-1-(2,5-difluoro-4-(((3S,6R)-3-methyl-1,1-dioxido-6-phenyl-1,2-thiazinan-2-yl)methyl)phenyl)-3-hydroxycyclobutyl)oxazol-2(3H)-one

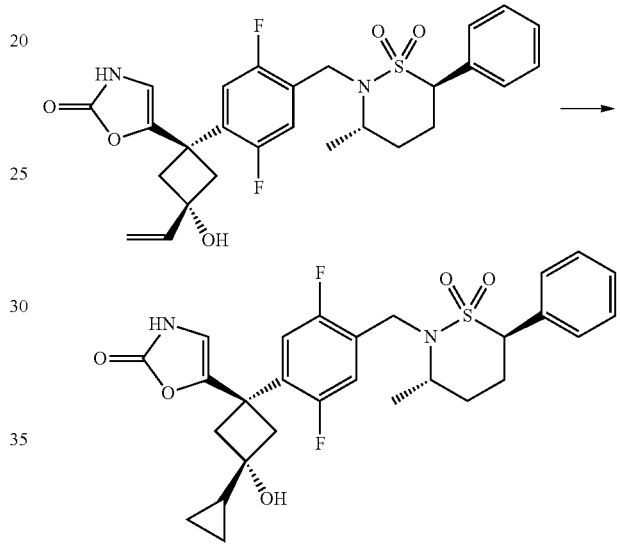

Diethylzinc (1.0 M in hexanes, 7.1 mL, 7.1 mmol) was added to anhydrous CH$_2$Cl$_2$ (10 mL) and the solution was cooled to 0° C. A solution of trifluoroacetic acid (0.55 mL, 7.1 mmol) in CH$_2$Cl$_2$ (10 mL) was added to the diethylzinc solution dropwise and the resulting mixture was stirred at 0° C. for 20 minutes. A solution of diiodomethane (0.58 mL, 7.1 mmol) in CH$_2$Cl$_2$ (10 mL) was then added and the reaction was stirred at 0° C. for an additional 20 minutes. 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-vinylcyclobutyl)oxazol-2(3H)-one (750 mg, 1.41 mmol) was then dissolved in CH$_2$Cl$_2$ (10 mL) and added to the CF$_3$CO$_2$ZnCH$_2$I solution. The resulting solution was stirred at room temperature for 30 minutes, then quenched with saturated aqueous ammonium chloride (75 mL), extracted with CH$_2$Cl$_2$ (3×25 mL), dried with MgSO$_4$, concentrated and purified by reverse phase preparative HPLC (acetonitrile 20-60%/0.1% formic acid in water) to give the title compound as a white solid (301 mg).

$^1$H NMR (400 MHz, DMSO-d6) δ 10.38 (s, 1H), 7.51-7.43 (m, 2H), 7.43-7.31 (m, 3H), 7.23-7.11 (m, 2H), 6.74 (s, 1H), 4.62-4.46 (m, 2H), 4.36 (d, J=17.7 Hz, 1H), 4.23-4.03 (m, 1H), 2.73 (d, J=13.1 Hz, 2H), 2.55 (d, J=12.1 Hz, 2H), 2.45-2.35 (m, 1H), 2.18-2.03 (m, 1H), 1.87-1.71 (m, 1H), 1.71-1.59 (m, 1H), 1.13 (d, J=6.7 Hz, 3H), 1.05 (p, J=6.9 Hz, 1H), 0.35-0.20 (m, 4H); LCMS ES$^+$545.1 [M+1]$^+$.

Example 26: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-(1-methylcyclopropyl)cyclobutyl)oxazol-2(3H)-one

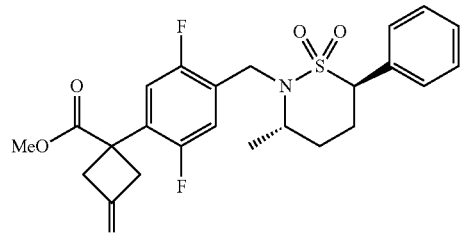

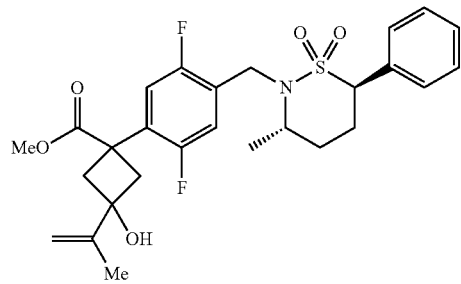

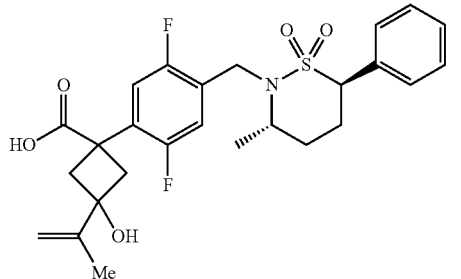

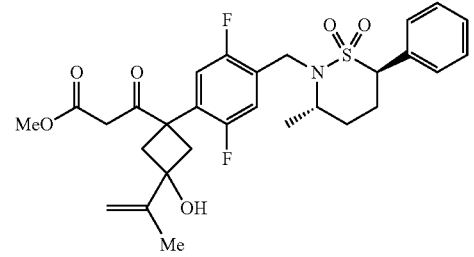

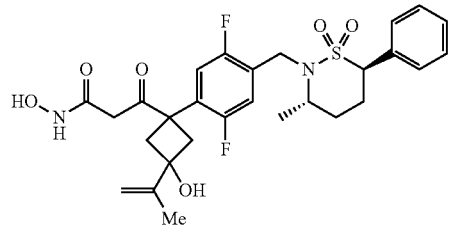

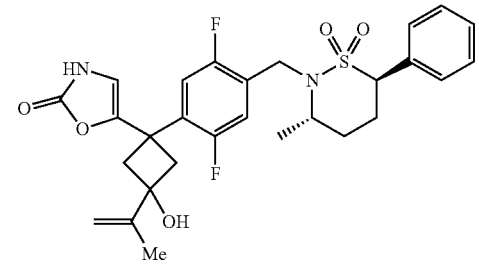

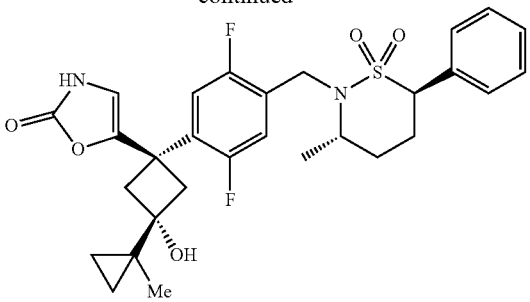

Step 1: Methyl 1-(2,5-difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutane-1-carboxylate A solution of methyl 1-(2,5-difluoro-4-(((3S,6R)-3-methyl-1,1-dioxido-6-phenyl-1,2-thiazinan-2-yl)methyl)phenyl)-3-oxacyclobutane-1-carboxylate (3.62 g, 7.58 mmol) in anisole (100 mL) and tetrahydrofuran (30 mL) was cooled to −30° C. Isopropenylmagnesium bromide (0.55M in THF, 34 mL) was then added dropwise and the reaction was stirred at −30° C. for 60 minutes. The resulting mixture was quenched with saturated aqueous ammonium chloride (200 mL) and the product was extracted with i-PrOAc (3×50 mL) and CH$_2$Cl$_2$ (50 mL), dried with MgSO$_4$, concentrated and purified silica gel column chromatography (i-PrOAc 30-60%/heptane) to give the title compound as a white solid (2.29 g). LCMS ES$^+$ 520.1 [M+1]$^+$.

Step 2: 1-(2,5-Difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutane-1-carboxylic Acid To a solution of methyl 1-(2,5-difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutane-1-carboxylate (2.29 g, 4.41 mmol) in tetrahydrofuran (50 mL) and water (15 mL) was added lithium hydroxide (3.78 g, 88.1 mmol) and the reaction was stirred at 60° C. for 16 hours. The resulting mixture was diluted with more water (100 mL) and the pH was adjusted to 1 with concentrated aqueous hydrochloric acid. The product was extracted with CH$_2$Cl$_2$ (3×50 mL), dried with MgSO$_4$ and concentrated to give the title compound (2.2 g). LCMS ES$^+$ 506.1 [M+1]$^+$.

Step 3: Methyl 3-(1-(2,5-difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutyl)-3-oxopropanoate A round-bottom flask was charged with 1-(2,5-difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutane-1-carboxylic acid (2.2 g, 4.4 mmol) and tetrahydrofuran (50 mL), followed by 1,1'-carbonyldiimidazole (756 mg, 4.6 mmol), and the reaction was stirred at room temperature for 5 hours. Magnesium chloride (476 mg, 5.0 mmol) and potassium 3-methoxy-3-oxopropanoate (797 mg, 5.0 mmol) were added and the reaction was heated to 50° C. and stirred at that temperature for 16 hours. The reaction mixture was then filtered, concentrated on silica gel and purified by silica gel column chromatography (i-PrOAc 0-100%/heptane) to give the title compound as a white solid (890 mg). LCMS ES+ 562.1 [M+1]+.

Step 4: 3-(1-(2,5-Difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutyl)-N-hydroxy-3-oxopropanamide A round bottom flask was charged with methyl 3-(1-(2,5-difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutyl)-3-oxopropanoate (890 mg, 1.58 mmol) and methanol (10 mL), and the resulting solution was cooled to −30° C. To the cooled solution was added sodium hydroxide (0.25M in MeOH, 7.0 mL) and the reaction was stirred at −30° C. for 10 minutes. To this solution was then added a solution of hydroxylamine hydrochloride (287 mg, 3.96 mmol) in sodium hydroxide (0.25M in MeOH, 16 mL) and water (2 mL). The resulting mixture was stirred at −30° C. for 10 minutes and then aged in a freezer at −25° C. for 16 hours. The reaction was diluted with saturated aqueous ammonium chloride (50 mL), extracted with i-PrOAc (3×10 mL) and CH$_2$Cl$_2$ (20 mL), dried with MgSO$_4$, concentrated and purified by silica gel column chromatography (MeOH 0-30%/CH$_2$Cl$_2$) to give the title compound as a white solid (424 mg). LCMS ES+ 563.1 [M+1]+.

Step 5: 5-(1-(2,5-Difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutyl)oxazol-2(3H)-one A solution of 3-(1-(2,5-difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutyl)-N-hydroxy-3-oxopropanamide (424 mg, 0.75 mmol) in tetrahydrofuran (4 mL) was cooled to 0° C. N,N-Diisopropylethylamine (0.33 mL, 1.88 mmol) was added, followed by 4-nitrobenzenesulfonyl chloride (204 mg, 0.83 mmol) and the reaction was stirred at 0° C. to room temperature for 16 hours. The resulting mixture was quenched with saturated aqueous ammonium chloride (50 mL), extracted with CH$_2$Cl$_2$ (3×15 mL), dried with MgSO$_4$, concentrated and purified by silica gel column chromatography (MeOH 0-30%/CH$_2$Cl$_2$) to give the title compound as a white solid (174 mg). LCMS ES+ 545.1 [M+1]+.

Step 6: 5-((1R,3S)-1-(2,5-Difluoro-4-(((3S,6R)-3-methyl-1,1-dioxido-6-phenyl-1,2-thiazinan-2-yl)methyl)phenyl)-3-hydroxy-3-(1-methylcyclopropyl)cyclobutyl)oxazol-2(3H)-one Diethylzinc (1.0 M in hexanes, 1.6 mL, 1.6 mmol) was added to anhydrous CH$_2$Cl$_2$ (2 mL) and the solution was cooled to 0° C. A solution of trifluoroacetic acid (0.12 mL, 1.6 mmol) in CH$_2$Cl$_2$ (2 mL) was added to the diethylzinc solution dropwise and the resulting mixture was stirred at 0° C. for 20 minutes. A solution of diiodomethane (0.13 mL, 1.6 mmol) in CH$_2$Cl$_2$ (2 mL) was then added and the reaction was stirred at 0° C. for an additional 20 minutes. 5-(1-(2,5-Difluoro-4-(((3S,6R)-3-methyl-1,1-dioxido-6-phenyl-1,2-thiazinan-2-yl)methyl)phenyl)-3-hydroxy-3-(prop-1-en-2-yl)cyclobutyl)oxazol-2(3H)-one (174 mg, 0.32 mmol) was then dissolved in CH$_2$Cl$_2$ (2 mL) and added to the CF$_3$CO$_2$ZnCH$_2$I solution. The resulting solution was stirred at room temperature for 30 minutes, then quenched with saturated aqueous ammonium chloride (25 mL), extracted with CH$_2$Cl$_2$ (3×10 mL), dried with MgSO$_4$, concentrated and purified by chiral supercritical fluid chromatography to give the title compound as a single diastereomer (26.3 mg).

1H NMR (400 MHz, DMSO-d6) δ 10.34 (s, 1H), 7.50-7.43 (m, 2H), 7.43-7.30 (m, 3H), 7.25-7.09 (m, 2H), 6.63 (s, 1H), 4.62-4.45 (m, 2H), 4.36 (d, J=17.8 Hz, 1H), 4.21-4.03 (m, 1H), 2.65-2.57 (m, 2H), 2.46-2.37 (m, 3H), 2.15-2.05 (m, 1H), 1.89-1.72 (m, 1H), 1.72-1.61 (m, 1H), 1.13 (d, J=6.7 Hz, 3H), 1.01 (s, 3H), 0.44-0.34 (m, 2H), 0.21-0.13 (m, 2H). LCMS ES+ 559.2 [M+1]+

Compounds of the above examples, together with additional compounds made using the same or similar procedures, are shown in Table 4 together with IC$_{50}$ values for RORc.

TABLE 4

| | Structure | Name | IC$_{50}$ |
|---|---|---|---|
| 1 | 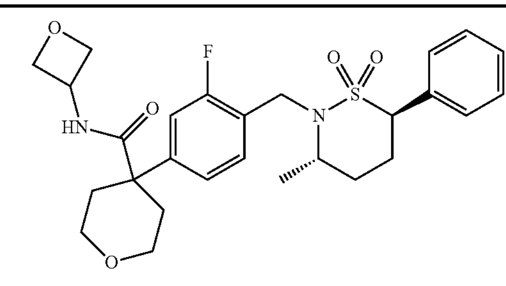 | 4-[3-fluoro-4-[[(3S,6R)-3-methyl-1,1-dioxo-6-phenyl-thiazinan-2-yl]methyl]phenyl]-N-(oxetan-3-yl)tetrahydropyran-4-carboxamide | 0.11 |
| 2 | 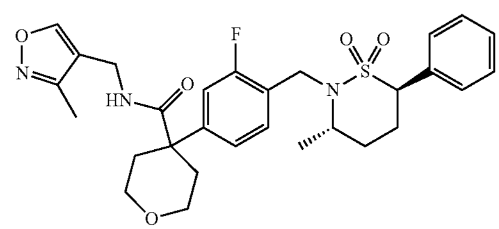 [SMILES: Cc1nocc1CNC(=O)C1(c2ccc(CN3[C@@H](C)CC[C@H](c4ccccc4)S3(=O)=O)c(F)c2)CCOCC1] | 4-[3-fluoro-4-[[(3S,6R)-3-methyl-1,1-dioxo-6-phenyl-thiazinan-2-yl]methyl]phenyl]-N-[(3-methylisoxazol-4-yl)methyl]tetrahydropyran-4-carboxamide | 0.0638 |

TABLE 4-continued

| | Structure | Name | IC$_{50}$ |
|---|---|---|---|
| 3 | 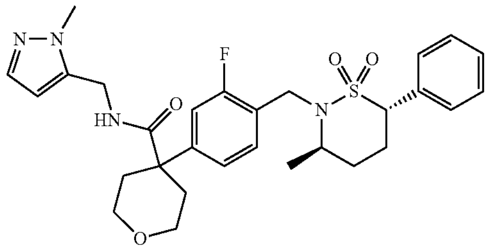 [SMILES: C[C@@H]1CC[C@@H](c2ccccc2)S(=O)(=O)N1Cc1ccc(C2(C(=O)NCc3ccnn3C)CCOCC2)cc1F] | 4-[3-fluoro-4-[[(3S,6R)-3-methyl-1,1-dioxo-6-phenyl-thiazinan-2-yl]methyl]phenyl]-N-[(2-methylpyrazol-3-yl)methyl]tetrahydropyran-4-carboxamide | 0.0582 |
| 4 | 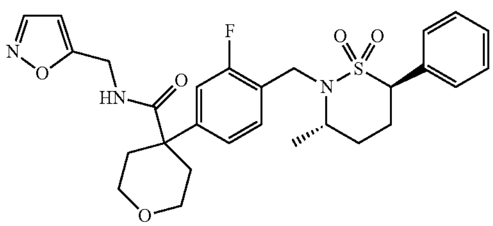 [SMILES: C[C@H]1CC[C@H](c2ccccc2)S(=O)(=O)N1Cc1ccc(C2(C(=O)NCc3ccno3)CCOCC2)cc1F] | 4-[3-fluoro-4-[[(3S,6R)-3-methyl-1,1-dioxo-6-phenyl-thiazinan-2-yl]methyl]phenyl]-N-(isoxazol-5-ylmethyl)tetrahydropyran-4-carboxamide | 0.0757 |
| 5 | 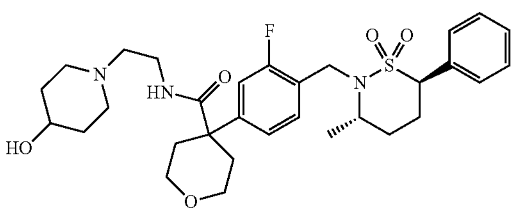 [SMILES: C[C@H]1CC[C@H](c2ccccc2)S(=O)(=O)N1Cc1ccc(C2(C(=O)NCCN3CCC(O)CC3)CCOCC2)cc1F] | 4-[3-fluoro-4-[[(3S,6R)-3-methyl-1,1-dioxo-6-phenyl-thiazinan-2-yl]methyl]phenyl]-N-[2-(4-hydroxy-1-piperidyl)ethyl]tetrahydropyran-4-carboxamide | 1.86 |
| 6 | 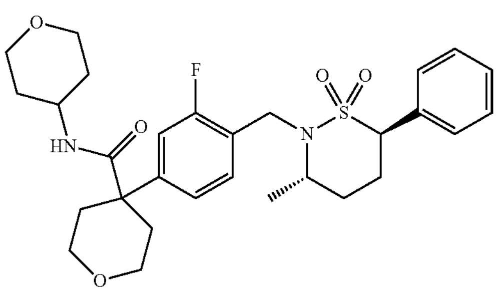 [SMILES: C[C@H]1CC[C@H](c2ccccc2)S(=O)(=O)N1Cc1ccc(C2(C(=O)NC3CCOCC3)CCOCC2)cc1F] | 4-[3-fluoro-4-[[(3S,6R)-3-methyl-1,1-dioxo-6-phenyl-thiazinan-2-yl]methyl]phenyl]-N-tetrahydropyran-4-yl-tetrahydropyran-4-carboxamide | 0.171 |
| 7 | 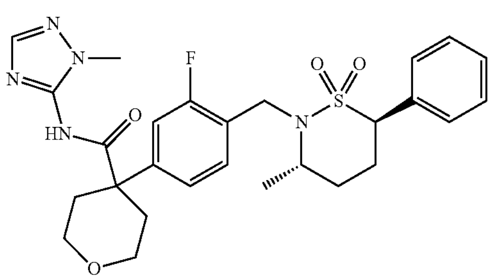 [SMILES: C[C@H]1CC[C@H](c2ccccc2)S(=O)(=O)N1Cc1ccc(C2(C(=O)Nc3ncnn3C)CCOCC2)cc1F] | 4-[3-fluoro-4-[[(3S,6R)-3-methyl-1,1-dioxo-6-phenyl-thiazinan-2-yl]methyl]phenyl]-N-(2-methyl-1,2,4 triazol-3-yl)tetrahydropyran-4-carboxamide | 0.299 |
| 8 | 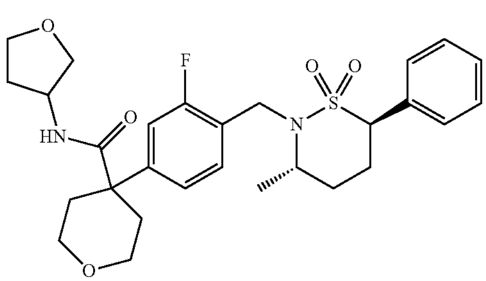 [SMILES: C[C@H]1CC[C@H](c2ccccc2)S(=O)(=O)N1Cc1ccc(C2(C(=O)NC3CCOC3)CCOCC2)cc1F] | 4-[3-fluoro-4-[[(3S,6R)-3-methyl-1,1-dioxo-6-phenyl-thiazinan-2-yl]methyl]phenyl]-N-tetrahydrofuran-3-yl-tetrahydropyran-4-carboxamide | 0.101 |

TABLE 4-continued

| | Structure | Name | IC$_{50}$ |
|---|---|---|---|
| 9 | 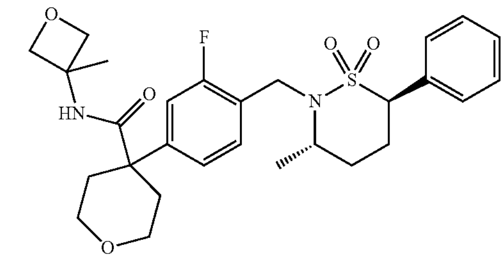 [SMILES: C[C@H]1CC[C@H](c2ccccc2)S(=O)(=O)N1Cc1ccc(C2(C(=O)NC3(C)COC3)CCOCC2)cc1F] | 4-[3-fluoro-4-[[(3S,6R)-3-methyl-1,1-dioxo-6-phenyl-thiazinan-2-yl]methyl]phenyl]-N-(3-methyloxetan-3-yl)tetrahydropyran-4-carboxamide | 0.144 |
| 10 | 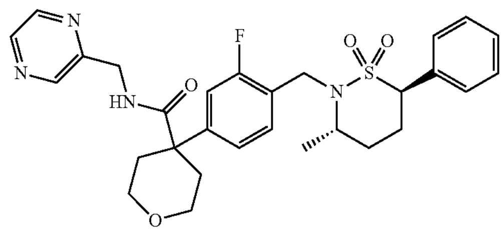 [SMILES: C[C@H]1CC[C@H](c2ccccc2)S(=O)(=O)N1Cc1ccc(C2(C(=O)NCc3cnccn3)CCOCC2)cc1F] | 4-[3-fluoro-4-[[(3S,6R)-3-methyl-1,1-dioxo-6-phenyl-thiazinan-2-yl]methyl]phenyl]-N-(pyrazin-2-ylmethyl)tetrahydropyran-4-carboxamide | 0.173 |
| 11 | 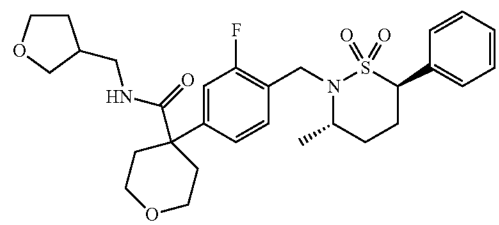 [SMILES: C[C@H]1CC[C@H](c2ccccc2)S(=O)(=O)N1Cc1ccc(C2(C(=O)NCC3CCOC3)CCOCC2)cc1F] | 4-[3-fluoro-4-[[(3S,6R)-3-methyl-1,1-dioxo-6-phenyl-thiazinan-2-yl]methyl]phenyl]-N-(tetrahydrofuran-3-ylmethyl)tetrahydropyran-4-carboxamide | 0.161 |
| 12 | 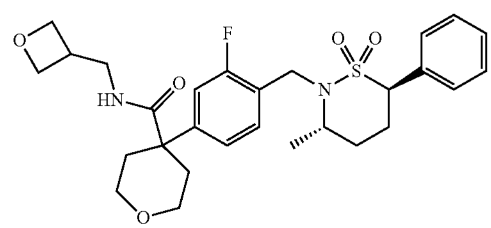 [SMILES: C[C@H]1CC[C@H](c2ccccc2)S(=O)(=O)N1Cc1ccc(C2(C(=O)NCC3COC3)CCOCC2)cc1F] | 4-[3-fluoro-4-[[(3S,6R)-3-methyl-1,1-dioxo-6-phenyl-thiazinan-2-yl]methyl]phenyl]-N-(oxetan-3-ylmethyl)tetrahydropyran-4-carboxamide | 0.0179 |
| 13 | 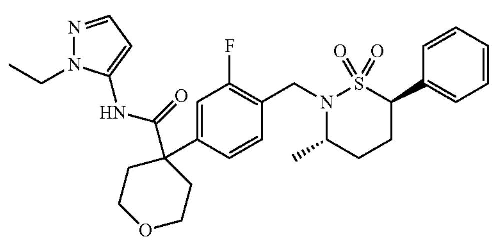 [SMILES: CCn1nccc1NC(=O)C1(c2ccc(CN3[C@@H](C)CC[C@H](c4ccccc4)S3(=O)=O)c(F)c2)CCOCC1] | N-(2-ethylpyrazol-3-yl)-4-[3-fluoro-4-[[(3S,6R)-3-methyl-1,1-dioxo-6-phenyl-thiazinan-2-yl]methyl]phenyl]tetrahydropyran-4-carboxamide | 0.0632 |
| 14 | 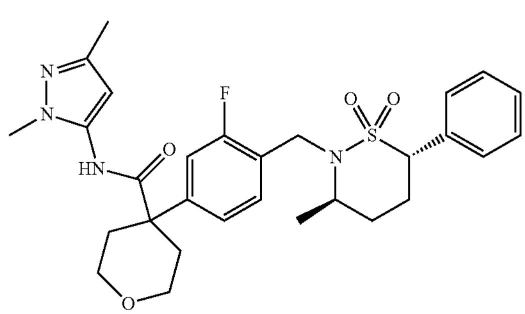 [SMILES: Cc1cc(NC(=O)C2(c3ccc(CN4[C@H](C)CC[C@@H](c5ccccc5)S4(=O)=O)c(F)c3)CCOCC2)n(C)n1] | N-(2,5-dimethylpyrazol-3-yl)-4-[3-fluoro-4-[[(3S,6R)-3-methyl-1,1-dioxo-6-phenyl-thiazinan-2-yl]methyl]phenyl]tetrahydropyran-4-carboxamide | 0.0636 |

TABLE 4-continued

| | Structure | Name | IC$_{50}$ |
|---|---|---|---|
| 15 | 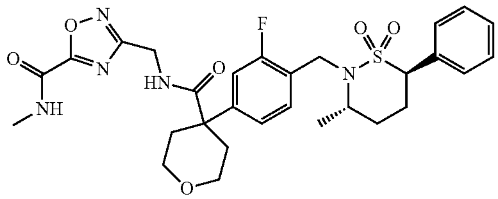 [SMILES: CNC(=O)c1nc(CNC(=O)C2(c3ccc(CN4[C@@H](C)CC[C@H](c5ccccc5)S4(=O)=O)c(F)c3)CCOCC2)no1] | 3-[[[4-[3-fluoro-4-[[(3S,6R)-3-methyl-1,1-dioxo-6-phenyl-thiazinan-2-yl]methyl]phenyl]tetrahydropyran-4-carbonyl]amino]methyl]-N-methyl-1,2,4-oxadiazole-5-carboxamide | 0.0094 |
| 16 | 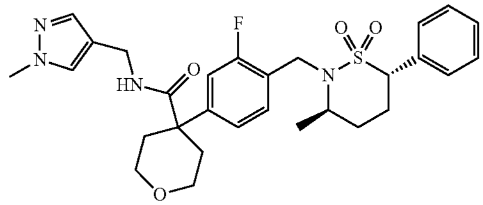 [SMILES: C[C@@H]1CC[C@@H](c2ccccc2)S(=O)(=O)N1Cc1ccc(C2(C(=O)NCc3cnn(C)c3)CCOCC2)cc1F] | 4-[3-fluoro-4-[[(3S,6R)-3-methyl-1,1-dioxo-6-phenyl-thiazinan-2-yl]methyl]phenyl]-N-[(1-methylpyrazol-4-yl)methyl]tetrahydropyran-4-carboxamide | 0.0454 |
| 17 | 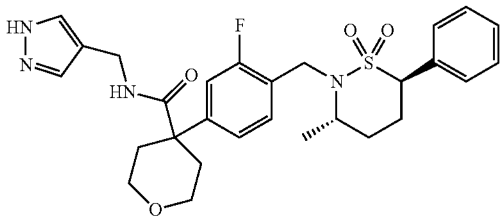 [SMILES: C[C@H]1CC[C@H](c2ccccc2)S(=O)(=O)N1Cc1ccc(C2(C(=O)NCc3cn[nH]c3)CCOCC2)cc1F] | 4-[3-fluoro-4-[[(3S,6R)-3-methyl-1,1-dioxo-6-phenyl-thiazinan-2-yl]methyl]phenyl]-N-(1H-pyrazol-4-ylmethyl)tetrahydropyran-4-carboxamide | 0.0325 |
| 18 | 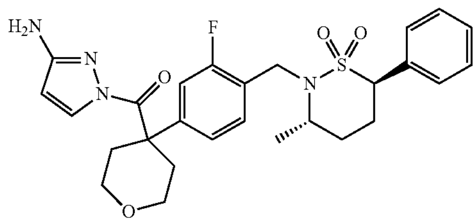 [SMILES: C[C@H]1CC[C@H](c2ccccc2)S(=O)(=O)N1Cc1ccc(C2(C(=O)n3ccc(N)n3)CCOCC2)cc1F] | (3-aminopyrazol-1-yl)-[4-[3-fluoro-4-[[(3S,6R)-3-methyl-1,1-dioxo-6-phenyl-thiazinan-2-yl]methyl]phenyl]tetrahydropyran-4-yl]methanone | 0.0079 |
| 19 | 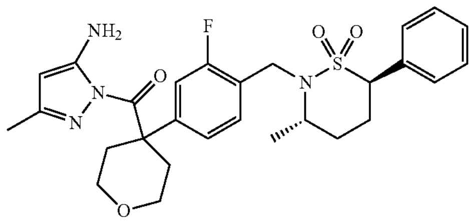 [SMILES: Cc1cc(N)n(C(=O)C2(c3ccc(CN4[C@@H](C)CC[C@H](c5ccccc5)S4(=O)=O)c(F)c3)CCOCC2)n1] | (5-amino-3-methyl-pyrazol-1-yl)-[4-[3-fluoro-4-[[(3S,6R)-3-methyl-1,1-dioxo-6-phenyl-thiazinan-2-yl]methyl]phenyl]tetrahydropyran-4-yl]methanone | 0.0123 |
| 20 | 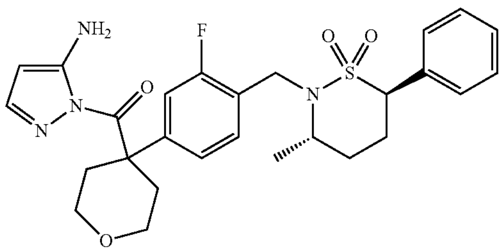 [SMILES: C[C@H]1CC[C@H](c2ccccc2)S(=O)(=O)N1Cc1ccc(C2(C(=O)n3nccc3N)CCOCC2)cc1F] | (5-aminopyrazol-1-yl)-[4-[3-fluoro-4-[[(3S,6R)-3-methyl-1,1-dioxo-6-phenyl-thiazinan-2-yl]methyl]phenyl]tetrahydropyran-4-yl]methanone | 0.0196 |
| 21 | 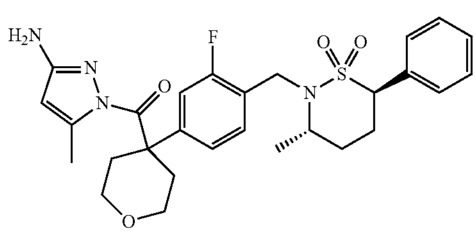 [SMILES: Cc1cc(N)nn1C(=O)C1(c2ccc(CN3[C@@H](C)CC[C@H](c4ccccc4)S3(=O)=O)c(F)c2)CCOCC1] | (3-amino-5-methyl-pyrazol-1-yl)-[4-[3-fluoro-4-[[(3S,6R)-3-methyl-1,1-dioxo-6-phenyl-thiazinan-2-yl]methyl]phenyl]tetrahydropyran-4-yl]methanone | 0.0019 |

TABLE 4-continued

| | Structure | Name | IC$_{50}$ |
|---|---|---|---|
| 22 | 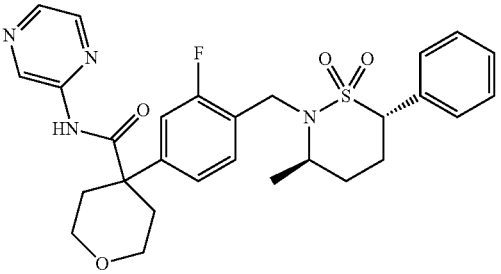 [SMILES: C[C@@H]1CC[C@@H](c2ccccc2)S(=O)(=O)N1Cc1ccc(C2(C(=O)Nc3cnccn3)CCOCC2)cc1F] | 4-[3-fluoro-4-[[(3S,6R)-3-methyl-1,1-dioxo-6-phenyl-thiazinan-2-yl]methyl]phenyl]-N-pyrazin-2-yl-tetrahydropyran-4-carboxamide | 0.0289 |
| 23 | 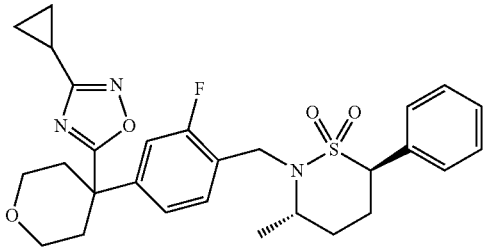 [SMILES: C[C@H]1CC[C@H](c2ccccc2)S(=O)(=O)N1Cc1ccc(C2(c3nc(C4CC4)no3)CCOCC2)cc1F] | (3S,6R)-2-[[4-[4-(3-cyclopropyl-1,2,4-oxadiazol-5-yl)tetrahydropyran-4-yl]-2-fluoro-phenyl]methyl]-3-methyl-6-phenyl-thiazinane 1,1-dioxide | 0.0143 |
| 24 | 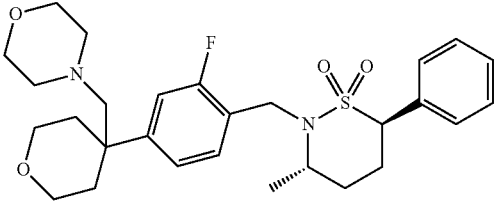 [SMILES: C[C@H]1CC[C@H](c2ccccc2)S(=O)(=O)N1Cc1ccc(C2(CN3CCOCC3)CCOCC2)cc1F] | (3S,6R)-2-[[2-fluoro-4-[4-(morpholinomethyl)tetrahydropyran-4-yl]phenyl]methyl]-3-methyl-6-phenyl-thiazinane 1,1-dioxide | 0.0111 |
| 25 | 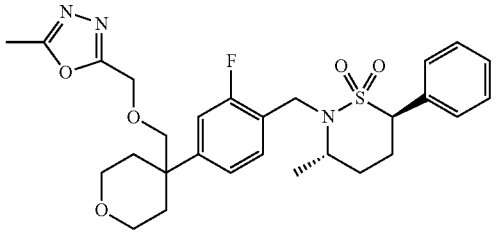 [SMILES: Cc1nnc(COCC2(c3ccc(CN4[C@@H](C)CC[C@H](c5ccccc5)S4(=O)=O)c(F)c3)CCOCC2)o1] | (3S,6R)-2-[[2-fluoro-4-[4-[(5-methyl-1,3,4-oxadiazol-2-yl)methoxymethyl]tetrahydropyran-4-yl]phenyl]methyl]-3-methyl-6-phenyl-thiazinane 1,1-dioxide | 0.0903 |
| 26 | 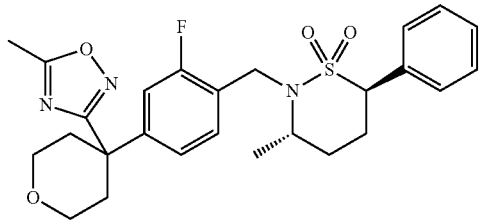 [SMILES: Cc1nc(C2(c3ccc(CN4[C@@H](C)CC[C@H](c5ccccc5)S4(=O)=O)c(F)c3)CCOCC2)no1] | (3S,6R)-2-[[2-fluoro-4-[4-(5-methyl-1,2,4-oxadiazol-3-yl)tetrahydropyran-4-yl]phenyl]methyl]-3-methyl-6-phenyl-thiazinane 1,1-dioxide | 0.0395 |
| 27 | 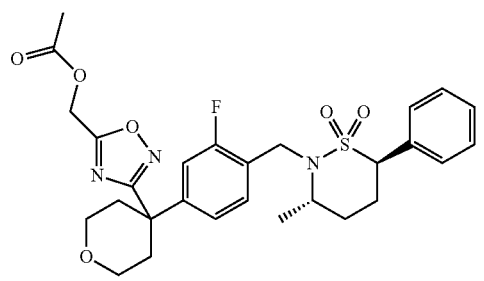 [SMILES: CC(=O)OCc1nc(C2(c3ccc(CN4[C@@H](C)CC[C@H](c5ccccc5)S4(=O)=O)c(F)c3)CCOCC2)no1] | [3-[4-[3-fluoro-4-[[(3S,6R)-3-methyl-1,1-dioxo-6-phenyl-thiazinan-2-yl]methyl]phenyl]tetrahydropyran-4-yl]-1,2,4-oxadiazol-5-yl]methyl acetate | 0.109 |

TABLE 4-continued

| | Structure | Name | IC$_{50}$ |
|---|---|---|---|
| 28 | 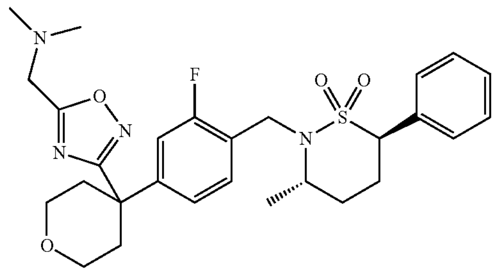 [SMILES: C[C@H]1CC[C@H](c2ccccc2)S(=O)(=O)N1Cc1ccc(C2(c3noc(CN(C)C)n3)CCOCC2)cc1F] | 1-[3-[4-[3-fluoro-4-[[(3S,6R)-3-methyl-1,1-dioxo-6-phenyl-thiazinan-2-yl]methyl]phenyl]tetrahydropyran-4-yl]-1,2,4-oxadiazol-5-yl]-N,N-dimethyl-methanamine | 0.465 |
| 29 | 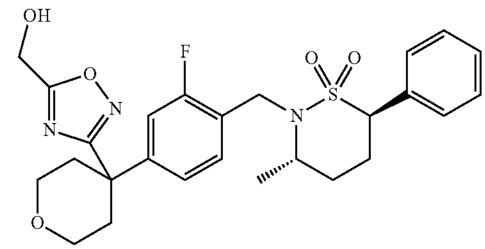 [SMILES: C[C@H]1CC[C@H](c2ccccc2)S(=O)(=O)N1Cc1ccc(C2(c3noc(CO)n3)CCOCC2)cc1F] | [3-[4-[3-fluoro-4-[[(3S,6R)-3-methyl-1,1-dioxo-6-phenyl-thiazinan-2-yl]methyl]phenyl]tetrahydropyran-4-yl]-1,2,4-oxadiazol-5-yl]methanol | 0.0636 |
| 30 | 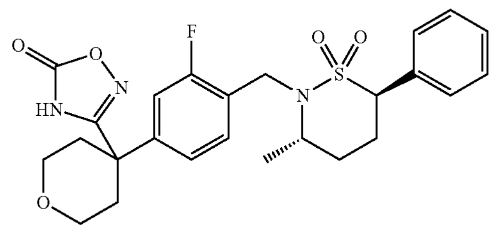 [SMILES: C[C@H]1CC[C@H](c2ccccc2)S(=O)(=O)N1Cc1ccc(C2(c3noc(=O)[nH]3)CCOCC2)cc1F] | 3-[4-[3-fluoro-4-[[(3S,6R)-3-methyl-1,1-dioxo-6-phenyl-thiazinan-2-yl]methyl]phenyl]tetrahydropyran-4-yl]-4H-1,2,4-oxadiazol-5-one | 0.245 |
| 31 | 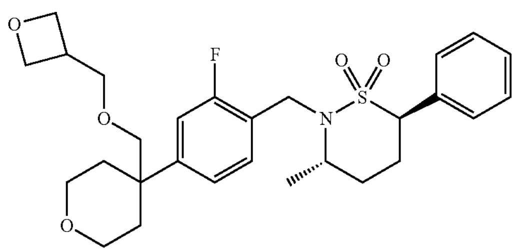 [SMILES: C[C@H]1CC[C@H](c2ccccc2)S(=O)(=O)N1Cc1ccc(C2(COCC3COC3)CCOCC2)cc1F] | (3S,6R)-2-[[2-fluoro-4-[4-(oxetan-3-ylmethoxymethyl)tetrahydropyran-4-yl]phenyl]methyl]-3-methyl-6-phenyl-thiazinane 1,1-dioxide | 0.0445 |
| 32 | 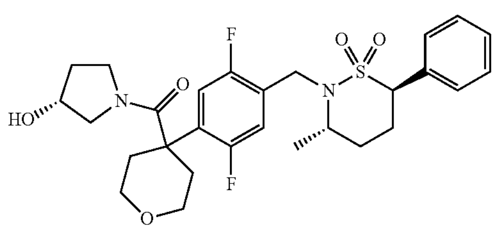 [SMILES: C[C@H]1CC[C@H](c2ccccc2)S(=O)(=O)N1Cc1cc(F)c(C2(C(=O)N3CC[C@@H](O)C3)CCOCC2)cc1F] | [4-[2,5-difluoro-4-[[(3S,6R)-3-methyl-1,1-dioxo-6-phenyl-thiazinan-2-yl]methyl]phenyl]tetrahydropyran-4-yl]-[(3R)-3-hydroxypyrrolidin-1-yl]methanone | 0.079 |
| 33 | 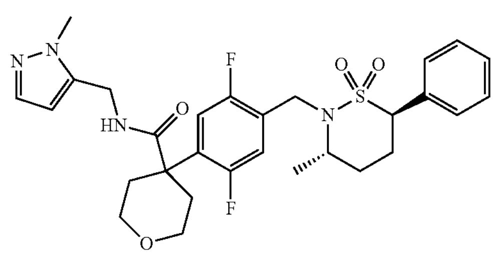 [SMILES: C[C@H]1CC[C@H](c2ccccc2)S(=O)(=O)N1Cc1cc(F)c(C2(C(=O)NCc3ccnn3C)CCOCC2)cc1F] | 4-[2,5-difluoro-4-[[(3S,6R)-3-methyl-1,1-dioxo-6-phenyl-thiazinan-2-yl]methyl]phenyl]-N-[(2-methylpyrazol-3-yl)methyl]tetrahydropyran-4-carboxamide | 0.0234 |

TABLE 4-continued

| | Structure | Name | IC$_{50}$ |
|---|---|---|---|
| 34 | 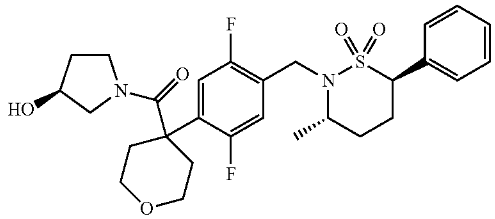 [SMILES: C[C@H]1CC[C@H](c2ccccc2)S(=O)(=O)N1Cc1cc(F)c(C2(C(=O)N3CC[C@H](O)C3)CCOCC2)cc1F] | [4-[2,5-difluoro-4-[[(3S,6R)-3-methyl-1,1-dioxo-6-phenyl-thiazinan-2-yl]methyl]phenyl]tetrahydropyran-4-yl]-[(3S)-3-hydroxypyrrolidin-1-yl]methanone | 0.0985 |
| 35 | 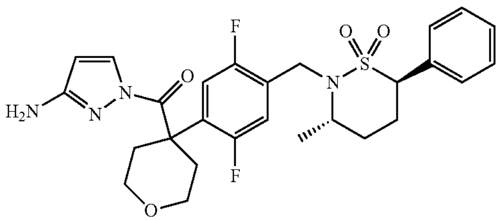 [SMILES: C[C@H]1CC[C@H](c2ccccc2)S(=O)(=O)N1Cc1cc(F)c(C2(C(=O)n3ccc(N)n3)CCOCC2)cc1F] | (3-aminopyrazol-1-yl)-[4-[2,5-difluoro-4-[[(3S,6R)-3-methyl-1,1-dioxo-6-phenyl-thiazinan-2-yl]methyl]phenyl]tetrahydropyran-4-yl]methanone | 0.010 |
| 346 | 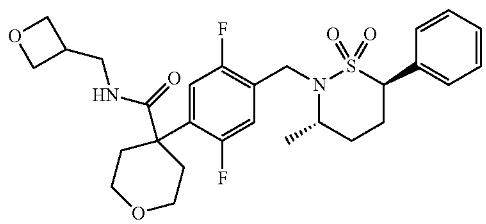 | 4-[2,5-difluoro-4-[[(3S,6R)-3-methyl-1,1-dioxo-6-phenyl-thiazinan-2-yl]methyl]phenyl]-N-(oxetan-3-ylmethyl)tetrahydropyran-4-carboxamide | 0.0474 |
| 37 | 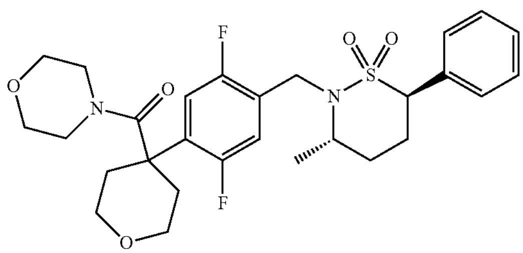 [SMILES: C[C@H]1CC[C@H](c2ccccc2)S(=O)(=O)N1Cc1cc(F)c(C2(C(=O)N3CCOCC3)CCOCC2)cc1F] | [4-[2,5-difluoro-4-[[(3S,6R)-3-methyl-1,1-dioxo-6-phenyl-thiazinan-2-yl]methyl]phenyl]tetrahydropyran-4-yl]-morpholino-methanone | 0.106 |
| 38 | 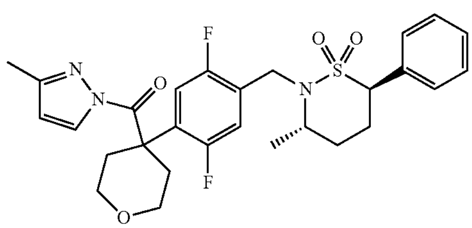 [SMILES: Cc1ccn(C(=O)C2(c3cc(F)c(CN4[C@@H](C)CC[C@H](c5ccccc5)S4(=O)=O)cc3F)CCOCC2)n1] | [4-[2,5-difluoro-4-[[(3S,6R)-3-methyl-1,1-dioxo-6-phenyl-thiazinan-2-yl]methyl]phenyl]tetrahydropyran-4-yl]-(3-methylpyrazol-1-yl)methanone | 0.035 |
| 39 | 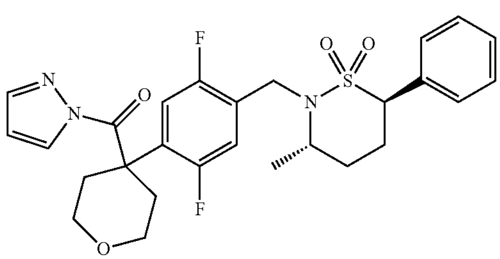 [SMILES: C[C@H]1CC[C@H](c2ccccc2)S(=O)(=O)N1Cc1cc(F)c(C2(C(=O)n3cccn3)CCOCC2)cc1F] | [4-[2,5-difluoro-4-[[(3S,6R)-3-methyl-1,1-dioxo-6-phenyl-thiazinan-2-yl]methyl]phenyl]tetrahydropyran-4-yl]-pyrazol-1-yl-methanone | 0.0273 |

TABLE 4-continued

| | Structure | Name | IC$_{50}$ |
|---|---|---|---|
| 40 | 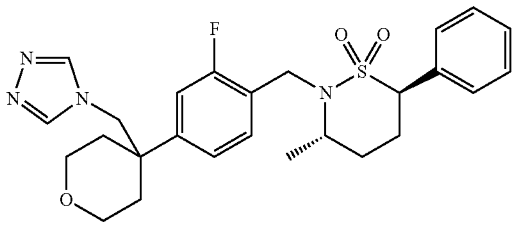 [SMILES: C[C@H]1CC[C@H](c2ccccc2)S(=O)(=O)N1Cc1ccc(C2(Cn3cnnc3)CCOCC2)cc1F] | (3S,6R)-2-[[2-fluoro-4-[4-(1,2,4-triazol-4-ylmethyl)tetrahydropyran-4-yl]phenyl]methyl]-3-methyl-6-phenyl-thiazinane 1,1-dioxide | 0.118 |
| 41 | 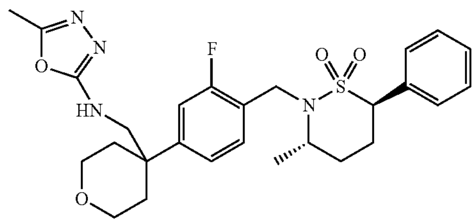 [SMILES: Cc1nnc(NCC2(c3ccc(CN4[C@@H](C)CC[C@H](c5ccccc5)S4(=O)=O)c(F)c3)CCOCC2)o1] | N-[[4-[3-fluoro-4-[[(3S,6R)-3-methyl-1,1-dioxo-6-phenyl-thiazinan-2-yl]methyl]phenyl]tetrahydropyran-4-yl]methyl]-5-methyl-1,3,4-oxadiazol-2-amine | 0.0418 |
| 42 | 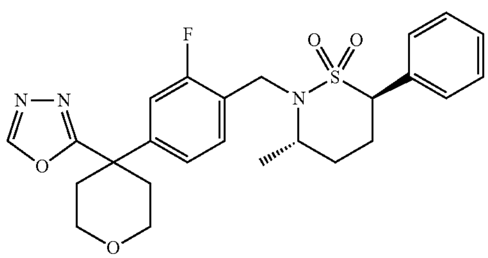 [SMILES: C[C@H]1CC[C@H](c2ccccc2)S(=O)(=O)N1Cc1ccc(C2(c3nnco3)CCOCC2)cc1F] | (3S,6R)-2-[[2-fluoro-4-[4-(1,3,4-oxadiazol-2-yl)tetrahydropyran-4-yl]phenyl]methyl]-3-methyl-6-phenyl-thiazinane 1,1-dioxide | 0.0546 |
| 43 | 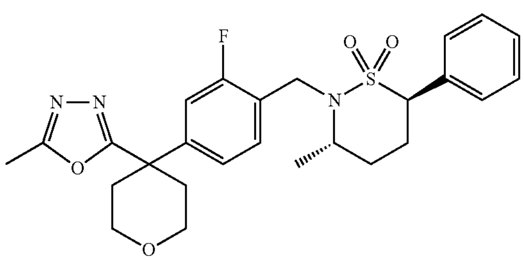 [SMILES: Cc1nnc(C2(c3ccc(CN4[C@@H](C)CC[C@H](c5ccccc5)S4(=O)=O)c(F)c3)CCOCC2)o1] | (3S,6R)-2-[[2-fluoro-4-[4-(5-methyl-1,3,4-oxadiazol-2-yl)tetrahydropyran-4-yl]phenyl]methyl]-3-methyl-6-phenyl-thiazinane 1,1-dioxide | 0.142 |
| 44 | 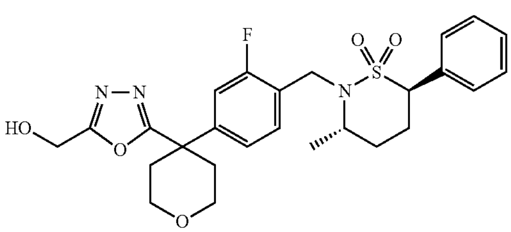 [SMILES: C[C@H]1CC[C@H](c2ccccc2)S(=O)(=O)N1Cc1ccc(C2(c3nnc(CO)o3)CCOCC2)cc1F] | [5-[4-[3-fluoro-4-[[(3S,6R)-3-methyl-1,1-dioxo-6-phenyl-thiazinan-2-yl]methyl]phenyl]tetrahydropyran-4-yl]-1,3,4-oxadiazol-2-yl]methanol | 0.102 |
| 45 | 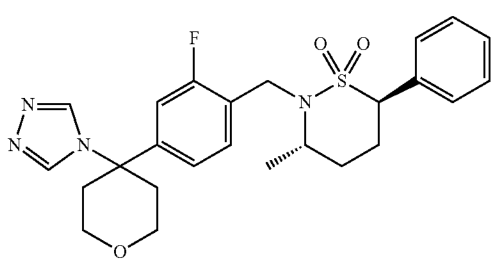 [SMILES: C[C@H]1CC[C@H](c2ccccc2)S(=O)(=O)N1Cc1ccc(C2(n3cnnc3)CCOCC2)cc1F] | (3S,6R)-2-[[2-fluoro-4-[4-(1,2,4-triazol-4-yl)tetrahydropyran-4-yl]phenyl]methyl]-3-methyl-6-phenyl-thiazinane 1,1-dioxide | 0.0877 |

TABLE 4-continued

| | Structure | Name | IC$_{50}$ |
|---|---|---|---|
| 46 | 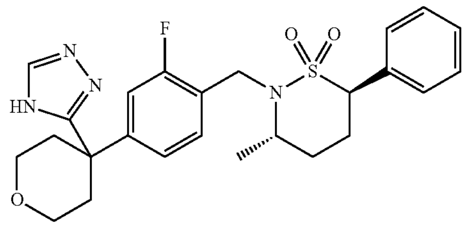 [SMILES: C[C@H]1CC[C@H](c2ccccc2)S(=O)(=O)N1Cc1ccc(C2(c3nnc[nH]3)CCOCC2)cc1F] | (3S,6R)-2-[[2-fluoro-4-[4-(4H-1,2,4-triazol-3-yl)tetrahydropyran-4-yl]phenyl]methyl]-3-methyl-6-phenyl-thiazinane 1,1-dioxide | 0.0266 |
| 47 | 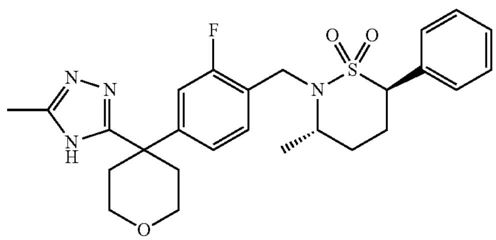 [SMILES: Cc1nnc(C2(c3ccc(CN4[C@@H](C)CC[C@H](c5ccccc5)S4(=O)=O)c(F)c3)CCOCC2)[nH]1] | (3S,6R)-2-[[2-fluoro-4-[4-(5-methyl-4H-1,2,4-triazol-3-yl)tetrahydropyran-4-yl]phenyl]methyl]-3-methyl-6-phenyl-thiazinane 1,1-dioxide | 0.114 |
| 48 | 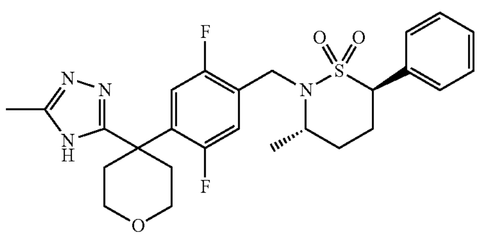 [SMILES: Cc1nnc(C2(c3cc(F)c(CN4[C@@H](C)CC[C@H](c5ccccc5)S4(=O)=O)cc3F)CCOCC2)[nH]1] | (3S,6R)-2-[[2,5-difluoro-4-[4-(5-methyl-4H-1,2,4-triazol-3-yl)tetrahydropyran-4-yl]phenyl]methyl]-3-methyl-6-phenyl-thiazinane 1,1-dioxide | 0.0216 |
| 49 | 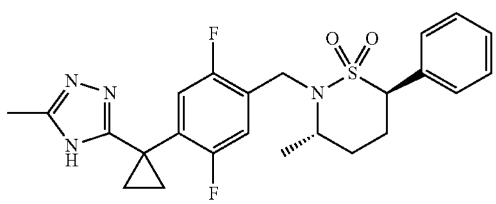 [SMILES: Cc1nnc(C2(c3cc(F)c(CN4[C@@H](C)CC[C@H](c5ccccc5)S4(=O)=O)cc3F)CC2)[nH]1] | (3S,6R)-2-[[2,5-difluoro-4-[1-(5-methyl-4H-1,2,4-triazol-3-yl)cyclopropyl]phenyl]methyl]-3-methyl-6-phenyl-thiazinane 1,1-dioxide | 0.0404 |
| 50 | 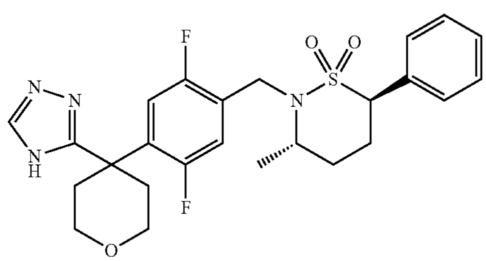 [SMILES: C[C@H]1CC[C@H](c2ccccc2)S(=O)(=O)N1Cc1cc(F)c(C2(c3nnc[nH]3)CCOCC2)cc1F] | (3S,6R)-2-[[2,5-difluoro-4-[4-(4H-1,2,4-triazol-3-yl)tetrahydropyran-4-yl]phenyl]methyl]-3-methyl-6-phenyl-thiazinane 1,1-dioxide | 0.0286 |
| 51 | 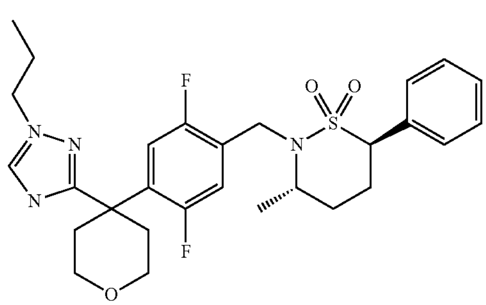 | (3S,6R)-2-[[2,5-difluoro-4-[4-(1-propyl-1,2,4-triazol-3-yl)tetrahydropyran-4-yl]phenyl]methyl]-3-methyl-6-phenyl-thiazinane 1,1-dioxide | 0.026 |

TABLE 4-continued

| | Structure | Name | IC$_{50}$ |
|---|---|---|---|
| 52 | 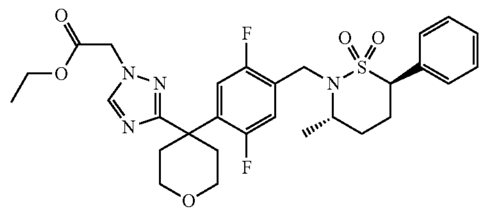 [SMILES: CCOC(=O)Cn1cnc(C2(c3cc(F)c(CN4[C@@H](C)CC[C@H](c5ccccc5)S4(=O)=O)cc3F)CCOCC2)n1] | ethyl 2-[3-[4-[2,5-difluoro-4-[[(3S,6R)-3-methyl-1,1-dioxo-6-phenyl-thiazinan-2-yl]methyl]phenyl]tetrahydropyran-4-yl]-1,2,4-triazol-1-yl]acetate | 0.071 |
| 53 | 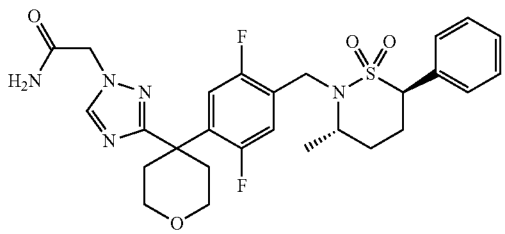 [SMILES: C[C@H]1CC[C@H](c2ccccc2)S(=O)(=O)N1Cc1cc(F)c(C2(c3ncn(CC(N)=O)n3)CCOCC2)cc1F] | 2-[3-[4-[2,5-difluoro-4-[[(3S,6R)-3-methyl-1,1-dioxo-6-phenyl-thiazinan-2-yl]methyl]phenyl]tetrahydropyran-4-yl]-1,2,4-triazol-1-yl]acetamide | 0.103 |
| 54 | 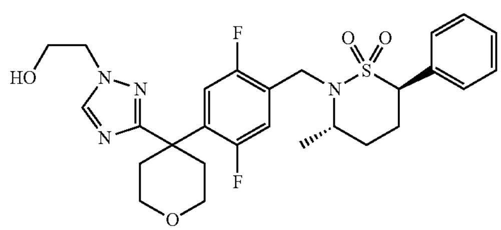 [SMILES: C[C@H]1CC[C@H](c2ccccc2)S(=O)(=O)N1Cc1cc(F)c(C2(c3ncn(CCO)n3)CCOCC2)cc1F] | 2-[3-[4-[2,5-difluoro-4-[[(3S,6R)-3-methyl-1,1-dioxo-6-phenyl-thiazinan-2-yl]methyl]phenyl]tetrahydropyran-4-yl]-1,2,4-triazol-1-yl]ethanol | 0.057 |
| 55 | 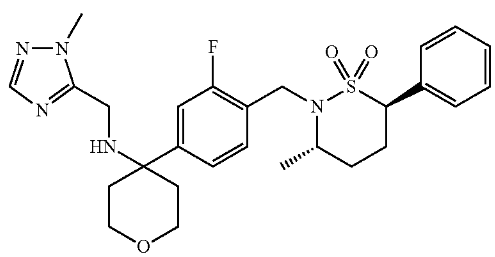 [SMILES: C[C@H]1CC[C@H](c2ccccc2)S(=O)(=O)N1Cc1ccc(C2(NCc3ncnn3C)CCOCC2)cc1F] | 4-[3-fluoro-4-[[(3S,6R)-3-methyl-1,1-dioxo-6-phenyl-thiazinan-2-yl]methyl]phenyl]-N-[(2-methyl-1,2,4-triazol-3-yl)methyl]tetrahydropyran-4-amine | 0.0107 |
| 56 | 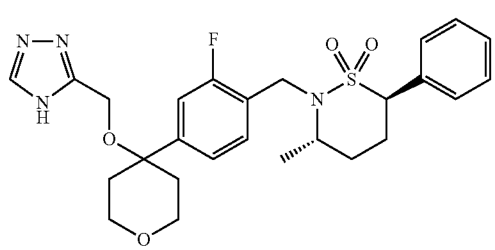 [SMILES: C[C@H]1CC[C@H](c2ccccc2)S(=O)(=O)N1Cc1ccc(C2(OCc3nnc[nH]3)CCOCC2)cc1F] | (3S,6R)-2-[[2-fluoro-4-[4-(4H-1,2,4-triazol-3-ylmethoxy)tetrahydropyran-4-yl]phenyl]methyl]-3-methyl-6-phenyl-thiazinane 1,1-dioxide | 0.0072 |
| 57 | 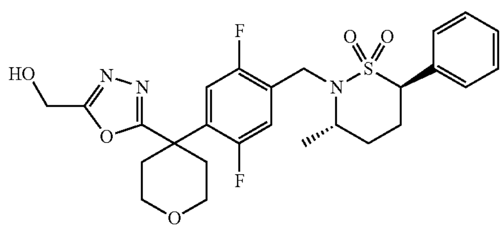 [SMILES: C[C@H]1CC[C@H](c2ccccc2)S(=O)(=O)N1Cc1cc(F)c(C2(c3nnc(CO)o3)CCOCC2)cc1F] | [5-[4-[2,5-difluoro-4-[[(3S,6R)-3-methyl-1,1-dioxo-6-phenyl-thiazinan-2-yl]methyl]phenyl]tetrahydropyran-4-yl]-1,3,4-oxadiazol-2-yl]methanol | 0.0282 |

TABLE 4-continued

| | Structure | Name | IC$_{50}$ |
|---|---|---|---|
| 58 | 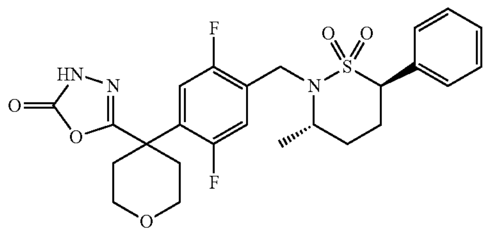 [SMILES: C[C@H]1CC[C@H](c2ccccc2)S(=O)(=O)N1Cc1cc(F)c(C2(c3n[nH]c(=O)o3)CCOCC2)cc1F] | 5-[4-[2,5-difluoro-4-[[(3S,6R)-3-methyl-1,1-dioxo-6-phenyl-thiazinan-2-yl]methyl]phenyl]tetrahydropyran-4-yl]-3H-1,3,4-oxadiazol-2-one | 0.0066 |
| 59 | 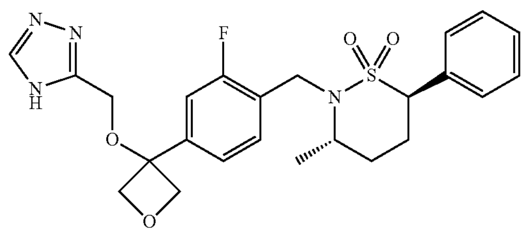 [SMILES: C[C@H]1CC[C@H](c2ccccc2)S(=O)(=O)N1Cc1ccc(C2(OCc3nnc[nH]3)COC2)cc1F] | (3S,6R)-2-[[2-fluoro-4-[3-(4H-1,2,4-triazol-3-ylmethoxy)oxetan-3-yl]phenyl]methyl]-3-methyl-6-phenyl-thiazinane 1,1-dioxide | 0.0232 |
| 60 | 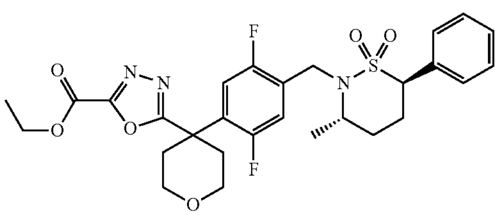 [SMILES: CCOC(=O)c1nnc(C2(c3cc(F)c(CN4[C@@H](C)CC[C@H](c5ccccc5)S4(=O)=O)cc3F)CCOCC2)o1] | ethyl 5-[4-[2,5-difluoro-4-[[(3S,6R)-3-methyl-1,1-dioxo-6-phenyl-thiazinan-2-yl]methyl]phenyl]tetrahydropyran-4-yl]-1,3,4-oxadiazole-2-carboxylate | 0.0042 |
| 61 | 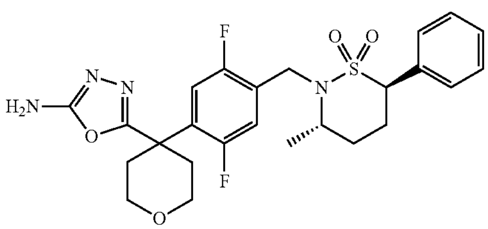 [SMILES: C[C@H]1CC[C@H](c2ccccc2)S(=O)(=O)N1Cc1cc(F)c(C2(c3nnc(N)o3)CCOCC2)cc1F] | 5-[4-[2,5-difluoro-4-[[(3S,6R)-3-methyl-1,1-dioxo-6-phenyl-thiazinan-2-yl]methyl]phenyl]tetrahydropyran-4-yl]-1,3,4-oxadiazol-2-amine | 0.0192 |
| 62 | 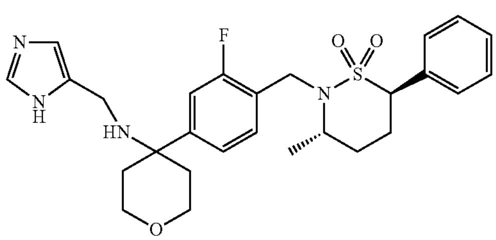 [SMILES: C[C@H]1CC[C@H](c2ccccc2)S(=O)(=O)N1Cc1ccc(C2(NCc3cnc[nH]3)CCOCC2)cc1F] | 4-[3-fluoro-4-[[(3S,6R)-3-methyl-1,1-dioxo-6-phenyl-thiazinan-2-yl]methyl]phenyl]-N-(1H-imidazol-5-ylmethyl)tetrahydropyran-4-amine | 0.0205 |
| 63 | 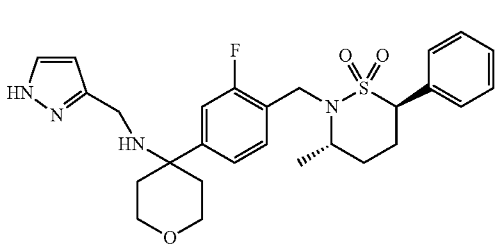 [SMILES: C[C@H]1CC[C@H](c2ccccc2)S(=O)(=O)N1Cc1ccc(C2(NCc3cc[nH]n3)CCOCC2)cc1F] | 4-[3-fluoro-4-[[(3S,6R)-3-methyl-1,1-dioxo-6-phenyl-thiazinan-2-yl]methyl]phenyl]-N-(1H-pyrazol-3-ylmethyl)tetrahydropyran-4-amine | 0.0067 |

TABLE 4-continued

| | Structure | Name | IC$_{50}$ |
|---|---|---|---|
| 64 | 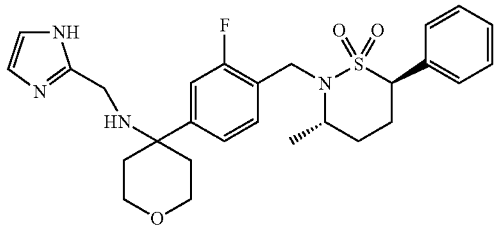 [SMILES: C[C@H]1CC[C@H](c2ccccc2)S(=O)(=O)N1Cc1ccc(C2(NCc3ncc[nH]3)CCOCC2)cc1F] | 4-[3-fluoro-4-[[(3S,6R)-3-methyl-1,1-dioxo-6-phenyl-thiazinan-2-yl]methyl]phenyl]-N-(1H-imidazol-2-ylmethyl)tetrahydropyran-4-amine | 0.0101 |
| 65 | 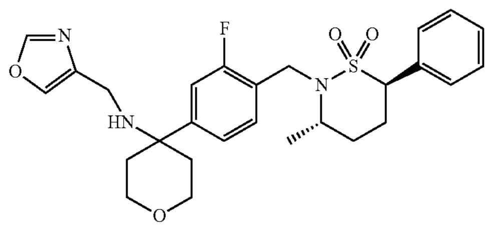 [SMILES: C[C@H]1CC[C@H](c2ccccc2)S(=O)(=O)N1Cc1ccc(C2(NCc3cocn3)CCOCC2)cc1F] | 4-[3-fluoro-4-[[(3S,6R)-3-methyl-1,1-dioxo-6-phenyl-thiazinan-2-yl]methyl]phenyl]-N-(oxazol-4-ylmethyl)tetrahydropyran-4-amine | 0.0036 |
| 66 | 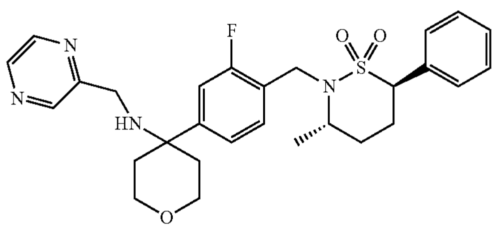 [SMILES: C[C@H]1CC[C@H](c2ccccc2)S(=O)(=O)N1Cc1ccc(C2(NCc3cnccn3)CCOCC2)cc1F] | 4-[3-fluoro-4-[[(3S,6R)-3-methyl-1,1-dioxo-6-phenyl-thiazinan-2-yl]methyl]phenyl]-N-(pyrazin-2-ylmethyl)tetrahydropyran-4-amine | 0.0066 |
| 67 | 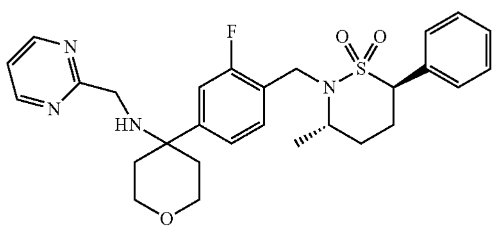 [SMILES: C[C@H]1CC[C@H](c2ccccc2)S(=O)(=O)N1Cc1ccc(C2(NCc3ncccn3)CCOCC2)cc1F] | 4-[3-fluoro-4-[[(3S,6R)-3-methyl-1,1-dioxo-6-phenyl-thiazinan-2-yl]methyl]phenyl]-N-(pyrimidin-2-ylmethyl)tetrahydropyran-4-amine | 0.0093 |
| 68 | 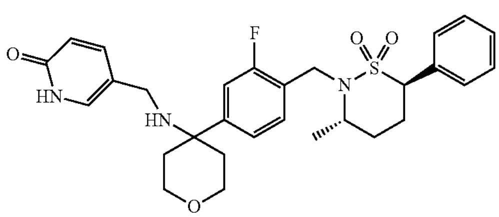 [SMILES: C[C@H]1CC[C@H](c2ccccc2)S(=O)(=O)N1Cc1ccc(C2(NCc3ccc(=O)[nH]c3)CCOCC2)cc1F] | 5-[[[4-[3-fluoro-4-[[(3S,6R)-3-methyl-1,1-dioxo-6-phenyl-thiazinan-2-yl]methyl]phenyl]tetrahydropyran-4-yl]amino]methyl]-1H-pyridin-2-one | 0.0389 |
| 69 | 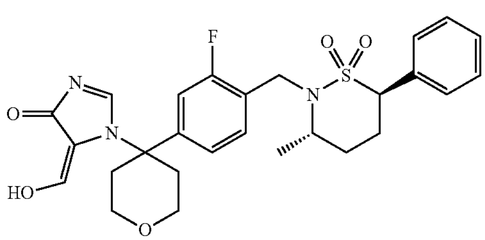 [SMILES: C[C@H]1CC[C@H](c2ccccc2)S(=O)(=O)N1Cc1ccc(C2(N3C=NC(=O)/C3=C\O)CCOCC2)cc1F] | (5E)-1-[4-[3-fluoro-4-[[(3S,6R)-3-methyl-1,1-dioxo-6-phenyl-thiazinan-2-yl]methyl]phenyl]tetrahydropyran-4-yl]-5-(hydroxymethylene)imidazol-4-one | 0.0833 |

TABLE 4-continued

| | Structure | Name | IC$_{50}$ |
|---|---|---|---|
| 70 | 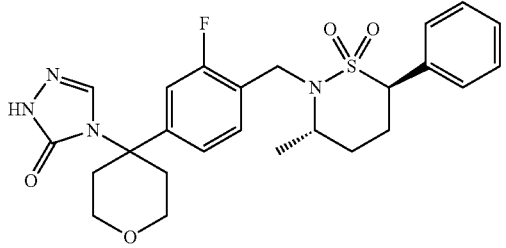 [SMILES: C[C@H]1CC[C@H](c2ccccc2)S(=O)(=O)N1Cc1ccc(C2(n3cn[nH]c3=O)CCOCC2)cc1F] | 4-[4-[3-fluoro-4-[[(3S,6R)-3-methyl-1,1-dioxo-6-phenyl-thiazinan-2-yl]methyl]phenyl]tetrahydropyran-4-yl]-1H-1,2,4-triazol-5-one | 0.113 |
| 71 | 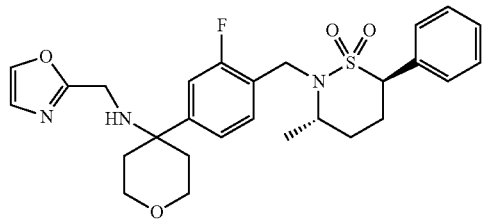 [SMILES: C[C@H]1CC[C@H](c2ccccc2)S(=O)(=O)N1Cc1ccc(C2(NCc3ncco3)CCOCC2)cc1F] | 4-[3-fluoro-4-[[(3S,6R)-3-methyl-1,1-dioxo-6-phenyl-thiazinan-2-yl]methyl]phenyl]-N-(oxazol-2-ylmethyl)tetrahydropyran-4-amine | 0.0025 |
| 72 | 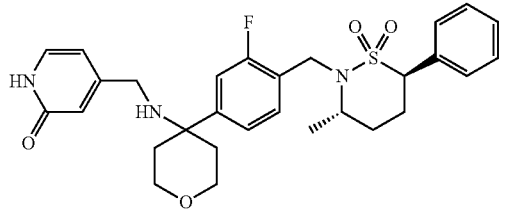 [SMILES: C[C@H]1CC[C@H](c2ccccc2)S(=O)(=O)N1Cc1ccc(C2(NCc3cc[nH]c(=O)c3)CCOCC2)cc1F] | 4-[[[4-[3-fluoro-4-[[(3S,6R)-3-methyl-1,1-dioxo-6-phenyl-thiazinan-2-yl]methyl]phenyl]tetrahydropyran-4-yl]amino]methyl]-1H-pyridin-2-one | 0.0106 |
| 73 | 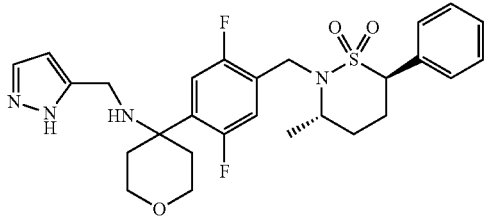 [SMILES: C[C@H]1CC[C@H](c2ccccc2)S(=O)(=O)N1Cc1cc(F)c(C2(NCc3ccn[nH]3)CCOCC2)cc1F] | 4-[2,5-difluoro-4-[[(3S,6R)-3-methyl-1,1-dioxo-6-phenyl-thiazinan-2-yl]methyl]phenyl]-N-(1H-pyrazol-5-ylmethyl)tetrahydropyran-4-amine | 0.0029 |
| 74 | 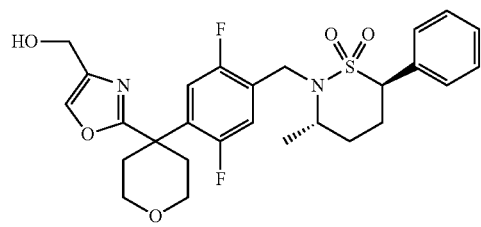 [SMILES: C[C@H]1CC[C@H](c2ccccc2)S(=O)(=O)N1Cc1cc(F)c(C2(c3nc(CO)co3)CCOCC2)cc1F] | [2-[4-[2,5-difluoro-4-[[(3S,6R)-3-methyl-1,1-dioxo-6-phenyl-thiazinan-2-yl]methyl]phenyl]tetrahydropyran-4-yl]oxazol-4-yl]methanol | 0.0128 |
| 75 | 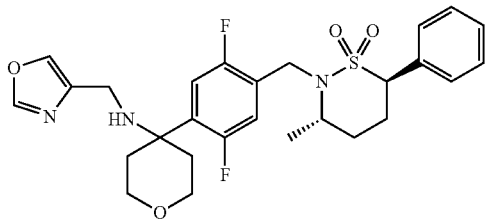 [SMILES: C[C@H]1CC[C@H](c2ccccc2)S(=O)(=O)N1Cc1cc(F)c(C2(NCc3cocn3)CCOCC2)cc1F] | 4-[2,5-difluoro-4-[[(3S,6R)-3-methyl-1,1-dioxo-6-phenyl-thiazinan-2-yl]methyl]phenyl]-N-(oxazol-4-ylmethyl)tetrahydropyran-4-amine | 0.0064 |

TABLE 4-continued

| | Structure | Name | IC$_{50}$ |
|---|---|---|---|
| 76 | 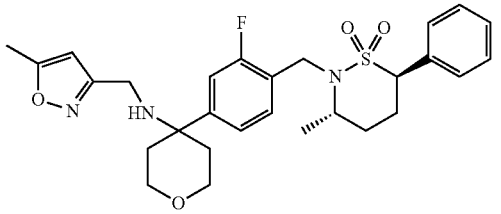 [SMILES: Cc1cc(CNC2(c3ccc(CN4[C@@H](C)CC[C@H](c5ccccc5)S4(=O)=O)c(F)c3)CCOCC2)no1] | 4-[3-fluoro-4-[[(3S,6R)-3-methyl-1,1-dioxo-6-phenyl-thiazinan-2-yl]methyl]phenyl]-N-[(5-methylisoxazol-3-yl)methyl]tetrahydropyran-4-amine | 0.0046 |
| 77 | 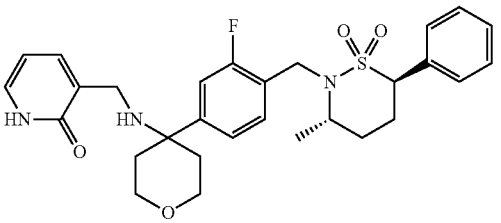 [SMILES: C[C@H]1CC[C@H](c2ccccc2)S(=O)(=O)N1Cc1ccc(C2(NCc3ccc[nH]c3=O)CCOCC2)cc1F] | 3-[[[4-[3-fluoro-4-[[(3S,6R)-3-methyl-1,1-dioxo-6-phenyl-thiazinan-2-yl]methyl]phenyl]tetrahydropyran-4-yl]amino]methyl]-1H-pyridin-2-one | 0.0872 |
| 78 | 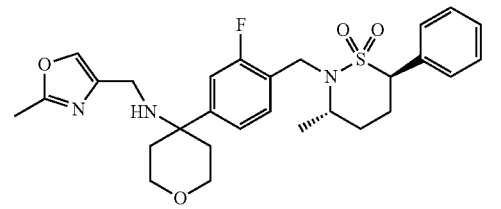 [SMILES: Cc1nc(CNC2(c3ccc(CN4[C@@H](C)CC[C@H](c5ccccc5)S4(=O)=O)c(F)c3)CCOCC2)co1] | 4-[3-fluoro-4-[[(3S,6R)-3-methyl-1,1-dioxo-6-phenyl-thiazinan-2-yl]methyl]phenyl]-N-[(2-methyloxazol-4-yl)methyl]tetrahydropyran-4-amine; hydrochloride | 0.0302 |
| 79 | 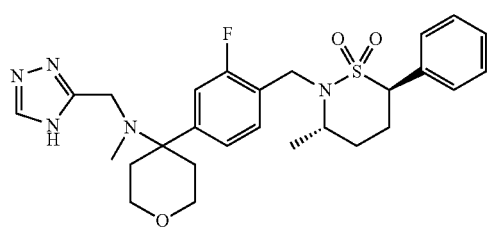 [SMILES: C[C@H]1CC[C@H](c2ccccc2)S(=O)(=O)N1Cc1ccc(C2(N(C)Cc3nnc[nH]3)CCOCC2)cc1F] | 4-[3-fluoro-4-[[(3S,6R)-3-methyl-1,1-dioxo-6-phenyl-thiazinan-2-yl]methyl]phenyl]-N-methyl-N-(4H-1,2,4-triazol-3-ylmethyl)tetrahydropyran-4-amine | 0.0771 |
| 80 | 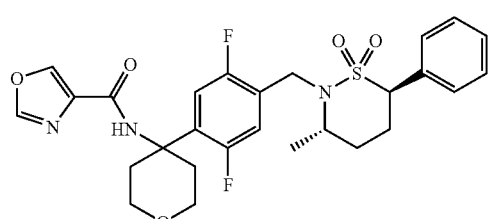 | N-[4-[2,5-difluoro-4-[[(3S,6R)-3-methyl-1,1-dioxo-6-phenyl-thiazinan-2-yl]methyl]phenyl]tetrahydropyran-4-yl]oxazole-4-carboxamide | 0.0048 |
| 81 | 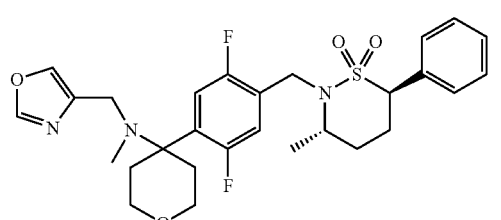 | 4-[2,5-difluoro-4-[[(3S,6R)-3-methyl-1,1-dioxo-6-phenyl-thiazinan-2-yl]methyl]phenyl]-N-methyl-N-(oxazol-4-ylmethyl)tetrahydropyran-4-amine | 0.0088 |
| 82 | 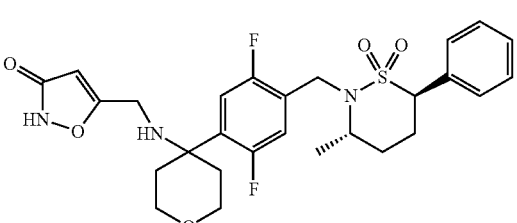 | 5-[[[4-[2,5-difluoro-4-[[(3S,6R)-3-methyl-1,1-dioxo-6-phenyl-thiazinan-2-yl]methyl]phenyl]tetrahydropyran-4-yl]amino]methyl]isoxazol-3-one | 0.0057 |

TABLE 4-continued

| | Structure | Name | IC$_{50}$ |
|---|---|---|---|
| 83 | 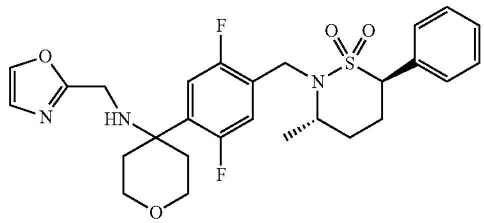 [SMILES: C[C@H]1CC[C@H](c2ccccc2)S(=O)(=O)N1Cc1cc(F)c(C2(NCc3ncco3)CCOCC2)cc1F] | 4-[2,5-difluoro-4-[[(3S,6R)-3-methyl-1,1-dioxo-6-phenyl-thiazinan-2-yl]methyl]phenyl]-N-(oxazol-2-ylmethyl)tetrahydropyran-4-amine | 0.0037 |
| 84 | 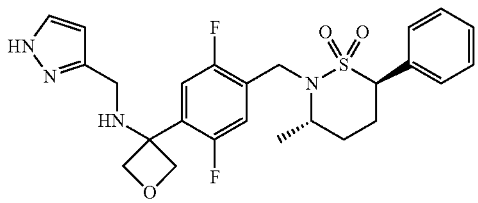 [SMILES: C[C@H]1CC[C@H](c2ccccc2)S(=O)(=O)N1Cc1cc(F)c(C2(NCc3cc[nH]n3)COC2)cc1F] | 3-[2,5-difluoro-4-[[(3S,6R)-3-methyl-1,1-dioxo-6-phenyl-thiazinan-2-yl]methyl]phenyl]-N-(1H-pyrazol-3-ylmethyl)oxetan-3-amine | 0.0057 |
| 85 | 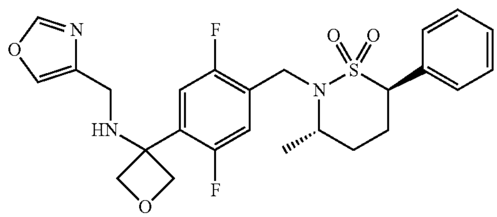 [SMILES: C[C@H]1CC[C@H](c2ccccc2)S(=O)(=O)N1Cc1cc(F)c(C2(NCc3cocn3)COC2)cc1F] | 3-[2,5-difluoro-4-[[(3S,6R)-3-methyl-1,1-dioxo-6-phenyl-thiazinan-2-yl]methyl]phenyl]-N-(oxazol-4-ylmethyl)oxetan-3-amine | 0.0041 |
| 86 | 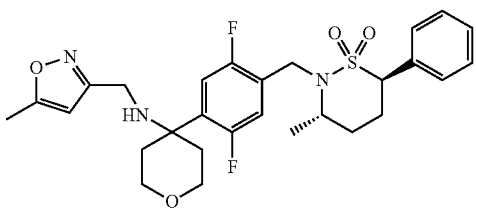 [SMILES: Cc1cc(CNC2(c3cc(F)c(CN4[C@@H](C)CC[C@H](c5ccccc5)S4(=O)=O)cc3F)CCOCC2)no1] | 4-[2,5-difluoro-4-[[(3S,6R)-3-methyl-1,1-dioxo-6-phenyl-thiazinan-2-yl]methyl]phenyl]-N-[(5-methylisoxazol-3-yl)methyl]tetrahydropyran-4-amine | 0.005 |
| 87 | 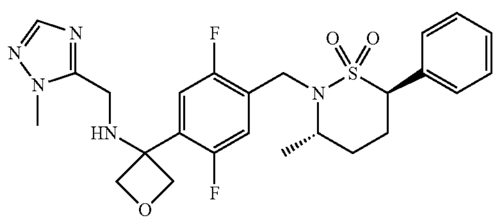 [SMILES: C[C@H]1CC[C@H](c2ccccc2)S(=O)(=O)N1Cc1cc(F)c(C2(NCc3ncnn3C)COC2)cc1F] | 3-[2,5-difluoro-4-[[(3S,6R)-3-methyl-1,1-dioxo-6-phenyl-thiazinan-2-yl]methyl]phenyl]-N-[(2-methyl-1,2,4-triazol-3-yl)methyl]oxetan-3-amine | 0.008 |
| 88 | 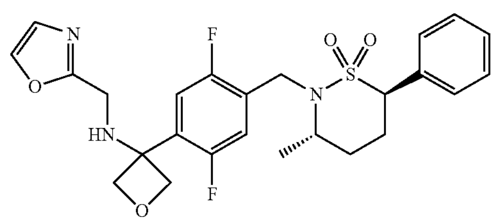 [SMILES: C[C@H]1CC[C@H](c2ccccc2)S(=O)(=O)N1Cc1cc(F)c(C2(NCc3ncco3)COC2)cc1F] | 3-[2,5-difluoro-4-[[(3S,6R)-3-methyl-1,1-dioxo-6-phenyl-thiazinan-2-yl]methyl]phenyl]-N-(oxazol-2-ylmethyl)oxetan-3-amine | 0.0082 |
| 89 | 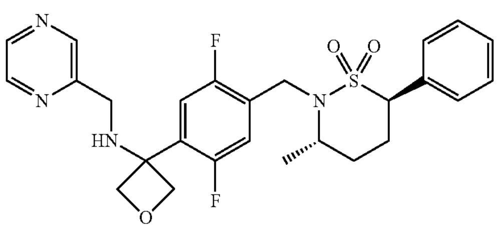 [SMILES: C[C@H]1CC[C@H](c2ccccc2)S(=O)(=O)N1Cc1cc(F)c(C2(NCc3cnccn3)COC2)cc1F] | 3-[2,5-difluoro-4-[[(3S,6R)-3-methyl-1,1-dioxo-6-phenyl-thiazinan-2-yl]methyl]phenyl]-N-(pyrazin-2-ylmethyl)oxetan-3-amine | 0.0071 |

TABLE 4-continued

| | Structure | Name | IC$_{50}$ |
|---|---|---|---|
| 90 | 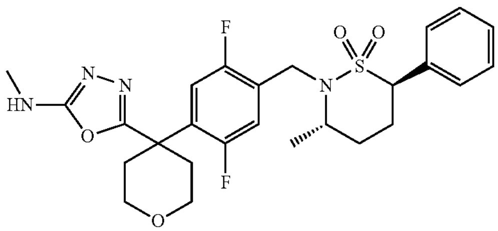 [SMILES: CNc1nnc(C2(c3cc(F)c(CN4[C@@H](C)CC[C@H](c5ccccc5)S4(=O)=O)cc3F)CCOCC2)o1] | 5-[4-[2,5-difluoro-4-[[(3S,6R)-3-methyl-1,1-dioxo-6-phenyl-thiazinan-2-yl]methyl]phenyl]tetrahydropyran-4-yl]-N-methyl-1,3,4-oxadiazol-2-amine | 0.0137 |
| 91 | 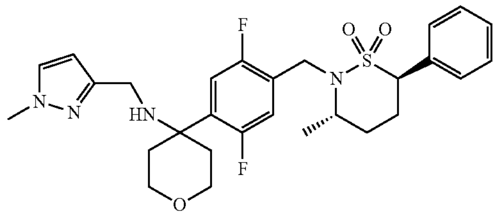 [SMILES: C[C@H]1CC[C@H](c2ccccc2)S(=O)(=O)N1Cc1cc(F)c(C2(NCc3ccn(C)n3)CCOCC2)cc1F] | 4-[2,5-difluoro-4-[[(3S,6R)-3-methyl-1,1-dioxo-6-phenyl-thiazinan-2-yl]methyl]phenyl]-N-[(1-methylpyrazol-3-yl)methyl]tetrahydropyran-4-amine | 0.0826 |
| 92 | 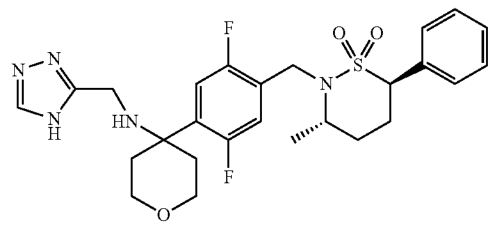 [SMILES: C[C@H]1CC[C@H](c2ccccc2)S(=O)(=O)N1Cc1cc(F)c(C2(NCc3nnc[nH]3)CCOCC2)cc1F] | 4-[2,5-difluoro-4-[[(3S,6R)-3-methyl-1,1-dioxo-6-phenyl-thiazinan-2-yl]methyl]phenyl]-N-(4H-1,2,4-triazol-3-ylmethyl)tetrahydropyran-4-amine | 0.0236 |
| 93 | 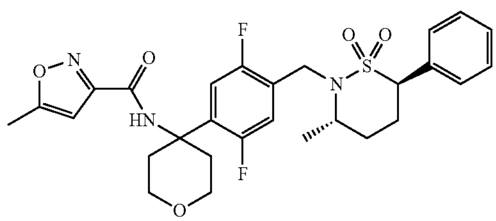 [SMILES: Cc1cc(C(=O)NC2(c3cc(F)c(CN4[C@@H](C)CC[C@H](c5ccccc5)S4(=O)=O)cc3F)CCOCC2)no1] | N-[4-[2,5-difluoro-4-[[(3,6R)-3-methyl-1,1-dioxo-6-phenyl-thiazinan-2-yl]methyl]phenyl]tetrahydropyran-4-yl]-5-methyl-isoxazole-3-carboxamide | 0.044 |
| 94 | 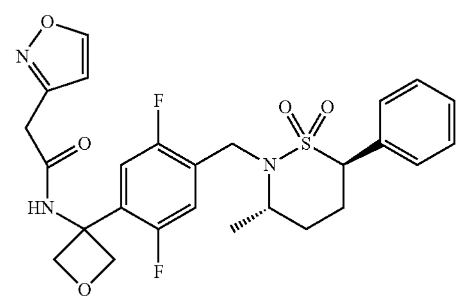 [SMILES: C[C@H]1CC[C@H](c2ccccc2)S(=O)(=O)N1Cc1cc(F)c(C2(NC(=O)Cc3ccon3)COC2)cc1F] | N-[3-[2,5-difluoro-4-[[(3S,6R)-3-methyl-1,1-dioxo-6-phenyl-thiazinan-2-yl]methyl]phenyl]oxetan-3-yl]-2-isoxazol-3-yl-acetamide | 0.0179 |
| 95 | 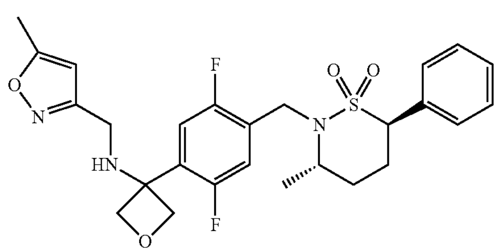 [SMILES: Cc1cc(CNC2(c3cc(F)c(CN4[C@@H](C)CC[C@H](c5ccccc5)S4(=O)=O)cc3F)COC2)no1] | 3-[2,5-difluoro-4-[[(3S,6R)-3-methyl-1,1-dioxo-6-phenyl-thiazinan-2-yl]methyl]phenyl]-N-[(5-methylisoxazol-3-yl)methyl]oxetan-3-amine | 0.0206 |

TABLE 4-continued

| | Structure | Name | IC$_{50}$ |
|---|---|---|---|
| 96 | 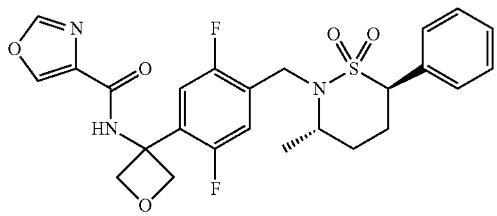 [SMILES: C[C@H]1CC[C@H](c2ccccc2)S(=O)(=O)N1Cc1cc(F)c(C2(NC(=O)c3cocn3)COC2)cc1F] | N-[3-[2,5-difluoro-4-[[(3S,6R)-3-methyl-1,1-dioxo-6-phenyl-thiazinan-2-yl]methyl]phenyl]oxetan-3-yl]oxazole-4-carboxamide | 0.0356 |
| 97 | 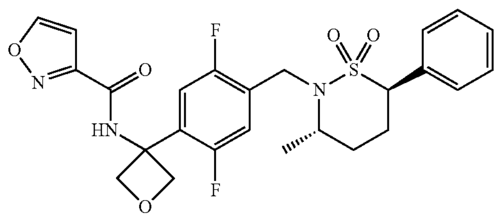 [SMILES: C[C@H]1CC[C@H](c2ccccc2)S(=O)(=O)N1Cc1cc(F)c(C2(NC(=O)c3ccon3)COC2)cc1F] | N-[3-[2,5-difluoro-4-[[(3S,6R)-3-methyl-1,1-dioxo-6-phenyl-thiazinan-2-yl]methyl]phenyl]oxetan-3-yl]isoxazole-3-carboxamide | 0.0224 |
| 98 | 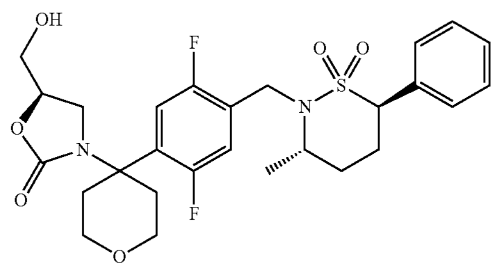 [SMILES: C[C@H]1CC[C@H](c2ccccc2)S(=O)(=O)N1Cc1cc(F)c(C2(N3C[C@H](CO)OC3=O)CCOCC2)cc1F] | (5R)-3-[4-[2,5-difluoro-4-[[(3S,6R)-3-methyl-1,1-dioxo-6-phenyl-thiazinan-2-yl]methyl]phenyl]tetrahydropyran-4-yl]-5-(hydroxymethyl)oxazolidin-2-one | 0.0676 |
| 99 | 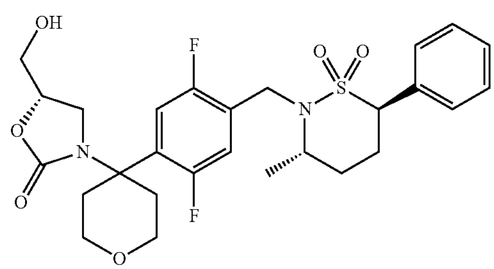 [SMILES: C[C@H]1CC[C@H](c2ccccc2)S(=O)(=O)N1Cc1cc(F)c(C2(N3C[C@@H](CO)OC3=O)CCOCC2)cc1F] | (5S)-3-[4-[2,5-difluoro-4-[[(3S,6R)-3-methyl-1,1-dioxo-6-phenyl-thiazinan-2-yl]methyl]phenyl]tetrahydropyran-4-yl]-5-(hydroxymethyl)oxazolidin-2-one | 0.0587 |
| 100 | 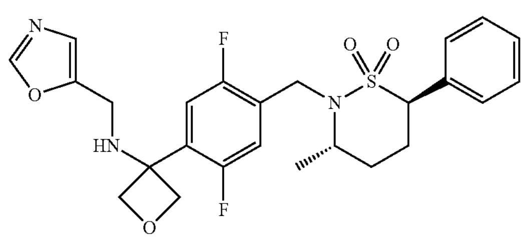 [SMILES: C[C@H]1CC[C@H](c2ccccc2)S(=O)(=O)N1Cc1cc(F)c(C2(NCc3cnco3)COC2)cc1F] | 3-[2,5-difluoro-4-[[(3S,6R)-3-methyl-1,1-dioxo-6-phenyl-thiazinan-2-yl]methyl]phenyl]-N-(oxazol-5-ylmethyl)oxetan-3-amine | 0.0341 |
| 101 | 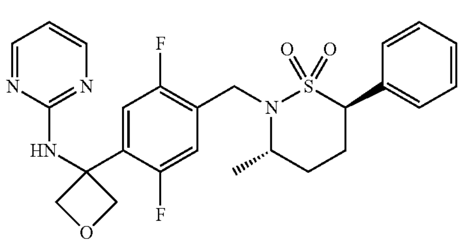 | N-[3-[2,5-difluoro-4-[[(3S,6R)-3-methyl-1,1-dioxo-6-phenyl-thiazinan-2-yl]methyl]phenyl]oxetan-3-yl]pyrimidin-2-amine | 0.0607 |

TABLE 4-continued

| | Structure | Name | IC$_{50}$ |
|---|---|---|---|
| 102 | 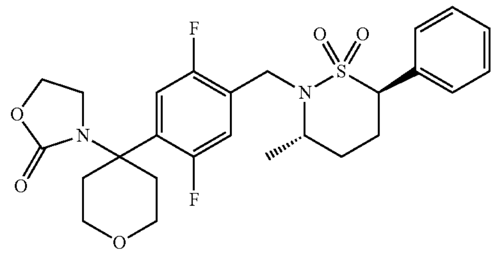 [SMILES: C[C@H]1CC[C@H](c2ccccc2)S(=O)(=O)N1Cc1cc(F)c(C2(N3CCOC3=O)CCOCC2)cc1F] | 3-[4-[2,5-difluoro-4-[[(3S,6R)-3-methyl-1,1-dioxo-6-phenyl-thiazinan-2-yl]methyl]phenyl]tetrahydropyran-4-yl]oxazolidin-2-one | 0.0553 |
| 103 | 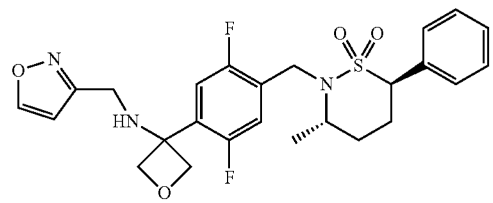 [SMILES: C[C@H]1CC[C@H](c2ccccc2)S(=O)(=O)N1Cc1cc(F)c(C2(NCc3ccon3)COC2)cc1F] | 3-[2,5-difluoro-4-[[(3S,6R)-3-methyl-1,1-dioxo-6-phenyl-thiazinan-2-yl]methyl]phenyl]-N-(isoxazol-3-ylmethyl)oxetan-3-amine | 0.0015 |
| 104 | 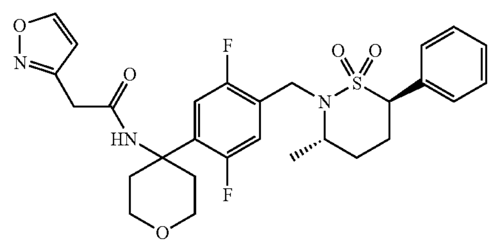 [SMILES: C[C@H]1CC[C@H](c2ccccc2)S(=O)(=O)N1Cc1cc(F)c(C2(NC(=O)Cc3ccon3)CCOCC2)cc1F] | N-[4-[2,5-difluoro-4-[[(3S,6R)-3-methyl-1,1-dioxo-6-phenyl-thiazinan-2-yl]methyl]phenyl]tetrahydropyran-4-yl]-2-isoxazol-3-yl-acetamide | 0.0026 |
| 105 | 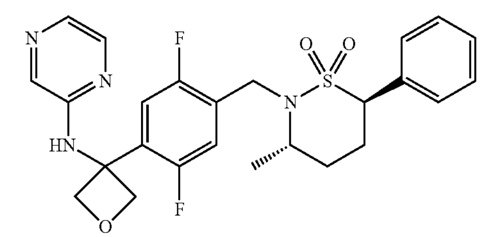 [SMILES: C[C@H]1CC[C@H](c2ccccc2)S(=O)(=O)N1Cc1cc(F)c(C2(Nc3cnccn3)COC2)cc1F] | N-[3-[2,5-difluoro-4-[[(3S,6R)-3-methyl-1,1-dioxo-6-phenyl-thiazinan-2-yl]methyl]phenyl]oxetan-3-yl]pyrazin-2-amine | 0.0022 |
| 106 | 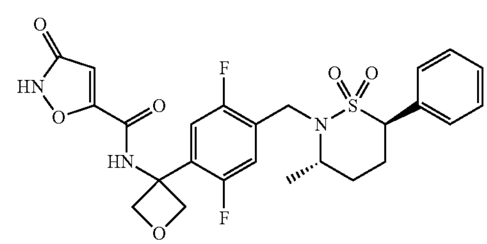 [SMILES: C[C@H]1CC[C@H](c2ccccc2)S(=O)(=O)N1Cc1cc(F)c(C2(NC(=O)c3cc(=O)[nH]o3)COC2)cc1F] | N-[3-[2,5-difluoro-4-[[(3S,6R)-3-methyl-1,1-dioxo-6-phenyl-thiazinan-2-yl]methyl]phenyl]oxetan-3-yl]-3-oxo-isoxazole-5-carboxamide | 0.0051 |
| 107 | 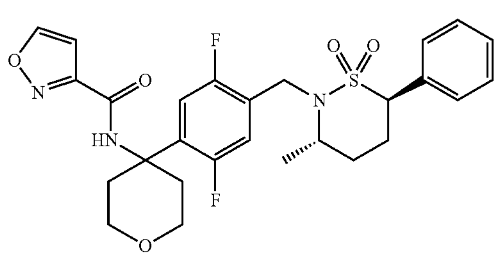 [SMILES: C[C@H]1CC[C@H](c2ccccc2)S(=O)(=O)N1Cc1cc(F)c(C2(NC(=O)c3ccon3)CCOCC2)cc1F] | N-[4-[2,5-difluoro-4-[[(3S,6R)-3-methyl-1,1-dioxo-6-phenyl-thiazinan-2-yl]methyl]phenyl]tetrahydropyran-4-yl]isoxazole-3-carboxamide | 0.0027 |

TABLE 4-continued

| | Structure | Name | IC$_{50}$ |
|---|---|---|---|
| 108 | 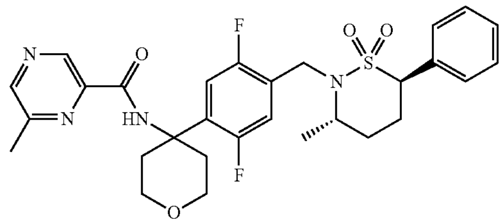 [SMILES: Cc1cncc(C(=O)NC2(c3cc(F)c(CN4[C@@H](C)CC[C@H](c5ccccc5)S4(=O)=O)cc3F)CCOCC2)n1] | N-[4-[2,5-difluoro-4-[[(3S,6R)-3-methyl-1,1-dioxo-6-phenyl-thiazinan-2-yl]methyl]phenyl]tetrahydropyran-4-yl]-6-methyl-pyrazine-2-carboxamide | 0.0192 |
| 109 | 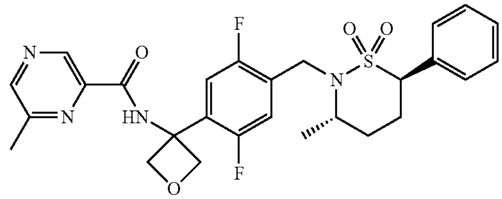 [SMILES: Cc1cncc(C(=O)NC2(c3cc(F)c(CN4[C@@H](C)CC[C@H](c5ccccc5)S4(=O)=O)cc3F)COC2)n1] | N-[3-[2,5-difluoro-4-[[(3S,6R)-3-methyl-1,1-dioxo-6-phenyl-thiazinan-2-yl]methyl]phenyl]oxetan-3-yl]-6-methyl-pyrazine-2-carboxamide | 0.112 |
| 110 | 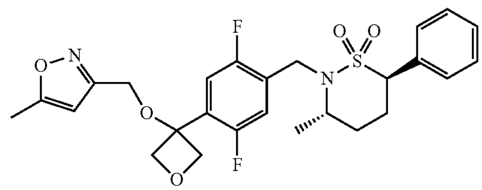 [SMILES: Cc1cc(COC2(c3cc(F)c(CN4[C@@H](C)CC[C@H](c5ccccc5)S4(=O)=O)cc3F)COC2)no1] | (3S,6R)-2-[[2,5-difluoro-4-[3-[(5-methylisoxazol-3-yl)methoxy]oxetan-3-yl]phenyl]methyl]-3-methyl-6-phenyl-thiazinane 1,1-dioxide | 0.0013 |
| 111 | 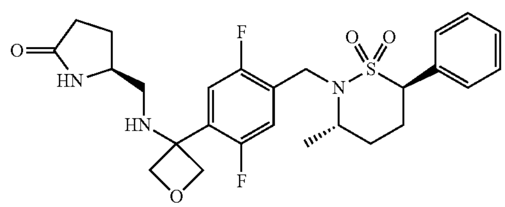 [SMILES: C[C@H]1CC[C@H](c2ccccc2)S(=O)(=O)N1Cc1cc(F)c(C2(NC[C@@H]3CCC(=O)N3)COC2)cc1F] | (5S)-5-[[[3-[2,5-difluoro-4-[[(3S,6R)-3-methyl-1,1-dioxo-6-phenyl-thiazinan-2-yl]methyl]phenyl]oxetan-3-yl]amino]methyl]pyrrolidin-2-one | 0.0898 |
| 112 | 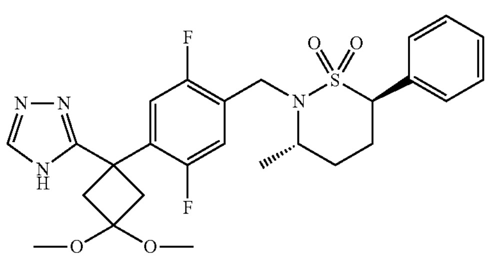 [SMILES: COC1(OC)CC(c2nnc[nH]2)(c2cc(F)c(CN3[C@@H](C)CC[C@H](c4ccccc4)S3(=O)=O)cc2F)C1] | (3S,6R)-2-[[4-[3,3-dimethoxy-1-(4H-1,2,4-triazol-3-yl)cyclobutyl]-2,5-difluoro-phenyl]methyl]-3-methyl-6-phenyl-thiazinane 1,1-dioxide | 0.0046 |
| 113 | 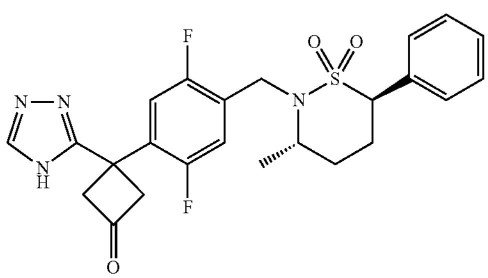 [SMILES: C[C@H]1CC[C@H](c2ccccc2)S(=O)(=O)N1Cc1cc(F)c(C2(c3nnc[nH]3)CC(=O)C2)cc1F] | 3-[2,5-difluoro-4-[[(3S,6R)-3-methyl-1,1-dioxo-6-phenyl-thiazinan-2-yl]methyl]phenyl]-3-(4H-1,2,4-triazol-3-yl)cyclobutanone | 0.0081 |

| | Structure | Name | IC$_{50}$ |
|---|---|---|---|
| 114 | 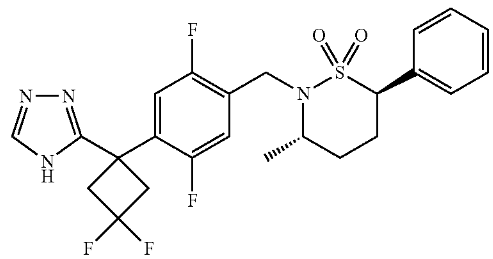 [SMILES: C[C@H]1CC[C@H](c2ccccc2)S(=O)(=O)N1Cc1cc(F)c(C2(c3nnc[nH]3)CC(F)(F)C2)cc1F] | (3S,6R)-2-[[4-[3,3-difluoro-1-(4H-1,2,4-triazol-3-yl)cyclobutyl]-2,5-difluoro-phenyl]methyl]-3-methyl-6-phenyl-thiazinane 1,1-dioxide | 0.0036 |
| 115 | 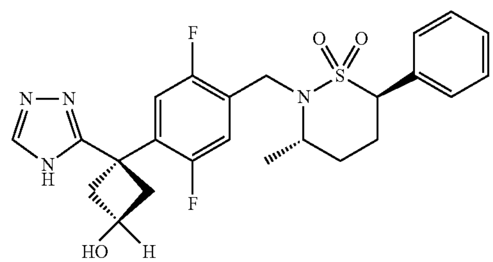 [SMILES: C[C@H]1CC[C@H](c2ccccc2)S(=O)(=O)N1Cc1cc(F)c([C@]2(c3nnc[nH]3)C[C@@H](O)C2)cc1F] | 3-[2,5-difluoro-4-[[(3S,6R)-3-methyl-1,1-dioxo-6-phenyl-thiazinan-2-yl]methyl]phenyl]-3-(4H-1,2,4-triazol-3-yl)cyclobutanol | 0.0078 |
| 116 | 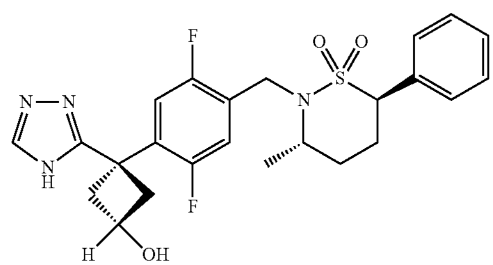 [SMILES: C[C@H]1CC[C@H](c2ccccc2)S(=O)(=O)N1Cc1cc(F)c([C@]2(c3nnc[nH]3)C[C@H](O)C2)cc1F] | 3-[2,5-difluoro-4-[[(3S,6R)-3-methyl-1,1-dioxo-6-phenyl-thiazinan-2-yl]methyl]phenyl]-3-(4H-1,2,4-triazol-3-yl)cyclobutanol | 0.0379 |
| 117 | 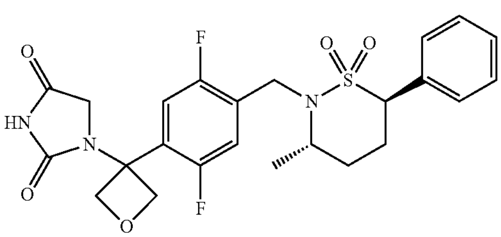 [SMILES: C[C@H]1CC[C@H](c2ccccc2)S(=O)(=O)N1Cc1cc(F)c(C2(N3CC(=O)NC3=O)COC2)cc1F] | 1-[3-[2,5-difluoro-4-[[(3S,6R)-3-methyl-1,1-dioxo-6-phenyl-thiazinan-2-yl]methyl]phenyl]oxetan-3-yl]imidazolidine-2,4-dione | 0.0259 |
| 118 | 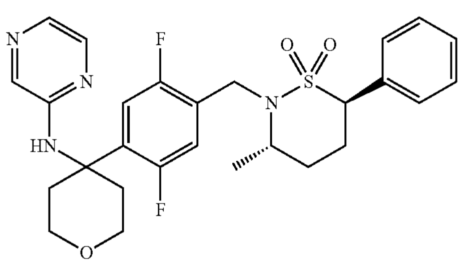 [SMILES: C[C@H]1CC[C@H](c2ccccc2)S(=O)(=O)N1Cc1cc(F)c(C2(Nc3cnccn3)CCOCC2)cc1F] | N-[4-[2,5-difluoro-4-[[(3S,6R)-3-methyl-1,1-dioxo-6-phenyl-thiazinan-2-yl]methyl]phenyl]tetrahydropyran-4-yl]pyrazin-2-amine | 0.0052 |
| 119 | 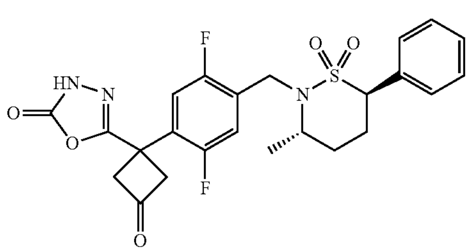 [SMILES: C[C@H]1CC[C@H](c2ccccc2)S(=O)(=O)N1Cc1cc(F)c(C2(c3n[nH]c(=O)o3)CC(=O)C2)cc1F] | 5-[1-[2,5-difluoro-4-[[(3S,6R)-3-methyl-1,1-dioxo-6-phenyl-thiazinan-2-yl]methyl]phenyl]-3-oxo-cyclobutyl]-3H-1,3,4-oxadiazol-2-one | 0.0018 |

TABLE 4-continued

| | Structure | Name | IC$_{50}$ |
|---|---|---|---|
| 120 | 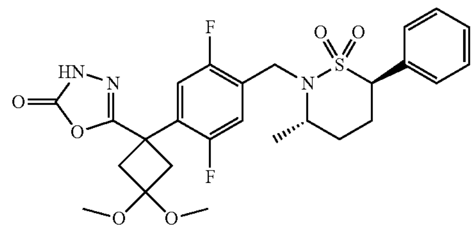 [SMILES: COC1(OC)CC(c2n[nH]c(=O)o2)(c2cc(F)c(CN3[C@@H](C)CC[C@H](c4ccccc4)S3(=O)=O)cc2F)C1] | 5-[1-[2,5-difluoro-4-[[(3S,6R)-3-methyl-1,1-dioxo-6-phenyl-thiazinan-2-yl]methyl]phenyl]-3,3-dimethoxy-cyclobutyl]-3H-1,3,4-oxadiazol-2-one | 0.0057 |
| 121 | 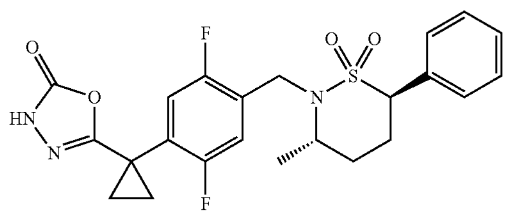 [SMILES: C[C@H]1CC[C@H](c2ccccc2)S(=O)(=O)N1Cc1cc(F)c(C2(c3n[nH]c(=O)o3)CC2)cc1F] | 5-[1-[2,5-difluoro-4-[[(3S,6R)-3-methyl-1,1-dioxo-6-phenyl-thiazinan-2-yl]methyl]phenyl]cyclopropyl]-3H-1,3,4-oxadiazol-2-one | 0.0195 |
| 122 | 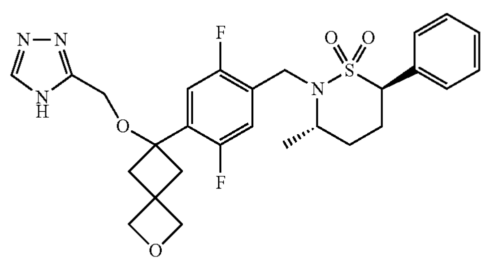 [SMILES: C[C@H]1CC[C@H](c2ccccc2)S(=O)(=O)N1Cc1cc(F)c(C2(OCc3nnc[nH]3)CC3(COC3)C2)cc1F] | (3S,6R)-2-[[2,5-difluoro-4-[6-(4H-1,2,4-triazol-3-ylmethoxy)-2-oxaspiro[3.3]heptan-6-yl]phenyl]methyl]-3-methyl-6-phenyl-thiazinane 1,1-dioxide | 0.0027 |
| 123 | 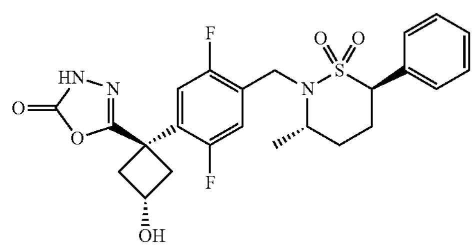 [SMILES: C[C@H]1CC[C@H](c2ccccc2)S(=O)(=O)N1Cc1cc(F)c([C@]2(c3n[nH]c(=O)o3)C[C@H](O)C2)cc1F] | trans-5-[1-[2,5-difluoro-4-[[(3S,6R)-3-methyl-1,1-dioxo-6-phenyl-thiazinan-2-yl]methyl]phenyl]-3-hydroxy-cyclobutyl]-3H-1,3,4-oxadiazol-2-one | 0.0018 |
| 124 | 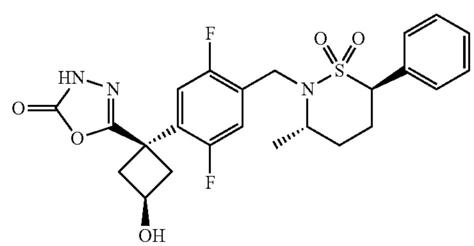 [SMILES: C[C@H]1CC[C@H](c2ccccc2)S(=O)(=O)N1Cc1cc(F)c([C@]2(c3n[nH]c(=O)o3)C[C@@H](O)C2)cc1F] | cis-5-[1-[2,5-difluoro-4-[[(3S,6R)-3-methyl-1,1-dioxo-6-phenyl-thiazinan-2-yl]methyl]phenyl]-3-hydroxy-cyclobutyl]-3H-1,3,4-oxadiazol-2-one | 0.0021 |
| 125 | 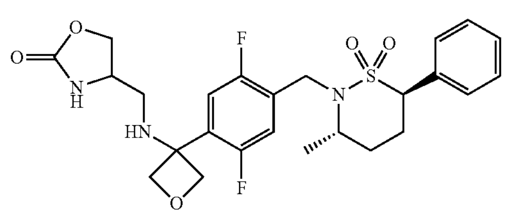 [SMILES: C[C@H]1CC[C@H](c2ccccc2)S(=O)(=O)N1Cc1cc(F)c(C2(NCC3COC(=O)N3)COC2)cc1F] | 4-[[[3-[2,5-difluoro-4-[[(3S,6R)-3-methyl-1,1-dioxo-6-phenyl-thiazinan-2-yl]methyl]phenyl]oxetan-3-yl]amino]methyl]oxazolidin-2-one | 0.0566 |

TABLE 4-continued

| | Structure | Name | IC$_{50}$ |
|---|---|---|---|
| 126 | 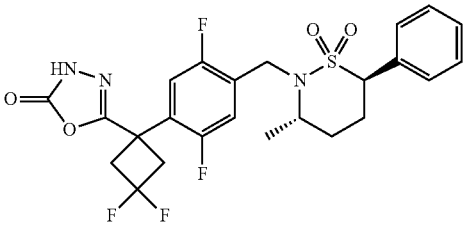 [SMILES: C[C@H]1CC[C@H](c2ccccc2)S(=O)(=O)N1Cc1cc(F)c(C2(c3n[nH]c(=O)o3)CC(F)(F)C2)cc1F] | 5-[1-[2,5-difluoro-4-[[(3S,6R)-3-methyl-1,1-dioxo-6-phenyl-thiazinan-2-yl]methyl]phenyl]-3,3-difluoro-cyclobutyl]-3H-1,3,4-oxadiazol-2-one | 0.0027 |
| 127 | 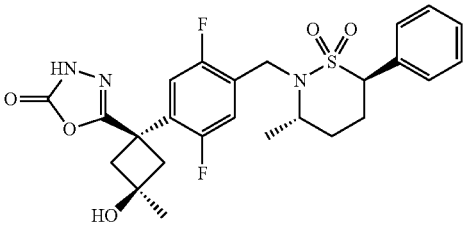 [SMILES: C[C@H]1CC[C@H](c2ccccc2)S(=O)(=O)N1Cc1cc(F)c([C@]2(c3n[nH]c(=O)o3)C[C@@](C)(O)C2)cc1F] | cis-5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3H-1,3,4-oxadiazol-2-one | 0.0072 |
| 128 | 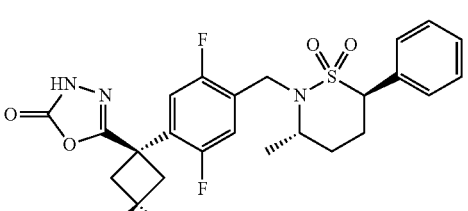 | trans-5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3H-1,3,4-oxadiazol-2-one | 0.0034 |
| 129 | 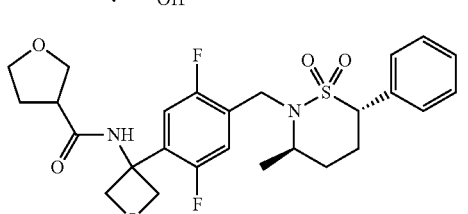 | N-[3-[2,5-difluoro-4-[[(3S,6R)-3-methyl-1,1-dioxo-6-phenyl-thiazinan-2-yl]methyl]phenyl]oxetan-3-yl]tetrahydrofuran-3-carboxamide | 0.0323 |
| 130 | 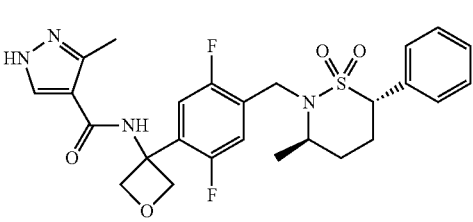 [SMILES: Cc1n[nH]cc1C(=O)NC1(c2cc(F)c(CN3[C@H](C)CC[C@@H](c4ccccc4)S3(=O)=O)cc2F)COC1] | N-[3-[2,5-difluoro-4-[[(3S,6R)-3-methyl-1,1-dioxo-6-phenyl-thiazinan-2-yl]methyl]phenyl]oxetan-3-yl]-3-methyl-1H-pyrazole-4-carboxamide | 0.126 |
| 131 | 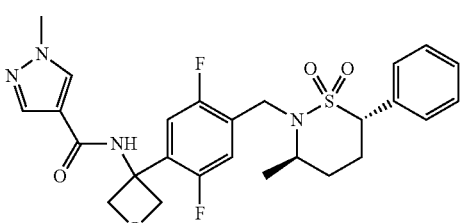 | N-[3-[2,5-difluoro-4-[[(3S,6R)-3-methyl-1,1-dioxo-6-phenyl-thiazinan-2-yl]methyl]phenyl]oxetan-3-yl]-1-methyl-pyrazole-4-carboxamide | 0.208 |
| 132 | 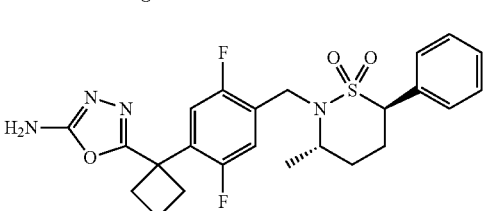 | 5-[1-[2,5-difluoro-4-[[(3S,6R)-3-methyl-1,1-dioxo-6-phenyl-thiazinan-2-yl]methyl]phenyl]-3,3-difluoro-cyclobutyl]-1,3,4-oxadiazol-2-amine | 0.0128 |

TABLE 4-continued

| | Structure | Name | IC$_{50}$ |
|---|---|---|---|
| 133 | 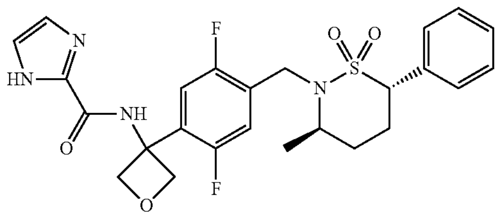 [SMILES: C[C@@H]1CC[C@@H](c2ccccc2)S(=O)(=O)N1Cc1cc(F)c(C2(NC(=O)c3ncc[nH]3)COC2)cc1F] | N-[3-[2,5-difluoro-4-[[(3S,6R)-3-methyl-1,1-dioxo-6-phenyl-thiazinan-2-yl]methyl]phenyl]oxetan-3-yl]-1H-imidazole-2-carboxamide | 0.133 |
| 134 | 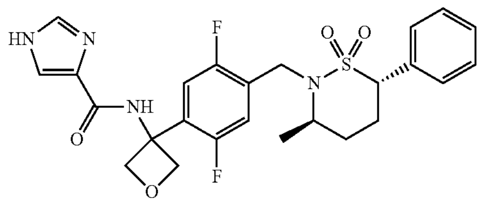 [SMILES: C[C@@H]1CC[C@@H](c2ccccc2)S(=O)(=O)N1Cc1cc(F)c(C2(NC(=O)c3c[nH]cn3)COC2)cc1F] | N-[3-[2,5-difluoro-4-[[(3S,6R)-3-methyl-1,1-dioxo-6-phenyl-thiazinan-2-yl]methyl]phenyl]oxetan-3-yl]-1H-imidazole-4-carboxamide | 0.0507 |
| 135 | 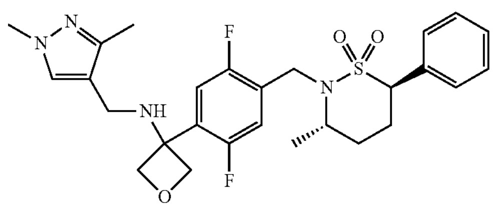 [SMILES: Cc1nn(C)cc1CNC1(c2cc(F)c(CN3[C@@H](C)CC[C@H](c4ccccc4)S3(=O)=O)cc2F)COC1] | 3-[2,5-difluoro-4-[[(3S,6R)-3-methyl-1,1-dioxo-6-phenyl-thiazinan-2-yl]methyl]phenyl]-N-[(1,3-dimethylpyrazol-4-yl)methyl]oxetan-3-amine | 0.201 |
| 136 | 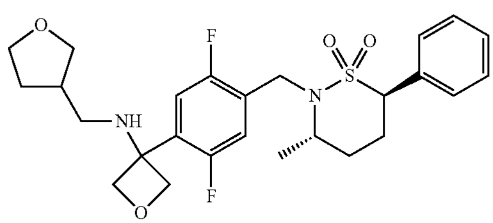 [SMILES: C[C@H]1CC[C@H](c2ccccc2)S(=O)(=O)N1Cc1cc(F)c(C2(NCC3CCOC3)COC2)cc1F] | 3-[2,5-difluoro-4-[[(3S,6R)-3-methyl-1,1-dioxo-6-phenyl-thiazinan-2-yl]methyl]phenyl]-N-(tetrahydrofuran-3-ylmethyl)oxetan-3-amine | 0.0239 |
| 137 | 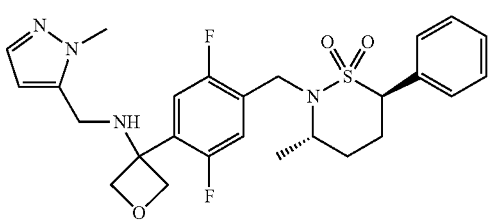 [SMILES: C[C@H]1CC[C@H](c2ccccc2)S(=O)(=O)N1Cc1cc(F)c(C2(NCc3ccnn3C)COC2)cc1F] | 3-[2,5-difluoro-4-[[(3S,6R)-3-methyl-1,1-dioxo-6-phenyl-thiazinan-2-yl]methyl]phenyl]-N-[(2-methylpyrazol-3-yl)methyl]oxetan-3-amine | 0.0894 |
| 138 | 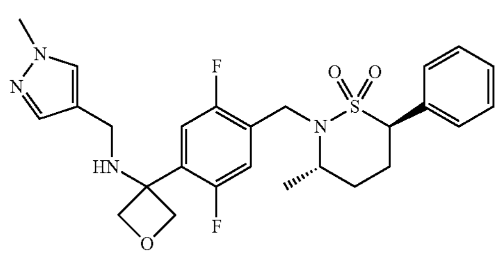 [SMILES: C[C@H]1CC[C@H](c2ccccc2)S(=O)(=O)N1Cc1cc(F)c(C2(NCc3cnn(C)c3)COC2)cc1F] | 3-[2,5-difluoro-4-[[(3S,6R)-3-methyl-1,1-dioxo-6-phenyl-thiazinan-2-yl]methyl]phenyl]-N-[(1-methylpyrazol-4-yl)methyl]oxetan-3-amine | 0.0694 |
| 139 | 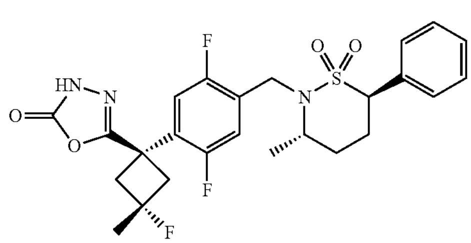 [SMILES: C[C@H]1CC[C@H](c2ccccc2)S(=O)(=O)N1Cc1cc(F)c([C@]2(c3n[nH]c(=O)o3)C[C@](C)(F)C2)cc1F] | trans 5-[1-[2,5-difluoro-4-[[(3S,6R)-3-methyl-1,1-dioxo-6-phenyl-thiazinan-2-yl]methyl]phenyl]-3-fluoro-3-methyl-cyclobutyl]-3H-1,3,4-oxadiazol-2-one | 0.0039 |

TABLE 4-continued

| | Structure | Name | IC$_{50}$ |
|---|---|---|---|
| 140 | 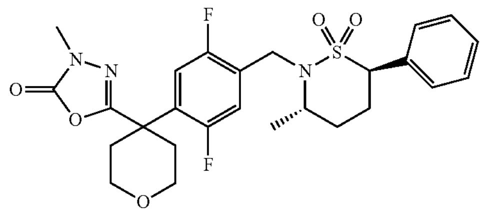 [SMILES: C[C@H]1CC[C@H](c2ccccc2)S(=O)(=O)N1Cc1cc(F)c(C2(c3nn(C)c(=O)o3)CCOCC2)cc1F] | 5-[4-[2,5-difluoro-4-[[(3S,6R)-3-methyl-1,1-dioxo-6-phenyl-thiazinan-2-yl]methyl]phenyl]tetrahydropyran-4-yl]-3-methyl-1,3,4-oxadiazol-2-one | 0.0128 |
| 141 | 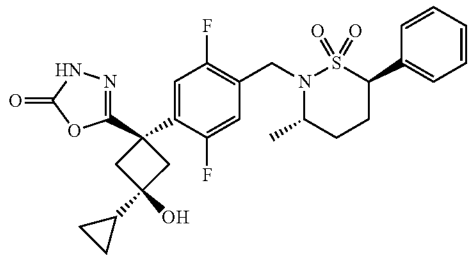 [SMILES: C[C@H]1CC[C@H](c2ccccc2)S(=O)(=O)N1Cc1cc(F)c([C@]2(c3n[nH]c(=O)o3)C[C@](O)(C3CC3)C2)cc1F] | cis 5-[3-cyclopropyl-1-[2,5-difluoro-4-[[(3S,6R)-3-methyl-1,1-dioxo-6-phenyl-thiazinan-2-yl]methyl]phenyl]-3-hydroxy-cyclobutyl]-3H-1,3,4-oxadiazol-2-one | 0.0092 |
| 142 | 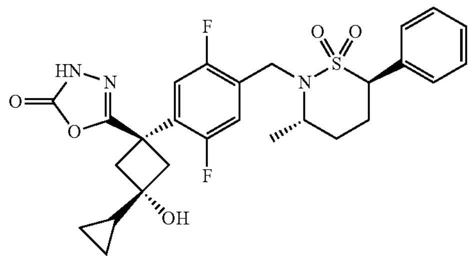 [SMILES: C[C@H]1CC[C@H](c2ccccc2)S(=O)(=O)N1Cc1cc(F)c([C@]2(c3n[nH]c(=O)o3)C[C@@](O)(C3CC3)C2)cc1F] | trans 5-[3-cyclopropyl-1-[2,5-difluoro-4-[[(3S,6R)-3-methyl-1,1-dioxo-6-phenyl-thiazinan-2-yl]methyl]phenyl]-3-hydroxy-cyclobutyl]-3H-1,3,4-oxadiazol-2-one | 0.0043 |
| 143 | 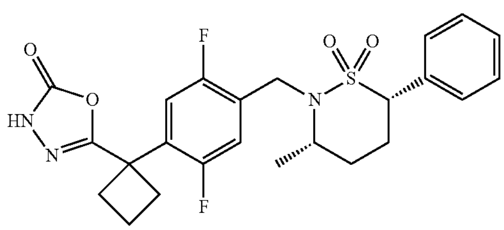 [SMILES: C[C@H]1CC[C@@H](c2ccccc2)S(=O)(=O)N1Cc1cc(F)c(C2(c3n[nH]c(=O)o3)CCC2)cc1F] | 5-[1-[2,5-difluoro-4-[[(3S,6S)-3-methyl-1,1-dioxo-6-phenyl-thiazinan-2-yl]methyl]phenyl]cyclobutyl]-3H-1,3,4-oxadiazol-2-one | 0.151 |
| 144 | 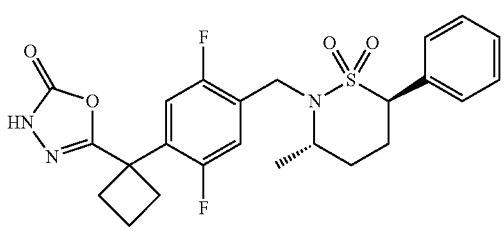 [SMILES: C[C@H]1CC[C@H](c2ccccc2)S(=O)(=O)N1Cc1cc(F)c(C2(c3n[nH]c(=O)o3)CCC2)cc1F] | 5-[1-[2,5-difluoro-4-[[(3S,6R)-3-methyl-1,1-dioxo-6-phenyl-thiazinan-2-yl]methyl]phenyl]cyclobutyl]-3H-1,3,4-oxadiazol-2-one | 0.0094 |
| 145 | 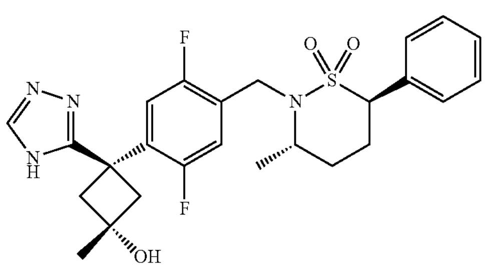 [SMILES: C[C@H]1CC[C@H](c2ccccc2)S(=O)(=O)N1Cc1cc(F)c([C@]2(c3nnc[nH]3)C[C@](C)(O)C2)cc1F] | trans 3-[2,5-difluoro-4-[[(3S,6R)-3-methyl-1,1-dioxo-6-phenyl-thiazinan-2-yl]methyl]phenyl]-1-methyl-3-(4H-1,2,4-triazol-3-yl)cyclobutanol | 0.007 |

TABLE 4-continued

| | Structure | Name | IC$_{50}$ |
|---|---|---|---|
| 146 | 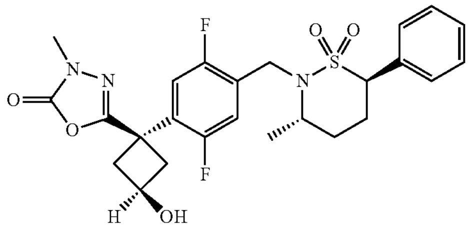 [SMILES: C[C@H]1CC[C@H](c2ccccc2)S(=O)(=O)N1Cc1cc(F)c([C@]2(c3nn(C)c(=O)o3)C[C@@H](O)C2)cc1F] | cis 5-[1-[2,5-difluoro-4-[[(3S,6R)-3-methyl-1,1-dioxo-6-phenyl-thiazinan-2-yl]methyl]phenyl]-3-hydroxy-cyclobutyl]-3-methyl-1,3,4-oxadiazol-2-one | 0.0176 |
| 147 | 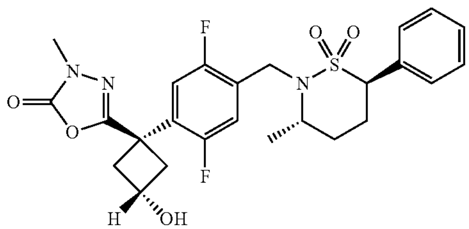 [SMILES: C[C@H]1CC[C@H](c2ccccc2)S(=O)(=O)N1Cc1cc(F)c([C@]2(c3nn(C)c(=O)o3)C[C@H](O)C2)cc1F] | trans 5-[1-[2,5-difluoro-4-[[(3S,6R)-3-methyl-1,1-dioxo-6-phenyl-thiazinan-2-yl]methyl]phenyl]-3-hydroxy-cyclobutyl]-3-methyl-1,3,4-oxadiazol-2-one | 0.0046 |
| 148 | 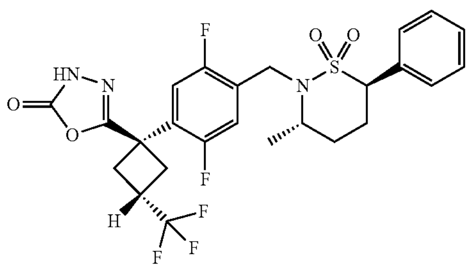 [SMILES: C[C@H]1CC[C@H](c2ccccc2)S(=O)(=O)N1Cc1cc(F)c([C@]2(c3n[nH]c(=O)o3)C[C@H](C(F)(F)F)C2)cc1F] | cis 5-[1-[2,5-difluoro-4-[[(3S,6R)-3-methyl-1,1-dioxo-6-phenyl-thiazinan-2-yl]methyl]phenyl]-3-hydroxy-3-(trifluoromethyl)cyclobutyl]-3H-1,3,4-oxadiazol-2-one | 0.011 |
| 149 | 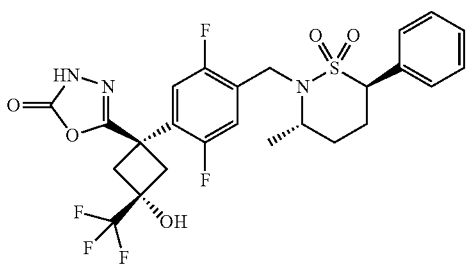 [SMILES: C[C@H]1CC[C@H](c2ccccc2)S(=O)(=O)N1Cc1cc(F)c([C@]2(c3n[nH]c(=O)o3)C[C@@](O)(C(F)(F)F)C2)cc1F] | trans 5-[1-[2,5-difluoro-4-[[(3S,6R)-3-methyl-1,1-dioxo-6-phenyl-thiazinan-2-yl]methyl]phenyl]-3-hydroxy-3-(trifluoromethyl)cyclobutyl]-3H-1,3,4-oxadiazol-2-one | 0.0053 |
| 150 | 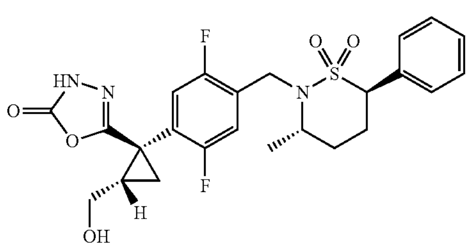 [SMILES: C[C@H]1CC[C@H](c2ccccc2)S(=O)(=O)N1Cc1cc(F)c([C@]2(c3n[nH]c(=O)o3)C[C@@H]2CO)cc1F] | 5-[(1S,2S)-1-[2,5-difluoro-4-[[(3S,6R)-3-methyl-1,1-dioxo-6-phenyl-thiazinan-2-yl]methyl]phenyl]-2-(hydroxymethyl)cyclopropyl]-3H-1,3,4-oxadiazol-2-one | 0.039 |
| 151 | 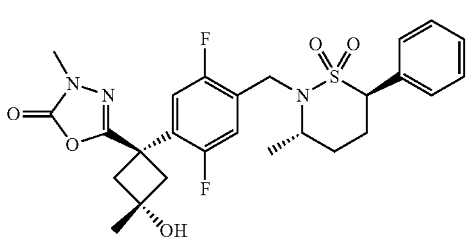 [SMILES: C[C@H]1CC[C@H](c2ccccc2)S(=O)(=O)N1Cc1cc(F)c([C@]2(c3nn(C)c(=O)o3)C[C@](C)(O)C2)cc1F] | trans 5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3-methyl-1,3,4-oxadiazol-2-one | 0.0069 |

TABLE 4-continued

| | Structure | Name | IC$_{50}$ |
|---|---|---|---|
| 152 | 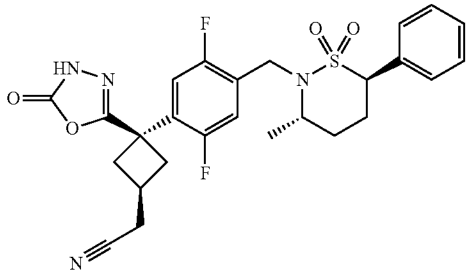 [SMILES: C[C@H]1CC[C@H](c2ccccc2)S(=O)(=O)N1Cc1cc(F)c([C@]2(c3n[nH]c(=O)o3)C[C@@H](CC#N)C2)cc1F] | cis 2-[3-[2,5-difluoro-4-[[(3S,6R)-3-methyl-1,1-dioxo-6-phenyl-thiazinan-2-yl]methyl]phenyl]-3-(2-oxo-3H-1,3,4-oxadiazol-5-yl)cyclobutyl]acetonitrile | 0.0071 |
| 153 | 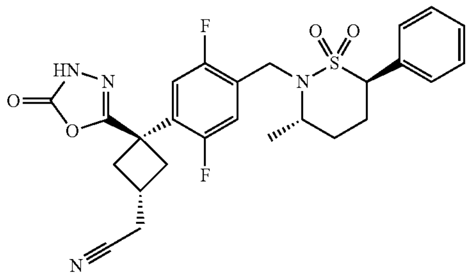 [SMILES: C[C@H]1CC[C@H](c2ccccc2)S(=O)(=O)N1Cc1cc(F)c([C@]2(c3n[nH]c(=O)o3)C[C@H](CC#N)C2)cc1F] | trans 2-[3-[2,5-difluoro-4-[[(3S,6R)-3-methyl-1,1-dioxo-6-phenyl-thiazinan-2-yl]methyl]phenyl]-3-(2-oxo-3H-1,3,4-oxadiazol-5-yl)cyclobutyl]acetonitrile | 0.0087 |
| 154 | 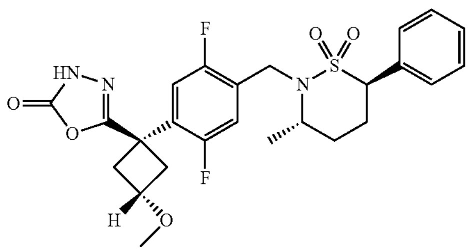 [SMILES: CO[C@H]1C[C@@](c2n[nH]c(=O)o2)(c2cc(F)c(CN3[C@@H](C)CC[C@H](c4ccccc4)S3(=O)=O)cc2F)C1] | trans 5-[1-[2,5-difluoro-4-[[(3S,6R)-3-methyl-1,1-dioxo-6-phenyl-thiazinan-2-yl]methyl]phenyl]-3-methoxy-cyclobutyl]-3H-1,3,4-oxadiazol-2-one | 0.0062 |
| 155 | 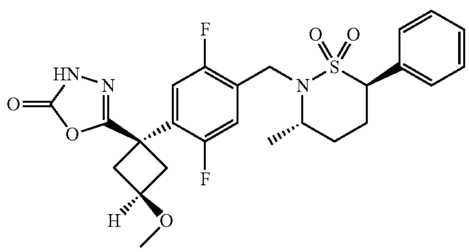 [SMILES: CO[C@H]1C[C@](c2n[nH]c(=O)o2)(c2cc(F)c(CN3[C@@H](C)CC[C@H](c4ccccc4)S3(=O)=O)cc2F)C1] | cis 5-[1-[2,5-difluoro-4-[[(3S,6R)-3-methyl-1,1-dioxo-6-phenyl-thiazinan-2-yl]methyl]phenyl]-3-methoxy-cyclobutyl]-3H-1,3,4-oxadiazol-2-one | 0.0113 |
| 156 | 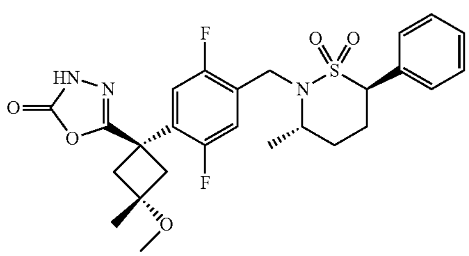 [SMILES: CO[C@]1(C)C[C@](c2n[nH]c(=O)o2)(c2cc(F)c(CN3[C@@H](C)CC[C@H](c4ccccc4)S3(=O)=O)cc2F)C1] | trans 5-[1-[2,5-difluoro-4-[[(3S,6R)-3-methyl-1,1-dioxo-6-phenyl-thiazinan-2-yl]methyl]phenyl]-3-methoxy-3-methyl-cyclobutyl]-3H-1,3,4-oxadiazol-2-one | 0.0040 |
| 157 | 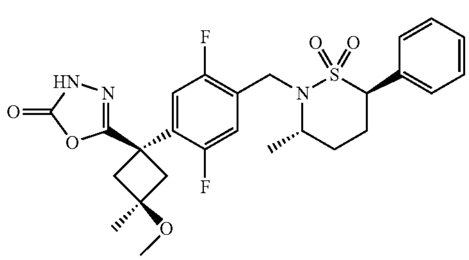 [SMILES: CO[C@]1(C)C[C@@](c2n[nH]c(=O)o2)(c2cc(F)c(CN3[C@@H](C)CC[C@H](c4ccccc4)S3(=O)=O)cc2F)C1] | cis 5-[1-[2,5-difluoro-4-[[(3S,6R)-3-methyl-1,1-dioxo-6-phenyl-thiazinan-2-yl]methyl]phenyl]-3-methoxy-3-methyl-cyclobutyl]-3H-1,3,4-oxadiazol-2-one | 0.0074 |

TABLE 4-continued

| | Structure | Name | IC$_{50}$ |
|---|---|---|---|
| 158 | 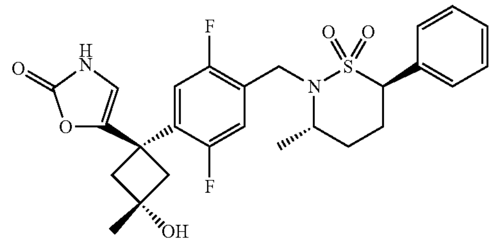 [SMILES: C[C@H]1CC[C@H](c2ccccc2)S(=O)(=O)N1Cc1cc(F)c([C@]2(c3c[nH]c(=O)o3)C[C@](C)(O)C2)cc1F] | 5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3H-oxazol-2-one | 0.0032 |
| 159 | 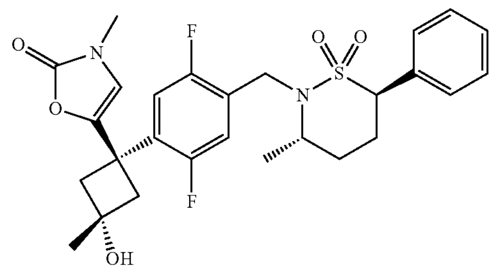 [SMILES: C[C@H]1CC[C@H](c2ccccc2)S(=O)(=O)N1Cc1cc(F)c([C@]2(c3cn(C)c(=O)o3)C[C@](C)(O)C2)cc1F] | 5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-3-methyl-oxazol-2-one | 0.0028 |
| 160 | 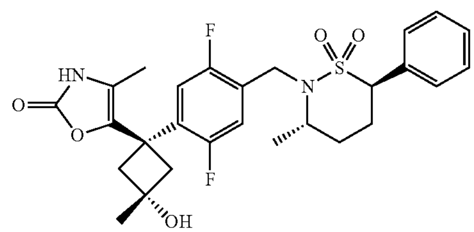 [SMILES: Cc1[nH]c(=O)oc1[C@]1(c2cc(F)c(CN3[C@@H](C)CC[C@H](c4ccccc4)S3(=O)=O)cc2F)C[C@@](C)(O)C1] | 5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-4-methyl-3H-oxazol-2-one | 0.0136 |
| 161 | 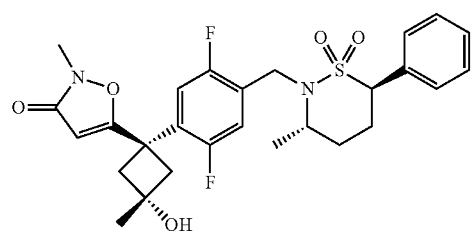 [SMILES: C[C@H]1CC[C@H](c2ccccc2)S(=O)(=O)N1Cc1cc(F)c([C@]2(c3cc(=O)n(C)o3)C[C@](C)(O)C2)cc1F] | 5-[1-[2,5-difluoro-4-[[(3S,6R)-3-methyl-1,1-dioxo-6-phenyl-thiazinan-2-yl]methyl]phenyl]-3-hydroxy-3-methyl-cyclobutyl]-2-methyl-isoxazol-3-one | 0.0052 |
| 162 | 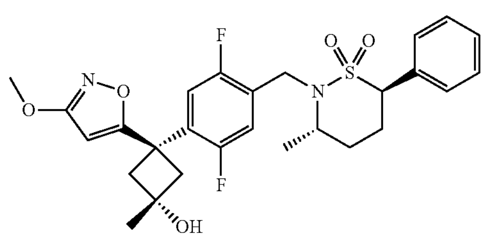 [SMILES: COc1cc([C@]2(c3cc(F)c(CN4[C@@H](C)CC[C@H](c5ccccc5)S4(=O)=O)cc3F)C[C@@](C)(O)C2)on1] | 3-[2,5-difluoro-4-[[(3S,6R)-3-methyl-1,1-dioxo-6-phenyl-thiazinan-2-yl]methyl]phenyl]-3-(3-methoxyisoxazol-5-yl)-1-methyl-cyclobutanol | 0.0036 |
| 163 | 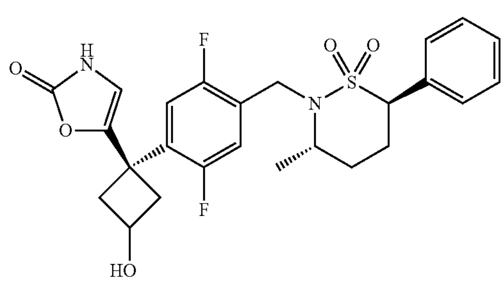 | 5-[1-[2,5-difluoro-4-[[rac-(3S,6R)-3-methyl-1,1-dioxo-6-phenyl-thiazinan-2-yl]methyl]phenyl]-3-hydroxy-cyclobutyl]-3H-oxazol-2-one | 0.0043 |

TABLE 4-continued

| | Structure | Name | IC$_{50}$ |
|---|---|---|---|
| 164 | 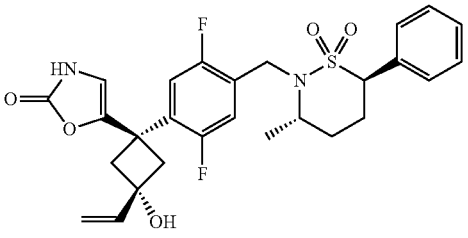 [SMILES: C=C[C@]1(O)C[C@@](c2c[nH]c(=O)o2)(c2cc(F)c(CN3[C@@H](C)CC[C@H](c4ccccc4)S3(=O)=O)cc2F)C1] | 5-[1-[2,5-difluoro-4-[[(3S,6R)-3-methyl-1,1-dioxo-6-phenyl-thiazinan-2-yl]methyl]phenyl]-3-hydroxy-3-vinyl-cyclobutyl]-3H-oxazol-2-one | 0.0061 |
| 165 | 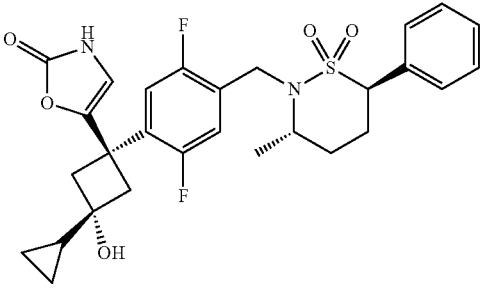 [SMILES: C[C@H]1CC[C@H](c2ccccc2)S(=O)(=O)N1Cc1cc(F)c([C@]2(c3c[nH]c(=O)o3)C[C@@](O)(C3CC3)C2)cc1F] | 5-[3-cyclopropyl-1-[2,5-difluoro-4-[[(3S,6R)-3-methyl-1,1-dioxo-6-phenyl-thiazinan-2-yl]methyl]phenyl]-3-hydroxy-cyclobutyl]-3H-oxazol-2-one | 0.0067 |
| 166 | 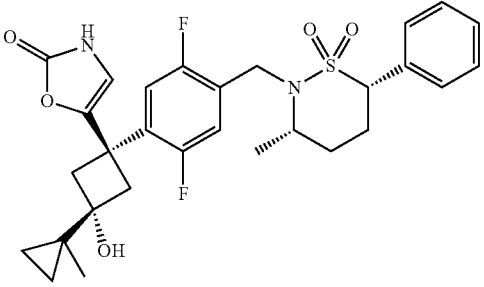 [SMILES: C[C@H]1CC[C@@H](c2ccccc2)S(=O)(=O)N1Cc1cc(F)c([C@]2(c3c[nH]c(=O)o3)C[C@@](O)(C3(C)CC3)C2)cc1F] | 5-[1-[2,5-difluoro-4-[[rac-(3S,6S)-3-methyl-1,1-dioxo-6-phenyl-thiazinan-2-yl]methyl]phenyl]-3-hydroxy-3-(1-methylcyclopropyl)cyclobutyl]-3H-oxazol-2-one | 0.0155 |
| 167 | 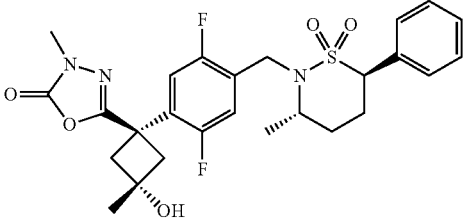 [SMILES: C[C@H]1CC[C@H](c2ccccc2)S(=O)(=O)N1Cc1cc(F)c([C@]2(c3nn(C)c(=O)o3)C[C@](C)(O)C2)cc1F] | 5-[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]-2-methyl-4H-1,2,4-triazol-3-one | 0.0192 |
| 168 | 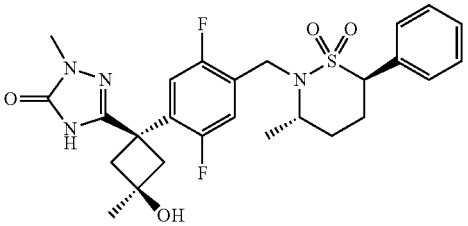 [SMILES: C[C@H]1CC[C@H](c2ccccc2)S(=O)(=O)N1Cc1cc(F)c([C@]2(c3nn(C)c(=O)[nH]3)C[C@@](C)(O)C2)cc1F] | 5-[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]-2-methyl-4H-1,2,4-triazol-3-one | 0.0398 |
| 169 | 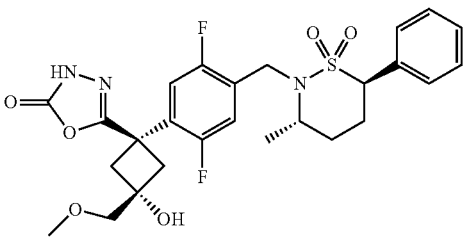 [SMILES: COC[C@]1(O)C[C@@](c2n[nH]c(=O)o2)(c2cc(F)c(CN3[C@@H](C)CC[C@H](c4ccccc4)S3(=O)=O)cc2F)C1] | 5-[1-[2,5-difluoro-4-[[rac-(3S,6R)-3-methyl-1,1-dioxo-6-phenyl-thiazinan-2-yl]methyl]phenyl]-3-hydroxy-3-(methoxymethyl)cyclobutyl]-3H-1,3,4-oxadiazol-2-one | 0.0064 |

TABLE 4-continued

| | Structure | Name | IC$_{50}$ |
|---|---|---|---|
| 170 | 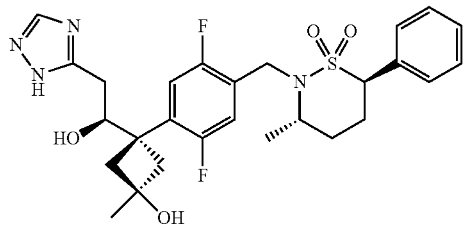 [SMILES: C[C@H]1CC[C@H](c2ccccc2)S(=O)(=O)N1Cc1cc(F)c([C@]2([C@@H](O)Cc3ncn[nH]3)C[C@](C)(O)C2)cc1F] | 3-[2,5-difluoro-4-[[rac-(3S,6R)-3-methyl-1,1-dioxo-6-phenyl-thiazinan-2-yl]methyl]phenyl]-1-methyl-3-[rac-(1S)-1-hydroxy-2-(1H-1,2,4-triazol-5-yl)ethyl]cyclobutanol | 0.0295 |
| 171 | 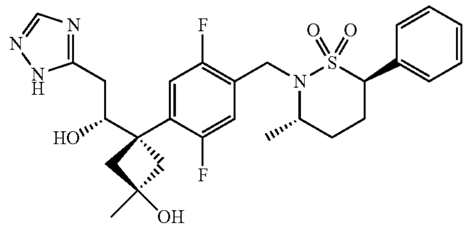 [SMILES: C[C@H]1CC[C@H](c2ccccc2)S(=O)(=O)N1Cc1cc(F)c([C@]2([C@H](O)Cc3ncn[nH]3)C[C@](C)(O)C2)cc1F] | 3-[2,5-difluoro-4-[[rac-(3S,6R)-3-methyl-1,1-dioxo-6-phenyl-thiazinan-2-yl]methyl]phenyl]-1-methyl-3-[rac-(1R)-1-hydroxy-2-(1H-1,2,4-triazol-5-yl)ethyl]cyclobutanol | 0.0503 |
| 172 | 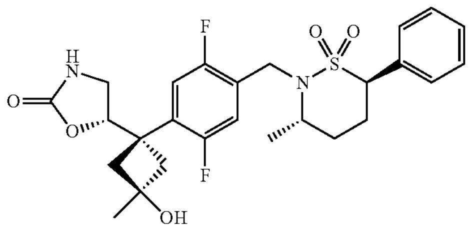 [SMILES: C[C@H]1CC[C@H](c2ccccc2)S(=O)(=O)N1Cc1cc(F)c([C@]2([C@H]3CNC(=O)O3)C[C@](C)(O)C2)cc1F] | rac-(5S)-5-[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]oxazolidin-2-one | 0.0519 |
| 173 | 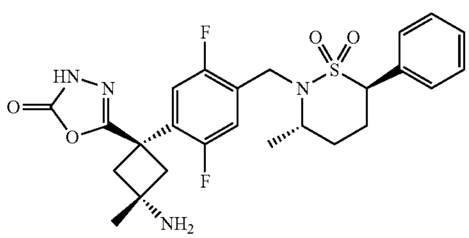 [SMILES: C[C@H]1CC[C@H](c2ccccc2)S(=O)(=O)N1Cc1cc(F)c([C@]2(c3n[nH]c(=O)o3)C[C@](C)(N)C2)cc1F] | 5-[3-amino-1-[2,5-difluoro-4-[[rac-(3S,6R)-3-methyl-1,1-dioxo-6-phenyl-thiazinan-2-yl]methyl]phenyl]-3-methyl-cyclobutyl]-3H-1,3,4-oxadiazol-2-one; hydrochloride | 0.18 |
| 174 | 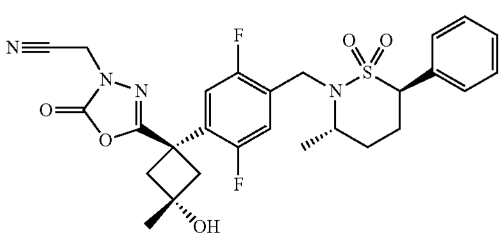 [SMILES: C[C@H]1CC[C@H](c2ccccc2)S(=O)(=O)N1Cc1cc(F)c([C@]2(c3nn(CC#N)c(=O)o3)C[C@](C)(O)C2)cc1F] | 2-[5-[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]-2-oxo-1,3,4-oxadiazol-3-yl]acetonitrile | 0.023 |
| 175 | 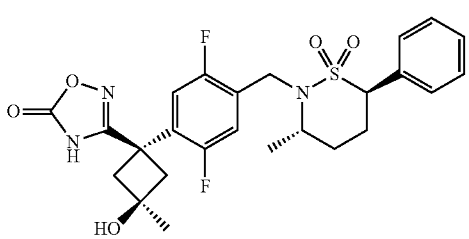 [SMILES: C[C@H]1CC[C@H](c2ccccc2)S(=O)(=O)N1Cc1cc(F)c([C@]2(c3noc(=O)[nH]3)C[C@@](C)(O)C2)cc1F] | 3-[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]-4H-1,2,4-oxadiazol-5-one | 0.062 |

TABLE 4-continued

| | Structure | Name | IC$_{50}$ |
|---|---|---|---|
| 176 | 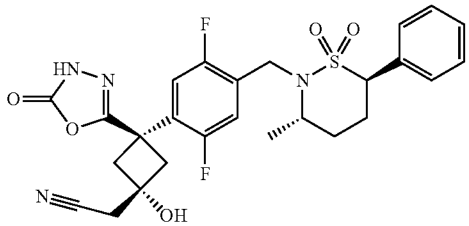 [SMILES: C[C@H]1CC[C@H](c2ccccc2)S(=O)(=O)N1Cc1cc(F)c([C@]2(c3n[nH]c(=O)o3)C[C@@](O)(CC#N)C2)cc1F] | 2-[3-[2,5-difluoro-4-[[rac-(3S,6R)-3-methyl-1,1-dioxo-6-phenyl-thiazinan-2-yl]methyl]phenyl]-1-hydroxy-3-(2-oxo-3H-1,3,4-oxadiazol-5-yl)cyclobutyl]acetonitrile | 0.0054 |
| 177 | 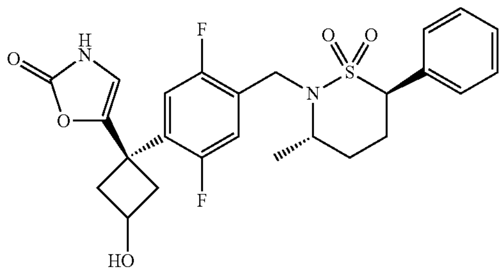 | 5-[1-[2,5-difluoro-4-[[rac-(3S,6R)-3-methyl-1,1-dioxo-6-phenyl-thiazinan-2-yl]methyl]phenyl]-3-hydroxy-cyclobutyl]-3H-oxazol-2-one | 0.0043 |
| 178 | 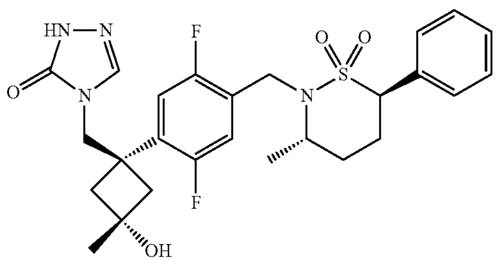 [SMILES: C[C@H]1CC[C@H](c2ccccc2)S(=O)(=O)N1Cc1cc(F)c([C@]2(Cn3cn[nH]c3=O)C[C@](C)(O)C2)cc1F] | 4-[[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]methyl]-1H-1,2,4-triazol-5-one | 0.0061 |
| 179 | 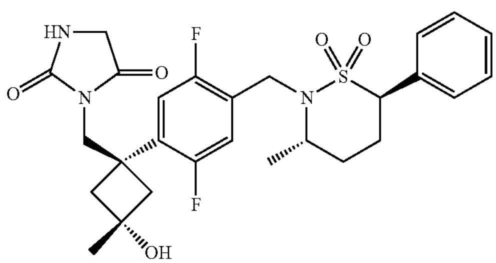 [SMILES: C[C@H]1CC[C@H](c2ccccc2)S(=O)(=O)N1Cc1cc(F)c([C@]2(CN3C(=O)CNC3=O)C[C@](C)(O)C2)cc1F] | 3-[[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]methyl]imidazolidine-2,4-dione | 6.9 |
| 180 | 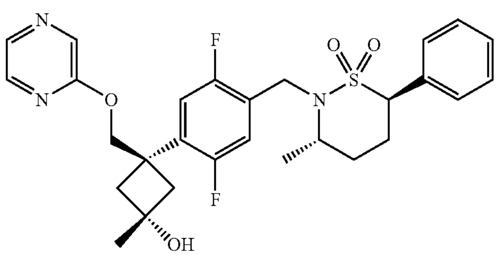 [SMILES: C[C@H]1CC[C@H](c2ccccc2)S(=O)(=O)N1Cc1cc(F)c([C@]2(COc3cnccn3)C[C@](C)(O)C2)cc1F] | 3-[2,5-difluoro-4-[[rac-(3S,6R)-3-methyl-1,1-dioxo-6-phenyl-thiazinan-2-yl]methyl]phenyl]-1-methyl-3-(pyrazin-2-yloxymethyl)cyclobutanol | 0.0080 |
| 181 | 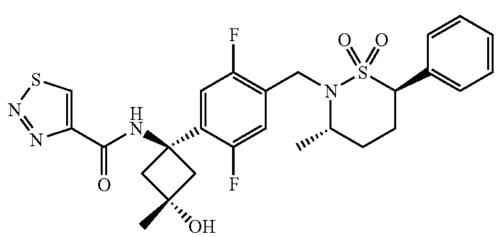 [SMILES: C[C@H]1CC[C@H](c2ccccc2)S(=O)(=O)N1Cc1cc(F)c([C@]2(NC(=O)c3csnn3)C[C@](C)(O)C2)cc1F] | N-[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]thiadiazole-4-carboxamide | 0.013 |

TABLE 4-continued

| | Structure | Name | IC$_{50}$ |
|---|---|---|---|
| 182 | 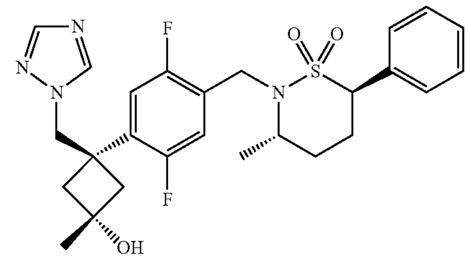 [SMILES: C[C@H]1CC[C@H](c2ccccc2)S(=O)(=O)N1Cc1cc(F)c([C@]2(Cn3cncn3)C[C@](C)(O)C2)cc1F] | 3-[2,5-difluoro-4-[[rac-(3S,6R)-3-methyl-1,1-dioxo-6-phenyl-thiazinan-2-yl]methyl]phenyl]-1-methyl-3-(1,2,4-triazol-1-ylmethyl)cyclobutanol | 0.0073 |
| 183 | 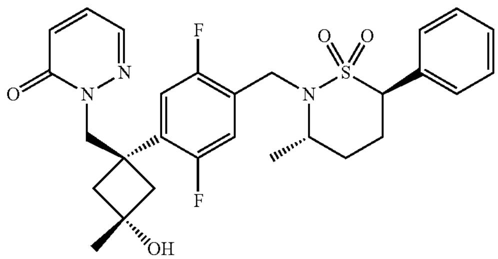 [SMILES: C[C@H]1CC[C@H](c2ccccc2)S(=O)(=O)N1Cc1cc(F)c([C@]2(Cn3ncccc3=O)C[C@](C)(O)C2)cc1F] | 2-[[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]methyl]pyridazin-3-one | 0.17 |
| 184 | 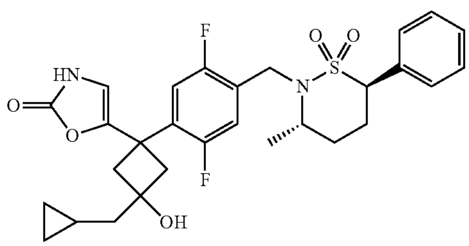 [SMILES: C[C@H]1CC[C@H](c2ccccc2)S(=O)(=O)N1Cc1cc(F)c(C2(c3c[nH]c(=O)o3)CC(O)(CC3CC3)C2)cc1F] | 5-[3-(cyclopropylmethyl)-1-[2,5-difluoro-4-[[rac-(3S,6R)-3-methyl-1,1-dioxo-6-phenyl-thiazinan-2-yl]methyl]phenyl]-3-hydroxy-cyclobutyl]-3H-oxazol-2-one | 0.0062 |
| 185 | 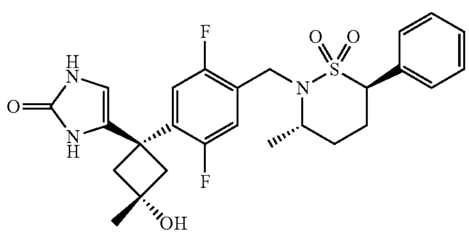 [SMILES: C[C@H]1CC[C@H](c2ccccc2)S(=O)(=O)N1Cc1cc(F)c([C@]2(c3c[nH]c(=O)[nH]3)C[C@](C)(O)C2)cc1F] | 4-[1-[2,5-difluoro-4-[[rac-(3S,6R)-3-methyl-1,1-dioxo-6-phenyl-thiazinan-2-yl]methyl]phenyl]-3-hydroxy-3-methyl-cyclobutyl]-1,3-dihydroimidazol-2-one | 0.019 |
| 186 | 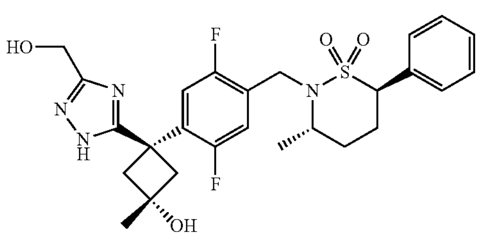 [SMILES: C[C@H]1CC[C@H](c2ccccc2)S(=O)(=O)N1Cc1cc(F)c([C@]2(c3nc(CO)n[nH]3)C[C@](C)(O)C2)cc1F] | 3-[2,5-difluoro-4-[[rac-(3S,6R)-3-methyl-1,1-dioxo-6-phenyl-thiazinan-2-yl]methyl]phenyl]-3-[3-(hydroxymethyl)-1H-1,2,4-triazol-5-yl]-1-methyl-cyclobutanol | 0.0044 |
| 187 | 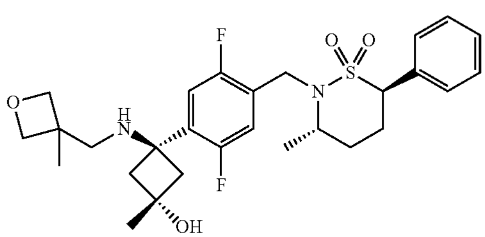 [SMILES: C[C@H]1CC[C@H](c2ccccc2)S(=O)(=O)N1Cc1cc(F)c([C@]2(NCC3(C)COC3)C[C@](C)(O)C2)cc1F] | 3-[2,5-difluoro-4-[[rac-(3S,6R)-3-methyl-1,1-dioxo-6-phenyl-thiazinan-2-yl]methyl]phenyl]-1-methyl-3-[(3-methyloxetan-3-yl)methylamino]cyclobutanol | 0.0100 |

Proton NMR data for selected compounds in Table 4 are shown below, with compound numbers corresponding to those shown in Table 4.

Compound 15: $^1$H NMR (400 MHz, DMSO-$d_6$) δ 9.25 (s, 1H), 8.47 (t, J=5.6 Hz, 1H), 7.53-7.43 (m, 3H), 7.43-7.32 (m, 3H), 7.24 (dd, J=8.2, 1.8 Hz, 1H), 7.13 (dd, J=12.2, 1.9 Hz, 1H), 4.57-4.47 (m, 2H), 4.43 (d, J=5.5 Hz, 2H), 4.36 (d, J=17.5 Hz, 1H), 4.19-4.06 (m, 1H), 3.80-3.70 (m, 2H), 3.52 (t, J=11.2 Hz, 2H), 2.80 (s, 3H), 2.47-2.38 (m, 3H), 2.15-2.05 (m, 1H), 1.92-1.74 (m, 3H), 1.71-1.62 (m, 1H), 1.09 (d, J=6.8 Hz, 3H).

Compound 16: $^1$H NMR (400 MHz, DMSO-$d_6$) δ 8.01 (t, J=5.8 Hz, 1H), 7.51-7.43 (m, 3H), 7.43-7.34 (m, 3H), 7.30-7.28 (m, 1H), 7.20 (dd, J=8.1, 1.9 Hz, 1H), 7.13-7.07 (m, 2H), 4.58-4.46 (m, 2H), 4.36 (d, J=17.5 Hz, 1H), 4.19-4.08 (m, 1H), 4.06 (d, J=5.7 Hz, 2H), 3.79-3.66 (m, 5H), 3.48-3.37 (m, 2H), 2.47-2.37 (m, 3H), 2.15-2.04 (m, 1H), 1.89-1.74 (m, 3H), 1.72-1.62 (m, 1H), 1.09 (d, J=6.9 Hz, 3H).

Compound 17: H NMR (500 MHz, DMSO-$d_6$) δ 12.55 (s, 1H), 8.07 (t, J=5.8 Hz, 1H), 7.50-7.44 (m, 3H), 7.44-7.18 (m, 6H), 7.10 (dd, J=12.3, 1.8 Hz, 1H), 4.58-4.47 (m, 2H), 4.36 (d, J=17.5 Hz, 1H), 4.18-4.06 (m, 3H), 3.77-3.69 (m, 2H), 3.45-3.36 (m, 2H), 2.48-2.38 (m, 3H), 2.15-2.05 (m, 1H), 1.90-1.74 (m, 3H), 1.71-1.61 (m, 1H), 1.08 (d, J=6.8 Hz, 3H).

Compound 33: $^1$H NMR (400 MHz, DMSO-$d_6$) δ 7.98 (t, J=5.6 Hz, 1H), 7.50-7.44 (m, 2H), 7.44-7.34 (m, 3H), 7.26-7.15 (m, 3H), 5.87 (d, J=1.9 Hz, 1H), 4.61-4.47 (m, 2H), 4.37 (d, J=17.9 Hz, 1H), 4.34-4.21 (m, 2H), 4.19-4.07 (m, 1H), 3.73-3.54 (m, 7H), 2.48-2.38 (m, 1H), 2.38-2.28 (m, 2H), 2.16-2.06 (m, 1H), 2.01-1.88 (m, 2H), 1.88-1.73 (m, 1H), 1.73-1.63 (m, 1H), 1.11 (d, J=6.9 Hz, 3H).

Compound 35: $^1$H NMR (400 MHz, DMSO-$d_6$) δ 8.04 (d, J=3.0 Hz, 1H), 7.48-7.42 (m, 2H), 7.42-7.32 (m, 4H), 7.08 (dd, J=12.2, 6.3 Hz, 1H), 5.76 (d, J=2.9 Hz, 1H), 5.31 (s, 2H), 4.57-4.44 (m, 2H), 4.35 (d, J=17.8 Hz, 1H), 4.14-4.01 (m, 1H), 3.82-3.72 (m, 2H), 3.72-3.58 (m, 2H), 2.70-2.57 (m, 2H), 2.46-2.31 (m, 1H), 2.17-2.02 (m, 3H), 1.87-1.72 (m, 1H), 1.72-1.60 (m, 1H), 1.09 (d, J=6.9 Hz, 3H).

Compound 36: $^1$H NMR (400 MHz, DMSO-$d_6$) δ 7.64 (t, J=5.8 Hz, 1H), 7.49-7.43 (m, 2H), 7.43-7.34 (m, 3H), 7.25-7.13 (m, 2H), 4.61-4.43 (m, 4H), 4.41-4.31 (m, 1H), 4.22-4.14 (m, 2H), 4.14-4.06 (m, 1H), 3.74-3.53 (m, 4H), 3.42-3.36 (m, 1H), 3.29-3.21 (m, 1H), 3.04-2.95 (m, 1H), 2.47-2.37 (m, 1H), 2.35-2.25 (m, 2H), 2.16-2.05 (m, 1H), 1.99-1.87 (m, 2H), 1.86-1.73 (m, 1H), 1.73-1.61 (m, 1H), 1.11 (d, J=6.9 Hz, 3H).

Compound 38: H NMR (400 MHz, DMSO-$d_6$) δ 8.28 (d, J=2.9 Hz, 1H), 7.53-7.32 (m, 6H), 7.05 (dd, J=12.1, 6.3 Hz, 1H), 6.27 (d, J=2.9 Hz, 1H), 4.57-4.44 (m, 2H), 4.36 (d, J=17.6 Hz, 1H), 4.14-4.00 (m, 1H), 3.84-3.62 (m, 4H), 2.63-2.55 (m, 2H), 2.45-2.32 (m, 1H), 2.30-2.14 (m, 2H), 2.14-2.06 (m, 1H), 1.96 (s, 3H), 1.87-1.74 (m, 1H), 1.71-1.59 (m, 1H), 1.04 (d, J=6.8 Hz, 3H).

Compound 39: $^1$H NMR (400 MHz, DMSO-$d_6$) δ 8.43 (d, J=2.8 Hz, 1H), 7.61 (d, J=2.1 Hz, 1H), 7.50 (dd, J=11.4, 6.5 Hz, 1H), 7.47-7.42 (m, 2H), 7.42-7.33 (m, 3H), 7.07 (dd, J=12.1, 6.3 Hz, 1H), 6.46 (dd, J=3.3, 1.1 Hz, 1H), 4.57-4.44 (m, 2H), 4.35 (d, J=17.8 Hz, 1H), 4.13-4.02 (m, 1H), 3.84-3.75 (m, 2H), 3.75-3.64 (m, 2H), 2.61-2.53 (m, 2H), 2.45-2.37 (m, 1H), 2.29-2.16 (m, 2H), 2.13-2.05 (m, 1H), 1.86-1.72 (m, 1H), 1.71-1.61 (m, 1H), 1.06 (d, J=6.8 Hz, 3H).

Compound 59: $^1$H NMR (400 MHz, DMSO-$d_6$) δ 13.96 (1H, s), 8.31-8.21 (1H, m), 7.59 (1H, t, J=8.0 Hz), 7.46-7.33 (6H, m), 4.82-4.72 (4H, m), 4.57-4.49 (2H, m), 4.40 (1H, d, J=17.6 Hz), 4.28 (2H, s), 4.16-4.07 (1H, m), 2.44-2.37 (1H, m), 2.12-2.05 (1H, m), 1.88-1.75 (1H, m), 1.68-1.61 (1H, m), 1.11-1.07 (3H, m).

Compound 119: $^1$H NMR (400 MHz, DMSO-$d_6$) δ 7.49-7.27 (7H, m), 4.62-4.53 (2H, m), 4.41 (1H, d, J=17.9 Hz), 4.18-4.10 (1H, m), 3.95-3.81 (3H, m), 2.48-2.40 (1H, m), 2.14-2.08 (1H, m), 1.91-1.76 (1H, m), 1.68 (1H, dd, J=2.3, 14.2 Hz), 1.40 (1H, s), 1.18-1.07 (3H, m).

Compound 120: $^1$H NMR (400 MHz, DMSO-$d_6$) δ 7.45-7.29 (6H, m), 7.21 (1H, dd, J=6.2, 11.1 Hz), 4.57-4.46 (2H, m), 4.35 (1H, d, J=17.8 Hz), 4.13-4.05 (1H, m), 3.05-2.99 (9H, m), 2.74 (2H, dd, J=4.5, 12.0 Hz), 2.44-2.35 (1H, m), 2.11-2.03 (1H, m), 1.83-1.70 (1H, m), 1.64 (1H, dd, J=2.3, 14.2 Hz), 1.10 (3H, d, J=6.9 Hz).

Compound 123: $^1$H NMR (400 MHz, DMSO-$d_6$) δ 7.46-7.34 (5H, m), 7.22-7.14 (2H, m), 5.30 (1H, d, J=6.9 Hz), 4.57-4.47 (2H, m), 4.38-4.23 (2H, m), 4.14-4.04 (1H, m), 3.12-3.03 (2H, m), 2.45-2.32 (3H, m), 2.11-2.05 (1H, m), 1.84-1.71 (1H, m), 1.64 (1H, dd, J=2.3, 14.2 Hz), 1.12-1.08 (3H, m).

Compound 127: $^1$H NMR (400 MHz, DMSO-$d_6$) δ 12.23-12.11 (1H, m), 7.48-7.35 (6H, m), 7.27-7.20 (1H, m), 5.22-5.20 (1H, m), 4.61-4.50 (2H, m), 4.38 (1H, d, J=17.6 Hz), 4.16-4.02 (1H, m), 2.90-2.82 (2H, m), 2.70 (2H, dd, J=4.2, 12.0 Hz), 2.48-2.38 (1H, m), 2.14-2.06 (1H, m), 1.85-1.63 (2H, m), 1.15-1.08 (6H, m).

Compound 128: $^1$H NMR (400 MHz, DMSO-$d_6$) δ 7.48-7.44 (2H, m), 7.43-7.35 (3H, m), 7.29-7.18 (2H, m), 5.19-5.18 (1H, m), 4.61-4.49 (2H, m), 4.41-4.34 (1H, m), 4.16-4.10 (1H, m), 2.94 (2H, d, J=13.2 Hz), 2.66 (2H, d, J=13.2 Hz), 2.47-2.37 (1H, m), 2.14-2.06 (1H, m), 1.86-1.73 (1H, m), 1.67 (1H, dd, J=2.4, 14.2 Hz), 1.27 (3H, s), 1.13 (3H, d, J=7.3 Hz).

Compound 132: $^1$H NMR (400 MHz, DMSO-$d_6$) δ 7.49-7.24 (6H, m), 7.07-7.04 (2H, m), 4.61-4.51 (2H, m), 4.39 (1H, d, J=17.9 Hz), 4.18-4.09 (1H, m), 3.56-3.36 (4H, m), 2.48-2.39 (1H, m), 2.13-2.07 (1H, m), 1.85-1.64 (2H, m), 1.20-1.12 (3H, m).

Compound 139: $^1$H NMR (400 MHz, DMSO-$d_6$) δ 12.35-12.25 (1H, m), 7.49-7.33 (6H, m), 7.28-7.21 (1H, m), 4.61-4.50 (2H, m), 4.38 (1H, d, J=18.1 Hz), 4.16-4.09 (1H, m), 3.18-3.07 (2H, m), 3.04-2.90 (1H, m), 2.46-2.38 (1H, m), 2.15-2.05 (1H, m), 1.84-1.73 (1H, m), 1.67 (1H, dd, J=1.7, 13.9 Hz), 1.55-1.52 (1H, m), 1.49-1.46 (1H, m), 1.40 (2H, s), 1.15-1.08 (3H, m).

Compound 141: $^1$H NMR (400 MHz, DMSO-$d_6$) δ 12.18-12.13 (1H, m), 7.48-7.30 (6H, m), 7.23 (1H, dd, J=6.2, 11.1 Hz), 4.96 (1H, s), 4.60-4.49 (2H, m), 4.38 (1H, d, J=17.8 Hz), 4.16-4.08 (1H, m), 2.85-2.77 (2H, m), 2.67-2.59 (2H, m), 2.47-2.32 (1H, m), 2.14-2.06 (1H, m), 1.86-1.74 (1H, m), 1.70-1.63 (1H, m), 1.14-1.11 (3H, m), 0.89-0.80 (1H, m), 0.22-0.12 (4H, m).

Compound 142: $^1$H NMR (400 MHz, DMSO-$d_6$) δ 7.49-7.19 (6H, m), 4.96 (1H, s), 4.61-4.50 (2H, m), 4.38 (1H, d, J=17.9 Hz), 4.17-4.00 (1H, m), 2.93 (2H, d, J=13.2 Hz), 2.62 (2H, d, J=12.3 Hz), 2.14-2.06 (1H, m), 1.85-1.74 (1H, m), 1.66 (1H, dd, J=2.1, 14.2 Hz), 1.18-1.12 (3H, m), 1.11-1.02 (1H, m), 0.32-0.25 (3H, m).

Compound 145: $^1$H NMR (400 MHz, DMSO-$d_6$) δ 13.75-13.67 (1H, m), 8.32-8.30 (1H, m), 7.48-7.36 (5H, m), 7.19-7.07 (2H, m), 5.03 (1H, s), 4.58-4.45 (2H, m), 4.33 (1H, d, J=17.7 Hz), 4.14-4.00 (1H, m), 3.07-3.00 (2H, m), 2.74-2.67 (2H, m), 2.13-2.05 (1H, m), 1.84-1.72 (1H, m), 1.66 (1H, dd, J=2.2, 14.3 Hz), 1.20-1.04 (6H, m).

Compound 153: $^1$H NMR (400 MHz, DMSO-$d_6$) δ 12.23-12.23 (1H, s), 7.51-7.36 (6H, m), 7.25 (1H, dd, J=6.2, 11.3 Hz), 4.61-4.51 (2H, m), 4.40 (1H, d, J=17.8 Hz), 4.16-4.08

(1H, m), 2.85-2.81 (2H, m), 2.73 (2H, d, J=6.2 Hz), 2.68-2.54 (3H, m), 2.48-2.38 (1H, m), 2.14-2.07 (1H, m), 1.87-1.75 (1H, m), 1.71-1.64 (1H, m), 1.14 (3H, d, J=6.9 Hz)

Compound 167: $^1$H NMR (400 MHz, DMSO-d$_6$) $\square_H$ 11.53 (1H, s), 7.48-7.36 (5H, m), 7.21-7.12 (2H, m), 5.07 (1H, s), 4.59-4.46 (2H, m), 4.35 (1H, d, J=17.8 Hz), 4.15-4.08 (1H, m), 3.21 (3H, s), 2.92 (2H, d, J=12.5 Hz), 2.61-2.54 (2H, m), 2.47-2.31 (1H, m), 2.13-2.06 (1H, m), 1.85-1.62 (2H, m), 1.16 (3H, s), 1.12 (3H, d, J=6.8 Hz)

Compound 169: $^1$H NMR (400 MHz, DMSO-d$_6$) δ 12.21 (1H, s), 7.48-7.36 (5H, m), 7.31 (1H, dd, J=6.5, 10.3 Hz), 7.23 (1H, dd, J=6.2, 11.0 Hz), 5.29 (1H, s), 4.61-4.49 (2H, m), 4.38 (1H, d, J=17.9 Hz), 4.18-4.08 (1H, m), 3.30 (2H, s), 3.28 (3H, s), 3.04 (2H, d, J=13.7 Hz), 2.57 (2H, d, J=14.0 Hz), 2.47-2.39 (1H, m), 2.13-2.06 (1H, m), 1.85-1.74 (1H, m), 1.67 (1H, dd, J=2.2, 14.3 Hz), 1.14 (3H, d, J=6.5 Hz)

Compound 170: $^1$H NMR (400 MHz, DMSO-d$_6$) δ 13.49 (1H, s), 7.82 (1H, br. s), 7.49-7.37 (5H, m), 7.15 (1H, dd, J=6.3, 11.3 Hz), 6.99 (1H, dd, J=6.4, 10.9 Hz), 5.26 (1H, s), 4.77 (1H, s), 4.60-4.48 (2H, m), 4.37 (1H, d, J=17.7 Hz), 4.17-4.11 (2H, m), 2.67-2.63 (2H, m), 2.47-2.28 (4H, m), 2.22-2.07 (2H, m), 1.85-1.76 (1H, m), 1.72-1.65 (1H, m), 1.31 (3H, s), 1.15 (3H, d, J=6.8 Hz)

Compound 171: $^1$H NMR (400 MHz, DMSO-d$_6$) δ 7.48-7.35 (6H, m), 7.22-7.13 (2H, m), 4.89 (1H, s), 4.75 (1H, dd, J=6.6, 8.8 Hz), 4.59-4.47 (2H, m), 4.36 (1H, d, J=17.8 Hz), 4.13 (1H, ddd, J=2.0, 6.9, 11.8 Hz), 3.30-3.25 (1H, m), 3.01 (1H, dd, J=6.9, 8.7 Hz), 2.57-2.52 (1H, m), 2.48-2.34 (4H, m), 2.14-2.06 (1H, m), 1.87-1.75 (1H, m), 1.67 (1H, dd, J=2.2, 14.2 Hz), 1.31 (3H, s), 1.12 (3H, d, J=6.8 Hz)

Example 27 In Vitro RORc Ligand Binding Assay

This assay was used to determine a compound's potency in inhibiting activity of RORc by determining, Ki$_{app}$, IC$_{50}$, or percent inhibition values. Consumables used in this Example are shown in Table 5 below.

TABLE 2

| Consumable | Supplier and product code |
| --- | --- |
| GFB Unifilter plates | Perkin Elmer 6005177 |
| 3-[(3-Cholamidopropyl)dimethylammonio]-1-propanesulfonate (CHAPS) | Sigma C5070 |
| 96-well polypropylene U-bottom assay plate | Nunc 267245 |
| HEPES buffer, 1M | Sigma H3375 |
| Magnesium chloride (MgCl$_2$) | Sigma M8266 |
| D,L-Dithiothreitol (DTT) | Sigma D0632 |

TABLE 5

| Sodium chloride (NaCl) | Sigma 71382 |
| --- | --- |
| Bovine serum albumin (BSA) | Sigma A7030 [lyophilized powder, ≥98% (agarose gel electrophoresis), Essentially fatty acid free, essentially globulin free] |
| 25-hydroxycholesterol | Sigma H1015 |
| 25-[26,27-$^3$H]hydroxycholesterol | Perkin Elmer NET674250UC American Radiolabeled Chemicals ART0766 |
| RORc ligand binding domain | Genentech (e.g., PUR 28048), expressed in E. coli |
| Plate seals | Perkin Elmer 6005185 |
| Microscint 0 | Perkin Elmer 6013611 |

Filter Plate Preparation

On day of the assay, 100 uL of 0.05% CHAPS (in deionized H$_2$O) was added to all wells of the GFB Unifilter plate and allowed soak for 1 h. A wash buffer of 50 mM HEPES (pH 7.4), 150 mM NaCl, and 5 mM MgCl$_2$ was prepared to wash the filter plate. To prepare an assay buffer, BSA was added to the wash buffer to reach 0.01% and DTT was added to reach 1 mM.

Compounds

For IC$_{50}$ mode, 10 mM compound stocks were serially diluted in DMSO with DMSO to give 20× required final concentration in DMSO (15 uL compound+30 uL DMSO). The 20× compound stocks were diluted in DMSO with Assay Buffer 4-fold to reach 5× the final test concentration in 25% DMSO (10 uL compound+30 uL Assay Buffer). Solutions were mixed by aspiration several times with a pipette set on 50 uL volume. For the assay, 10 uL of 5× compound stock solutions in 25% DMSO were added to the assay plate in duplicate.

For two point screening, 10 mM stock compound solutions were diluted in DMSO to obtain 200 uM (20× the high test concentration) and then diluted 10-fold further to reach 20 uM (20× the low test concentration). The 20× stocks were diluted 4-fold with Assay Buffer (10 uL compound+30 uL Assay Buffer) to reach 5× the test concentrations (50 uM and 5 uM) and 10 uL were added to two assay plates for the duplicate wells. With each concentration tested on 2 plates, each set of 80 compounds used 4 assay plates (1 uM and 10 uM, with n=2).

Nonspecific Binding (NSB) Samples, Total Binding (TB) Samples and No Receptor (No R) Samples 25-hydroxycholesterol (1 uM) was used to determine the level of NSB signal is prepared in DMSO as for compounds above, then diluted in Assay Buffer to give a final concentration of 5 uM. For 25-hydroxycholesterol in 25% DMSO/75% Assay Buffer; 10 uL per well was used for NSB samples. Wells for Total Binding and No Receptor sample determination contained 10 uL of 25% DMSO/75% Assay Buffer per well.

Radioligand 25-[$^3$H]Hydroxycholesterol) Preparation

25-[$^3$H]hydroxycholesterol was dilute in Assay Buffer to obtain 15 nM and vortex to mix. Add 20 uL to all wells to reach 6 nM final in the assay.

Receptor Preparation

The optimal concentration for RORc receptor was found to be 0.6 ug/mL. Stock receptor solution was diluted in assay buffer to obtain 1.5 ug/mL in Assay Buffer. 20 uL was added to all wells. For No R samples, 20 uL Assay Buffer was substituted for receptor solution.

Sample addition to Plates and Incubation

Assay plates were 96-well polypropylene V-bottom plates. 10 uL of 5× compound in 25% DMSO/75% Assay Buffer was added to Test wells. 10 uL of 25% DMSO/75% Assay Buffer was added to Total Binding or No Receptor wells. 10 uL of 5 uM 25-hydroxycholesterol in 25% DMSO/75% Assay Buffer was added to NSB wells. 20 uL of 15 nM 25-[$^3$H]hydroxycholesterol prepared in Assay Buffer was added to all wells. 20 uL of 1.5 ug/mL RORc receptor was added to wells (or 40 uL Assay Buffer to No R wells). Following addition to the wells, the plates were incubated 3 h at 25° C.

Filtration

Using a Packard Filtermate Harvester, the filter plate were washed 4 times following transfer of the incubated samples. Plates were dry-filtered completely (2 h at 50° C. or overnight at room temperature). 50 uL Microscint 0 was added to all wells and read on Topcount protocol Inverted.

Final Concentrations

Final concentrations were as follows: 50 mM HEPES buffer (pH 7.4); 150 mM NaCl; 1 mM DTT; 5 mM MgCl$_2$; 0.01% BSA; 5% DMSO; 0.6 ug/mL RORc receptor; 6 nM 25-[$^3$H]hydroxycholesterol. For NSB wells, 1 uM 25-hydroxycholesterol was also present.

Example 28: RORc Coactivator Peptide Binding Assay

Assays were carried out in 16-microL reaction volumes in black 384 Plus F Proxiplates (Perkin-Elmer 6008269). All assay components except test ligand were mixed in coregulator buffer D (Invitrogen PV4420) containing 5 mM DTT and added to the plate at twice their final concentrations in a volume of 8 microL. Test ligands at 2× the final concentration were then added to the wells in 8 □L of coregulator buffer D containing 5 mM DTT and 4% DMSO. Final incubations contained 1× coregulator buffer D, 5 mM DTT, test ligand, 2% DMSO, 50 nM biotinyl-CPSSHSSLTERKH-KILHRLLQEGSPS (American Peptide Company; Vista, Calif.), 2 nM Europium anti-GST (Cisbio 61GSTKLB), 12.5 nM streptavidin-D2 (Cisbio 610SADAB), 50 mM KF, and 10 nM of bacterially-expressed human RORc ligand binding domain protein containing an N-terminal 6×His-GST-tag and residues 262-507 of Accession NP_005051. Ten test ligand concentrations were tested in duplicate. After the reaction plates were incubated for 3 h in the dark at room temperature (22-23° C.), the plate was read on an EnVision plate reader (PerkinElmer) following the Europium/D2 HTRF protocol (ex 320, em 615 and 665, 100 □s lag time, 100 flashes, 500 μs window). The time-resolved FRET signal at 665 nm was divided by that at 615 nm to generate the signal ratio of each well. The signal ratio of wells containing RORc and peptide but no test ligand were averaged and set to 0% Effect while the signal ratios of the blank wells containing coactivator peptide but no RORc were averaged and set to −100% Effect. RORc exhibits a basal (constitutive) signal in this assay and test ligands can increase or decrease the signal ratio relative to this basal signal level. RORc agonists increase the signal ratio in this assay and result in a positive % Effect value. Inverse agonists decrease the signal ratio, and result in a negative % Effect value. The EC$_{50}$ value is the concentration of test compound that provides half-maximal effect (increased or decreased assay signal) and is calculated by Genedata Screener® software (Genedata; Basel, Switzerland) using the following equation:

$$\% \text{ Effect} = S_0 + \{(S_{inf} - S_0)/[1+(10^{\log EC_{50}}/10^c)^n]\}$$

where $S_0$ equals the activity level at zero concentration of test compound, $S_{inf}$ is the activity level at infinite concentration of test compound, $EC_{50}$ is the concentration at which the activity reaches 50% of the maximal effect, c is the concentration in logarithmic units corresponding to the values on the x-axis of the dose-response curve plot, and n is the Hill coefficient (the slope of the curve at the $EC_{50}$).

Example 29: Arthritis Mouse Model 8 to 10-week old male DBA/1 (DBA/1OlaHsd, Harlan Laboratories) mice are housed in a specific pathogen free (SPF) animal facility. Arthritis is induced by two injections of collagen subcutaneously in the base of the tail. The initial injection (on day 0) uses bovine type II collagen (2 mg/ml from Chondrex, Redmond, Wash.) emulsified in equal volume of CFA containing 4 mg/ml of *M. tuberculosis* (Chondrex). The CII booster injection on Day 29 is emulsified in incomplete Freund's adjuvant (IFA). Each animal receives 0.1 ml of emulsion by subcutaneous/intradermal injection in the tail 2 to 3 cm from the body of the mouse. The booster injection site is in the vicinity of but different from the initial injection site and closer to the body of the animal. OR-1050 was formulated in HRC-6 as above. On weekdays, the animals receive two doses (a.m. and p.m.) of HRC-6 or 50 mg/kg OR-1050 p.o. (2.5 mls/kg). On weekends, a single dose of 100 mg/kg is administered (5 mls/kg).

The mice are observed daily for clinical symptoms of CIA based on the following qualitative scale. Each paw was examined individually and scored. Grade 0, normal; grade 1, mild but definite redness and swelling of the ankle or wrist, or apparent redness and swelling limited to individual digits, regardless of the number of affected digits; grade 2, moderate redness and swelling of ankle or wrist; grade 3, severe redness and swelling of the entire paw including digits; grade 4, maximally inflamed limb with involvement of multiple joints. To estimate cumulative disease severity for each animal, an area under the curve score is calculated for each animal by totaling the sum of the daily hind paw measurements between days 24 and 48.

Example 30: Muscular Sclerosis Mouse Model I

Experiments are conducted on female mice aged 4-6 weeks belong to the C57BL/6 strain weighing 17-20 g. Experimental autoimmune encephalomyelitis (EAE) is actively induced using 95% pure synthetic myelin oligodendrocyte glycoprotein peptide 35-55 (MOG$_{35-55}$) (Invitrogen). Each mouse is anesthetized and receives 200 ug of MOG$_{35-55}$ peptide and 15 ug of Saponin extract from Quilija bark emulsified in 100 uL of phosphate-buffered saline. A 25 uL volume is injected subcutaneously over four flank areas. Mice are also intraperitoneally injected with 200 ng of pertussis toxin in 200 uL of PBS. A second, identical injection of pertussis toxin is given after 48 h.

A compound of the invention is administered at selected doses. Control animals receive 25 uL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hind limbs); 2, unilateral partial hind limb paralysis; 2.5, bilateral hind limb paralysis; 3, complete bilateral hindlimb paralysis; 3.5, complete hindlimb paralysis and unilateral forelimb paralysis; 4, total paralysis of hind limbs and forelimbs (Eugster et al., Eur J Immunol 2001, 31, 2302-2312).

Inflammation and demyelination may be assessed by histology on sections from the CNS of EAE mice. Mice are sacrificed after 30 or 60 days and whole spinal cords are removed and placed in 0.32 M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabeled with anti-CD3+ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then re-suspended in PBS and counted. Cells at a density of about $3 \times 10^6$ cells/mL are incubated overnight with 20 ug/mL of MOG peptide. Supernatants from stimulated cells are assayed for IFNgamma protein levels using an appropriate mouse IFN-gamma immunoassay system.

Example 31: Muscular Sclerosis Mouse Model II

In this model, female rodents are anesthetized with isoflurane and injected with Freund's Incomplete Adjuvant containing 1 mg/mL neuronal antigen (e.g. myelin basic protein, myelin oligodendrocyte glycoprotein, proteolipid protein) and 4 mg/mL *mycobacterium tuberculosis* at two sites on the back on day 0 of this study. A compound of interest is then dosed daily in a sub-cutaneous, intra-peritoneally, or oral manner from day 0 until the end of study at an efficacious dose. Daily observations of degree of paralysis are taken as measures of efficacy.

Example 32: Psoriasis Mouse Model I

The severe, combined immunodeficient (SCID) mouse model can be used to evaluate the efficacy of compounds for treating psoriasis in humans (Boehncke, Ernst Schering Res Found Workshop 2005, 50, 213-34; and Bhagavathula et al., J Pharmacol Expt'l Therapeutics 2008, 324(3), 938-947). Briefly, SCID mice are used as tissue recipients. One biopsy for each normal or psoriatic volunteer (human) is transplanted onto the dorsal surface of a recipient mouse. Treatment is initiated 1 to 2 weeks after transplantation. Animals with the human skin transplants are divided into treatment groups. Animals are treated twice daily for 14 days. At the end of treatment, animals are photographed and then euthanized. The transplanted human tissue along with the surrounding mouse skin is surgically removed and fixed in 10% formalin and samples obtained for microscopy. Epidermal thickness is measured. Tissue sections are stained with an antibody to the proliferation-associated antigen Ki-67 and with an anti-human CD3.sup.+ monoclonal antibody to detect human T lymphocytes in the transplanted tissue. Sections are also probed with antibodies to c-myc and beta-catenin. A positive response to treatment is reflected by a reduction in the average epiderma thickness of the psoriatic skin transplants. A positive response is also associated with reduced expression of Ki-67 in keratinocytes.

Example 33: Psoriasis Mouse Model II

Using the Imidquimod model of skin inflammation (Fits et al, Journal of Immunology, 2009, 182: 5836-5845), 10-12 week old BALB/c, I117c+/+ or I117c−/−, or I117re+/+ or I117re−/− mice were administered 50 mg Aldara cream (5% Imidquimod in Graceway, 3M) in the shaved back and right ear daily for 5 days. Clinical scoring and ear thickness measurements were performed daily. Scoring was based upon the manifestation of psoriatic symptoms, such as erythema, scaling and thickness: 0, No disease. 1, Very mild erythema with very mild thickening and scaling involving a small area. 2, Mild erythema with mild thickening and scaling involving a small area. 3, Moderate erythema with moderate thickening and scaling (irregular and patchy) involving a small area (<25%). 4, Severe erythema with marked thickening and scaling (irregular and patchy) involving a moderate area (25-50%). 5, Severe erythema with marked thickening and scaling (irregular and patchy) involving a large area (>50%). Ear and back tissue were harvested on day 5 for histological evaluation. Efficacy of compounds is compared in the imiquimod (IMQ) mouse model of psoriasis. Balb/c mice (10 males/group) received daily topical IMQ (5% cream) on shaved back and right ear for 5 days as described above. Animals received oral dose of a representative compound or DMF (45 or 90 mg-eq MMF/kg twice daily) or vehicle from Day −5 to Day +5. Erythema score is the primary outcome measure. The Erythema score values of the compounds tested at an oral dose of 90 mg-eq MMF/kg BID for 10 days in male Balb/C mice are set forth in Table 3, below. The data shows that the compounds of the disclosure are equipotent to DMF.

Example 34: Irritable Bowel Disease Mouse Model I

Effectiveness in treatment of inflammatory bowel disease may be evaluated as described by Jurjus et al., J Pharmacol Toxicol Methods 2004, 50, 81-92; Villegas et al., Int'l Immunopharmacol 2003, 3, 1731-1741; and Murakami et al., Biochemical Pharmacol 2003, 66, 1253-1261. Briefly, female ICR mice are divided into treatment groups which are given either water (control), 5% DSS in tap water is given at the beginning of the experiment to induce colitis, or various concentrations of test compound. After administering test compound for 1 week, 5% DSS in tap water is also administered to the groups receiving test compound for 1 week. At the end of the experiment, all mice are sacrificed and the large intestine is removed. Colonic mucosa samples are obtained and homogenized. Proinflammatory mediators (e.g., IL-1alpha, IL-1beta, TNFalpha, PGE2, and PGF2alpha.) and protein concentrations are quantified. Each excised large intestine is histologically examined and the damage to the colon scored.

Example 35: Chronic Obstructive Pulmonary Disease Mouse Model

The cigarette smoke model of Martorana et al., Am J Respir Crit Care Med 2005, 172, 848-835; and Cavarra et al., Am J Respir Crit Care Med 2001, 164, 886-890 can be used for assessing efficacy in treating emphysema. Briefly, six-week old C57B1/6J male mice are exposed either to room air or to the smoke of five cigarettes for 20 minutes. For the acute study, mice are divided into three groups of 40 animals each. These groups are then divided into four subgroups of 10 mice each as follows: (1) no treatment/air-exposed; (2) no treatment/smoke-exposed; (3) a first dose of test compound plus smoke-exposed; and (4) a second dose of test compound. In the first group, trolox equivalent antioxidant capacity is assessed at the end of the exposure in bronchoalveolar lavage fluid. In the second group, cytokines and chemokines are determined in bronchoalveolar lavage fluid using a commercial cytokine panel at 4 hours; and in the third group bronchoalveolar lavage fluid cell count is assessed at 24 hours.

In a chronic study, the mice are exposed to either room air or to the smoke of three cigarettes/day, for 5 days/week, for 7 months. Five groups of animals are used: (1) no treatment/air-exposed; (2) a first dose of a test compound plus air-exposed; (3) no treatment/smoke-exposed; (4) a second dose of the test compound plus smoke-exposed; and (5) the first dose of the test compound plus smoke exposed. Seven months after chronic exposure to room air or cigarette smoke, 5 to 12 animals from each group are sacrificed and the lungs fixed intratracheally with formalin. Lung volume is measured by water displacement. Lungs are stained. Assessment of emphysema includes mean linear intercept and internal surface area. The volume density of macrophages, marked immunohistochemically with anti-mouse Mac-3 monoclonal antibodies is determined by point counting. A mouse is considered to have goblet cell metaplasia when at least one or more midsize bronchi/lung showed a positive periodic acid-Schiff staining for the determination of desmosine, fresh lungs are homogenized, processed, and analyzed by high-pressure liquid chromatography.

Example 36: Asthma Mouse Model

A single inhaled allergen challenge can induce an acute increase in airway responsiveness in some individuals and animal models. However, repeated allergen inhalations have demonstrated more pronounced, consistent, and prolonged increases in airway responsiveness. This mouse model of long-term repeated inhalations of allergen has been used to study the long term effect of allergic diseases in the lung, and to delineate the cells, mechanisms, molecules, and mediators involved in the induction of airway hyperresponsiveness of lung in humans.

Crystalline OVA is obtained from Pierce Chem. Co. (Rockford, Ill.) aluminum potassium sulfate (alum) from Sigma Chem. Co. (St. Louis, Mo.), pyrogen-free distilled water from Baxter, Healthcare Corporation (Deerfield, Ill.), 0.9% sodium chloride (normal saline) from Lymphomed (Deerfield, Ill.) and Trappsol™ HPB-L100 (aqueous hydroxypropylbeta cyclodextrin; 45 wt/vol % aqueous solution) from Cyclodextrin Technologies Development, Inc. (Gainesville, Fla.). The OVA (500 ug/ml in normal saline) is mixed with equal volumes of 10% (wt/vol) alum in distilled water. The mixture (pH 6.5 using 10 N NaOH) after incubation for 60 minutes at room temperature is centrifuged at 750 g for 5 minutes; the pellet resuspended to the original volume in distilled water and used within one hour. The selective 5-lipoxtgenase inhibitor, Zileuton (N-[1-benzo[b]thien-2-ylethyl]-N-hydroxyurea; J. Pharmacol Exp Ther. 1991; 256: 929-937) is dissolved in Trappsol™ Histatek, Inc. (Seattle, Wash.) to provide the mast cell degranulation inhibitor, f-Met-Leu-Phe-Phe ("HK-X").

Female BALB/c Once (6-8 wk of age) receive an i.p. injection of 0.2 ml (100 ug) of OVA with alum on the different protocols of Standard (J. Exp Med. 1996; 184: 1483-1494). Mice are anesthetized with 0.2 ml i.p. of ketamine (0.44 mg/ml)/xylazine (6.3 mg/ml) in normal saline before receiving an intranasal (i.n.) dose of 100 ug OVA in 0.05 ml normal saline and an i.n. dose of 50 ug OVA in 0.05 ml normal saline separately on different days. Two control groups are used: the first group receives normal saline with alum i.p. and normal saline without alum i.n.; and the second group receives OVA with alum i.p., OVA without alum i.n., and normal saline, alone.

The trachea and left lung (the right lung may be used for bronchoalveolar lavage ("BAL") as described below) are obtained and fixed in 10% neutral formaldehyde solution at room temperature for about 15 h. After being embedded in paraffin, the tissues are cut into 5-um sections and processed with the different staining or immunolabeling further. Discombe's eosinophil staining is used for counting the cell numbers with the counterstain of methylene blue. The eosinophil number per unit airway area (2,200 um$^2$) is determined by morphometry (J. Pathol. 1992; 166: 395-404; Am Rev Respir Dis. 1993; 147:448-456). Fibrosis is identified with the Masson's trichrome staining. Airway mucus is identified by the following staining method: methylene blue, hematoxylin and eosin, mucicarmine, alcian blue, and alcian blue/periodic acid-Schiff (PAS) reaction (Troyer, H., "Carbohydrates" in Principles and Techniques of Histochemistry, Little, Brown and Company, Boston, Mass., 1980: 89-121; Sheehan, D. C., et al., "Carbohydrates" in Theory and Practice of Histotechnology, Battle Press, Columbus, Ohio, 1980: 159-179) Mucin is stained with mucicarmine solution; metanil yellow counterstain is employed. Acidic mucin and sulfated mucosubstances are stained with alcian blue, pH 2.5; nuclear fast red counterstain is used. Neutral and acidic mucosubstances are identified by alcian blue, pH 2.5, and PAS reaction. The degree of mucus plugging of the airways (0.5-0.8 mm in diameter) is also assessed by morphometry. The percent occlusion of airway diameter by mucus is classified on a semiquantitative scale from 0 to 4+. The histologic and morphometric analyses may be performed by individuals blinded to the protocol design.

On day 28, 24 hours after the last i.n. administration of either normal saline or OVA, pulmonary mechanics to intravenous infusion of methacholine may be determined in mice in vivo by a plethysmographic method as previously described (10, 1958; 192: 364-368; J. Appl. Physiol. 1988; 64: 2318-2323; J. Exp. Med. 1996; 184: 1483-1494).

After tying off the left lung at the mainstem bronchus, the right lung may be lavaged three times with 0.4 ml of normal saline. Bronchoalveolar lavage (BAL) fluid cells from a 0.05-ml aliquot of the pooled sample are counted using a hemocytometer and the remaining fluid centrifuged at 4° C. for 10 minutes at 200 g. The supernatant may be stored at 70.degree. C. until eicosanoid analysis is performed. After resuspension of the cell pellet in normal saline containing 10% bovine serum albumin ("BSA"), BAL cell smears are made on glass slides. To stain eosinophils, dried slides are stained with Discombe's diluting fluid (0.05% aqueous eosin and 5% acetone (vol/vol) in distilled water; J. Exp. Med. 1970; 131: 1271-1287) for 5-8 minutes, rinsed with water for 0.5 minutes, and counterstained with 0.07% methylene blue for 2 minutes.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:
1. A compound of formula III:

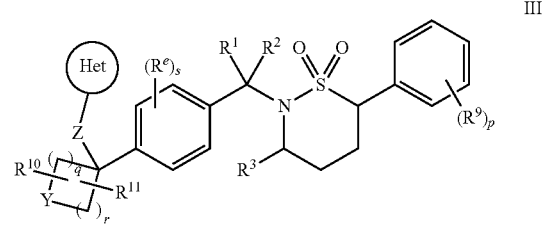

wherein:
s is from 0 to 3;
p is from 0 to 3;
q is 0, 1 or 2;
r is 1, 2 or 3;
Y is: —O—; or —CR$^f$R$^g$—
Z is:
  a bond;
  —C$_{1-6}$alkylene-;
  —NR$^p$—C$_{1-6}$alkylene;
  —C$_{1-6}$alkylene-NR$^p$—;
  —NR$^p$—;
  —C(O)—;
  —C(O)NR$^p$—;
  —C(O)NR$^p$—C$_{1-6}$alkylene;
  —NR$^p$C(O)—;
  —NR$^p$C(O)—C$_{1-6}$alkylene;
  —C$_{1-6}$alkylene—O—;
  —O—C$_{1-6}$alkylene-; or
  —C$_{1-6}$alkylene-O—C$_{1-6}$alkylene-;
Het is:
  heteroaryl selected from:
    oxazolyl;
    isoxazolyl;
    thiazolyl;
    isothiazolyl;
    pyrazolyl;
    triazolyl;
    oxadiazolyl;
    thiadiazolyl;
    pyridinyl;
    pyrimidinyl;
    pyrazinyl; or
    imidazolyl;
  each of which heteroaryl may be unsubstituted or substituted one or more times with R$^m$; or
  heterocyclyl selected from:
    oxetanyl;
    tetrahydrofuranyl;
    tetrahydropyranyl;
    pyrrolidinyl;
    piperidinyl;
    piperazinyl;
    oxazolidinyl;
    imidazolidinyl;
    morpoholinyl;
  each of which heterocyclyl may be unsubstituted or substituted one or more times with R$^n$;
R$^1$ and R$^2$ are hydrogen;
R$^3$ and R$^4$ each independently is hydrogen or C$_{1-6}$alkyl;
each R$^9$ is independently:
  C$_{1-6}$alkyl;
  halo;
  C$_{1-6}$alkoxy; or
  cyano;
  wherein the C$_{1-6}$alkyl moieties may be unsubstituted or substituted one or more times with halo;
R$^{10}$ is:
  hydrogen;
  oxo;
  hydroxy;
  cyano;
  halo; or
  C$_{1-6}$alkyl which may be unsubstituted or substituted one or more times with halo or oxo;
R$^{11}$ is:
  hydrogen;
  halo; or
  C$_{1-6}$alkyl which may be unsubstituted or substituted one or more times with halo or oxo;
each R$^e$ is independently:
  hydrogen;
  C$_{1-6}$alkyl;
  halo;
  C$_{1-6}$alkoxy; or
  cyano;
  wherein the C$_{1-6}$alkyl moieties may be unsubstituted or substituted one or more times with halo, hydroxy or C$_{1-6}$alkoxy;
R$^f$ is:
  hydrogen;
  halo;
  C$_{1-6}$alkoxy; or
  C$_{1-6}$alkyl which may be unsubstituted or substituted one or more times with halo, hydroxy, or C$_{1-6}$alkoxy;
R$^g$ is:
  hydrogen;
  C$_{1-6}$alkyl;
  C$_{3-6}$cycloalkyl which may be unsubstituted or substituted once or twice with C$_{1-6}$alkyl;
  C$_{2-6}$alkenyl;
  C$_{3-6}$cycloalkenyl;
  C$_{3-6}$cycloalkyl-C$_{1-6}$alkyl;
  halo;
  C$_{1-6}$alkyl-sulfonyl;
  C$_{3-6}$cycloalkyl-sulfonyl;
  C$_{3-6}$cycloalkyl-C$_{1-6}$alkyl-sulfonyl;
  C$_{1-6}$alkyl-sulfonyl-C$_{1-6}$alkyl;
  cyano;
  cyano-C$_{1-6}$alkyl;
  C$_{1-6}$alkoxy;
  amino;
  N—C$_{1-6}$alkyl-amino;
  N,N-di-C$_{1-6}$alkyl-amino;
  phenyl;
  hydroxy;
  wherein the C$_{1-6}$alkyl moieties may be unsubstituted or substituted one or more times with halo;
  or R$^f$ and R$^g$ together may form oxo;
each R$^m$ is independently:
  C$_{1-6}$alkyl;
  oxo;
  hydroxyl;
  amino; or
  hydroxyl-C$_{1-6}$alkyl;
each R$^n$ is independently:
  C$_{1-6}$alkyl;
  oxo;
  hydroxyl;
  hydroxyl-C$_{1-6}$alkyl; or
  halo;
R$^p$ is:
  hydrogen; or
  C$_{1-6}$alkyl; and
R$^x$ is: C$_{1-6}$alkyl; C$_{1-6}$alkoxy; hydroxy; halo; hydroxy-C$_{1-6}$alkyl; or cyano.

2. The compound of claim 1, wherein Z is: a bond; —NR$^p$—C$_{1-6}$alkylene; —C(O)—; —C(O)NR$^p$—; —C(O)NR$^x$—C$_{1-6}$alkylene; —NR$^x$C(O)—; —NR$^x$—C$_{1-6}$alkylene; —NR$^x$—; or —NR$^x$C(O)—C$_{1-6}$alkylene.

3. The compound of claim 1, wherein Z is: a bond; —NR$^p$—C$_{1-6}$alkylene; —C(O)—; —C(O)NR$^p$—; —NR$^x$—C$_{1-6}$alkylene; or —C(O)NR$^p$—.

4. The compound of claim 1, wherein Z is a bond.

5. The compound of claim 1, wherein Het is heteroaryl selected from: oxazolyl; isoxazolyl; pyrazolyl; triazolyl; or oxadiazolyl; each of which may be unsubstituted or substituted one or more times with R$^m$.

6. The compound of claim 1, wherein Het is: 3H-1,3,4-oxadiazol-2-one-5-yl; 3-methyl-1,3,4-oxadiazol-2-one-5-yl; 4H-1,2,4-triazol-3-yl; 3H-1,3,4-oxadiazol-2-one-5-yl; pyrazine-2-yl; 5-methylisoxazol-3-yl; isoxazol-3-yl; 3-oxo-isoxazole-5-yl; oxazol-2-yl; 2-methyl-1,2,4-triazol-3-yl; oxazol-4-yl; 1H-pyrazol-5-yl; pyrimidin-2-yl; 1H-pyrazol-3-yl; 1,3,4-oxadiazole-2-carboxylate-5-yl; 3-aminopyrazol-1-yl; or N-methyl-1,2,4-oxadiazole-5-carboxamide-3-yl.

7. The compound of claim 1, wherein R$^3$ is methyl.

8. The compound of claim 1, wherein R$^f$ is: hydrogen; halo; C$_{1-6}$alkyl; or halo-C$_{1-6}$alkyl.

9. The compound of claim 1, wherein R$^g$ is: hydrogen; halo; C$_{1-6}$alkyl; hydroxyl; C$_{1-6}$alkoxy; or halo-C$_{1-6}$alkyl.

10. A compound selected from:

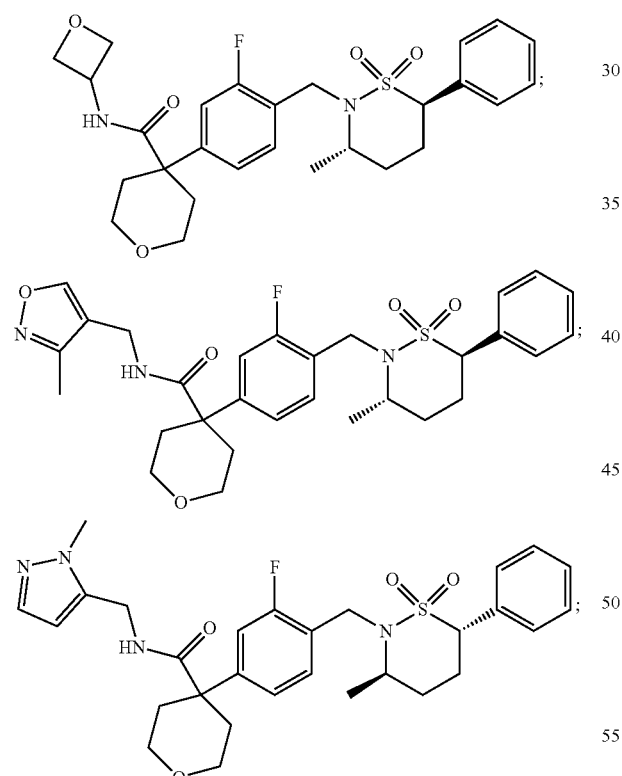

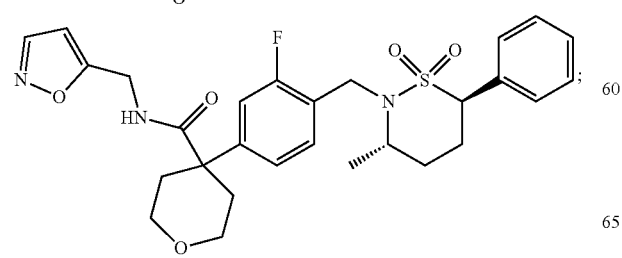

-continued

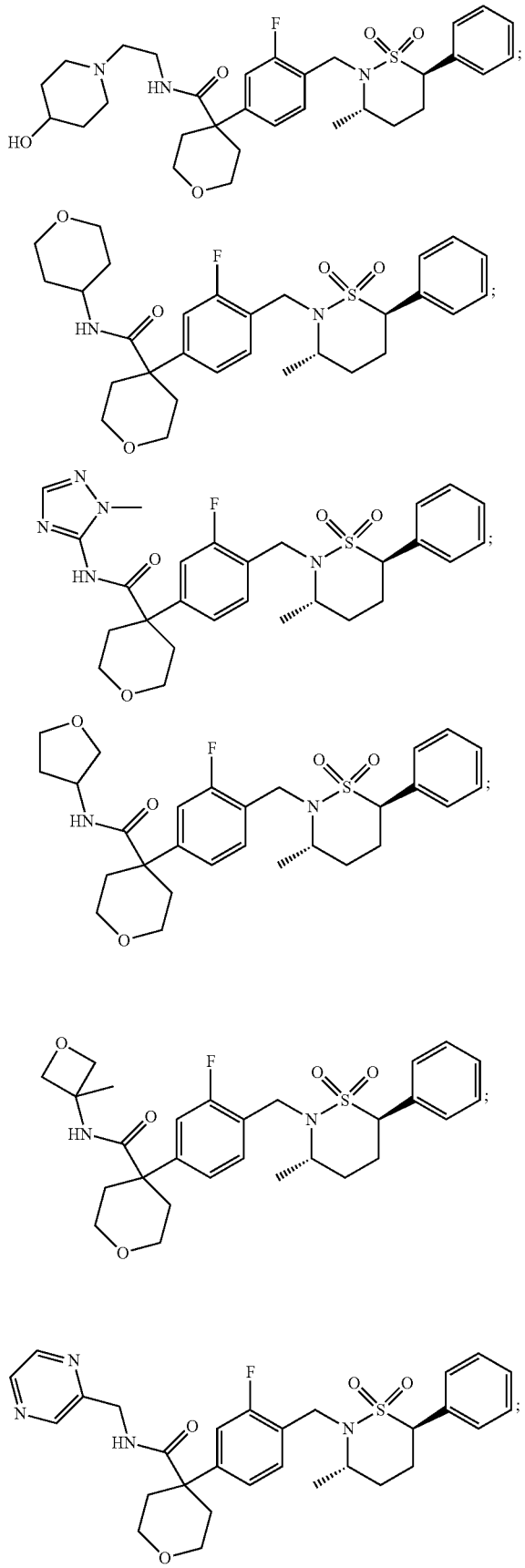

191
-continued
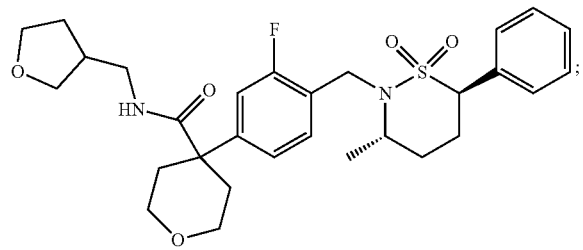
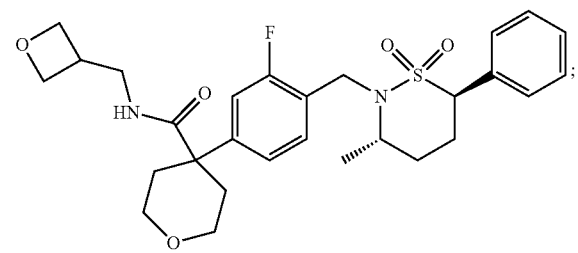
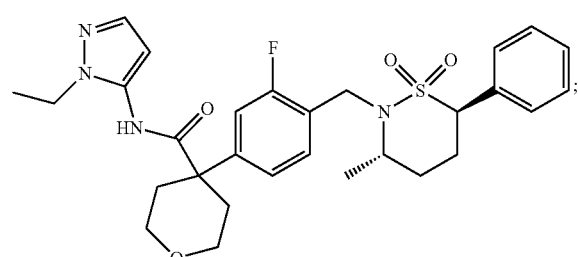
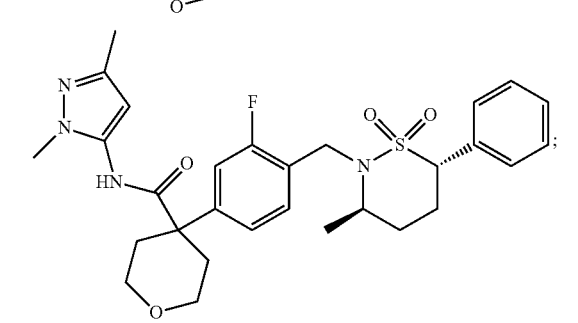
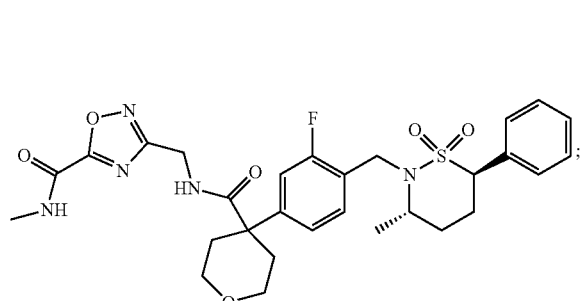
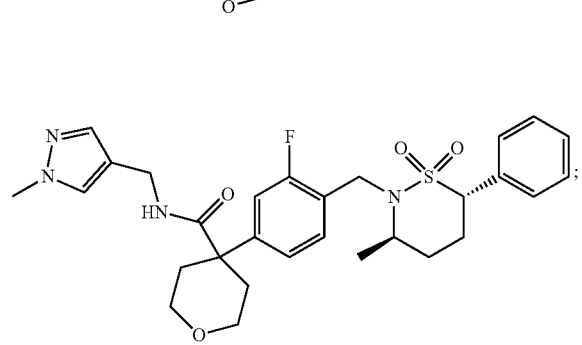
192
-continued
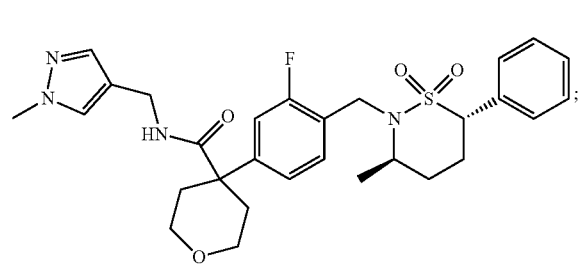

193
-continued
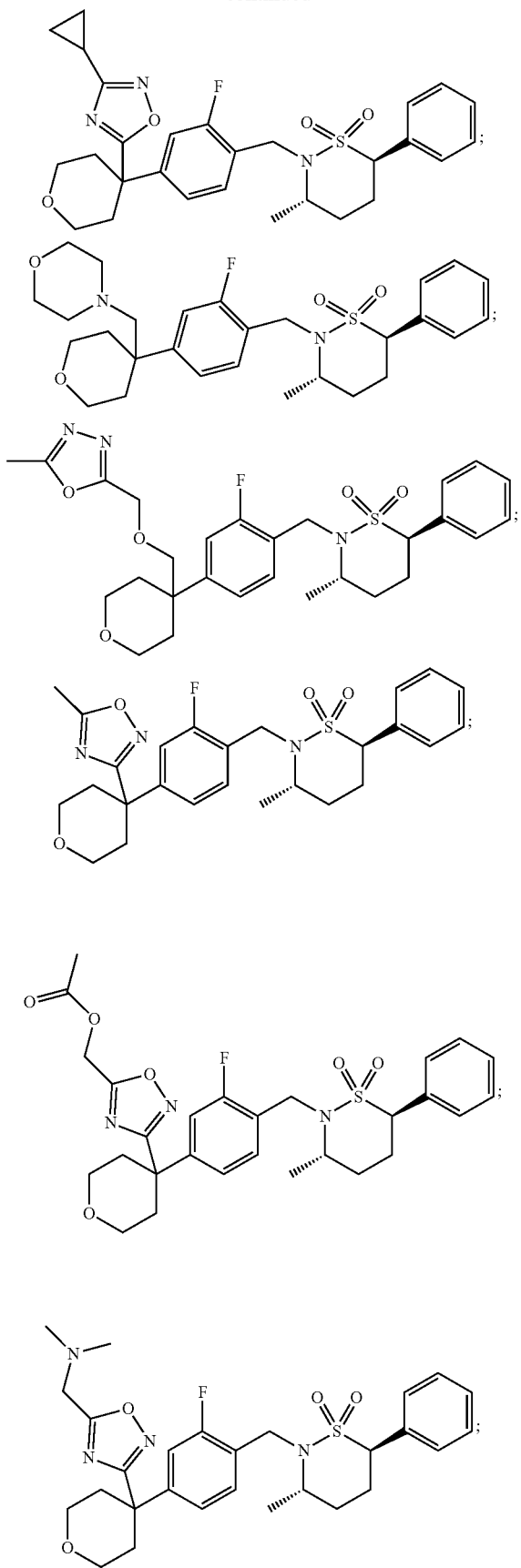
194
-continued
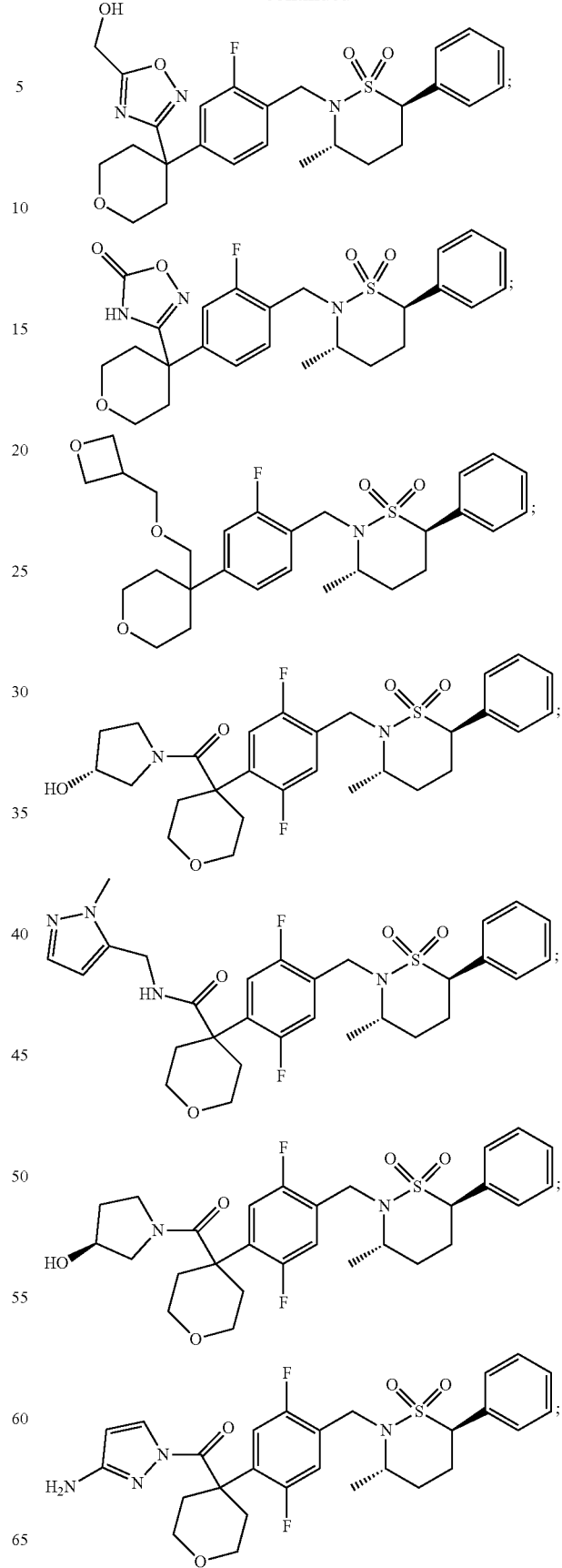

195
-continued
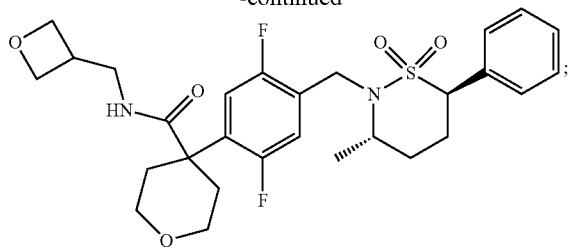
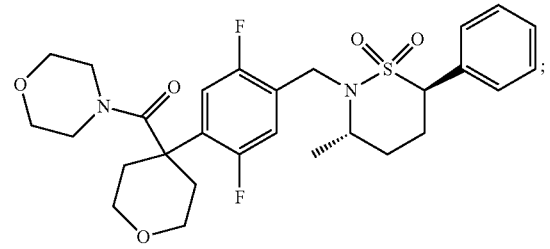
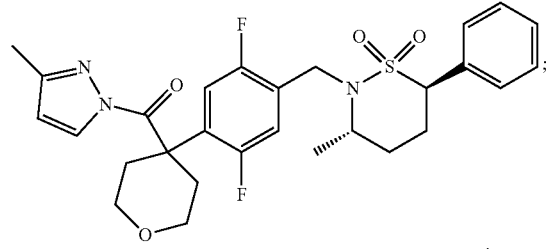
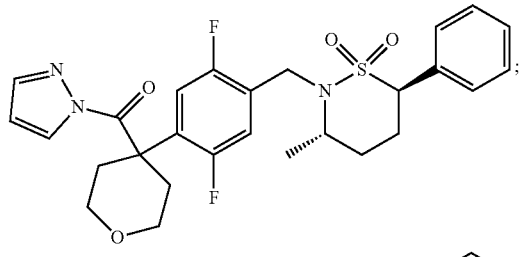
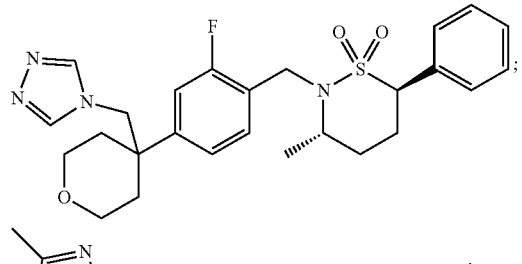
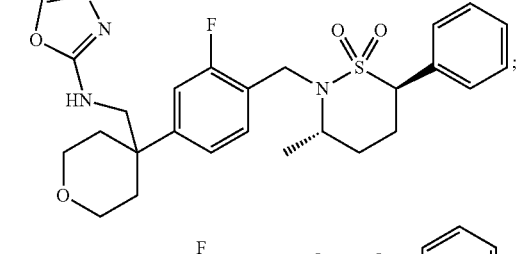
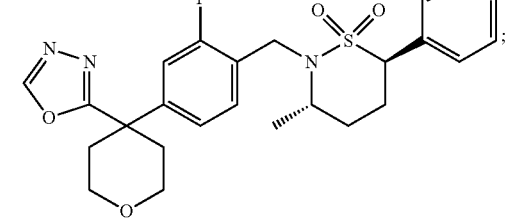
196
-continued
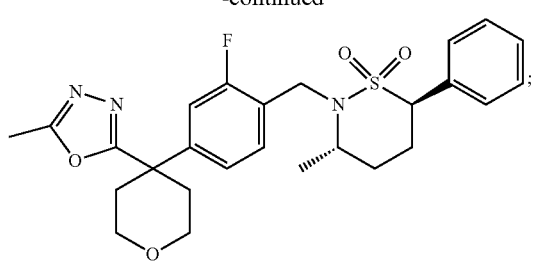
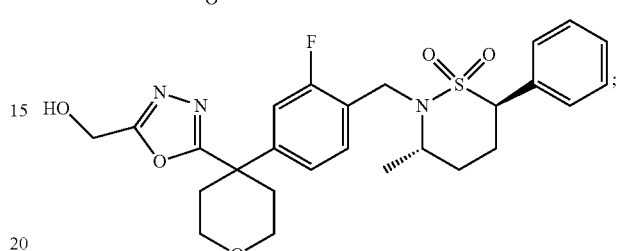
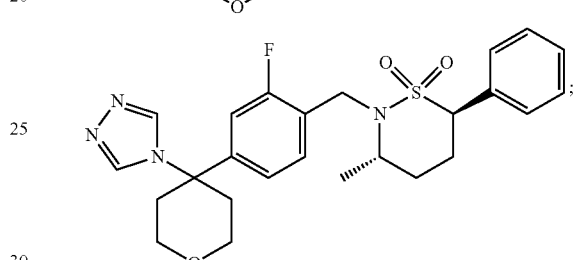
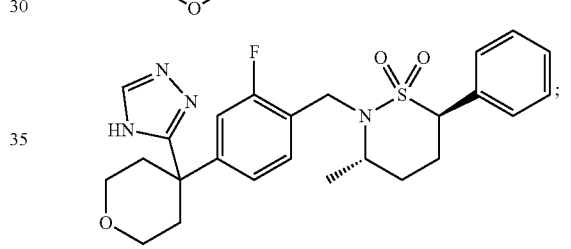
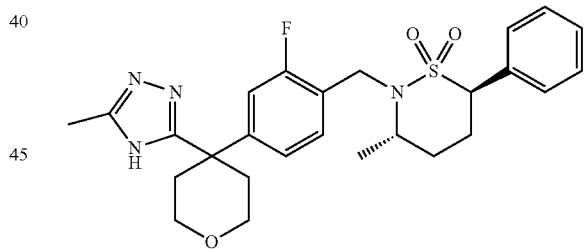
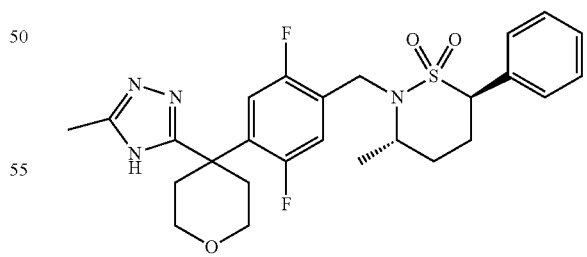
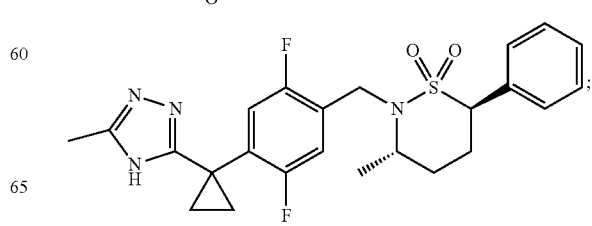

197
-continued
198
-continued
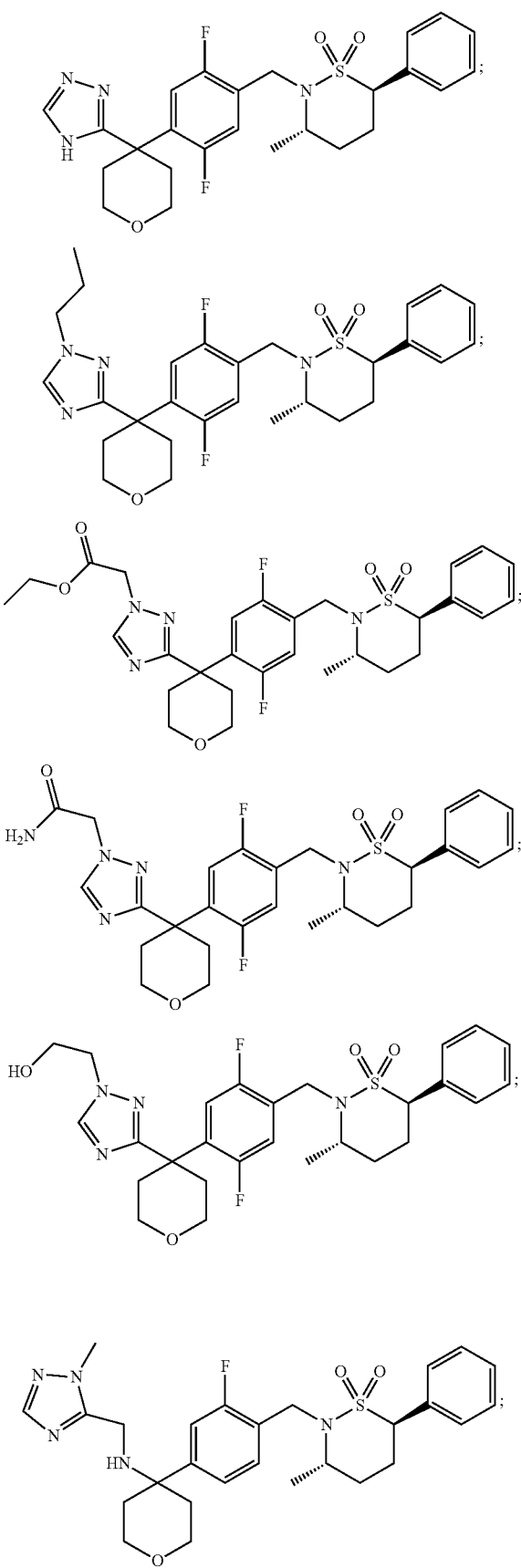
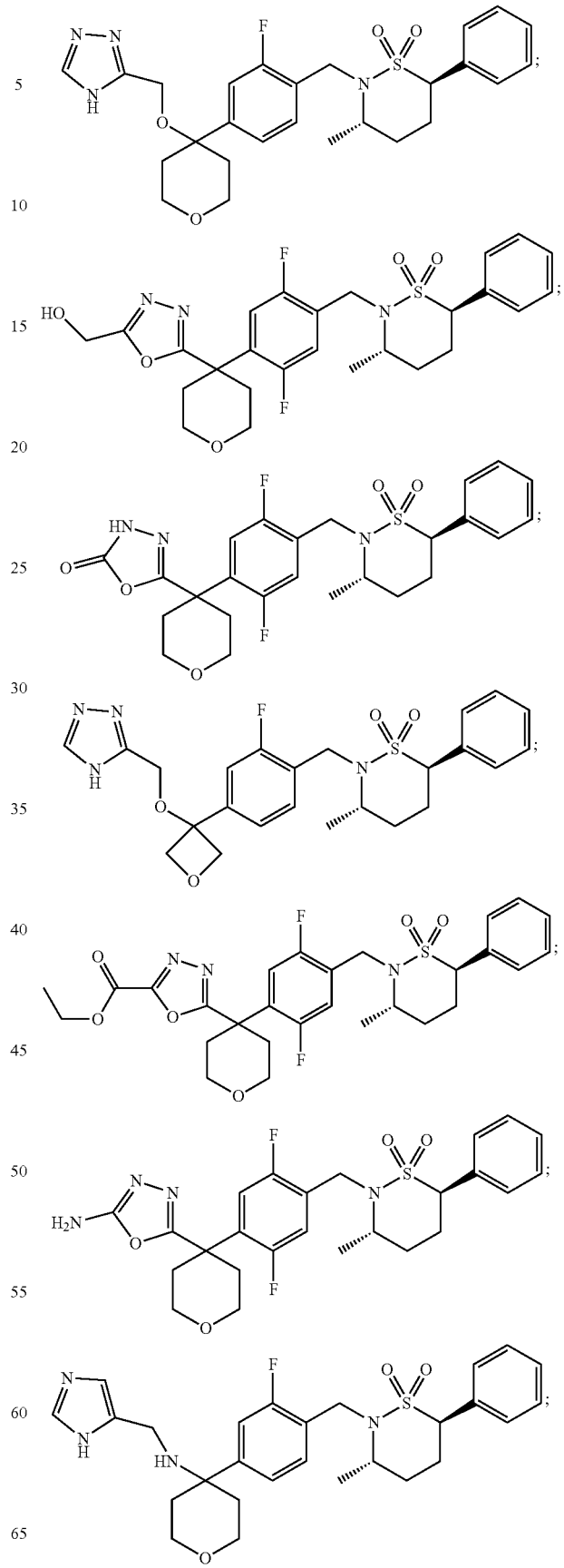

199
-continued
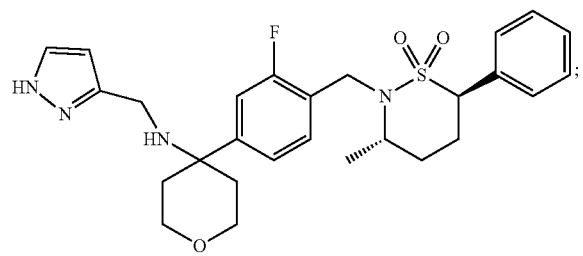
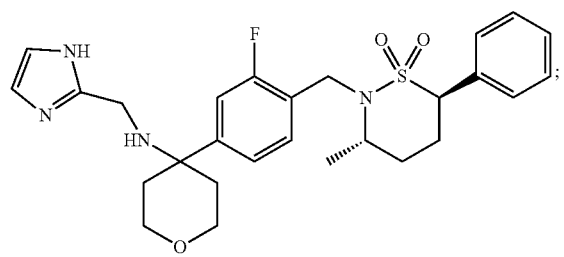
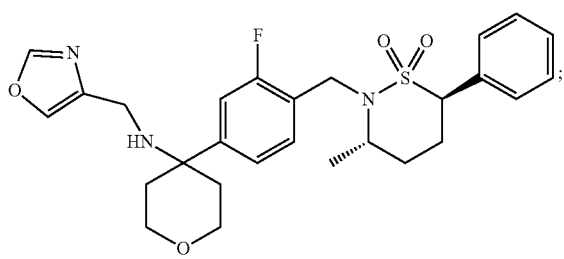
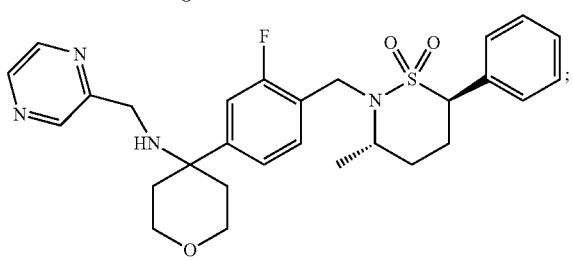
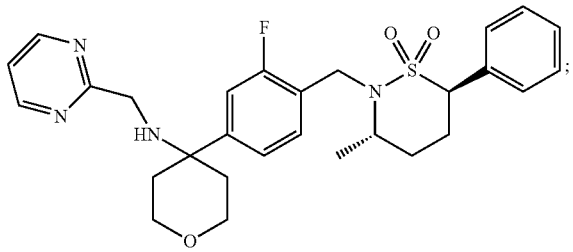
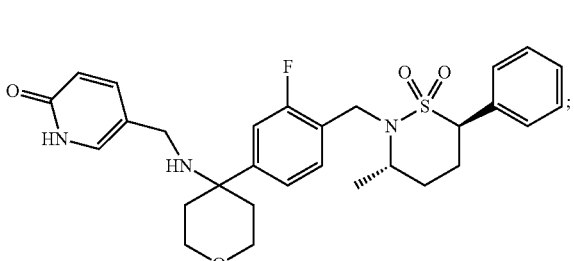
200
-continued
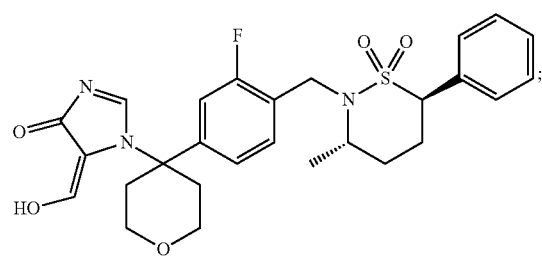
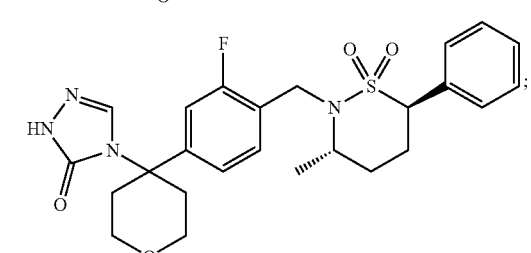
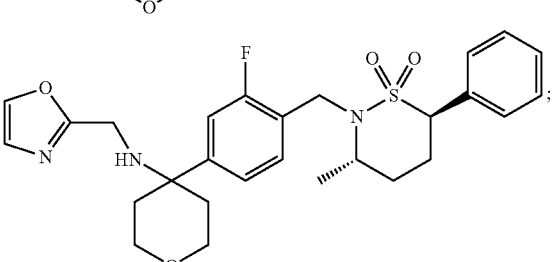
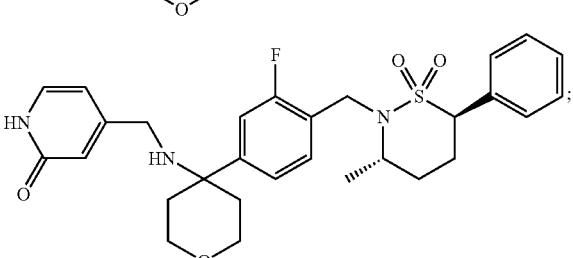
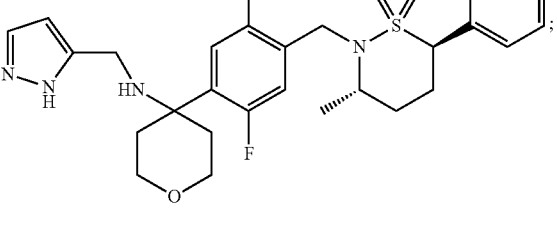
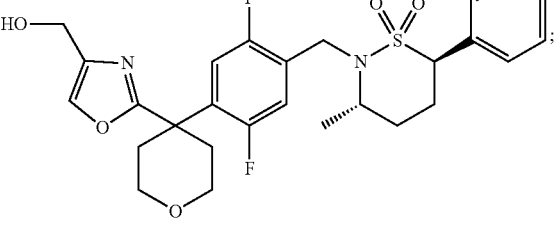

201
-continued
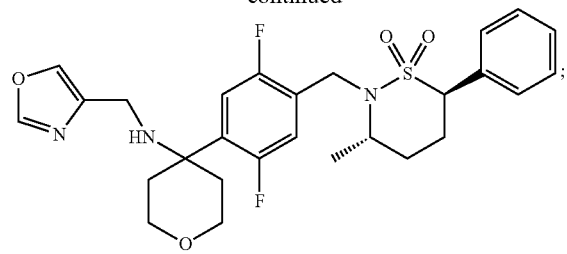
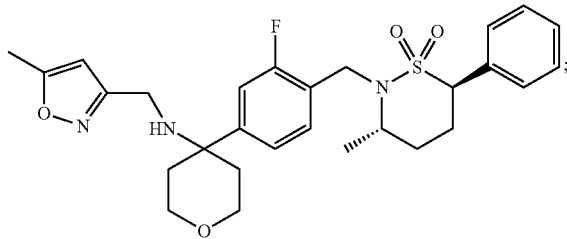
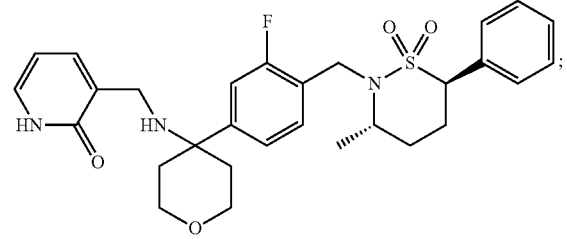
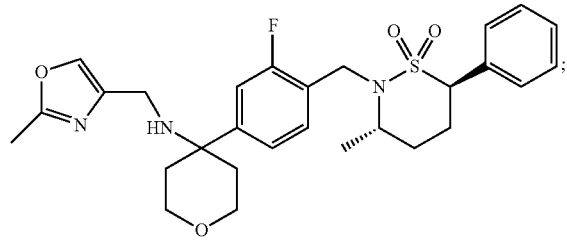
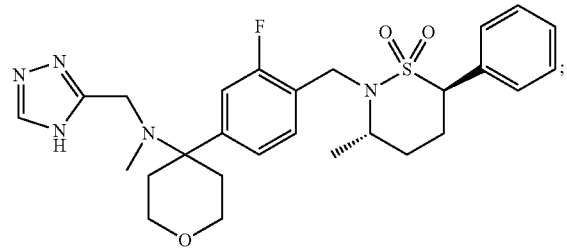
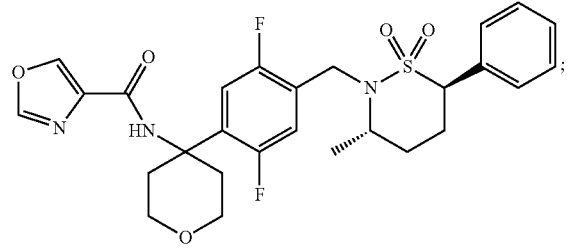
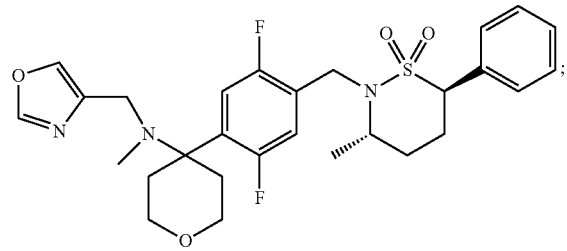
202
-continued
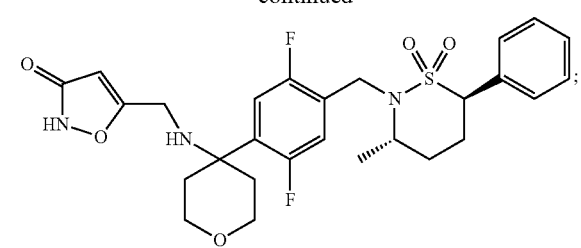
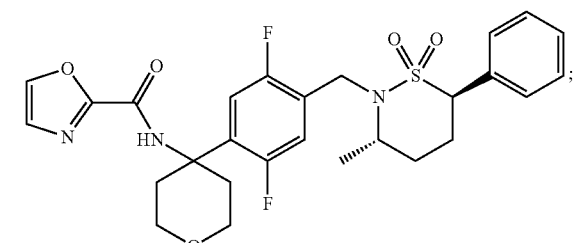
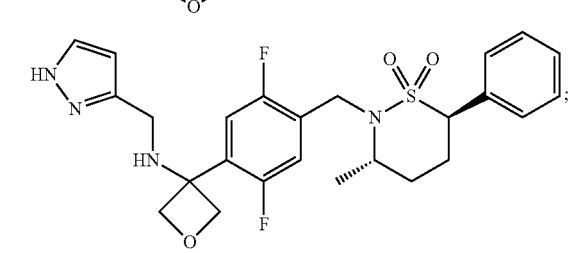
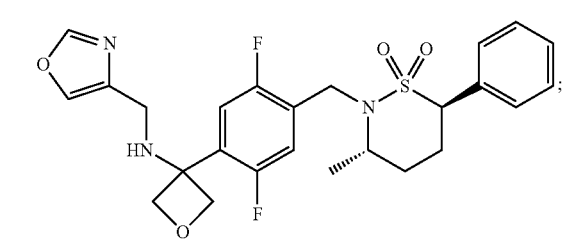
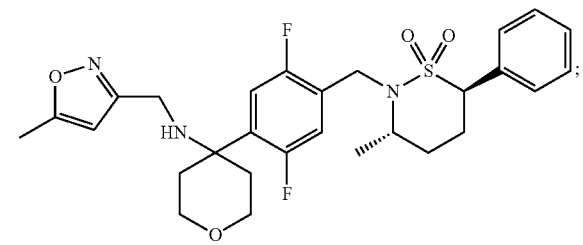
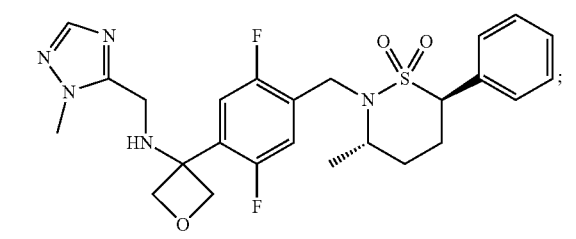
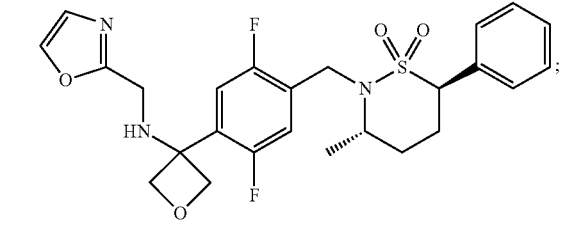

203
-continued
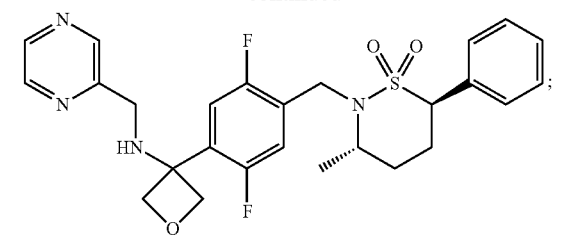
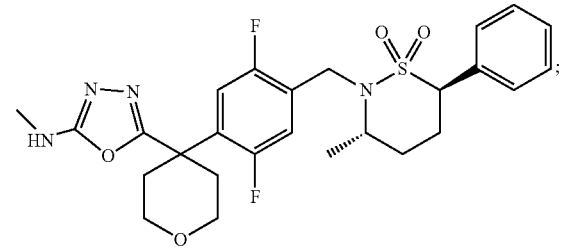
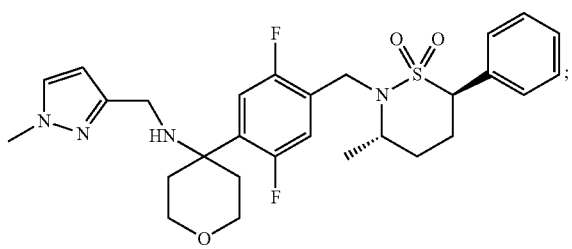
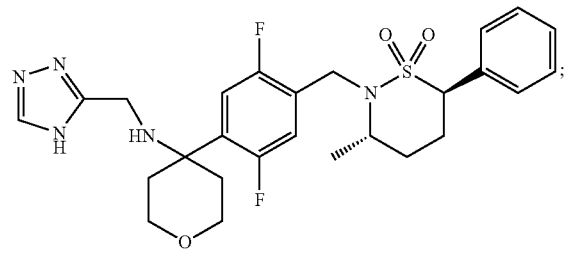
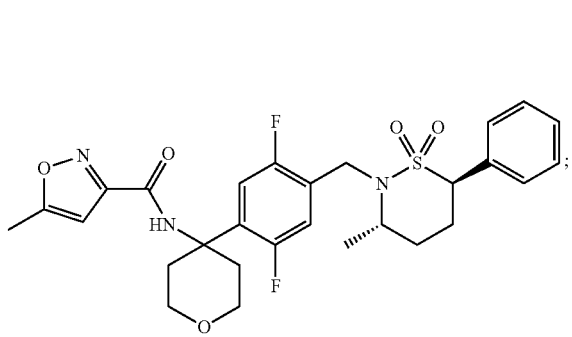
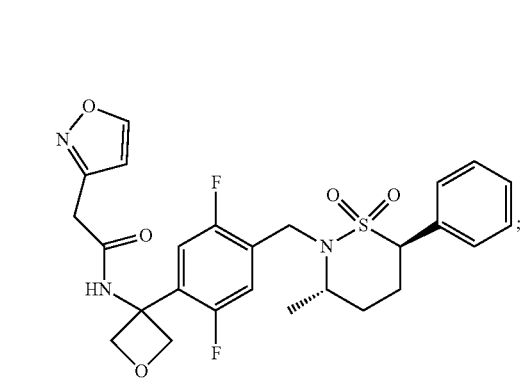
204
-continued
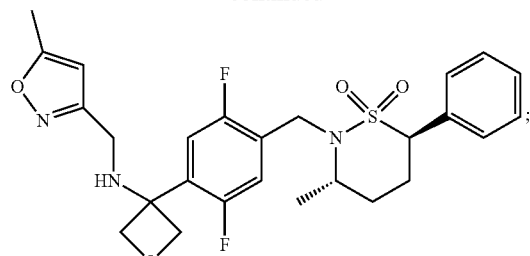
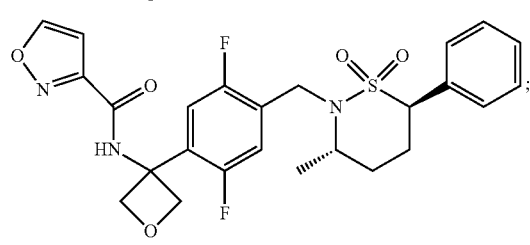
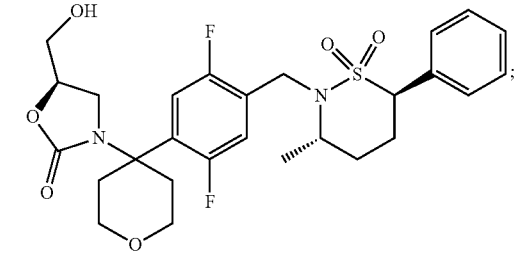
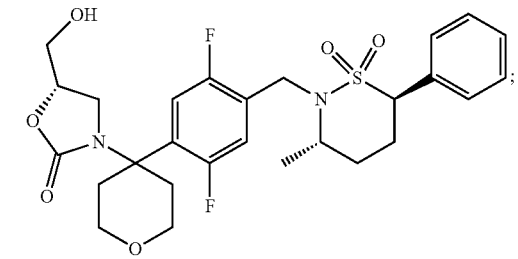
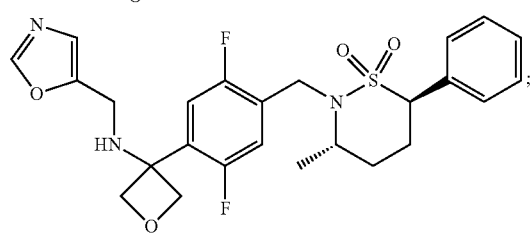
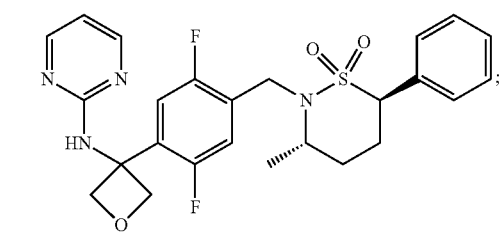

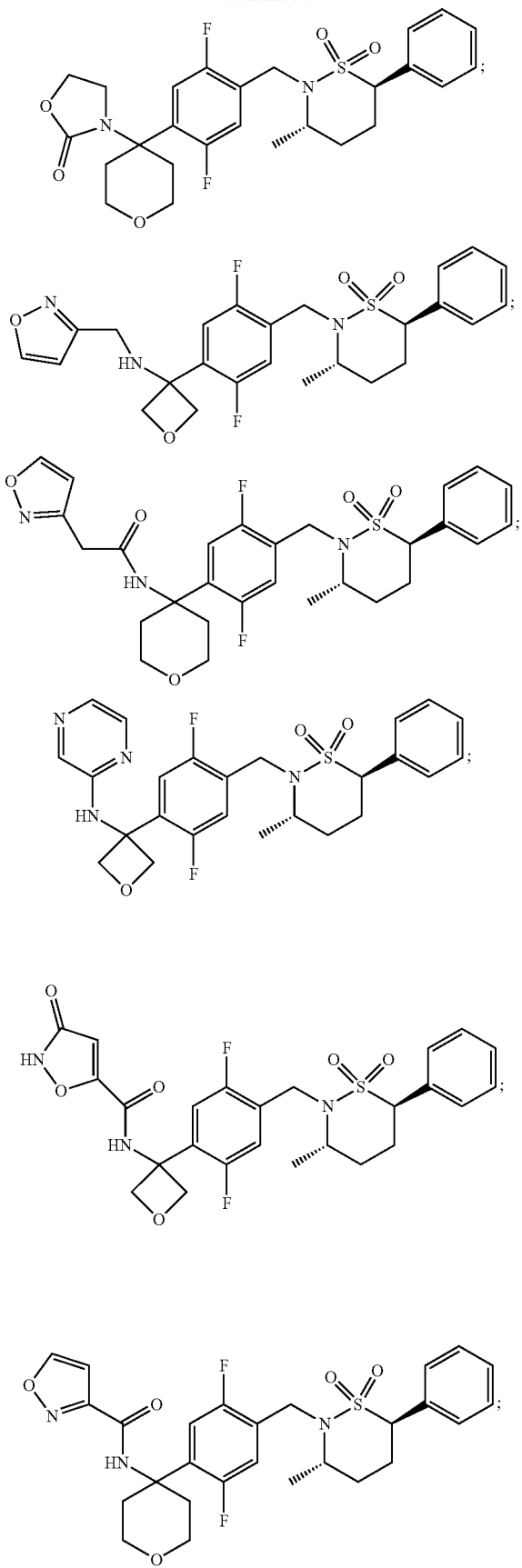
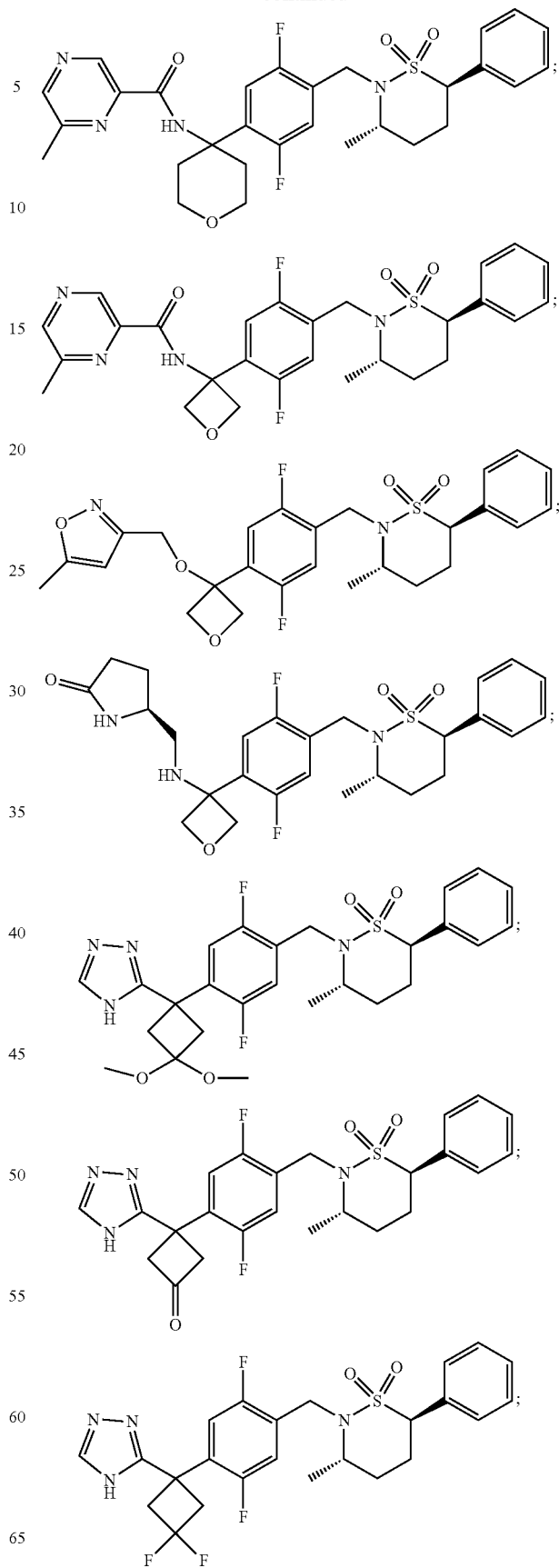

207
-continued
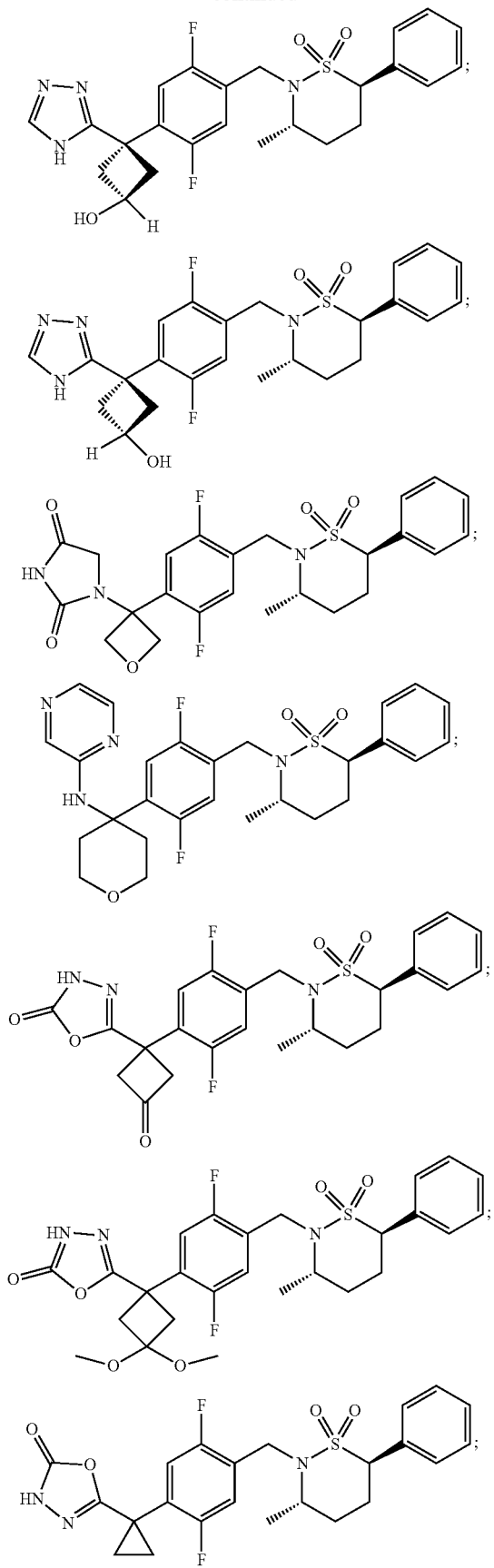
208
-continued
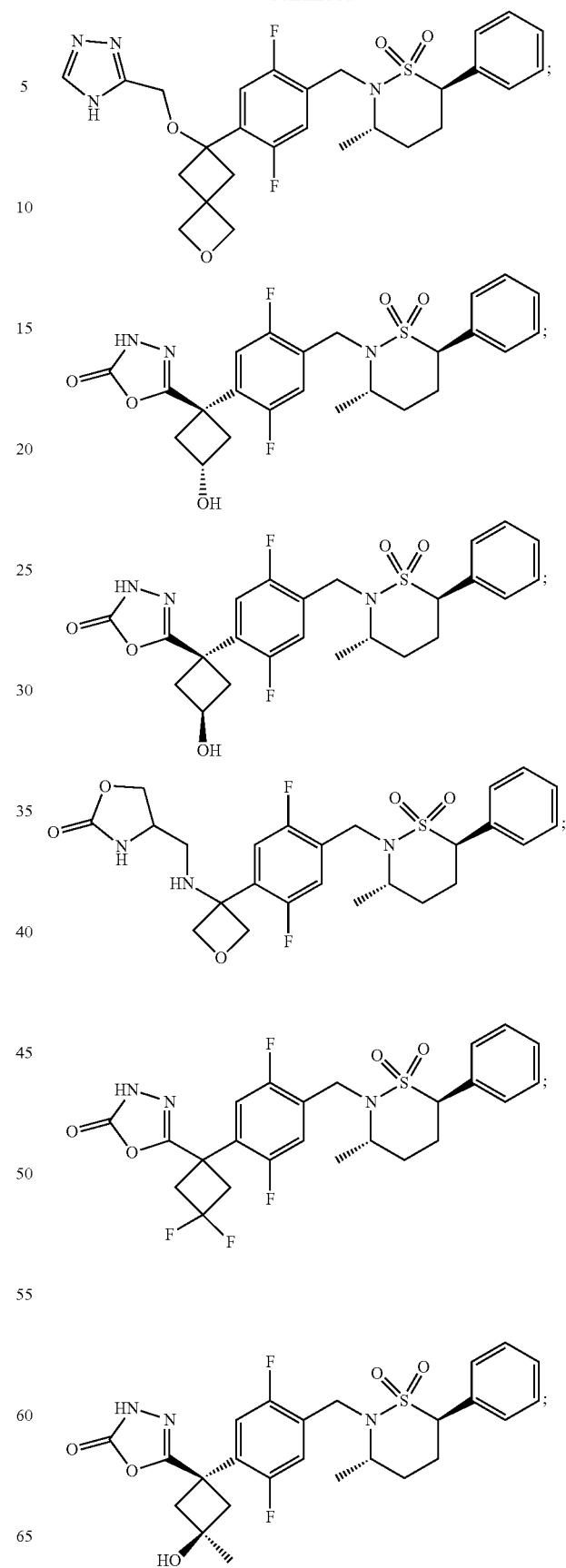

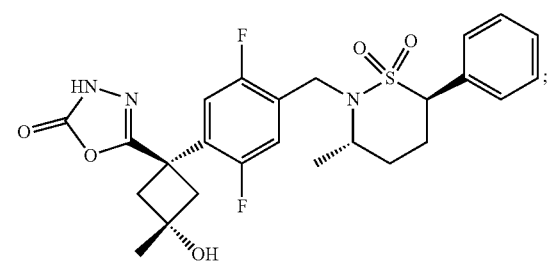
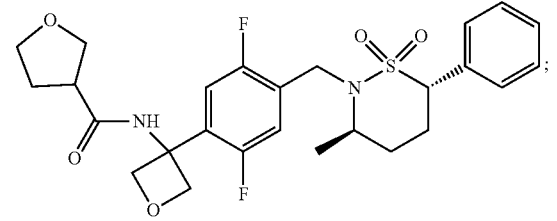
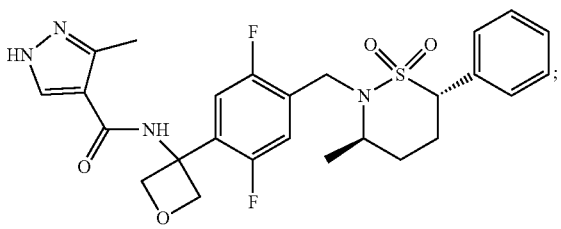
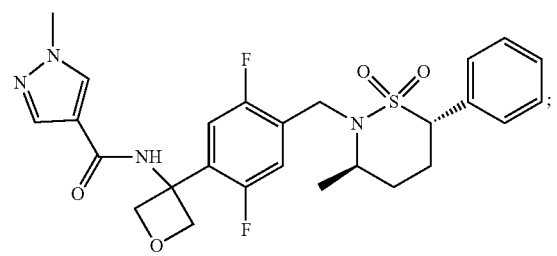
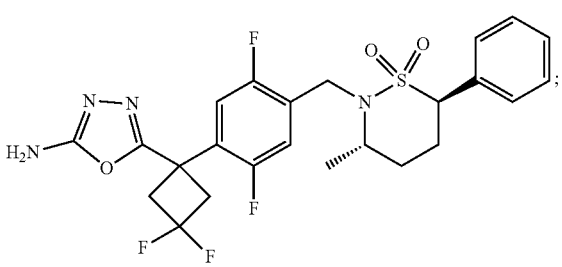
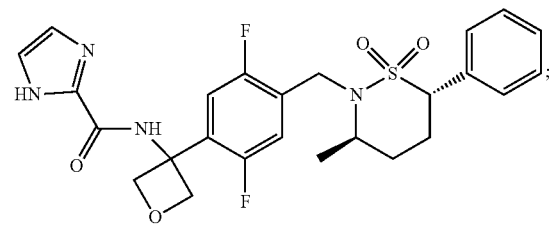
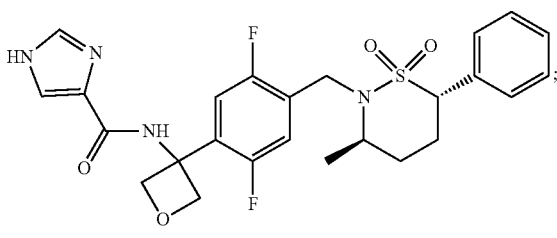
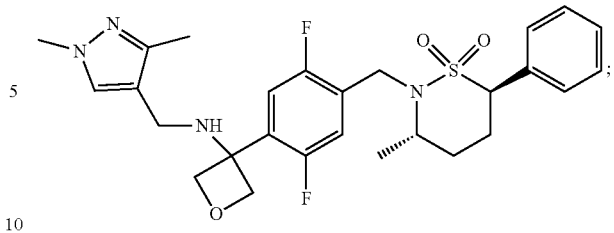
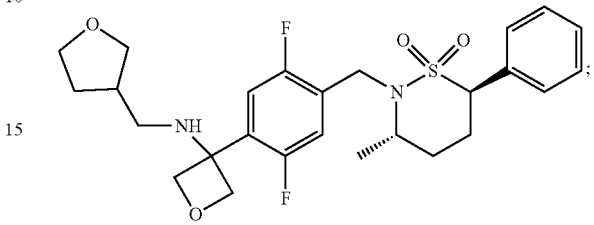
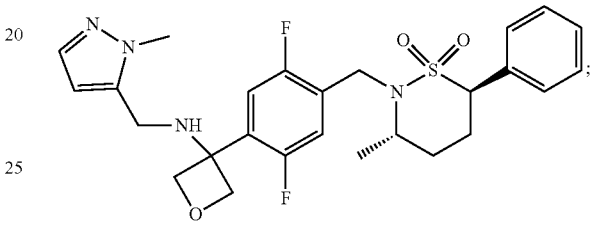
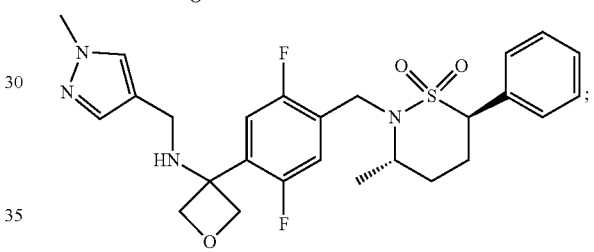
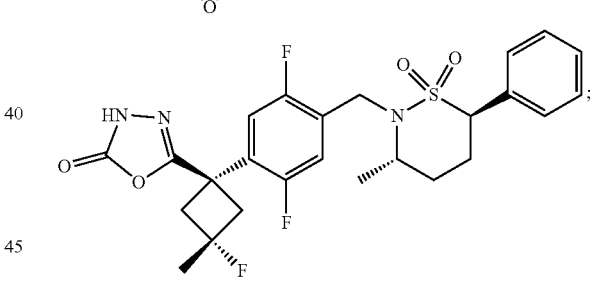
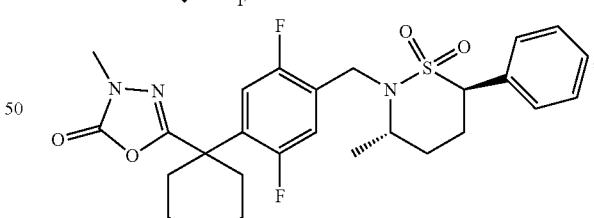
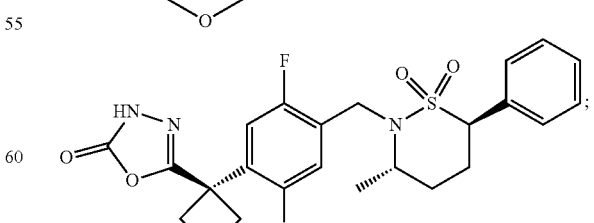
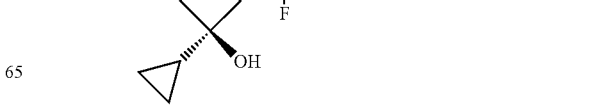

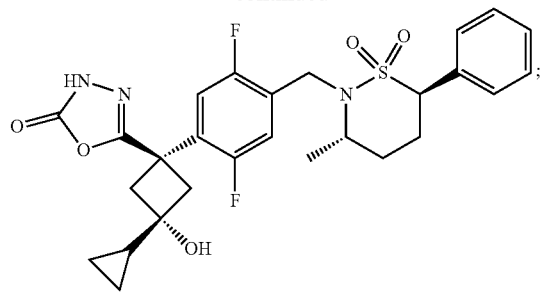
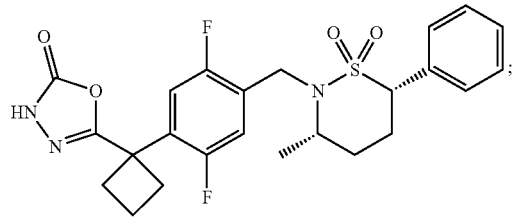
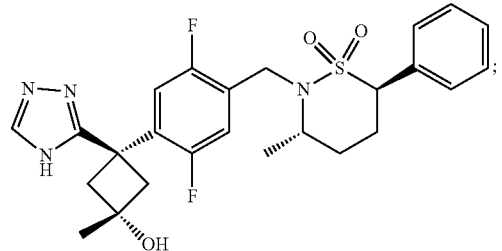
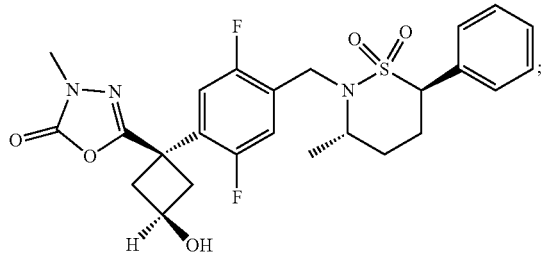
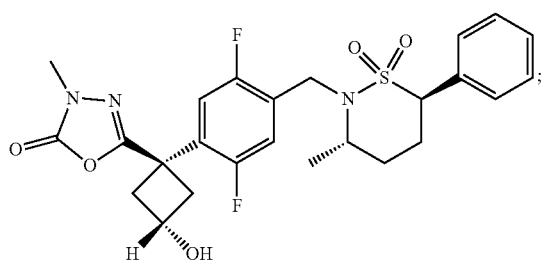
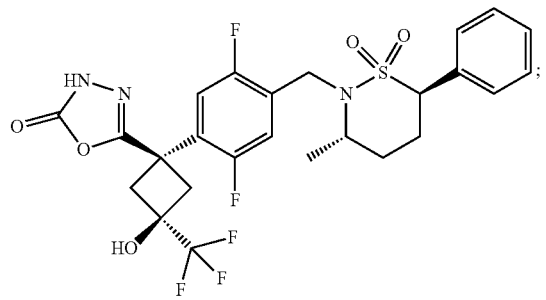
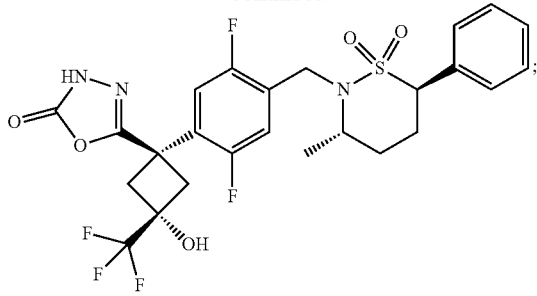
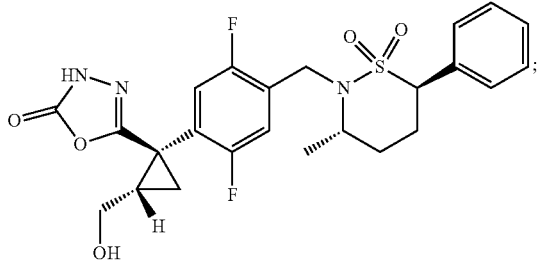
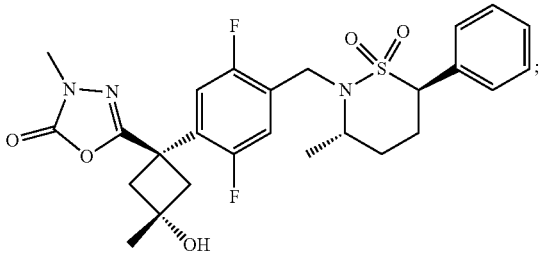
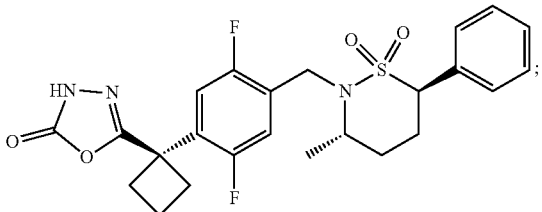
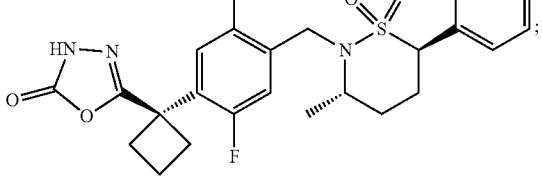
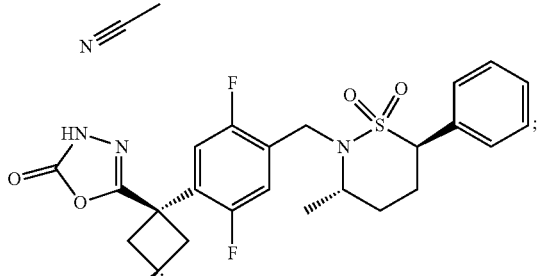

213
-continued
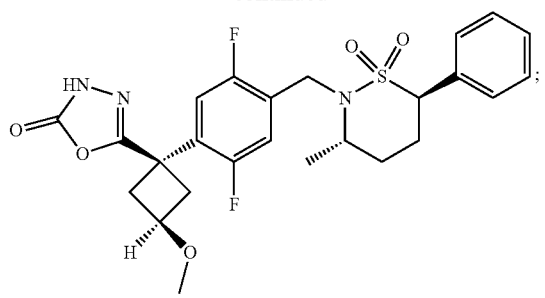
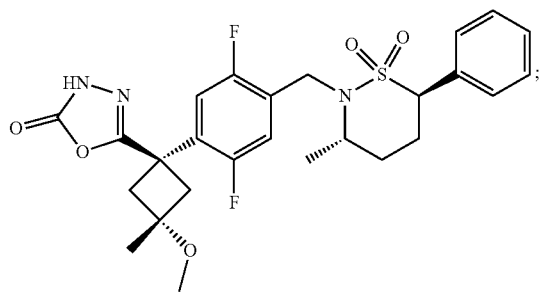
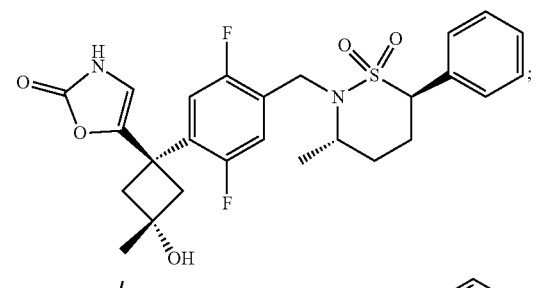
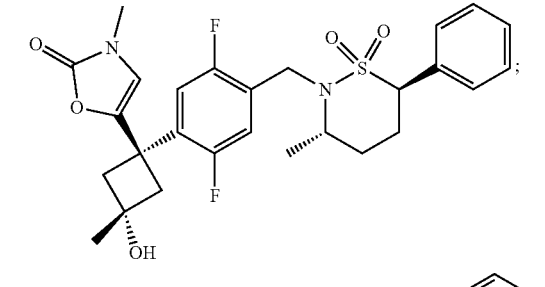
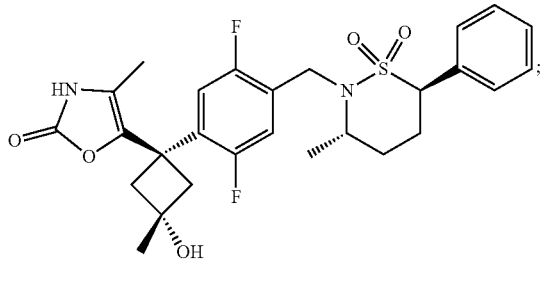
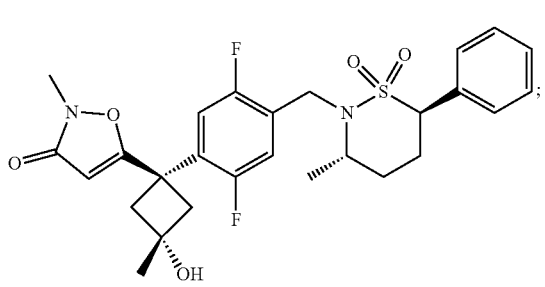
214
-continued
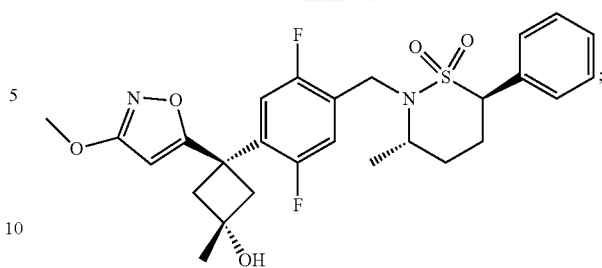
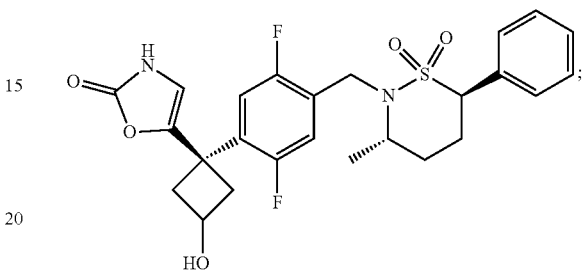
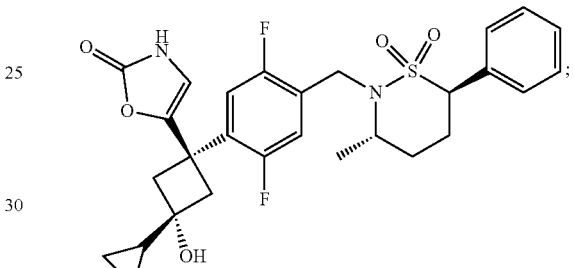
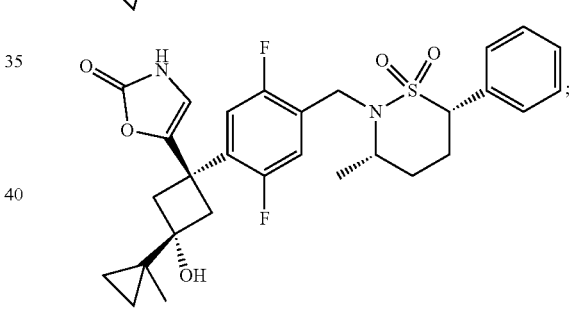
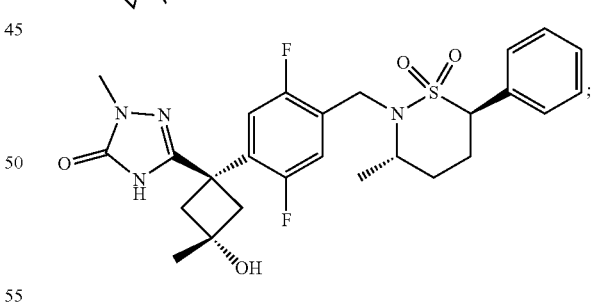
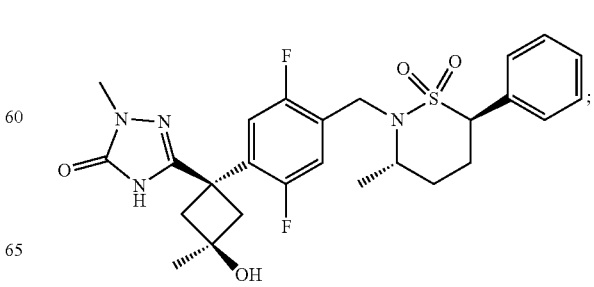

215
-continued
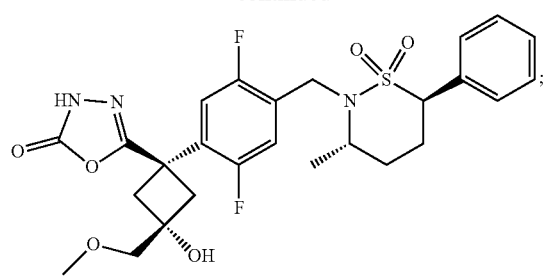
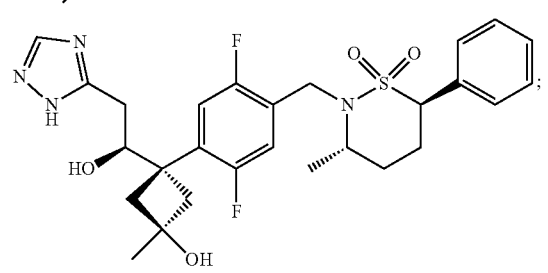
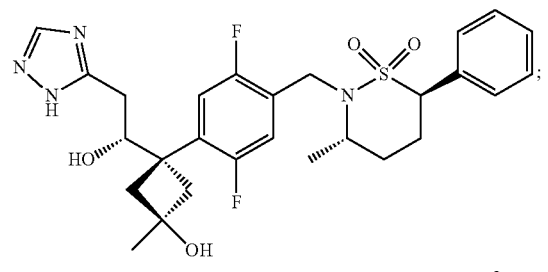
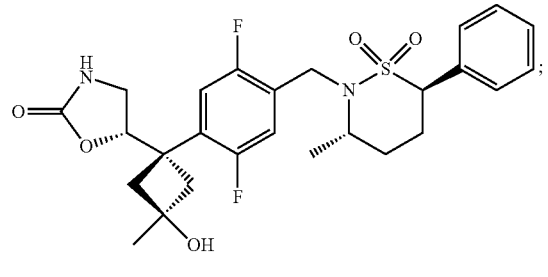
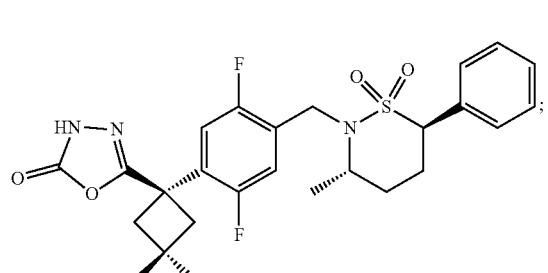
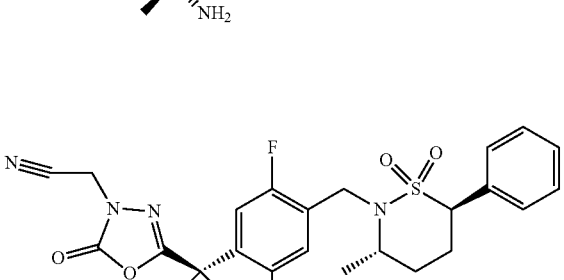
216
-continued
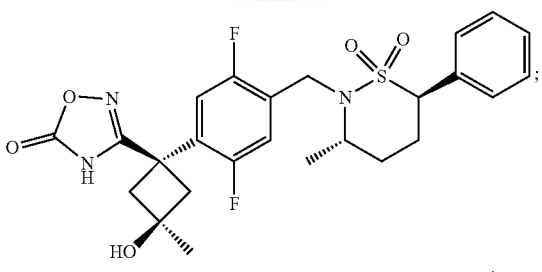
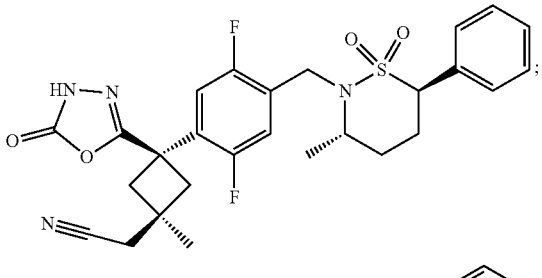
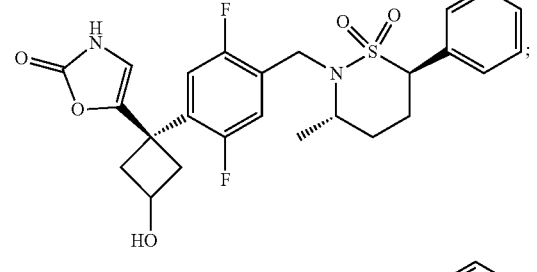
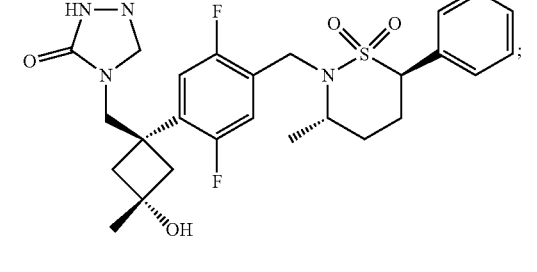
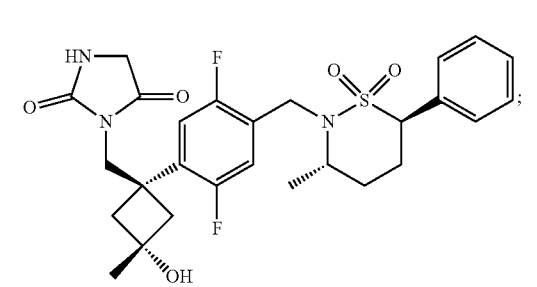
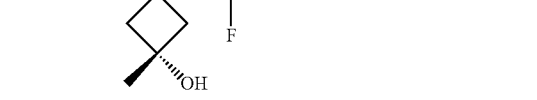

-continued
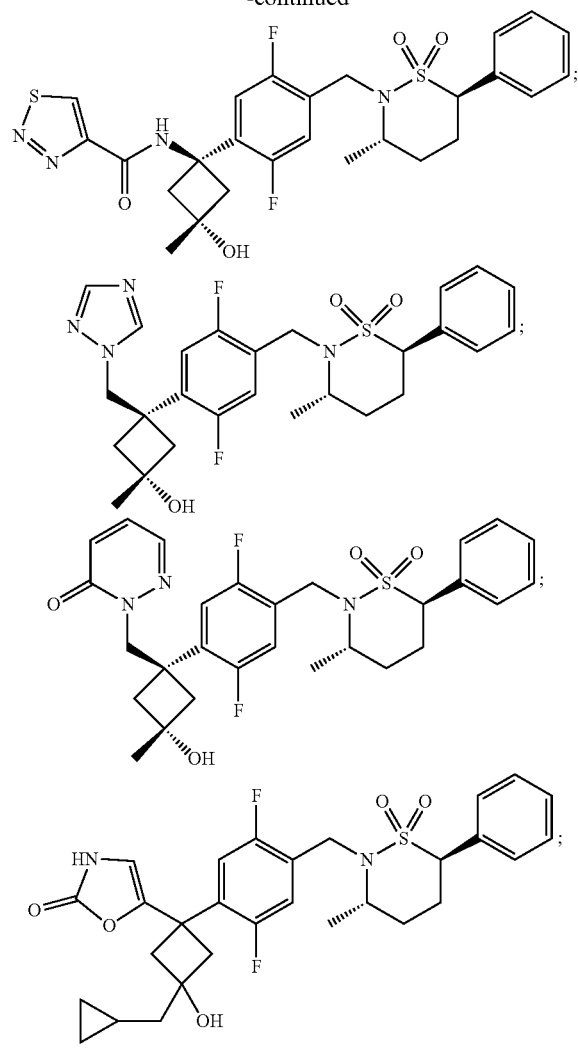
-continued
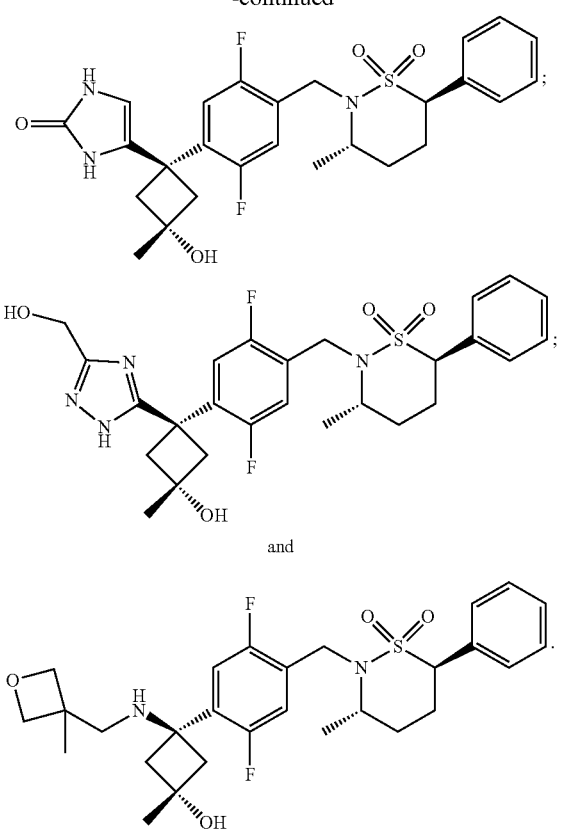
and
11. A composition comprising:
(a) a pharmaceutically acceptable carrier; and
(b) a compound of claim 1.
* * * * *